United States Patent
Crouse et al.

(10) Patent No.: US 9,440,964 B2
(45) Date of Patent: *Sep. 13, 2016

(54) PESTICIDAL COMPOSITIONS AND PROCESSES RELATED THERETO

(71) Applicant: Dow AgroSciences LLC, Indianapolis, IN (US)

(72) Inventors: Gary D. Crouse, Noblesville, IN (US); David A. Demeter, Fishers, IN (US); Thomas C. Sparks, Greenfield, IN (US); Nick X. Wang, Westfield, IN (US); William H. Dent, III, Indianapolis, IN (US); Carl DeAmicis, Indianapolis, IN (US); Noormohamed M. Niyaz, Indianapolis, IN (US); Erich W. Baum, Greenwood, IN (US); Lindsey G. Fischer, Indianapolis, IN (US); Natalie C. Giampietro, Carmel, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 14/670,470

(22) Filed: Mar. 27, 2015

(65) Prior Publication Data

US 2015/0197514 A1 Jul. 16, 2015

Related U.S. Application Data

(63) Continuation of application No. 13/546,010, filed on Jul. 11, 2012, now abandoned.

(60) Provisional application No. 61/506,743, filed on Jul. 12, 2011.

(51) Int. Cl.
| | |
|---|---|
| *C07D 417/12* | (2006.01) |
| *A01N 43/653* | (2006.01) |
| *A01N 43/78* | (2006.01) |
| *A01N 47/36* | (2006.01) |
| *A01N 47/42* | (2006.01) |
| *C07D 403/12* | (2006.01) |
| *C07D 417/14* | (2006.01) |
| *C07D 249/08* | (2006.01) |
| *A01N 43/82* | (2006.01) |
| *A01N 43/86* | (2006.01) |
| *C07D 271/107* | (2006.01) |
| *C07D 405/12* | (2006.01) |

(52) U.S. Cl.
CPC ........... *C07D 417/12* (2013.01); *A01N 43/653* (2013.01); *A01N 43/78* (2013.01); *A01N 43/82* (2013.01); *A01N 43/86* (2013.01); *A01N 47/36* (2013.01); *A01N 47/42* (2013.01); *C07D 249/08* (2013.01); *C07D 271/107* (2013.01); *C07D 403/12* (2013.01); *C07D 405/12* (2013.01); *C07D 417/14* (2013.01)

(58) Field of Classification Search
CPC .................................................... C07D 417/12
See application file for complete search history.

(56) References Cited

U.S. PATENT DOCUMENTS

| | | |
|---|---|---|
| 3,818,104 A | 6/1974 | Zilinkski |
| 3,932,436 A | 1/1976 | Grohe et al. |
| 4,017,529 A | 4/1977 | Fuchs |
| 4,867,780 A | 9/1989 | Woolard |
| 5,466,705 A | 11/1995 | Ozaki et al. |
| 6,136,335 A | 10/2000 | Uckun et al. |
| 6,417,187 B2 | 7/2002 | Hegde et al. |
| 2004/0138205 A1 | 7/2004 | Chen et al. |
| 2007/0027034 A1 | 2/2007 | Tank et al. |
| 2008/0262057 A1 | 10/2008 | Tisdell et al. |
| 2009/0137667 A1 | 5/2009 | Kabanov et al. |
| 2009/0209476 A1 | 8/2009 | Crouse et al. |
| 2010/0204164 A1 | 8/2010 | Crouse et al. |
| 2012/0053216 A1 | 3/2012 | Creemer et al. |
| 2012/0172217 A1 | 7/2012 | Brown et al. |
| 2012/0190543 A1 | 7/2012 | Lambert et al. |

(Continued)

FOREIGN PATENT DOCUMENTS

| | | |
|---|---|---|
| WO | 98/47894 A1 | 10/1998 |
| WO | 2009102736 A1 | 8/2009 |
| WO | 2011017513 A1 | 2/2011 |

OTHER PUBLICATIONS

Thomas A. Magee "Insecticidal Substituted 2-Butanone O-(Methylaminocarbonyl)oximes" Journal of Agricultural and Food Chemistry 1977, 25, 1376-1382.*
Kurtz, et. al. "Novel Insecticidal Oxathiolane and Oxathiane Oxime Carbamates" Journal of Agricultural and Food Chemistry 1987, 35, 106-114.*
Henrick et. al. "Ovicidal Activity and Its Relation to Chemical Structure for the Two-spotted Spider Mite (*Tetranychus urticae* Koch) in a New Class of Miticides Containing the Cyclopropyl Group" Journal of Agricultural and Food Chemistry 1976, 24, 1023-1029.*

(Continued)

*Primary Examiner* — David K. O'Dell
(74) *Attorney, Agent, or Firm* — Yung H. Lee

(57) ABSTRACT

This document discloses molecules having the following formula ("Formula One")

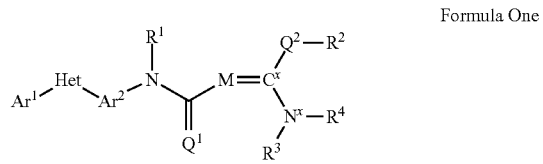

Formula One

The molecules disclosed in this document are related to the field of processes to produce molecules that are useful as pesticides (e.g., acaricides, insecticides, molluscicides, and nematicides), such molecules, and processes of using such molecules to control pests.

12 Claims, No Drawings

(56) References Cited

U.S. PATENT DOCUMENTS

2012/0202687 A1     8/2012     Crouse et al.
2012/0202688 A1     8/2012     Crouse et al.

OTHER PUBLICATIONS

Dekeyser et. al. "Synthesis and Miticidal and Insecticidal Activities of 4-(2-Fluoroethyl)-5,6-dihydro-4H-1,3,4-oxadiazines" Journal of Agricultural and Food Chemistry 1993, 41, 1329-1331.*
Pozharskii et. al. Heterocycles in Life and Society Wiley, 1997, pp. 1-6.*
Pitt "Heteroaromatic Rings of the Future" J. Med. Chem. 2009, 52, 2952-2963.*
Dorwald F. A. Side Reactions in Organic Synthesis, 2005, Wiley: VCH, Weinheim p. IX of Preface, pp. 1-16.*
Michael Schnürch, "Cross-Coupling Reactions on Azoles with Two and More Heteroatoms" European Journal of Organic Chemistry 2006, 15, 3283-3307.*
International Search Report and Written Opinion for PCT/US2012/046131 mailed Jan. 17, 2013.
L. Zhou, et al.: "Metabolites of an orally active antimicrobial prodrug, 2, 5-bis (4-amidophenyl) furan-bis-O-methylamidoxime, identified by liquid chromatography/tandem mass spectrometry" J. Mass Spectrom., vol. 39, 2004, pp. 351-360.
Yuan JJ et al: "Disposition of a Specific Cyclooxygenase-2 inhibitor, Valdecoxib, in human" Drug Metabolism and Deposition, Williams and Wilkins, Baltimore, MD, US, vol. 30, No. 9, Jan. 1, 2002.
Melucci et al., "Shaping Thiophene Oligomers into Fluorescent Nanobeads Forming Two-Dimensionally Patterned Assemblies by the Capillary Effect" Macromolecules (2005) vol. 38 pp. 10050-10054.
Braga et al., "Making Crystals from Crystals: a Green Route to Crystal Engineering and Polymorphism" Chemical Communications (2005) pp. 3635-3645.
Jain et al., "Polymorphism in Pharmacy" Indian Drugs (1986) vol. 23 No. 6, pp. 315-329.
Lieberman et al., "Pharmaceutical Dosage Forms" vol. 2, published 1990 by Marcel Dekker, Inc., pp. 462-472.
Vippagunta et al., "Crystalline Solids" Advanced Drug Delivery Reviews (2001) vol. 48 pp. 3-26.
J.S. Brimacombe, F. Hunedy, and A. Husan; "Syntheses of 6-Deoxy-2,4-and 3,4-Di-O-Methyl-D-Allose," Carbohydrate Research, 10 (1969) pp. 141-151, Elsevier Publishing Company, Amsterdam, Belgium.
Kenji Oshima, Ei-Ichi Kitazono, and Yasuhiro Aoyama; "Complexation-Induced Activation of Sugar OH Groups. Regioselective Alkylation of Methyl Fucopyranoside via Cyclic Phenylboronate in the Presence of Amine," Tetrahedron Letters, vol. 38, No. 28, pp. 5001-5004, 1997; Elseiver Science Ltd., Great Britian.
Ken-Ichi Sato, Hiroshi Seki, Akira Yoshitomo, Hiroshi Nanaumi, Yoshimitsu Takai and Yoshiharu Ishido; "Novel Synthetic Approaches to Man B1-4GLCNAc and LEX Units from N-Acetyllactosamine;" J. Carbohydrate Chemistry, 17(4&5), pp. 703-727, 1998, Marcel Dekker, Inc.
Elmarakby et al. Degradation of [14C]-Carfentrazone-ethyl under Aerobic Aquatic Conditions in Journal of Agricultural Food Chemistry, 2001, vol. 49, pp. 5285-5293. p. 5285, abstract; col. 2, para 2; col. 3, para 1, Figure 1.
Pedersen, et al. Synthesis and Insect Growth Regulating Activity of Thiosemicarbazones of Methyl 2-Pyridyl Ketones in Pest. Sci. 1984, vol. 25, pp. 462-470.

* cited by examiner

US 9,440,964 B2

PESTICIDAL COMPOSITIONS AND PROCESSES RELATED THERETO

CROSS REFERENCES TO RELATED APPLICATIONS

This Application is a continuation of, and claims the benefit of, U.S. patent application Ser. No. 13/546,010, which was filed on Jul. 11, 2012, and which claims priority from, and benefit of, U.S. provisional application 61/506,743 filed on Jul. 12, 2011. The entire contents of these applications are hereby incorporated by reference into this Application.

FIELD OF THE DISCLOSURE

The molecules disclosed in this document are related to the field of processes to produce molecules that are useful as pesticides (e.g., acaricides, insecticides, molluscicides, and nematicides), such molecules, and processes of using such molecules to control pests.

BACKGROUND OF THE DISCLOSURE

Pests cause millions of human deaths around the world each year. Furthermore, there are more than ten thousand species of pests that cause losses in agriculture. The worldwide agricultural losses amount to billions of U.S. dollars each year.

Termites cause damage to all kinds of private and public structures. The world-wide termite damage losses amount to billions of U.S. dollars each year.

Stored food pests eat and adulterate stored food. The world-wide stored food losses amount to billions of U.S. dollars each year, but more importantly, deprive people of needed food.

There is an acute need for new pesticides. Certain pests are developing resistance to pesticides in current use. Hundreds of pest species are resistant to one or more pesticides. The development of resistance to some of the older pesticides, such as DDT, the carbamates, and the organophosphates, is well known. But resistance has even developed to some of the newer pesticides.

Therefore, for many reasons, including the above reasons, a need exists for new pesticides.

DEFINITIONS

The examples given in the definitions are generally non-exhaustive and must not be construed as limiting the molecules disclosed in this document. It is understood that a substituent should comply with chemical bonding rules and steric compatibility constraints in relation to the particular molecule to which it is attached.

"Alkenyl" means an acyclic, unsaturated (at least one carbon-carbon double bond), branched or unbranched, substituent consisting of carbon and hydrogen, for example, vinyl, allyl, butenyl, pentenyl, and hexenyl.

"Alkenyloxy" means an alkenyl further consisting of a carbon-oxygen single bond, for example, allyloxy, butenyloxy, pentenyloxy, hexenyloxy.

"Alkoxy" means an alkyl further consisting of a carbon-oxygen single bond, for example, methoxy, ethoxy, propoxy, isopropoxy, butoxy, isobutoxy, and tert-butoxy.

"Alkyl" means an acyclic, saturated, branched or unbranched, substituent consisting of carbon and hydrogen, for example, methyl, ethyl, propyl, isopropyl, butyl, and tert-butyl.

"Alkynyl" means an acyclic, unsaturated (at least one carbon-carbon triple bond), branched or unbranched, substituent consisting of carbon and hydrogen, for example, ethynyl, propargyl, butynyl, and pentynyl.

"Alkynyloxy" means an alkynyl further consisting of a carbon-oxygen single bond, for example, pentynyloxy, hexynyloxy, heptynyloxy, and octynyloxy.

"Aryl" means a cyclic, aromatic substituent consisting of hydrogen and carbon, for example, phenyl, naphthyl, and biphenyl.

"Cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, norbornenyl, bicyclo[2.2.2]octenyl, tetrahydronaphthyl, hexahydronaphthyl, and octahydronaphthyl.

"Cycloalkenyloxy" means a cycloalkenyl further consisting of a carbon-oxygen single bond, for example, cyclobutenyloxy, cyclopentenyloxy, norbomenyloxy, and bicyclo[2.2.2]octenyloxy.

"Cycloalkyl" means a monocyclic or polycyclic, saturated substituent consisting of carbon and hydrogen, for example, cyclopropyl, cyclobutyl, cyclopentyl, norbomyl, bicyclo[2.2.2]octyl, and decahydronaphthyl.

"Cycloalkoxy" means a cycloalkyl further consisting of a carbon-oxygen single bond, for example, cyclopropyloxy, cyclobutyloxy, cyclopentyloxy, norbornyloxy, and bicyclo[2.2.2]octyloxy.

"Halo" means fluoro, chloro, bromo, and iodo.

"Haloalkoxy" means an alkoxy further consisting of, from one to the maximum possible number of identical or different, halos, for example, fluoromethoxy, trifluoromethoxy, 2,2-difluoropropoxy, chloromethoxy, trichloromethoxy, 1,1,2,2-tetrafluoroethoxy, and pentafluoroethoxy.

"Haloalkyl" means an alkyl further consisting of, from one to the maximum possible number of, identical or different, halos, for example, fluoromethyl, trifluoromethyl, 2,2-difluoropropyl, chloromethyl, trichloromethyl, and 1,1,2,2-tetrafluoroethyl.

"Heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen. Examples of aromatic heterocyclyls include, but are not limited to, benzofuranyl, benzoisothiazolyl, benzoisoxazolyl, benzoxazolyl, benzothienyl, benzothiazolyl, cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, and triazolyl. Examples of fully saturated heterocyclyls include, but are not limited to, piperazinyl, piperidinyl, morpholinyl, pyrrolidinyl, tetrahydrofuranyl, and tetrahydropyranyl. Examples of partially unsaturated heterocyclyls include, but are not limited to, 1,2,3,4-tetrahydro-quinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

DETAILED DESCRIPTION OF THE DISCLOSURE

This document discloses molecules having the following formula ("Formula One")

Formula One

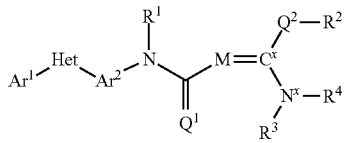

wherein:
(A) Ar¹ is selected from
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl have one or more substituents independently selected from H, F, Cl, Br, I, CN, NO$_2$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, substituted phenyl, and substituted phenoxy,
wherein such substituted phenyl and substituted phenoxy have one or more substituents independently selected from H, F, Cl, Br, I, CN, NO$_2$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl)phenyl, and phenoxy;

(B) Het is a 5- or 6-membered, saturated or unsaturated, heterocyclic ring, containing one or more heteroatoms independently selected from nitrogen, sulfur, or oxygen, and where Ar¹ and Ar² are not ortho to each other (but may be meta or para, such as, for a five-membered ring they are 1,3 and for a 6-membered ring they are either 1,3 or 1,4), and where said heterocyclic ring may also be substituted with one or more substituents independently selected from H, F, Cl, Br, I, CN, NO$_2$, oxo, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, substituted phenyl and substituted phenoxy,
wherein such substituted phenyl and substituted phenoxy have one or more substituents independently selected from H, F, Cl, Br, I, CN, NO$_2$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$^x$R$^y$, (C$_1$-C$_6$ alkyl)N-R$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), phenyl, and phenoxy;

(C) Ar² is selected from
(1) furanyl, phenyl, pyridazinyl, pyridyl, pyrimidinyl, thienyl, or
(2) substituted furanyl, substituted phenyl, substituted pyridazinyl, substituted pyridyl, substituted pyrimidinyl, or substituted thienyl,
wherein said substituted furanyl, substituted phenyl, substituted pyridazinyl, substituted pyridyl, substituted pyrimidinyl, and substituted thienyl, have one or more substituents independently selected from H, F, Cl, Br, I, CN, NO$_2$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, substituted phenyl and substituted phenoxy,
wherein such substituted phenyl and substituted phenoxy have one or more substituents independently selected from H, F, Cl, Br, I, CN, NO$_2$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_1$-C$_6$ haloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, and phenoxy);

(D) R¹ is selected from H, C$_1$-C$_6$ alkyl, C$_3$-C$_6$ cycloalkyl, C$_2$-C$_6$ alkenyl, C$_2$-C$_6$ alkynyl, S(=O)$_n$(C$_1$-C$_6$ alkyl), C(=O)NR$^x$R$^y$, (C$_1$-C$_6$ alkyl)NR$^x$R$^y$, C(=O)O(C$_1$-C$_6$ alkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)OC(=O)(C$_1$-C$_6$ alkyl), (C$_1$-C$_6$ alkyl)S(C$_1$-C$_6$ alkyl), (C$_1$-C$_6$ alkyl)OC(=O)O(C$_1$-C$_6$ alkyl),
wherein each alkyl, cycloalkyl, cycloalkoxy, alkoxy, alkenyl, and alkynyl are optionally substituted with one or more substituents independently selected from F, Cl, Br, I, CN, NO$_2$, oxo, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)NR$^x$R$^y$, (C$_1$-C$_6$ alkyl)

NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O) (C$_1$-C$_6$ alkyl)C(=O)O(C$_1$-C$_6$ alkyl), phenyl, and phenoxy;

(E) R$^2$ is selected from (K), H, C$_1$-C$_6$ alkyl, C$_3$-C$_6$ cycloalkyl, C$_2$-C$_6$ alkenyl, C$_2$-C$_6$ alkynyl, C(=O)(C$_1$-C$_6$ alkyl), (C$_1$-C$_6$ alkyl)O(C$_1$-C$_6$ alkyl), (C$_1$-C$_6$ alkyl)S(C$_1$-C$_6$ alkyl), C$_1$-C$_6$ alkylphenyl, C$_1$-C$_6$ alkyl-O-phenyl, C(=O) (Het-1), (Het-1); (C$_1$-C$_6$ alkyl)-(Het-1), C$_1$-C$_6$ alkyl-O—C(=O)C$_1$-C$_6$ alkyl, C$_1$-C$_6$ alkyl-O—C(=O)(C$_1$-C$_6$ alkyl), C$_1$-C$_6$ alkyl-O—C(=O)OC$_1$-C$_6$ alkyl, C$_1$-C$_6$ alkyl-O—C(=O)N(R$^x$R$^y$), C$_1$-C$_6$ alkylC(=O)N(R$^x$)C$_1$-C$_6$ alkyl-(Het-1), C$_1$-C$_6$ alkylC(=O)(Het-1), C$_1$-C$_6$ alkylC(=O)N(R$^x$)C$_1$-C$_6$ alkyl(N(R$^x$)(R$^y$))(C(=O)OH), C$_1$-C$_6$ alkylC(=O)N(R$^x$)C$_1$-C$_6$ alkylN(R$^x$)(R$^y$), C$_1$-C$_6$ alkylC(=O)N(R$^x$)C$_1$-C$_6$ alkylN(R$^x$)C(=O)—O—C$_1$-C$_6$ alkyl, C$_1$-C$_6$ alkylC(=O)N(R$^x$)C$_1$-C$_6$ alkyl(N(R$^x$)C(=O)—O—C$_1$-C$_6$ alkyl)(C(=O)OH), C$_1$-C$_6$ alkylC(=O)(Het-1)C(=O)—O—C$_1$-C$_6$ alkyl, C$_1$-C$_6$ alkyl-O—C(=O)—O—C$_1$-C$_6$ alkyl, C$_1$-C$_6$ alkyl-O—C(=O)C$_1$-C$_6$ alkyl, C$_1$-C$_6$ alkyl-O—C(=O)C$_3$-C$_6$ cycloalkyl, C$_1$-C$_6$ alkyl-O—C(=O)(Het-1), C$_1$-C$_6$ alkyl-O—C(=O)C$_1$-C$_6$ alkyl-N(R$^x$)C(=O)—O—C$_1$-C$_6$ alkyl, C$_1$-C$_6$ alkyl-NR$^x$R$^y$, (C$_1$-C$_6$ alkyl)S-(Het-1) or C$_1$-C$_6$ alkyl-O-(Het-1), wherein each alkyl, cycloalkyl, alkenyl, alkynyl, phenyl, and (Het-1) are optionally substituted with one or more substituents independently selected from F, Cl, Br, I, CN, NO$_2$, NR$^x$R$^y$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, C$_3$-C$_6$ cycloalkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, Si(C$_1$-C$_6$ alkyl)$_3$, S(=O)$_n$NR$^x$R$^y$, or (Het-1);

(F) R$^3$ is selected from phenyl, C$_1$-C$_6$ alkylphenyl, C$_1$-C$_6$ alkyl-O-phenyl, C$_2$-C$_6$ alkenyl-0-phenyl, (Het-1), C$_1$-C$_6$ alkyl(Het-1), or C$_1$-C$_6$ alkyl-O-(Het-1), wherein each alkyl, cycloalkyl, alkenyl, alkynyl, phenyl, and (Het-1) are optionally substituted with one or more substituents independently selected from F, Cl, Br, I, CN, NO$_2$, NR$^x$R$^y$, C$_1$-C$_6$ alkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, C$_3$-C$_6$ cycloalkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), O(C$_1$-C$_6$ alkyl), S(C$_1$-C$_6$ alkyl), C(=O)(C$_1$-C$_6$ alkyl)C(=O)O(C$_1$-C$_6$ alkyl), phenyl, phenoxy, and (Het-1);

(G) R$^4$ is selected from (K), H, or C$_1$-C$_6$ alkyl;

(H) M is N or C—R$^5$, wherein R$^5$ is selected from H, F, Cl, Br, I, CN, NO$_2$, C$_1$-C$_6$ alkyl, C$_1$-C$_6$ haloalkyl, C$_3$-C$_6$ cycloalkyl, C$_3$-C$_6$ halocycloalkyl, S(=O)$_n$(C$_1$-C$_6$ alkyl), S(=O)$_n$(C$_1$-C$_6$ haloalkyl), C(=O)NR$^x$R$^y$, C(=O)(C$_1$-C$_6$ alkyl), C(=O)O (C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), or phenyl;

(I) (1) Q$^1$ is selected from O or S,
(2) Q$^2$ is selected from O or S;

(J) R$^x$ and R$^y$ are independently selected from H, C$_1$-C$_6$ alkyl, C$_1$-C$_6$ haloalkyl, C$_3$-C$_6$ cycloalkyl, C$_3$-C$_6$ halocycloalkyl, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)(C$_1$-C$_6$ alkyl), C(=O)O(C$_1$-C$_6$ alkyl), C(=O)(C$_1$-C$_6$ haloalkyl), C(=O)O (C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), and phenyl, wherein each alkyl, cycloalkyl, cycloalkoxy, alkoxy, alkenyl, alkynyl, phenyl, phenoxy, and (Het-1), are optionally substituted with one or more substituents independently selected from F, Cl, Br, I, CN, NO$_2$, oxo, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, C$_3$-C$_6$ cycloalkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)OH, C(=O)(C$_1$-C$_6$ alkyl), C(=O)O(C$_1$-C$_6$ alkyl), C(=O)(C$_1$-C$_6$ haloalkyl), C(=O)O (C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, halophenyl, phenoxy, and (Het-1), or R$^x$ and R$^y$ together can optionally form a 5- to 7-membered saturated or unsaturated cyclic group which may contain one or more heteroatoms selected from nitrogen, sulfur, and oxygen, and where said cyclic group may be substituted with F, Cl, Br, I, CN, oxo, thioxo, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, C$_3$-C$_6$ cycloalkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, substituted phenyl, phenoxy, and (Het-1);

(K) R$^2$ and R$^4$ along with C$^x$(Q$^2$)(N$^x$), form a 4- to 7-membered saturated or unsaturated, hydrocarbyl cyclic group, which may contain one or more further heteroatoms selected from nitrogen, sulfur, and oxygen, wherein said hydrocarbyl cyclic group may optionally be substituted with R$^6$ and R$^7$, wherein R$^6$ and R$^7$ are independently selected from H, F, Cl, Br, I, CN, C$_1$-C$_6$ alkyl, oxo, thioxo, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_3$-C$_6$ cycloalkenyl, C$_2$-C$_6$ alkynyl, C$_3$-C$_6$ cycloalkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, substituted phenyl, phenoxy, or (Het-1);

(L) (Het-1) is a 5- or 6-membered, saturated or unsaturated, heterocyclic ring, containing one or more heteroatoms independently selected from nitrogen, sulfur or oxygen, wherein said heterocyclic ring may also be substituted with one or more substituents independently selected from H, F, Cl, Br, I, CN, NO$_2$, oxo, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), C(=O)(C$_1$-C$_6$ alkyl)C(=O)O(C$_1$-C$_6$ alkyl), phenyl, phenoxy, substituted phenyl and substituted phenoxy, wherein such substituted phenyl and substituted phenoxy have one or more substituents independently selected from H, F, Cl, Br, I, CN, NO$_2$, C$_1$-C$_6$ alkyl, C$_1$-C$_6$ haloalkyl, C$_3$-C$_6$ cycloalkyl, C$_3$-C$_6$ halocycloalkyl, C$_3$-C$_6$ cycloalkoxy, C$_3$-C$_6$ halocycloalkoxy, C$_1$-C$_6$ alkoxy, C$_1$-C$_6$ haloalkoxy, C$_2$-C$_6$ alkenyl, C$_2$-C$_6$ alkynyl, S(=O)$_n$(C$_1$-C$_6$ alkyl), S(=O)$_n$(C$_1$-C$_6$ haloalkyl), OSO$_2$(C$_1$-C$_6$ alkyl), OSO$_2$(C$_1$-C$_6$ haloalkyl), C(=O)H, C(=O)NR$^x$R$^y$, (C$_1$-C$_6$ alkyl)NR$^x$R$^y$, C(=O)(C$_1$-C$_6$ alkyl), C(=O)O(C$_1$-C$_6$ alkyl), C(=O)(C$_1$-C$_6$ haloalkyl), C(=O)O(C$_1$-C$_6$ haloalkyl), C(=O)(C$_3$-C$_6$ cycloalkyl), C(=O)O(C$_3$-C$_6$ cycloalkyl), C(=O)(C$_2$-C$_6$ alkenyl), C(=O)O(C$_2$-C$_6$ alkenyl), (C$_1$-C$_6$ alkyl)O(C$_1$-C$_6$ alkyl), (C$_1$-C$_6$ alkyl)S(C$_1$-C$_6$ alkyl), phenyl, and phenoxy; and (M) n is each individually 0, 1, or 2.

Many of the molecules of this invention may be depicted in two or more tautomeric forms such as when R$^1$, R$^2$, or R$^4$, is H (see for example, "Scheme TAU" below). For the sake of simplifying the schemes, all molecules have been depicted as existing as a single tautomer. Any and all alternative tautomers are included within the scope of this invention, and no inference should be made as to whether the molecule exists as the tautomeric form in which it is drawn.

Scheme TAU

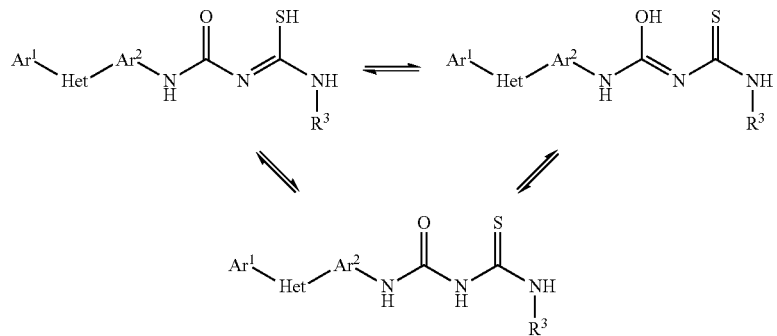

In another embodiment Ar$^1$ is a substituted phenyl.

In another embodiment Ar$^1$ is a substituted phenyl that has one or more substituents selected from C$_1$-C$_6$ haloalkyl and C$_1$-C$_6$ haloalkoxy.

In another embodiment Ar$^1$ is a substituted phenyl that has one or more substituents selected from CF$_3$, OCF$_3$, and OC$_2$F$_5$.

In another embodiment Het is selected from benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, tetrazolyl, thiazolinyl, thiazolyl, thienyl, triazinyl, triazolyl, piperazinyl, piperidinyl, morpholinyl, pyrrolidinyl, tetrahydrofuranyl, tetrahydropyranyl, 1,2,3,4-tetrahydroquinolinyl, 4,5-dihydro-oxazolyl, 4,5-dihydro-1H-pyrazolyl, 4,5-dihydro-isoxazolyl, and 2,3-dihydro-[1,3,4]-oxadiazolyl.

In another embodiment Het is triazolyl,

In another embodiment Het is 1,2,4 triazolyl.

In another embodiment Het is oxadiazolyl.

In another embodiment Het is 1,3,4 oxadiazolyl.

In another embodiment Het is pyrazolyl.

In another embodiment Ar$^2$ is phenyl.

In another embodiment Ar$^2$ is a substituted phenyl.

In another embodiment Ar$^2$ is a substituted phenyl that has one or more substituents selected from C$_1$-C$_6$ alkyl.

In another embodiment Ar$^2$ is a substituted phenyl that has one or more substituents wherein said substituent is CH$_3$.

In another embodiment R$^1$ is H.

In another embodiment R$^2$ is (K), H, C$_1$-C$_6$ alkyl, C$_1$-C$_6$ alkyl-O—C(=O)C$_1$-C$_6$ alkyl, C$_1$-C$_6$ alkyl-O—C(=O)N(R$^x$R$^y$), or (C$_1$-C$_6$ alkyl)S-(Het-1).

In another embodiment R$^2$ is (K), H, CH$_3$, C$_1$-C$_6$ alkyl, CH$_2$OC(=O)CH(CH$_3$)$_2$, CH$_2$OC(=O)N(H)(C(=O)OCH$_2$Ph), or CH$_2$S(3,4,5-trimethoxy-2-tetrahydropyran).

In another embodiment R$^3$ is substituted phenyl.

In another embodiment R$^3$ is substituted phenyl wherein said substituted phenyl has one or more substituents selected from F, Cl, C$_1$-C$_6$ alkyl, C$_3$-C$_6$ cycloalkyl, C$_1$-C$_6$ alkoxy, and phenyl.

In another embodiment R$^3$ is substituted phenyl wherein said substituted phenyl has one or more substituents selected from F, CH$_3$, 2-CH(CH$_3$)$_2$, CH(CH$_3$)(C$_2$H$_5$), OCH$_3$, and phenyl.

In another embodiment R$^3$ is substituted phenyl wherein said substituted phenyl has more than one substituent and at least one pair of said substituents are not ortho to each other.

In another embodiment R$^3$ is C$_1$-C$_6$ alkylphenyl.

In another embodiment R$^3$ is (Het-1).

In another embodiment R$^4$ is H.

In another embodiment M is N.

In another embodiment M is CR$^5$ wherein R$^5$ is selected from H, CN, and C(=O)(C$_1$-C$_6$ alkyl).

In another embodiment Q$^1$ is O.

In another embodiment Q$^2$ is S.

In another embodiment Q$^2$ is O.

In another embodiment R$^2$ and R$^4$ are (K) wherein R$^2$ and R$^4$ along with C$^x$(Q$^2$)(N$^x$), form a 4- to 7-membered saturated or unsaturated, hydrocarbyl cyclic group.

In another embodiment R$^2$ and R$^4$ are (K) wherein R$^2$ and R$^4$ along with C$^x$(Q$^2$)(N$^x$), form a 4- to 7-membered saturated or unsaturated, hydrocarbyl cyclic group, wherein said hydrocarbyl cyclic group is substituted with oxo or C$_1$-C$_6$ alkyl.

In another embodiment R$^2$ and R$^4$ are (K) wherein R$^2$ and R$^4$ along with C$^x$(Q$^2$)(N$^x$), form a 4- to 7-membered saturated or unsaturated, hydrocarbyl cyclic group, wherein the "link" between Q$^2$ and N$^x$ is CH$_2$C(=O), CH$_2$CH$_2$, CH$_2$CH$_2$CH$_2$, or CH$_2$CH(CH$_3$).

The molecules of this invention will generally have a molecular mass of about 400 Daltons to about 1200 Daltons. However, it is generally preferred if the molecular mass is from about 300 Daltons to about 1000 Daltons, and it is even more generally preferred if the molecular mass is from about 400 Daltons to about 750 Daltons.

Preparation of Triaryl-Intermediates

Molecules of this invention can be prepared by making a triaryl intermediate, Ar$^1$-Het-Ar$^2$, and then linking it to a desired intermediate to form a desired compound. A wide variety of triaryl intermediates can be used to prepare molecules of this invention, provided that such triaryl intermediates contain a suitable functional group on Ar$^2$ to which the rest of the desired intermediate can be attached. Suitable functional groups include an amino or isocyanate or a carboxyl group. These triaryl intermediates can be prepared by methods previously described in the chemical literature, including Crouse, et al., PCT Int. Appl. Publ. WO2009/102736 A1 (the entire disclosure of which is hereby incorporated by reference).

Preparation of Urea-Linked Compounds

Thiobiurets (thio-bisureas) and biurets can be prepared according to Scheme 1, Scheme 2, and Scheme 3, described as follows. S—R$^2$ thiourea precursors (3) are prepared from the corresponding thiourea (1) by treatment with R$^2$—X, where X is a halogen or methanesulfonate or a similar displaceable group. These are usually isolated as their hydrohalide (methanesulfonate) salts. Subsequent treatment of the S—R$^2$ thiourea precursors (3) with either an isocyanate (4) (see, for example, Pandey, A. K.; et. al., Ind J. Chem., Sect. B: Org. Chem. Incl. Med. Chem. (1982), 21B(2), 150-2) or with a p-nitrophenyl carbamate, such as (5), in the presence of a base, such as triethylamine or potassium carbonate or cesium carbonate, results in formation of an S-alkyl thiobiuret (6).

Scheme 1

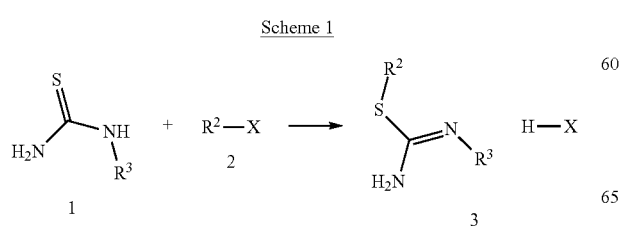

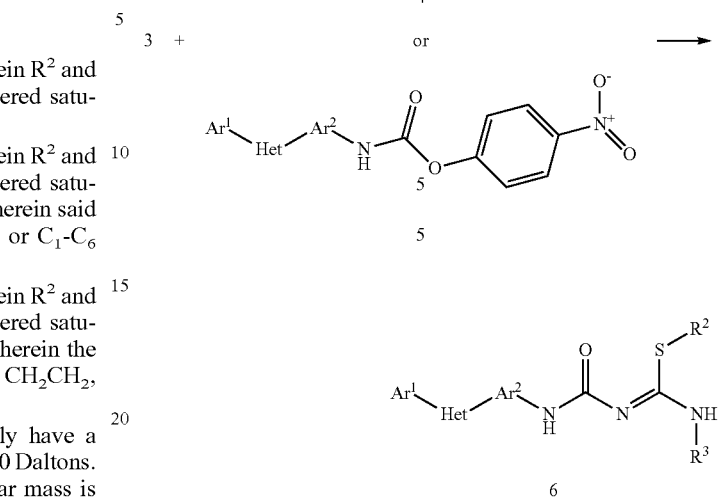

When R$^2$ is —CH$_2$OC(O)alkyl, treatment with ethanolic HCl at temperatures from about 0° C. to about 50° C., results in removal of R$^2$ and generation of the thiobiuret (7) (Scheme 2). Under more prolonged heating, for example, by heating in ethanolic HCl to the reflux temperature for from about 1 to about 24 hours, the thiobiuret is converted into a biuret (8), with oxygen replacing the sulfur atom.

Scheme 2

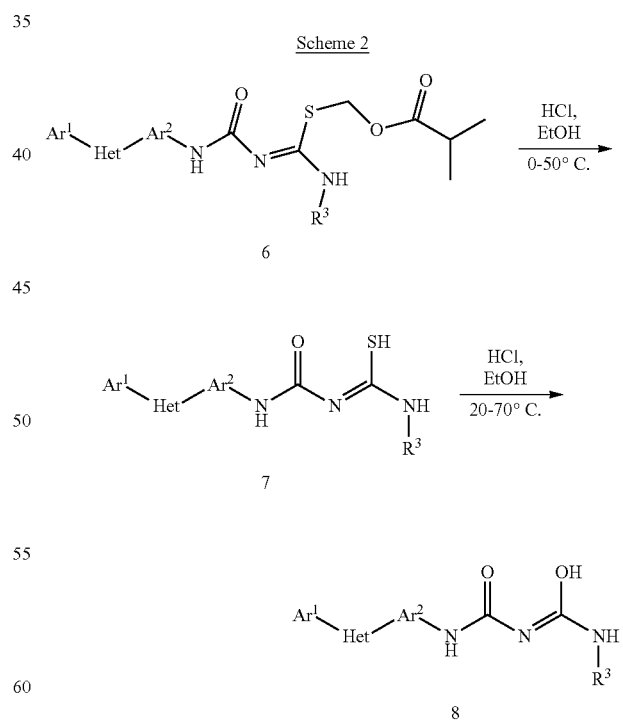

An alternative process to form thiobiurets has been described by Kaufmann, H. P.; Luthje, K. (Archiv Pharm.

und Ber. Deutschen Pharm. (1960), 293, 150-9) and Oertel, G., et al. (Farb. Bayer, DE 1443873 A 19681031 (1972). A carbamoyl isothiocyanate (9) is treated with an equivalent of an aniline to form (7) (Scheme 3). Yet another route to thiobiurets involves treatment of an N-aryl urea with $R^3$—NCS (N. Siddiqui, et. al., Eur. J. Med. Chem., 46 (2011), 2236-2242). Another route to biurets (8) involves treatment of an N-aryl urea with $R^3$ isocyanate (Briody, et. al., J. Chem. Soc., Perk. 2, 1977, 934-939).

between about 0° C. and about 100° C., can be used. Using conditions described above, it can be seen that other ring sizes and substitutions can be envisioned as well; the corresponding six-membered ring analog (10d), for example, can be prepared starting with a 1,3-dihalopropane precursor.

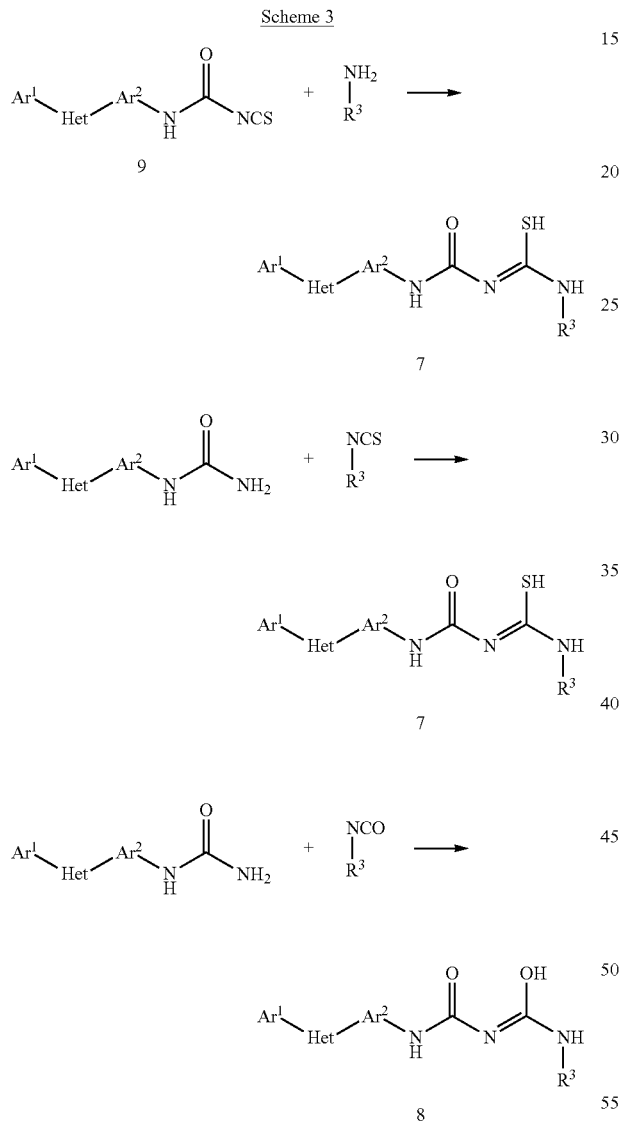

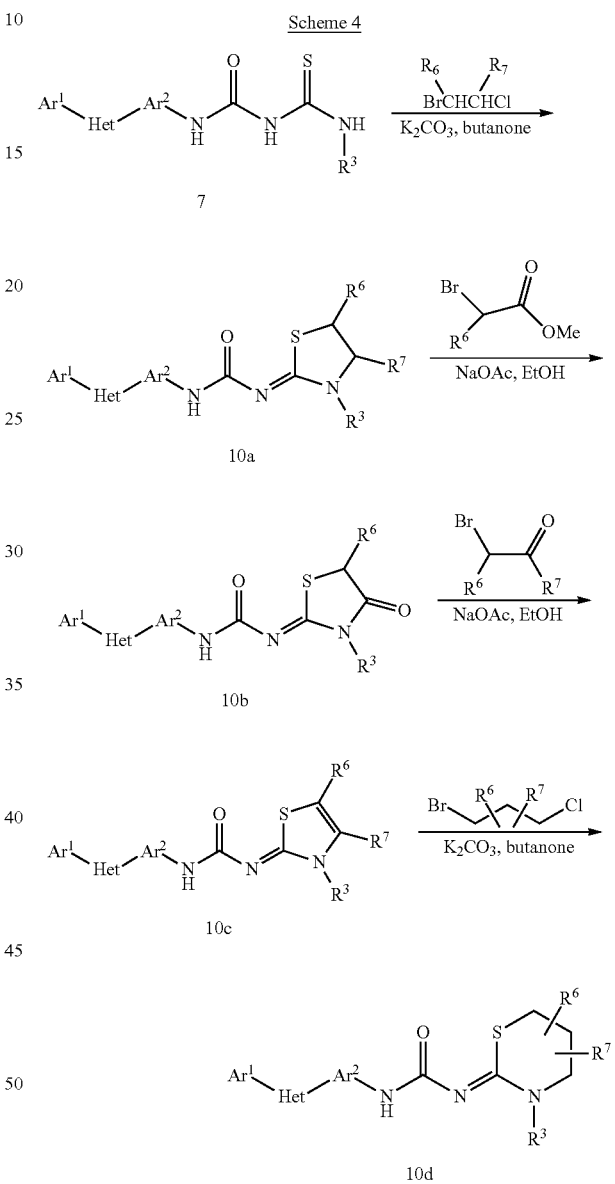

Thiobiurets (7) can be converted into a variety of cyclized analogs (10), by treatment with, for example, vicinal dihalides (for example, 1-bromo-2-chloroethane, to form 2-imino-1,3-thiazolines (10a)), or with methyl bromoacetate (to form 2-imino 1,3-thiazolin-4-ones (10b)), or with α-halo ketones (to form 2-imino-1,3-thiazoles (10c)), as depicted in Scheme 4. A base such as potassium carbonate or sodium acetate, in a protic solvent or aprotic solvent, at temperatures An alternative route to analogs of Formula (10b) is described in Scheme 5. Treatment of 2-imino-1,3-thiazolin-4-one (11) with an aryl isocyanate or with intermediate (5) (Scheme 1), in the presence of an amine base such as triethylamine, leads to the synthesis of (10b). Other routes to (10b) include addition of carbonyldiimidazole to (11) to produce an intermediate (12a), or addition of 4-nitrophenyl chloroformate to form (12b). Either (12a) or (12b) can then be made to react with an aniline $Ar^1$-Het-$Ar^2$—$NH_2$ to generate (10b).

Scheme 5

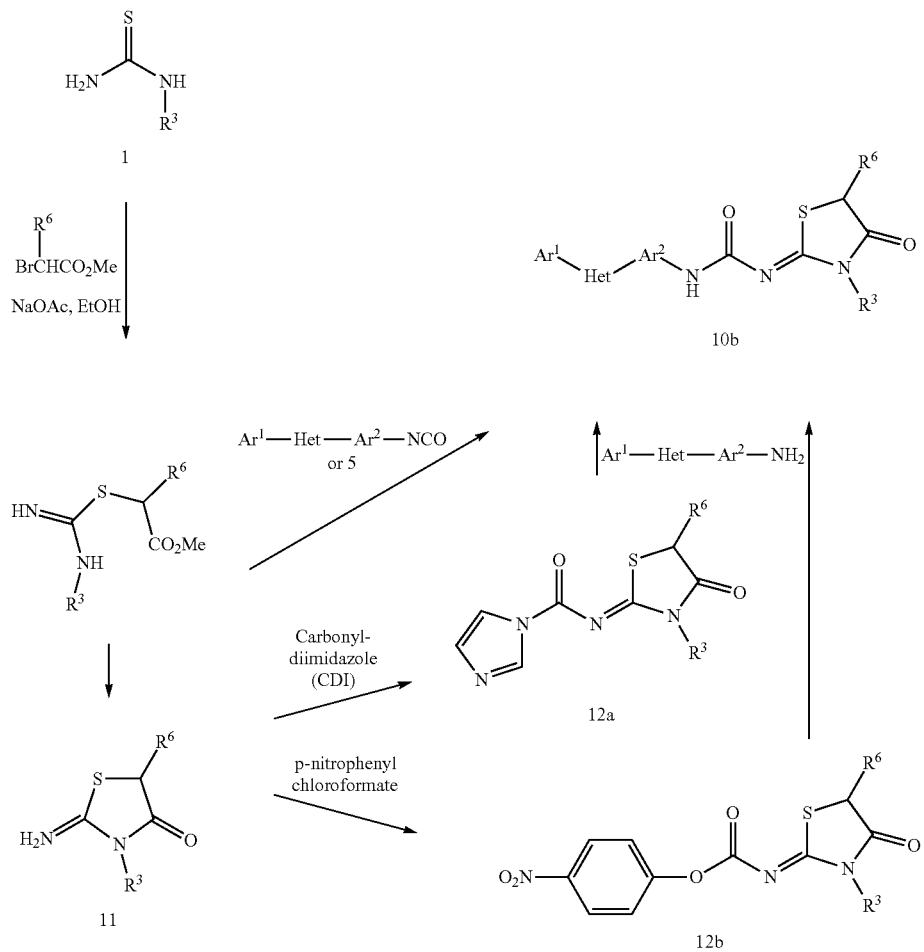

Another route to 1-(3-aryl thiazolidin-2-ylidene)-3-aryl ureas (10a) is shown in Scheme 6. Treatment of an aryl cyanamide (12) with a thiirane in the presence of a base such as potassium carbonate yields the 2-imino-1,3-thiazoline (14). The synthesis and subsequent acylation of 3-aryl-2-iminothiazolidines by this route is described by F. X. Woolard in U.S. Pat. No. 4,867,780 and references contained therein. Subsequent treatment of (14) with carbonyldiimidazole (to form 15a) or 4-nitrophenyl chloroformate (to form 15b), followed by addition of an aniline results in formation of (10a). Alternatively, reaction of (14) with an aryl isocyanate or 4-nitrophenyl carbamate (5) also produces (10a).

Scheme 6

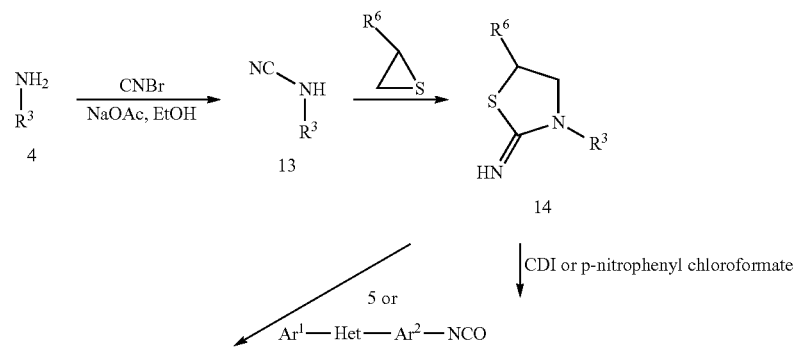

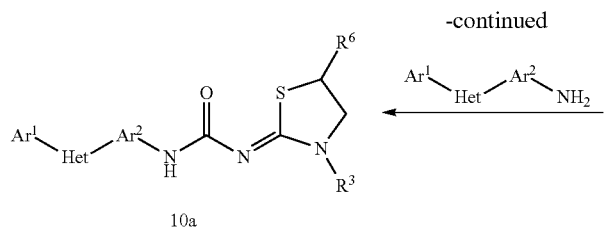
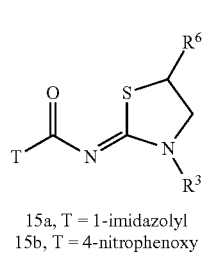

10a

15a, T = 1-imidazolyl
15b, T = 4-nitrophenoxy

By using the protocols described in Schemes 4 through 6, it can be seen that other analogs containing 4-, 5-, and 6-membered rings, and containing a variety of substitution patterns, can be produced. Other heterocyclic systems containing an exo-imino group are known, including but not limited to, 2-imino thiadiazolinones (16) (see Scheme 7); or 2-imino oxadiazolinones (17) (Syn. Comm., 2002, 32(5), 803-812); or 2-imino oxazolinones (18); or 2-imino thiadiazoles (19). These can also be used to prepare molecules (20)-(23), by appropriate substitution of precursors in the procedures described in Scheme 5 and Scheme 6.

Scheme 8

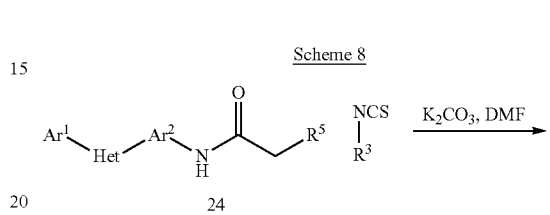

24

Scheme 7

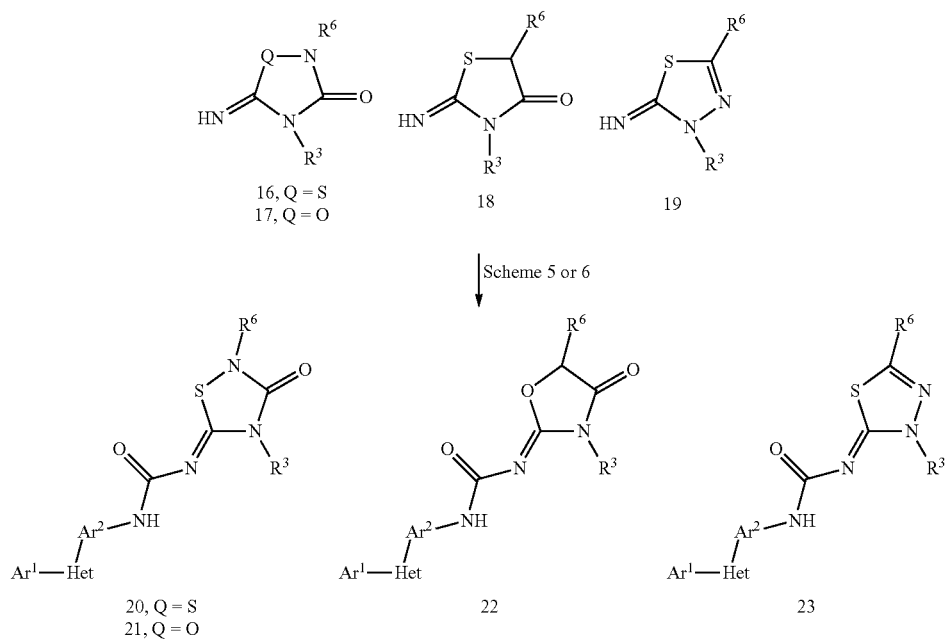

16, Q = S
17, Q = O

18

19

| Scheme 5 or 6

20, Q = S
21, Q = O

22

23

Malonyl monothioamides ((25) and (26)) and malonyl diamides (29) can be prepared as described in Scheme 8. Condensation of a β-ketoanilide or α-cyanoanilide (24) with $R^3$—NCS results in formation of 2-acyl malono-monothioamide (25). When $R^5$ is an acetyl group, deacylation occurs on refluxing in EtOH to form the malono-monothioamide (26). Thioamides can be cyclized in a manner similar to that described in Schemes 5 and 6, to produce cyclic analogs (27). The diamide (29) can be prepared from the corresponding monocarboxylic acid (28), by means of dicyclohexyl carbodiimide-1-hydroxy 7-azabenzotriazole coupling conditions. (for example, see Jones, J., in: The Chemical Synthesis of Peptides. Int. Ser. of Monographs on Chemistry, Oxford Univ. (Oxford, 1994), 23).

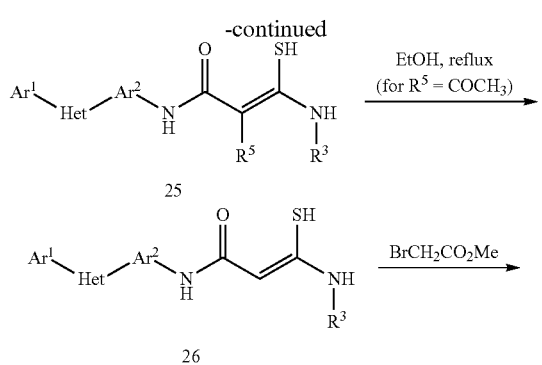

25

26

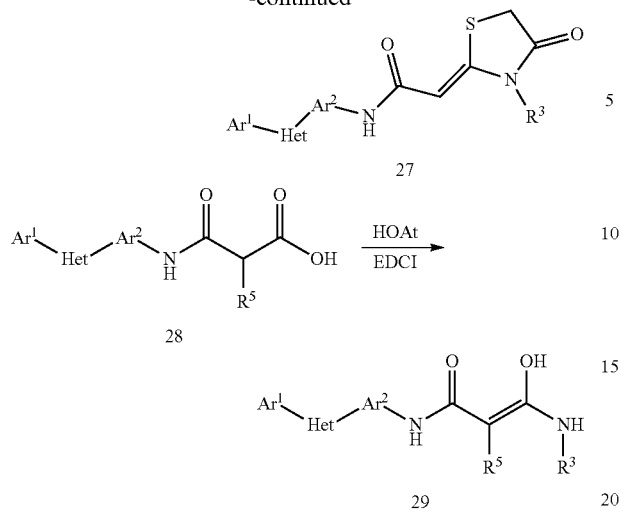

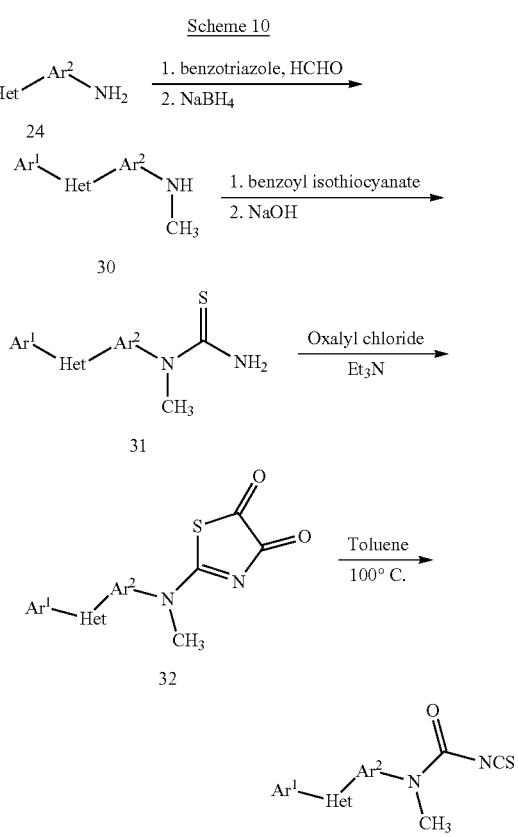

Further modifications by alkylation of the NH group of analogs such as (6), (10a), (10b), (10c), (20)-(23), and (27) can be effected by treating the appropriate molecule with an alkylating agent, $R^1$—X, where X is a halogen or methanesulfonyl group, or other similar leaving group (Scheme 9). The reaction requires use of a strong base such as sodium hydride (NaH) or potassium hexamethyldisilazane, in an aprotic solvent such as tetrahydrofuran or N,N-dimethylformamide

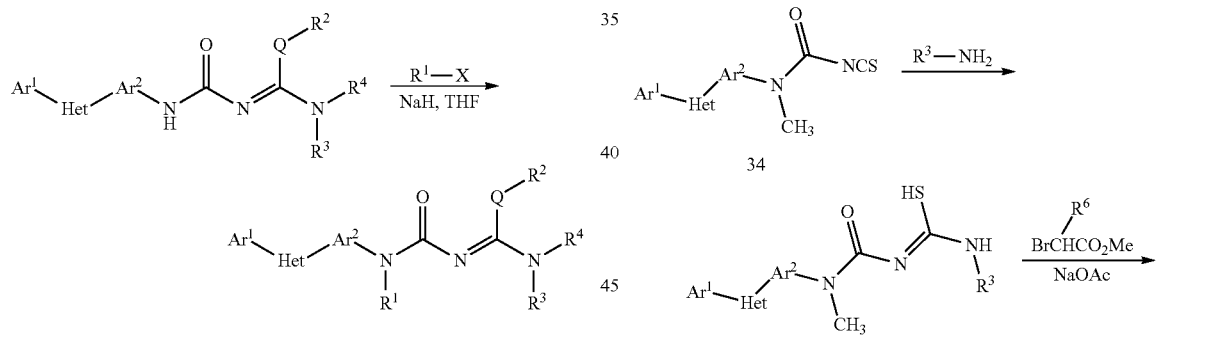

6, 10a, 10b, 10c, 20-23, 27

Analogs wherein $R^1$ is not H may also be prepared as in shown in Scheme 10. Alkylation of $Ar^1$-Het-$Ar^2$—$NH_2$, and conversion into thiourea (31), can be accomplished by a variety of known methods. For example, reaction with formaldehyde and benzotriazole, followed by reduction with sodium borohydride, generates the N-methyl analog (30). Conversion to (31) can be accomplished by treatment with thiophosgene and ammonia, or with benzoyl isothiocyanate followed by base-catalyzed cleavage of the benzoyl group. Treatment of (31) with oxalyl chloride and triethylamine, under conditions first described by J. Goerdeler and K. Jonas (Chem. Ber., 1966, 99(11), p. 3572-3581), results in formation of a 2-amino-1,3-thiazolin-4,5-dione (32). Pyrolysis of this intermediate in refluxing toluene then generates an N-carbonyl isothiocyanate (33), which on treatment with an amine $R^3$—$NH_2$ forms the thiobiuret (7b, $R^1$═$CH_3$). Thiobiurets where $R^1$ is not H can then be further elaborated using conditions described in Scheme 4, to form cyclic analogs such as 10e.

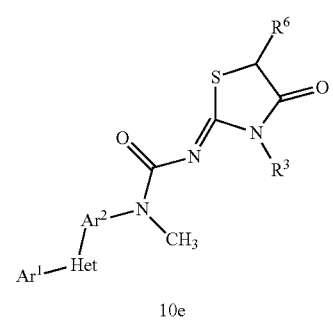

An aryl isocyanate, $Ar^1$—Het-$Ar^2$—NCO, can also be treated directly with an N-aryl thiourea in the presence of a catalytic amount of base such as cesium carbonate or sodium hydride, resulting in the formation of a thiobiuret (7) (Scheme 11).

Scheme 11

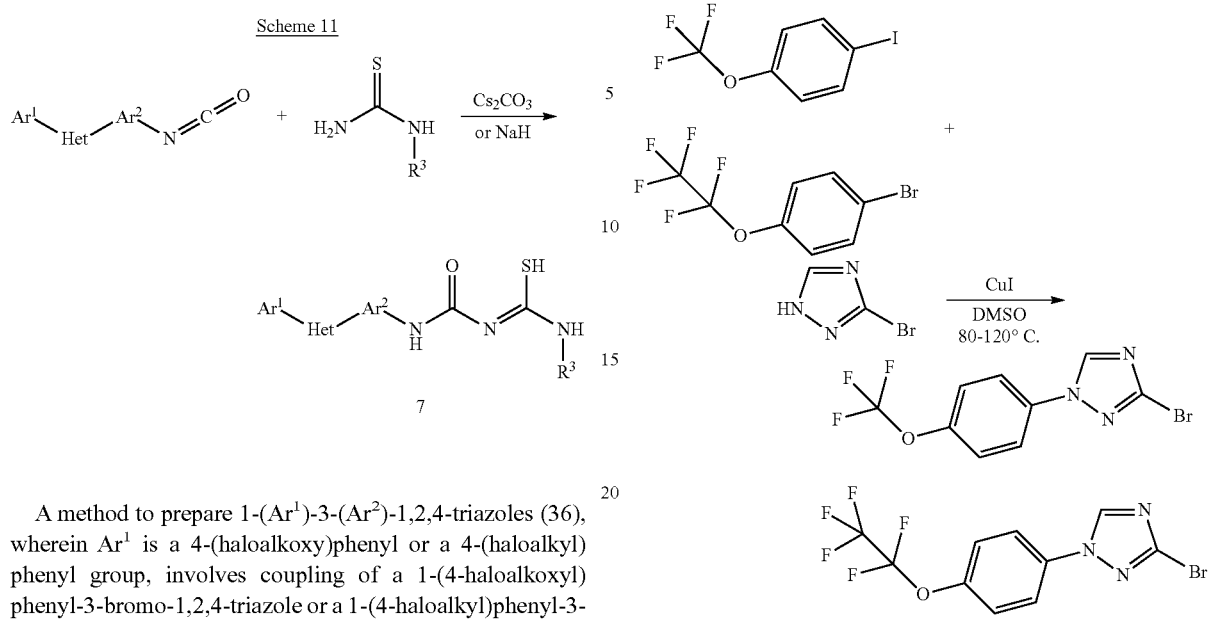

A method to prepare 1-(Ar$^1$)-3-(Ar$^2$)-1,2,4-triazoles (36), wherein Ar$^1$ is a 4-(haloalkoxy)phenyl or a 4-(haloalkyl) phenyl group, involves coupling of a 1-(4-haloalkoxyl) phenyl-3-bromo-1,2,4-triazole or a 1-(4-haloalkyl)phenyl-3-bromo-1,2,4-triazole (35, Scheme 12) with an aryl boronic acid or aryl boronic ester, under Suzuki conditions. The intermediates (35) in turn can be prepared by reacting 3-bromo-1H-1,2,4-triazole (Kroeger, C. F.; Miethchen, R., Chemische Berichte (1967), 100(7), 2250) (however 3-chloro-1H-1,2,4-triazole may be used) with a 4-haloalkoxy-1-halobenzene (where halo=independently I or Br or Cl or F), in the presence of a metal catalyst such as CuI or Cu$_2$O, and a base such as Cs$_2$CO$_3$, K$_3$PO$_4$, or K$_2$CO$_3$, with or without an added ligand such as quinolin-8-ol, or N,N'-dimethyl ethylenediamine or other 1,2-diamines, or glycine, in a polar aprotic solvent such as acetonitrile, DMF or DMSO at temperatures between about 70 and 150° C.

Scheme 12

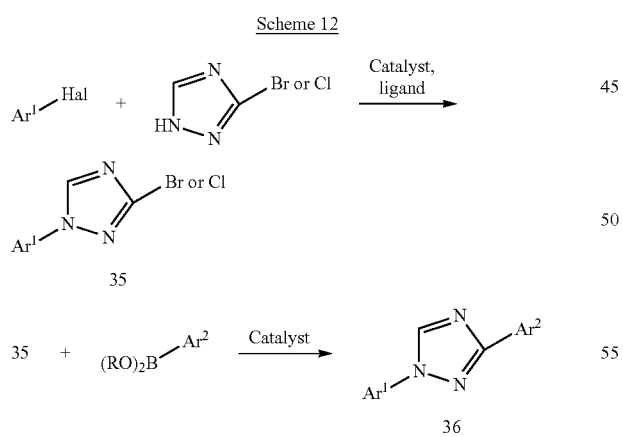

We also disclosed novel 1-Ar$^1$-3-bromo-1,2,4-triazoles, wherein Ar$^1$ is 4-(C$_1$-C$_6$-alkyl)phenyl, 4-(C$_1$-C$_6$-haloalkyl) phenyl, 4-(C$_1$-C$_6$ alkoxy)phenyl, 4-(C$_1$-C$_6$-haloalkoxy)phenyl, 4-(C$_1$-C$_6$ alkylthio)phenyl, or 4-(C$_1$-C$_6$-haloalkylthio) phenyl, as useful intermediates for the preparation of many of the molecules claimed in this invention (preparation is described in Scheme 12.

EXAMPLES

The examples are for illustration purposes and are not to be construed as limiting the invention disclosed in this document to only the embodiments disclosed in these examples.

Starting materials, reagents, and solvents that were obtained from commercial sources were used without further purification. Anhydrous solvents were purchased as Sure/Seal™ from Aldrich and were used as received. Melting points were obtained on an OptiMelt Automated Melting Point System from Stanford Research Systems and are uncorrected. Molecules are given their known names, named according to naming programs within MDL ISIS™/Draw 2.5, ChemBioDraw Ultra 12.0 or ACD Name Pro. If such programs are unable to name a molecule, the molecule is named using conventional naming rules. $^1$H NMR spectral data are in ppm (δ) and were recorded at 400 MHz, unless otherwise stated.

Example 1

Preparation of (E)-((N'-(4-methoxy-2-methylphenyl)-N-((4-(1-(4-(trifluoromethyl)phenyl)-1H-1,2,4-triazol-3-yl)phenyl)carbamoyl)carbamimidoyl)thio) methyl isobutyrate (Molecule A1)

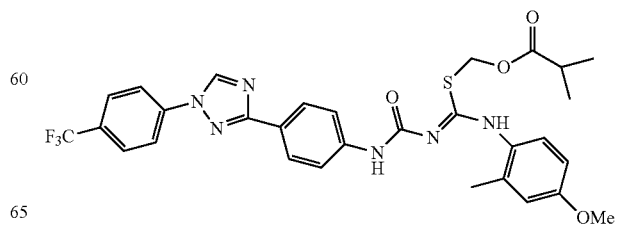

Step 1.

2-Methyl-4-methoxyphenyl thiourea (0.5 grams (g), 2.55 millimoles (mmol)) and bromomethyl isobutyrate were combined in 5 mL of acetone at ambient temperature, and the solution was allowed to stir for 18 hours (h). The solution was then cooled to 0° C. and the resulting solid was filtered and air-dried to give (E)-(N'-(4-methoxy-2-methylphenyl) carbamimidoylthio)methyl isobutyrate HBr (B1) (0.83 g, 82%): mp 127-130° C.; $^1$H NMR (CDCl$_3$) δ 11.34 (s, 1H), 10.29 (s, 1H), 8.32 (s, 1H), 7.09 (d, J=8.7 Hz, 1H), 6.79 (d, J=2.8 Hz, 1H), 6.74 (dd, J=8.7, 2.8 Hz, 1H), 3.81 (s, 3H), 2.69 (heptet, J=7.0 Hz, 1H), 2.31 (s, 3H), 1.22 (d, J=7.0 Hz, 6H); ESIMS m/z 297 ([M+H]$^+$).

Step 2.

The intermediate from Step 1 (0.40 g, 1.06 mmol) was dissolved in tetrahydrofuran (THF; 7 mL), and 4-nitrophenyl 4-(1-(4-(trifluoromethyl)phenyl)-1H-1,2,4-triazol-3-yl) phenylcarbamate (0.50 g, 1.06 mmol) was added. To this suspension was added N-ethyl-N-isopropylpropan-2-amine (Hünig's base; 0.25 g, 1.9 mmol), and the solution was allowed to stir at ambient temperature for 2 h. Evaporation of volatiles left a gummy oil which was purified by chromatography on silica gel. Elution with 0-50% ethyl acetate (EtOAc)-hexanes gave the title compound (425 mg, 61%) as a white solid: mp 160-164° C.; $^1$H NMR (CDCl$_3$) δ 11.24 (s, 1H), 8.64 (s, 1H), 8.17 (d, J=8.7 Hz, 2H), 7.92 (d, J=8.4 Hz, 2H), 7.80 (d, J=8.5 Hz, 2H), 7.67 (d, J=8.7 Hz, 2H), 7.41 (s, 1H), 7.12 (d, J=8.6 Hz, 1H), 6.79 (d, J=2.8 Hz, 1H), 6.74 (dd, J=8.4, 3.1 Hz, 1H), 5.65 (s, 2H), 3.82 (s, 3H), 2.59 (heptet, J=7.0 Hz, 1H), 2.27 (s, 3H), 1.18 (d, J=7.0 Hz, 6H); ESIMS m/z 627 ([M+H]$^+$).

Molecules A54-A62 in Table 1 were made in accordance with the procedures disclosed in Example 1. The following molecules (Examples 2-10) were prepared according to the conditions described in Example 1.

Example 2

(Z)-Methyl N-(4-methoxy-2-methylphenyl)-N'-((4-(1-(4-(trifluoromethyl)phenyl)-1H-1,2,4-triazol-3-yl)phenyl)carbamoyl)carbamimidothioate (Molecule A2)

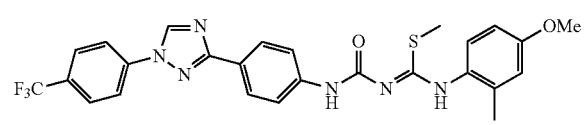 [SMILES: COc1ccc(N/C(=N/C(=O)Nc2ccc(-c3ncn(-c4ccc(C(F)(F)F)cc4)n3)cc2)SC)c(C)c1]

The title molecule was isolated as a white solid; 38 mg (11%), mp 172-175° C.; $^1$H NMR (CDCl$_3$) δ 11.29 (s, 1H), 8.64 (s, 1H), 8.17 (d, J=8.7 Hz, 2H), 7.92 (d, J=8.5 Hz, 2H), 7.80 (d, J=8.5 Hz, 2H), 7.66 (d, J=8.7 Hz, 2H), 7.33 (s, 1H), 7.16 (d, J=8.6 Hz, 1H), 6.80 (d, J=2.9 Hz, 1H), 6.75 (dd, J=8.6, 2.8 Hz, 1H), 3.82 (s, 3H), 2.38 (s, 3H), 2.30 (s, 3H); ESIMS m/z 541 ([M+H]$^+$).

Example 3

(E)-(N'-(2,6-Dimethylphenyl)-N-(4-(1-(4-(trifluoromethyl)phenyl)-1H-1,2,4-triazol-3-yl)phenylcarbamoyl) carbamimidoylthio) methyl isobutyrate (Molecule A3)

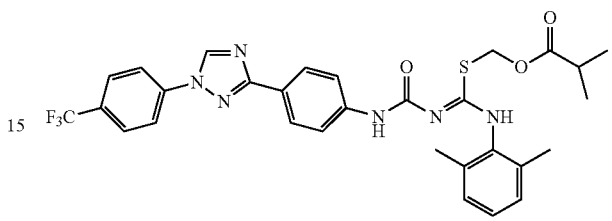

Step 1.

The intermediate (E)-(N'-(2,6-dimethylphenyl)carbamimidoylthio)methyl isobutyrate HBr (B2), was prepared from 1-(2,6-dimethylphenyl thiourea) using conditions described in Example 1. mp 129-131° C.; $^1$H NMR (CDCl$_3$) δ 11.51 (s, 1H), 10.45 (s, 1H), 8.25 (s, 1H), 7.23 (d, J=7.5 Hz, 1H), 7.12 (d, J=7.4 Hz, 2H), 5.59 (s, 2H), 2.69 (heptet, J=7.0 Hz, 1H), 2.30 (s, 6H), 1.23 (d, J=7.0 Hz, 6H); ESIMS m/z 280 ([M+H]$^+$).

Step 2.

Molecule A3 was prepared in a manner similar to that described in Example 1: 575 mg (59%) of a white solid, mp 173-176° C.; $^1$H NMR (CDCl$_3$) δ 11.21 (s, 1H), 8.65 (s, 1H), 8.18 (d, J=8.7 Hz, 2H), 7.92 (d, J=8.4 Hz, 2H), 7.80 (d, J=8.5 Hz, 2H), 7.68 (d, J=8.7 Hz, 2H), 7.20 (m, 1H), 7.14-7.04 (m, 2H), 5.65 (s, 2H), 2.59 (heptet, J=7.0 Hz, 1H), 2.29 (s, 6H), 1.18 (d, J=7.0 Hz, 6H); ESIMS m/z 611 ([M+H]$^+$).

Example 4

(E)-(N'-(2,6-Dimethylphenyl)-N-(4-(1-(4-(trifluoromethyoxy)phenyl)-1H-1,2,4-triazol-3-yl)phenylcarbamoyl) carbamimidoylthio)methyl isobutyrate (Molecule A4)

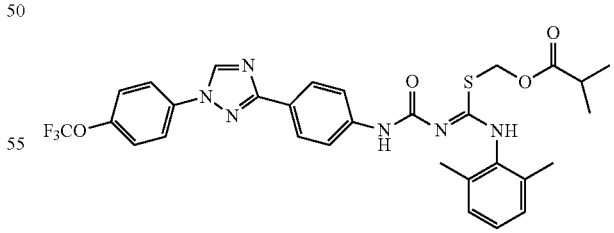

Molecule A4 was prepared in a manner similar to that described in Example 1: 860 mg (52%) of a white solid, mp 148-151° C.; $^1$H NMR (CDCl$_3$) δ 11.21 (s, 1H), 8.55 (s, 1H), 8.17 (d, J=8.7 Hz, 2H), 7.81 (d, J=8.7 Hz, 2H), 7.67 (d, J=8.7 Hz, 2H), 7.42 (br s, 1H), 7.39 (d, J=8.7 Hz, 2H), 7.21-7.10 (m, 3H), 5.65 (s, 2H), 2.67-2.52 (m, 1H), 2.29 (s, 6H), 1.18 (d, J=7.0 Hz, 6H); ESIMS m/z 627 ([M+H]$^+$).

Example 5

(Z)—((N-(2-Isopropylphenyl)-N'-((4-(1-(4-(trifluoromethoxy)phenyl)-1H-1,2,4-triazol-3-yl)phenyl) carbamoyl) carbamimidoyl)thio)methyl isobutyrate (Molecule A5)

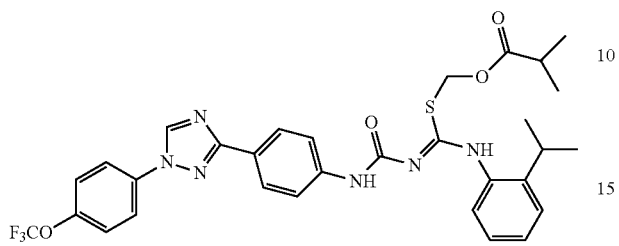

Step 1.

The intermediate (E)-(N'-(2-isopropylphenyl)carbamimidoylthio)methyl isobutyrate HBr (B3), was prepared from 1-(2-isopropylphenyl thiourea) using conditions described in Example 1; mp 80-85° C.; $^1$H NMR (CDCl$_3$) δ 11.70 (s, 1H), 10.45 (s, 1H), 8.27 (s, 1H), 7.47-7.36 (m, 1H), 7.23 m, 1H), 7.15 (d, J=7.4 Hz, 2H), 5.59 (s, 2H), 3.17 (m, 1H), 2.69 (heptet, J=7.0 Hz, 1H), 1.26 (d, J=6.9 Hz, 3H), 1.22 (d, J=6.9 Hz, 3H); ESIMS m/z 295 ([M+H]$^+$).

Step 2.

Molecule A5 was prepared in a manner similar to that described in Example 1: 382 mg (62%) of a white solid, mp 141-143° C.; $^1$H NMR (CDCl$_3$) δ 11.54 (s, 1H), 8.55 (d, J=3.7 Hz, 1H), 8.16 (d, J=8.6 Hz, 2H), 7.80 (d, J=9.1 Hz, 2H), 7.67 (d, J=8.6 Hz, 2H), 7.46-7.32 (m, 5H), 7.23-7.16 (m, 2H), 5.67 (s, 2H), 3.25-3.10 (m, 1H), 2.65-2.52 (m, 1H), 1.24 (d, J=6.9 Hz, 6H), 1.17 (d, J=7.0 Hz, 6H); ESIMS m/z 641 ([M+H]$^+$).

Example 6

(Z)—((N-(2-Isopropylphenyl)-N'-((4-(1-(4-(pentafluoroethoxy)phenyl)-1H-1,2,4-triazol-3-yl)phenyl) carbamoyl) carbamimidoyl)thio)methyl isobutyrate (Molecule A6)

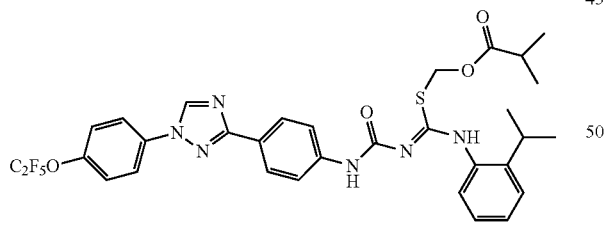

Molecule A6 was prepared in a manner similar to that described in Example 1: 300 mg (45%) of a white solid, mp 154-156° C.; $^1$H NMR (CDCl$_3$) δ 11.54 (s, 1H), 8.56 (d, J=3.7 Hz, 1H), 8.17 (d, J=8.7 Hz, 2H), 7.81 (d, J=9.1 Hz, 2H), 7.67 (d, J=8.7 Hz, 2H), 7.46-7.33 (m, 5H), 7.24-7.19 (m, 2H), 5.67 (s, 2H), 3.29-3.08 (m, 1H), 2.66-2.50 (m, 1H), 1.24 (d, J=6.9 Hz, 6H), 1.17 (d, J=7.0 Hz, 6H); ESIMS m/z 691 ([M+H]$^+$).

Example 7

(E)-(N'-(2,6-Dimethyl-4-methoxyphenyl)-N-(4-(1-(4-(trifluoromethyoxy)phenyl)-1H-1,2,4-triazol-3-yl)phenylcarbamoyl) carbamimidoylthio)methyl isobutyrate (Molecule A7)

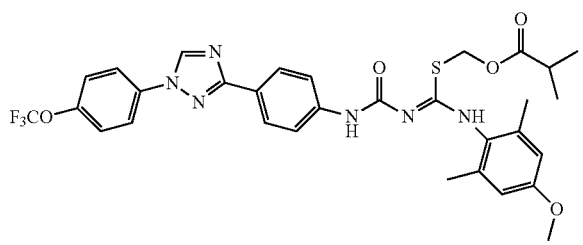 [SMILES: COc1cc(C)c(N/C(=N/C(=O)Nc2ccc(-c3ncn(-c4ccc(OC(F)(F)F)cc4)n3)cc2)SCOC(=O)C(C)C)c(C)c1]

Step 1.

The intermediate (E)-(N'-(2,6-dimethyl-4-methoxyphenyl)carbamimidoylthio)methyl isobutyrate HBr (B4), was prepared from 1-(2,6-dimethyl-4-methoxyphenyl thiourea) using conditions described in Step 1 of Example 1: mp 152-154° C.; $^1$H NMR (CDCl$_3$) δ 6.62 (s, 2H), 5.59 (s, 2H), 3.79 (s, 3H), 2.68 (heptet, J=7.0 Hz, 1H), 2.25 (s, 6H), 1.22 (d, J=7.0 Hz, 6H); ESIMS m/z 311 ([M+H]$^+$).

Step 2.

Molecule A7 was prepared in a manner similar to that described in Example 1: 955 mg (71%) of a white solid, mp 148-151° C.; $^1$H NMR (CDCl$_3$) δ 11.03 (s, 1H), 8.55 (s, 1H), 8.16 (d, J=8.7 Hz, 2H), 7.80 (d, J=9.1 Hz, 2H), 7.67 (d, J=8.7 Hz, 2H), 7.39 (m, 3H), 6.64 (s, 2H), 5.64 (s, 2H), 3.80 (s, 3H), 2.59 (heptet, J=7.0 Hz, 1H), 2.25 (s, 6H), 1.17 (d, J=7.0 Hz, 6H); ESIMS m/z 657 ([M+H]$^+$).

Example 8

(Z)—((N-(2,6-Dimethylphenyl)-N'-((4-(1-(4-(trifluoromethyl)phenyl)-1H-1,2,4-triazol-3-yl)phenyl)carbamoyl) carbamimidoyl)thio)methyl 2-(((benzyloxy)carbonyl)amino)acetate (Molecule A8)

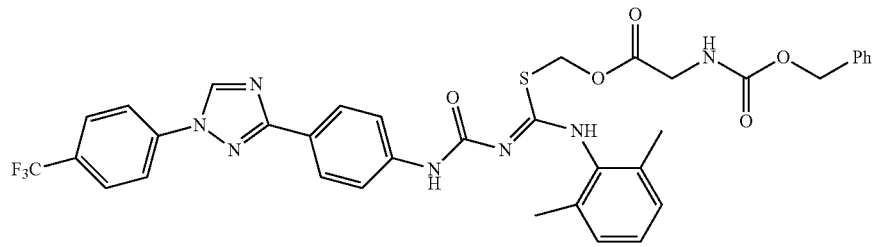 [SMILES: Cc1cccc(C)c1N/C(=N/C(=O)Nc1ccc(-c2ncn(-c3ccc(C(F)(F)F)cc3)n2)cc1)SCOC(=O)CNC(=O)OCc1ccccc1]

The intermediate, ((N-(2,6-dimethylphenyl)carbamimidoyl)thio)methyl 2-(((benzyloxy)carbonyl)amino)acetate HCl (B5), was prepared as described in Step 1 of Example 1, and was used without purification. Molecule A8 (30 mg, 15%) was isolated as a white solid, mp 142-148° C.; $^1$H NMR (CDCl$_3$) δ 11.26 (s, 1H), 8.64 (s, 1H), 8.16 (d, J=8.4 Hz, 2H), 7.91 (d, J=8.2 Hz, 2H), 7.79 (d, J=8.5 Hz, 2H), 7.71 (d, J=8.1 Hz, 2H), 7.54 (s, 1H), 7.34 (m, 5H), 7.15 (m, 3H), 5.69 (s, 2H), 5.23 (s, 1H), 5.13 (s, 2H), 4.02 (d, J=5.7 Hz, 2H), 2.29 (s, 6H); ESIMS m/z 732 ([M+H]$^+$).

Example 9

(E)-((N'-(4-Methoxy-2,6-dimethylphenyl)-N-((4-(1-(4-(trifluoromethyl)phenyl)-1H-1,2,4-triazol-3-yl)phenyl)carbamoyl) carbamimidoyl)thio)methyl 2-(((benzyloxy)carbonyl)amino)acetate (Molecule A9)

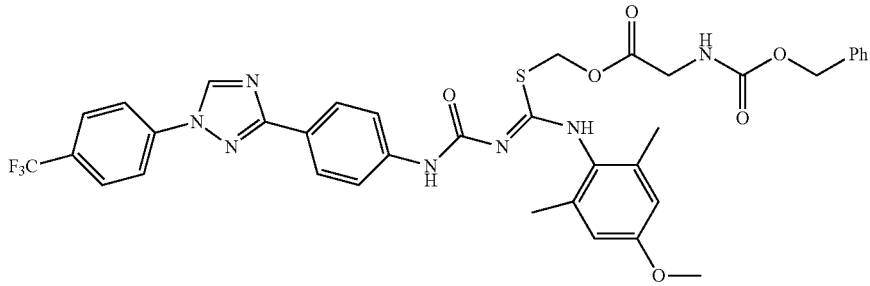 [SMILES: COc1cc(C)c(N/C(=N/C(=O)Nc2ccc(-c3ncn(-c4ccc(C(F)(F)F)cc4)n3)cc2)SCOC(=O)CNC(=O)OCc2ccccc2)c(C)c1]

The intermediate, ((N-(2,6-dimethyl-4-methoxyphenyl) carbamimidoyl)thio)methyl 2-(((benzyloxy)carbonyl) amino)acetate HCl (B6), was prepared as in Step 1 of Example 1, and was used without purification. Molecule A9 (330 mg, 46%) was isolated as a white solid, mp 142-148° C.; $^1$H NMR (CDCl$_3$) δ 11.07 (s, 1H), 8.55 (s, 1H), 8.15 (d, J=8.5 Hz, 2H), 7.80 (d, J=8.8 Hz, 2H), 7.70 (d, J=8.4 Hz, 2H), 7.52 (d, J=3.1 Hz, 1H), 7.44-7.31 (m, 7H), 6.64 (s, 2H), 5.67 (s, 2H), 5.23 (s, 1H), 5.12 (s, 2H), 4.02 (d, J=5.8 Hz, 2H), 3.80 (s, 3H), 2.21 (s, 6H); ESIMS m/z 778 ([M+H]$^+$).

Example 10

(Z)-(((2S,3R,4R,5S,6S)-3,4,5-Trimethoxy-6-methyltetrahydro-2H-pyran-2-yl)thio)methyl N-(4-methoxy-2-methylphenyl)-N'-((4-(1-(4-(trifluoromethoxy)phenyl)-1H-1,2,4-triazol-3-yl)phenyl) carbamoyl) carbamimidothioate (Molecule A10)

The intermediate, (((2S,3R,4R,5S,6S)-3,4,5-trimethoxy-6-methyltetrahydro-2H-pyran-2-yl)thio)methyl(4-methoxy-2-methylphenyl)carbamimidothioate HCl (B7), was prepared as in Step 1 of Example 1, and was used without purification. Molecule A10 (240 mg, 43%) was isolated as a white solid, mp 128-132° C.; $^1$H NMR (CDCl$_3$) δ 11.19 (s, 1H), 8.56 (s, 1H), 8.15 (d, J=8.4 Hz, 2H), 7.80 (J=8.4 Hz, 2H), 7.66 (d, J=8.5 Hz, 2H), 7.38 (d, J=8.3 Hz, 2H), 7.14 (d, J=8.6 Hz, 1H), 6.82-6.69 (m, 3H), 5.69 (s, 1H), 4.46 (d, J=13.9 Hz, 1H), 4.05 (d, J=13.9 Hz, 1H), 3.91 (dd, J=9.3, 6.2 Hz, 1H), 3.81 (s, 3H), 3.67 (dd, J=3.2, 1.5 Hz, 1H), 3.56 (s, 3H), 3.46 s, 3H), 3.44 (s, 3H), 3.38 (dd, J=9.3, 3.3 Hz, 1H), 3.21 (t, J=9.3 Hz, 1H), 2.29 (s, 3H), 1.32 (d, J=6.1 Hz, 3H); ESIMS m/z 777 ([M+H]$^+$).

Example 11

Preparation of N-[[(2,6-dimethylphenyl)amino]thioxomethyl]-N'-(4-(1-(4-(trifluoromethyoxy)phenyl)-1H-1,2,4-triazol-3-yl)phenyl urea (Molecule A11)

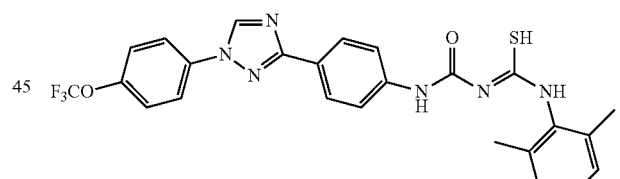

To a solution of Molecule A4 (660 mg, 1.05 mmol) in 75 mL of MeOH was added 20 mL of 1 N HCl, and the resulting

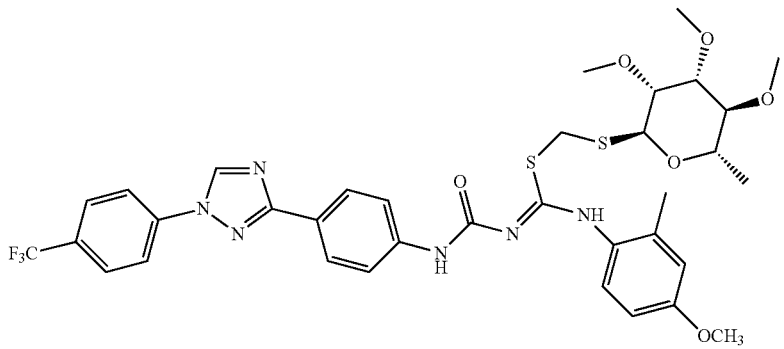 [SMILES: COc1ccc(N/C(=N/C(=O)Nc2ccc(-c3ncn(-c4ccc(C(F)(F)F)cc4)n3)cc2)SCS[C@@H]2O[C@@H](C)[C@H](OC)[C@@H](OC)[C@H]2OC)c(C)c1]

solution was heated at 55° C. for 36 h. The cooled solution was then diluted with another 50 mL of water and the resulting white solid was filtered and air-dried to give 470 mg (81%) of the title compound, mp 233-235° C. $^1$H NMR (CDCl$_3$) δ 8.54 (s, 1H), 8.12 (d, J=8.7 Hz, 2H), 7.79 (d, J=9.1 Hz, 2H), 7.62 (d, J=8.8 Hz, 2H), 7.44-7.29 (m, 4H), 7.22 (d, J=7.5 Hz, 2H), 4.01 (s, 2H), 2.17 (s, 6H); ESIMS m/z 527 ([M+H]$^+$).

Compounds A44 and A49-A52 in Table 1 were made in accordance with the procedures disclosed in Example 11.

Example 12

Preparation of N-[[(2,6-dimethylphenyl)amino]thioxomethyl]-N'-(4-(1-(4-(trifluoromethyl)phenyl)-1H-1,2,4-triazol-3-yl)phenyl urea (Molecule A12)

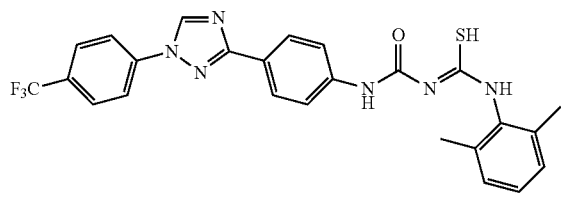 [SMILES: Cc1cccc(C)c1N/C(S)=N/C(=O)Nc1ccc(-c2ncn(-c3ccc(C(F)(F)F)cc3)n2)cc1]

To a solution of Molecule A3 (125 mg, 0.203 mmol) in 5 mL of MeOH was added 0.5 mL of 7 N NH$_3$ in MeOH. The resulting solution was allowed to stir at ambient temperature for 16 h. The solution was concentrated and chromatographed (0-100% EtOAc-hexanes) to give 28 mg (27%) of the thiobiuret as a white solid, mp 204-212° C. $^1$H NMR (DMSO-d$_6$) δ 11.30 (s, 1H), 10.20 (s, 1H), 9.52 (s, 1H), 9.51 (s, 1H), 8.19 (d, J=8.4 Hz, 2H), 8.11 (d, J=8.7 Hz, 2H), 7.99 (d, J=8.6 Hz, 2H), 7.62 (d, J=8.8 Hz, 2H), 7.20-7.09 (m, 3H), 2.20 (s, 6H); ESIMS m/z 511 ([M+H]$^+$).

Example 13

Preparation of 1-(2-isopropylphenyl)-3-[[4-[1-[4-(trifluoromethoxy)phenyl]-1,2,4-triazol-3-yl]phenyl] carbamoyl]urea (Molecule A13)

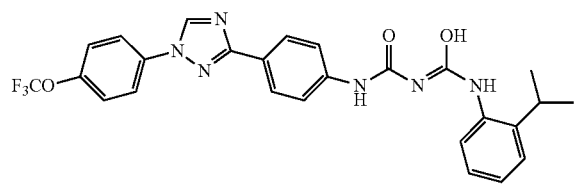 [SMILES: CC(C)c1ccccc1N/C(O)=N/C(=O)Nc1ccc(-c2ncn(-c3ccc(OC(F)(F)F)cc3)n2)cc1]

Molecule A5 (500 mg, 0.78 mmol) was added to 10 mL of THF and 2 mL of 1 N HCl and the solution was stirred for 24 h. The solution was then partitioned between EtOAc (30 mL) and saturated NaHCO$_3$ solution (15 mL). Separation and drying of the organic layer followed by removal of the solvent gave a crude solid which was chromatographed on silica gel to furnish 160 mg (38%) of the title compound as a white solid; mp 300° C. (dec); $^1$H NMR (DMSO-d$_6$) δ 9.86 (s, 1H), 9.57 (s, 1H), 9.37 (d, J=13.8 Hz, 2H), 8.15-7.98 (m, 4H), 7.74 (dd, J=7.9, 1.5 Hz, 1H), 7.67-7.53 (m, 4H), 7.33 (dd, J=7.5, 1.8 Hz, 1H), 7.24-7.06 (m, 2H), 3.20-2.99 (m, 1H), 1.22 (d, J=6.8 Hz, 6H); ESIMS m/z 525 ([M+H]$^+$).

Example 14

Preparation of (Z)-1-(3-(2,6-dimethylphenyl)-4-oxothiazolidin-2-ylidene)-3-(4-(1-(4-(trifluoromethoxy)phenyl)-1H-1,2,4-triazol-3-yl)phenyl) urea (Molecule A14)

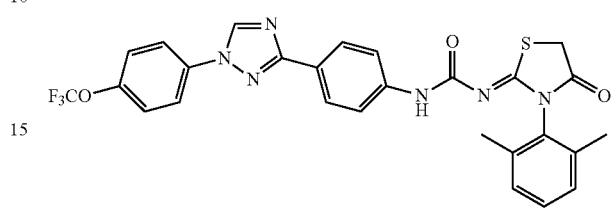

To a suspension of Molecule A11 (200 mg, 0.38 mmol) in 5 mL of EtOH was added sodium acetate (200 mg, 2.43 mmol) and methyl bromoacetate (0.14 g, 0.91 mmol), and the solution was heated at 60° C. for 3 h. The cooled solution was then diluted with 2 mL of water and the resulting white solid was filtered and air-dried to give 142 mg (64%) of the title compound, mp 190-196° C. $^1$H NMR (CDCl$_3$) δ 8.54 (s, 1H), 8.12 (d, J=8.7 Hz, 2H), 7.79 (d, J=9.1 Hz, 2H), 7.62 (d, J=8.8 Hz, 2H), 7.44-7.29 (m, 4H), 7.22 (d, J=7.5 Hz, 2H), 4.01 (s, 2H), 2.17 (s, 6H); ESIMS m/z 567 ([M+H]$^+$).

Compounds A35-A37, A65, A66, A69, A74-A77, A85-A88, A92-A95, A103-A105, A108-A111, A115, A117, A120-A121, and A125 in Table 1 were made in accordance with the procedures disclosed in Example 14.

Example 15

Preparation of (Z)-2-((2,6-dimethylphenyl)imino)-N-(4-(1-(4-(trifluoromethoxy)phenyl)-1H-1,2,4-triazol-3-yl)phenyl)thiazolidine-3-carboxamide (Molecule A15)

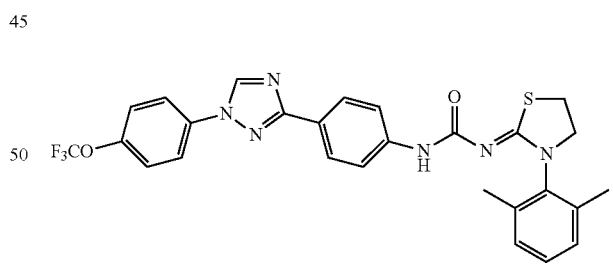

To a solution of Molecule A11 (350 mg, 0.665 mmol) in 7 mL of acetone was added potassium carbonate (200 mg, 1.44 mmol) and 1-chloro-2-bromoethane (0.20 g, 1.40 mmol), and the solution was heated at 50° C. for 5 h. The cooled solution was adsorbed onto silica gel and chromatographed (0-80% EtOAc-hexanes) to give 99 mg (26%) of Molecule A15: mp 145-150° C. $^1$H NMR (CDCl$_3$) δ 8.51 (s, 1H), 8.07 (d, J=7.9 Hz, 2H), 7.81-7.74 (m, 2H), 7.59 (d, J=6.8 Hz, 2H), 7.36 (d, J=8.3 Hz, 2H), 7.19 (m, 3H), 7.12 (s, 1H), 3.81 (t, J=7.7 Hz, 2H), 3.37 (t, J=7.6 Hz, 2H), 2.23 (s, 6H); ESIMS m/z 553 ([M+H]$^+$).

Example 16

Preparation of (Z)-2-((2,6-dimethylphenyl)imino)-N-(4-(1-(4-(trifluoromethoxy)phenyl)-1H-1,2,4-triazol-3-yl)phenyl)-1,3-thiazinane-3-carboxamide (Molecule A16)

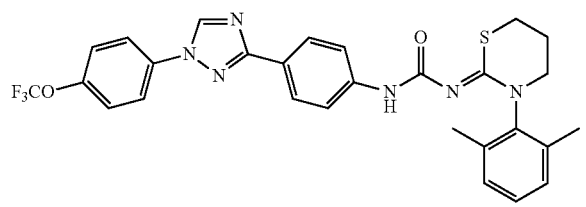 [SMILES: Cc1cccc(C)c1N1CCCS/C1=N\C(=O)Nc1ccc(-c2ncn(-c3ccc(OC(F)(F)F)cc3)n2)cc1]

To a solution of Molecule A11 (150 mg, 0.28 mmol) in 5 mL of acetone was added potassium carbonate (150 mg, 1.08 mmol) and 1-chloro-3-bromopropane (0.16 g, 1.00 mmol), and the solution was heated at 50° C. for 5 h. The cooled solution was adsorbed onto silica gel and chromatographed (0-70% EtOAc-hexanes) to give 22 mg (12%) of the thiazinane: mp 121-125° C. $^1$H NMR (CDCl$_3$) δ 12.81 (s, 1H), 8.54 (s, 1H), 8.16-8.09 (m, 2H), 7.79 (d, J=9.2 Hz, 2H), 7.63 (d, J=8.8 Hz, 2H), 7.38 (d, J=8.3 Hz, 2H), 7.18-6.96 (m, 3H), 4.22-4.09 (m, 2H), 3.00 (t, J=6.9 Hz, 2H), 2.25-2.13 (m, 8H); ESIMS m/z 567 ([M+H]$^+$).

Compounds A39 and A41 in Table 1 were made in accordance with the procedures disclosed in Example 16.

Example 17

Preparation of (Z)-2-((2,6-dimethylphenyl)imino)-N-(4-(1-(4-(trifluoromethoxy)phenyl)-1H-1,2,4-triazol-3-yl)phenyl)thiazolidine-3-carboxamide (Molecule A17)

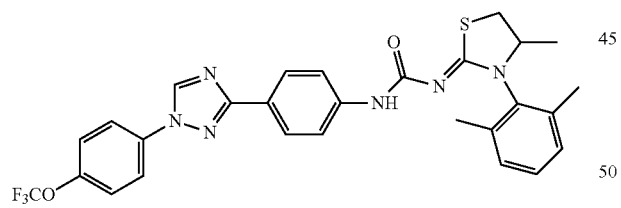

To a solution of Molecule A11 (150 mg, 0.28 mmol) in 5 mL of acetone was added potassium carbonate (100 mg, 0.72 mmol) and 1,2-dibromopropane (0.07 g, 1.20 mmol), and the solution was heated at 50° C. for 12 h. The cooled solution was adsorbed onto silica gel and chromatographed (0-80% EtOAc-hexanes) to give 29 mg (18%) of the title compound as a light tan solid; mp 105-115° C. $^1$H NMR (CDCl$_3$) δ 8.52 (s, 1H), 8.07 (d, J=8.3 Hz, 2H), 7.83-7.73 (m, 2H), 7.59 (d, J=8.2 Hz, 2H), 7.37 (d, J=8.3 Hz, 2H), 7.20 (m, 4H), 4.24 (dd, J=14.5, 6.6 Hz, 1H), 3.58-3.41 (m, 4H), 3.02 (dd, J=11.0, 8.6 Hz, 1H), 2.25 (s, 3H), 2.21 (s, 3H), 1.21 (d, J=6.4 Hz, 3H); ESIMS m/z 567 ([M+H]$^+$).

Compounds A38 and A40 in Table 1 were made in accordance with the procedures disclosed in Example 17.

Example 18

Preparation of (Z)-1-(3-(2-(sec-butyl)phenyl)-4-oxothiazolidin-2-ylidene)-3-(4-(1-(4-(trifluoromethoxy)phenyl)-1H-1,2,4-triazol-3-yl)phenyl)urea (Molecule A18)

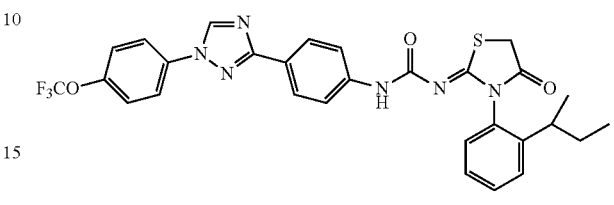

To a solution of 1-(2-(sec-butyl)phenylthiourea (1.40 g, 6.72 mmol) suspended in 5 mL of acetone was added methyl bromoacetate (1.23 g, 1.20 mmol), and the solution was allowed to stir at ambient temperature for 18 h. The solution was then diluted with 8 mL of diethyl ether and, after stirring for 30 min, the solvent was carefully decanted from a gummy oil. The intermediate, methyl 2-((N-(2-(sec-butyl)phenyl)carbamimidoyl)thio)acetate HBr (B8), was dissolved in 8 mL of dry tetrahydrofuran and 4-nitrophenyl(4-(1-(4-(trifluoromethoxy)phenyl)-1H-1,2,4-triazol-3-yl)phenyl)carbamate (3.26 g, 6.72 mmol) was added, followed by Hünig's base (2.6 g, 20 mmol). The solution was allowed to stir at ambient temperature for 3 h, then it was concentrated and the residue chromatographed (silica gel, 0-70% EtOAc-hexanes) to give 730 mg (18%) of the title compound as a solid, mp 169-177° C.; $^1$H NMR (400 MHz, CDCl$_3$) δ 8.53 (s, 1H), 8.12 (d, J=8.7 Hz, 2H), 7.81-7.74 (m, 2H), 7.63-7.56 (m, 2H), 7.52 (m, 1H), 7.45 (d, J=7.9 Hz, 1H), 7.41-7.32 (m, 3H), 7.28 (s, 1H), 7.11 (d, J=7.9 Hz, 1H), 4.03-3.95 (m, 2H), 2.43 (dd, J=13.5, 6.8 Hz, 1H), 1.73-1.56 (m, 2H), 1.20 (overlapping d, J=7.6 Hz, 3H), 0.78 (overlapping t, J=7.4 Hz, 3H); ESIMS m/z 594 ([M+H]$^+$).

The following molecule was prepared according to the conditions described in the previous example.

Example 19

Preparation of (Z)-1-(3-(2-isopropylphenyl)-4-oxothiazolidin-2-ylidene)-3-(4-(1-(4-(trifluoromethoxy)phenyl)-1H-1,2,4-triazol-3-yl)phenyl)urea (Molecule A19)

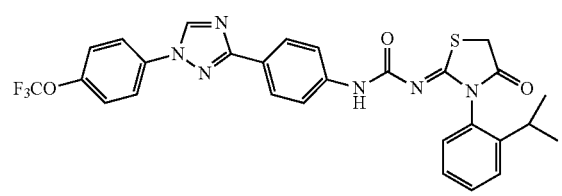 [SMILES: CC(C)c1ccccc1N1C(=O)CS/C1=N\C(=O)Nc1ccc(-c2ncn(-c3ccc(OC(F)(F)F)cc3)n2)cc1]

From 0.70 g (2.0 mmol) of the intermediate (E)-methyl 2-((N'-(2-isopropylphenyl)carbamimidoyl)thio)acetate, HBr (B9) and 850 mg (1.75 mmol) of 4-nitrophenyl(4-(1-(4-(trifluoromethoxy)phenyl)-1H-1,2,4-triazol-3-yl)phenyl)carbamate was obtained 320 mg (31%) of Molecule A19 as a light tan solid, mp 180-183° C.; $^1$H NMR (CDCl$_3$) δ 8.53 (s, 1H), 8.12 (d, J=8.7 Hz, 2H), 7.80-7.74 (m, 2H), 7.60 (d, J=8.8 Hz, 2H), 7.54-7.45 (m, 2H), 7.40-7.34 (m, 3H), 7.32 (s, 1H), 7.10 (d, J=7.5 Hz, 1H), 3.98 (d, J=2.5 Hz, 2H), 2.73 (heptet, J=6.9 Hz, 1H), 1.22 (dd, J=6.8, 5.0 Hz, 6H); ESIMS m/z 581 ([M+H]⁺).

Example 20

Preparation of (E)-3-hydroxy-2-((2-isopropylphenyl)carbamothioyl)-N-(4-(1-(4-(trifluoromethoxy)phenyl)-1H-1,2,4-triazol-3-yl)phenyl)but-2-enamide (Molecule A20)

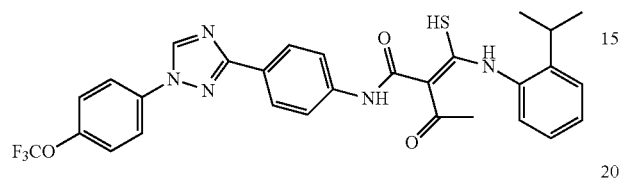

Step 1.
A solution of 4-(1-(4-(trifluoromethoxy)phenyl)-1H-1,2,4-triazol-3-yl)aniline (1.0 g, 3.12 mmol) and t-butyl acetoacetate (0.494 g, 3.12 mmol) in 8 mL of toluene was heated at 90° C. for 2 h, then cooled. The resulting solid was filtered and air-dried to give 1.12 g (89%) of 3-oxo-N-(4-(1-(4-(trifluoromethoxy)phenyl)-1H-1,2,4-triazol-3-yl)phenyl)-butanamide as a tan solid (B10); mp 159-164° C. ¹H NMR (CDCl₃) δ 9.35 (s, 1H), 8.55 (s, 1H), 8.19-8.09 (d, J=8.7 Hz, 2H), 7.83-7.74 (d, J=9.1 Hz, 2H), 7.74-7.63 (d, J=8.7 Hz, 2H), 7.43-7.32 (d, J=8.3 Hz, 2H), 3.62 (s, 2H), 2.34 (s, 3H); ¹³C NMR (101 MHz, CDCl₃) δ 205.34, 163.43, 163.02, 148.34, 141.49, 138.84, 135.55, 127.37, 126.50, 122.37, 121.67, 121.16, 120.03, 49.56, 31.36; ESIMS m/z 581 ([M+H]⁺).

Step 2.
A portion of the solid from Step 1 (0.50 g, 1.24 mmol) was dissolved in 5 mL of dry N,N-dimethylformamide (DMF) and stirred at ambient temperature while potassium carbonate (0.25 g, 1.81 mmol) and 2-isopropylphenyl isothiocyanate (0.25 g, 1.41 mmol) were added. The solution was stirred for 18 h, then it was poured into 15 mL of water, extracted with ether, and the solvent evaporated. Chromatography of the crude product (0-70% EtOAc-hexanes) gave 350 mg of the title compound as an off-white solid. mp 141-144° C. ¹H NMR (400 MHz, CDCl₃) δ 15.35-14.58 (m, 1H), 10.93 (s, 1H), 8.57 (m, 3H), 8.31-8.11 (m, 6H), 7.71 (m, 12H), 7.56-7.30 (m, 15H), 5.35 (s, 1H), 3.02 (heptet, J=6.9 Hz, 1H), 2.52 (s, 3H), 1.35-1.11 (m, 6H); ESIMS m/z 582 ([M+H]⁺).

Example 21

Preparation of 3-((2-isopropylphenyl)amino)-3-thioxo-N-(4-(1-(4-(trifluoromethoxy)phenyl)-1H-1,2,4-triazol-3-yl)phenyl)propanamide (Molecule A21)

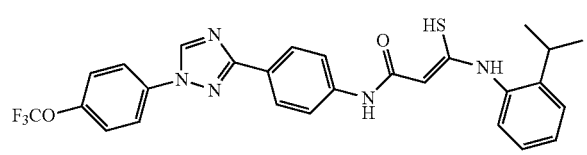 [SMILES: CC(C)c1ccccc1N/C(S)=C/C(=O)Nc1ccc(-c2ncn(-c3ccc(OC(F)(F)F)cc3)n2)cc1]

Molecule A20 (0.410 g, 0.71 mmol) was heated in 5 mL of MeOH for 90 min, then it was cooled, concentrated and chromatographed (0-70% EtOAc-hexanes) to give 288 mg (75%) of Molecule A21 as a yellow solid, mp 173-178° C. ¹H NMR (CDCl₃) δ 10.46 (s, 1H), 8.57 (s, 1H), 8.38 (s, 1H), 8.19 (d, J=8.7 Hz, 2H), 7.80 (d, J=9.1 Hz, 2H), 7.67 (d, J=8.8 Hz, 2H), 7.47-7.31 (m, 6H), 4.10 (s, 2H), 3.04 (heptet, J=6.7 Hz, 1H), 1.22 (d, J=6.9 Hz, 6H); ESIMS m/z 540 ([M+H]⁺).

The conditions described in Examples 20 and 21 were used to prepare the molecules in Examples 22 and 23.

Example 22

Preparation of 3-thioxo-3-(o-tolylamino)-N-(4-(1-(4-(trifluoromethoxy)phenyl)-1H-1,2,4-triazol-3-yl)phenyl)propanamide (Molecule A22)

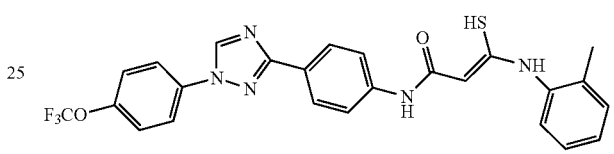

Using 2-methylphenyl isothiocyanate in place of 2-isopropylphenyl isothiocyanate in Step 2 of Example 20, there was obtained 33 mg (52%) of Molecule A22; ¹H NMR (CDCl₃) δ 10.76 (s, 1H), 8.84 (s, 1H), 8.56 (s, 1H), 8.15-8.13 (d, J=8.4 Hz, 2H), 7.81-7.74 (m, 3H), 7.66-7.33 (d, J=8.4 Hz, 2H), 7.58-7.50 (m, 1H), 7.43-7.20 (m, 4H), 4.10 (s, 2H), 2.28 (s, 3H); ESIMS m/z 511 ([M+H]⁺).

Example 23

Preparation of 3-((2,6-dimethylphenyl)amino)-3-thioxo-N-(4-(1-(4-(trifluoromethoxy)phenyl)-1H-1,2,4-triazol-3-yl)phenyl)propanamide (Molecule A23)

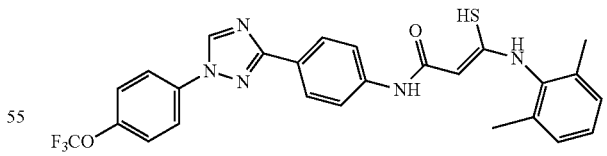

Using 2,6-dimethylphenyl isothiocyanate in place of 2-isopropylphenyl isothiocyanate in Step 2 of Example 20, there was obtained 185 mg (41%) of Molecule A23 as a light yellow solid, mp 178-182° C.; ¹H NMR (CDCl₃) δ 10.41 (s, 1H), 8.88 (s, 1H), 8.58 (s, 1H), 8.15 (d, J=8.7 Hz, 2H), 7.85-7.76 (m, 2H), 7.65 (d, J=8.7 Hz, 2H), 7.38 (d, J=8.4 Hz, 2H), 7.22-6.99 (m, 3H), 4.14 (s, 2H), 2.22 (s, 6H); ESIMS m/z 526 ([M+H]⁺).

Example 24

Preparation of (Z)-2-(3-(2-isopropylphenyl)-4-oxothiazolidin-2-ylidene)-N-(4-(1-(4-(trifluoromethoxy)phenyl)-1H-1,2,4-triazol-3-yl)phenyl)acetamide (Molecule A24)

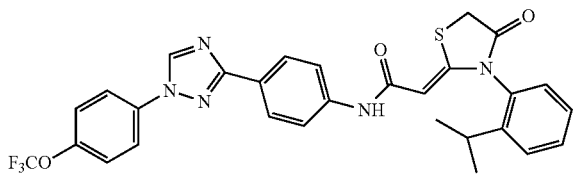 [SMILES: CC(C)c1ccccc1N1C(=O)CS/C1=C\C(=O)Nc1ccc(-c2ncn(-c3ccc(OC(F)(F)F)cc3)n2)cc1]

Molecule A21 (0.031 g, 0.057 mmol) was dissolved in 4 mL of EtOH and treated with 20 mg (0.13 mmol) of methyl bromoacetate and 20 mg (0.24 mmol) of sodium acetate, and the solution was heated to reflux for 2 h. The solution was then cooled, concentrated and chromatographed (0-70% EtOAc-hexanes) to give 27 mg (73%) of Molecule A24 as a tan solid. mp>250° C. (dec). $^1$H NMR (CDCl$_3$) δ 8.53 (s, 1H), 8.13-8.07 (m, 2H), 7.81-7.76 (m, 2H), 7.61 (d, J=8.6 Hz, 2H), 7.53 (d, J=3.9 Hz, 2H), 7.42-7.33 (m, 2H), 7.23-7.16 (m, 1H), 7.13 (d, J=7.7 Hz, 1H), 6.97 (s, 1H), 5.01 (s, 1H), 3.91 (s, 2H), 2.83-2.68 (m, 1H), 1.31-1.16 (m, 6H); ESIMS m/z 580 ([M+H]$^+$).

Example 25

Preparation of (Z)-2-cyano-3-((2-isopropylphenyl)amino)-3-mercapto-N-(4-(1-(4-(trifluoromethoxy)phenyl)-1H-1,2,4-triazol-3-yl)phenyl)acrylamide (Molecule A25)

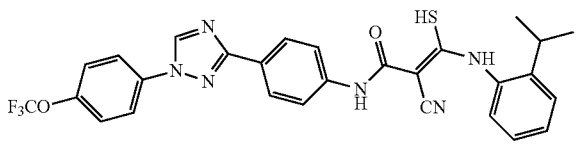 [SMILES: CC(C)c1ccccc1N/C(S)=C(\C#N)C(=O)Nc1ccc(-c2ncn(-c3ccc(OC(F)(F)F)cc3)n2)cc1]

Step 1.

Cyanoacetic acid (0.30 g, 3.53 mmol) and 4-(1-(4-(trifluoromethoxy)phenyl)-1H-1,2,4-triazol-3-yl)aniline (1.00 g, 3.12 mmol) were dissolved in 30 mL of dichloromethane, and then dicyclohexylcarbodiimide (0.695 g, 3.37 mmol) was added in one portion as a solid. The solution was allowed to stir for 2 h, then the solvent was removed and the residue was heated in 75 mL of EtOAc, cooled and filtered to remove dicyclohexyl urea. The filtrate was concentrated and the solid was recrystallized from EtOH to give 0.82 g (66%) of 2-cyano-N-(4-(1-(4-(trifluoromethoxy)phenyl)-1H-1,2,4-triazol-3-yl)phenyl)acetamide (B11) as a white solid, mp 250-252° C. $^1$H NMR (DMSO-d$_6$) δ 10.51 (s, 1H), 9.39 (s, 1H), 8.13-8.00 (m, 4H), 7.75-7.66 (m, 2H), 7.62 (d, J=8.3 Hz, 2H), 3.95 (s, 2H). ESIMS m/z 388 (M+H).

Step 2.

The cyanoacetanilide from Step 1 (0.30 g, 0.775 mmol) and 2-isopropylphenyl isothiocyanate (0.16 g, 0.903 mmol) were dissolved in 5 mL of DMF and stirred under N$_2$ while NaH (60%; 62 mg, 1.55 mmol) was added in one portion. The solution was allowed to stir at ambient temperature for 1 h, then it was poured into 20 mL of 1 N HCl. The gummy solid was collected and crystallized from EtOH/water to give 0.32 g (71%) of the title compound as a light yellow solid, mp 159-162° C. $^1$H NMR (CDCl$_3$) δ 12.56 (s, 1H), 8.56 (s, 1H), 8.18 (d, J=8.7 Hz, 2H), 7.85-7.77 (m, 2H), 7.68-7.60 (m, 3H), 7.45-7.36 (m, 4H), 7.32-7.27 (m, 1H), 7.20 (d, J=7.7 Hz, 1H), 4.42 (s, 1H), 3.11 (heptet, J=6.9 Hz, 1H), 1.26 (d, J=6.9 Hz, 6H); ESIMS m/z 565 ([M+H]$^+$).

The following molecules (Examples 26-30) were prepared according to the procedure described in the previous Example.

Example 26

(Z)-2-Cyano-3-mercapto-3-((4-methoxy-2-methylphenyl)amino)-N-(4-(1-(4-(trifluoromethoxy)phenyl)-1H-1,2,4-triazol-3-yl)phenyl)acrylamide (Molecule A26)

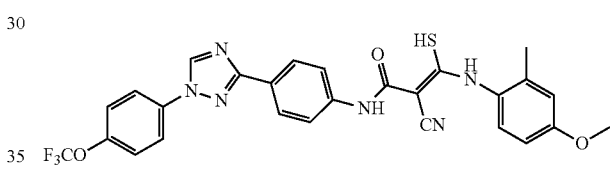

Molecule A26 was isolated as a light yellow solid, 103 mg (58%), mp 174-177° C.; $^1$H NMR (CDCl$_3$) δ 12.27 (s, 1H), 8.56 (s, 1H), 8.18 (d, J=8.7 Hz, 2H), 7.80 (d, J=9.1 Hz, 2H), 7.63 (d, J=8.9 Hz, 2H), 7.61 (s, 1H), 7.39 (d, J=8.3 Hz, 2H), 7.12 (d, J=8.6 Hz, 1H), 6.92-6.73 (m, 2H), 4.40 (s, 1H), 3.83 (s, 3H), 2.28 (s, 3H); ESIMS m/z 567 ([M+H]$^+$).

Example 27

(Z)-3-([1,1'-Biphenyl]-2-ylamino)-2-cyano-3-mercapto-N-(4-(1-(4-(trifluoromethoxy)phenyl)-1H-1,2,4-triazol-3-yl)phenyl)acrylamide (Molecule A27)

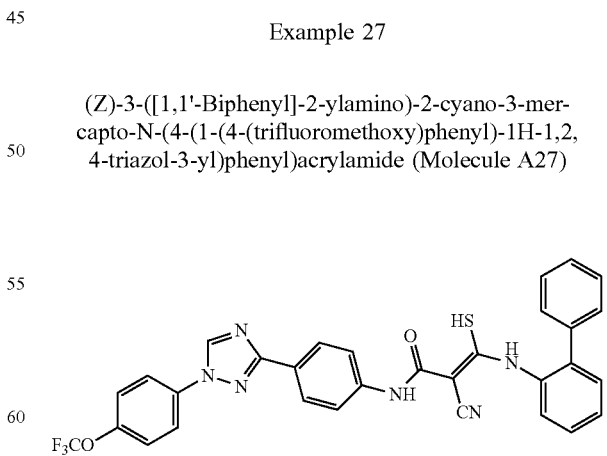

Molecule A27 was isolated as a light yellow solid, 60 mg (32%), mp 162-166° C.; $^1$H NMR (CDCl$_3$) δ 12.52 (s, 1H), 8.55 (s, 1H), 8.15 (d, J=8.6 Hz, 2H), 7.80 (m, 3H), 7.57-7.28 (m, 13H), 4.29 (s, 1H); ESIMS m/z 599 ([M+H]$^+$).

Example 28

(Z)-2-Cyano-3-mercapto-3-((2,6-dimethylphenyl)amino)-N-(4-(1-(4-(trifluoromethoxy)phenyl)-1H-1,2,4-triazol-3-yl)phenyl)acrylamide (Molecule A28)

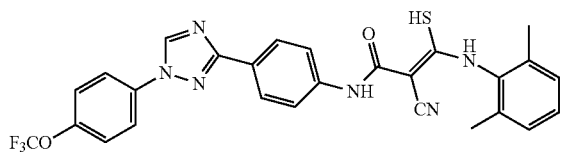 [SMILES: Cc1cccc(C)c1N/C(S)=C(\C#N)C(=O)Nc1ccc(-c2ncn(-c3ccc(OC(F)(F)F)cc3)n2)cc1]

Molecule A28 was isolated as a light yellow solid, 103 mg (59%), mp 196-199° C.; $^1$H NMR (CDCl$_3$) δ 12.24 (s, 1H), 8.56 (s, 1H), 8.18 (d, J=8.8 Hz, 2H), 7.80 (d, J=9.1 Hz, 2H), 7.64 (d, J=8.7 Hz, 2H), 7.42-7.33 (m, 2H), 7.23 (m, 1H), 7.17 (d, J=7.7 Hz, 2H), 4.30 (s, 1H), 2.28 (s, 6H); ESIMS m/z 551 ([M+H]$^+$).

Example 29

(Z)-2-Cyano-3-mercapto-3-(o-tolylamino)-N-(4-(1-(4-(trifluoromethoxy)phenyl)-1H-1,2,4-triazol-3-yl)phenyl)acrylamide (Molecule A29)

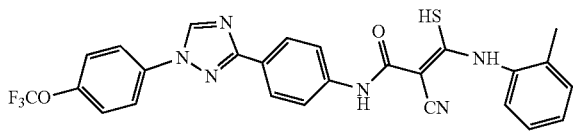 [SMILES: Cc1ccccc1N/C(S)=C(\C#N)C(=O)Nc1ccc(-c2ncn(-c3ccc(OC(F)(F)F)cc3)n2)cc1]

Molecule A29 was isolated as a light yellow solid, 121 mg (71%), mp 157-160° C.; $^1$H NMR (CDCl$_3$) δ 12.51 (s, 1H), 8.56 (s, 1H), 8.18 (d, J=8.8 Hz, 2H), 7.84-7.73 (m, 2H), 7.67-7.60 (m, 3H), 7.39 (d, J=8.3 Hz, 2H), 7.32 (m, 3H), 7.23 (m, 1H), 4.42 (s, 1H), 2.33 (s, 3H); ESIMS m/z 537 ([M+H]$^+$).

Example 30

(Z)-2-Cyano-3-((2,6-difluorophenyl)amino)-3-mercapto-N-(4-(1-(4-(trifluoromethoxy)phenyl)-1H-1,2,4-triazol-3-yl)phenyl)acrylamide (Molecule A30)

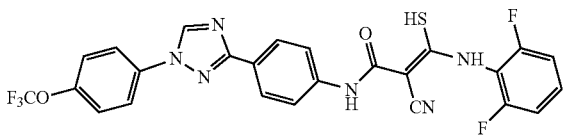 [SMILES: N#C/C(C(=O)Nc1ccc(-c2ncn(-c3ccc(OC(F)(F)F)cc3)n2)cc1)=C(/S)Nc1c(F)cccc1F]

Molecule A30 was isolated as a light yellow solid, 53 mg (28%), mp 135-142° C.; $^1$H NMR (CDCl$_3$) δ 12.31 (s, 1H), 8.64-8.50 (m, 1H), 8.19 (dd, J=13.9, 7.1 Hz, 2H), 7.80 (m, 2H), 7.65 (m, 2H), 7.39 (m, 3H), 7.14-6.86 (m, 3H), 4.97-4.11 (m, 1H); ESIMS m/z 559 ([M+H]$^+$).

Example 31

(Z)-2-Cyano-2-(3-(2-isopropylphenyl)-4-oxothiazolidin-2-ylidene)-N-(4-(1-(4-(trifluoromethoxy)phenyl)-1H-1,2,4-triazol-3-yl)phenyl)acetamide (Molecule A31)

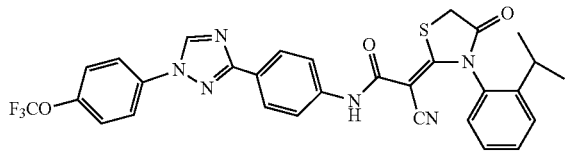 [SMILES: CC(C)c1ccccc1N1C(=O)CS/C1=C(/C#N)C(=O)Nc1ccc(-c2ncn(-c3ccc(OC(F)(F)F)cc3)n2)cc1]

Molecule A25 (0.058 g, 0.103 mmol) was dissolved in 3 mL of EtOH and treated with 35 mg (0.23 mmol) of methyl bromoacetate and 30 mg (0.37 mmol) of sodium acetate, and the solution was heated to reflux for 1 h. The solution was then cooled and the solid product was filtered and air-dried to give to give 46 mg (71%) of the thiazolinone as a light tan solid, mp 250-255° C.; $^1$H NMR (CDCl$_3$) δ 8.55 (s, 1H), 8.16 (d, J=8.8 Hz, 2H), 7.95 (s, 1H), 7.79 (d, J=9.1 Hz, 2H), 7.62 (d, J=8.8 Hz, 3H), 7.53 (dd, J=7.8, 1.2 Hz, 1H), 7.42-7.34 (m, 3H), 7.18 (dd, J=7.9, 1.2 Hz, 1H), 3.92 (d, J=1.3 Hz, 2H), 2.71 (heptet, J=6.8 Hz, 1H), 1.33 (d, J=6.9 Hz, 3H), 1.23 (d, J=6.8 Hz, 3H); ESIMS m/z 605 ([M+H]$^+$).

Example 32

Preparation of (Z)-3-(2,6-dimethylphenylamino)-3-hydroxy-1-(4-(1-(4-(trifluoromethoxy)phenyl)-1H-1,2,4-triazol-3-yl)phenyl)acrylamide (Molecule A32)

Step 1.

To a stirred solution of 4-(1-(4-(trifluoromethoxy)phenyl)-1H-1,2,4-triazol-3-yl)aniline (0.19 g; 0.593 mmol) and mono-benzyl malonic acid (0.138 g; 0.712 mmol) dissolved in DMF (6 mL) was added 1-hydroxy-7-azabenzotriazole (HOAt, 0.5 M in DMF; 2.14 mL; 1.068 mmol), followed by 1-(3-dimethylaminnopropyl)-3-ethylcarbodiimide hydrochloride (EDCI; 0.21 g; 1.068 mmol) and N-methyl morpholine (0.46 mL; 4.15 mmol). The mixture was stirred overnight. Water (25 mL) was then added and the solution was extracted with EtOAc (3×10 mL). The organic solution was washed with water (5×10 mL) and brine (10 mL), followed by drying over MgSO$_4$, filtration and concentration. The residue was applied to a 1 g Isolute SCX-2 column and eluted with a 9:1 CHCl$_3$/MeOH solution to afford the expected amide (B12), contaminated with about 10% of the dimethyl amide of the starting oxo-propanoic acid (0.26 g; 88%). $^1$H NMR (CDCl$_3$) δ 9.35 (s, 1H), 8.55 (s, 1H), 8.15 (d, J=8.7 Hz, 2H), 7.78 (d, J=9.0 Hz, 2H), 7.67 (d, J=8.7 Hz, 2H), 7.35 (m, 7H), 5.23 (s, 2H), 3.54 (s, 2H). $^{13}$C NMR (101 MHz, CDCl$_3$) δ 169.59, 167.45, 162.84, 141.53, 138.91, 135.58, 134.81, 128.77, 128.60, 128.52, 128.41, 128.36, 127.37, 122.39, 121.17, 119.97, 67.65, 41.76, 35.58. ESIMS m/z 496 ([M+H]$^+$)

Step 2.

The benzyl ester from Step 1 (0.26 g; 0.524 mmol) was dissolved in 4 mL of MeOH and eluted through the H-Cube hydrogenator at 50° C. (1 mL/min) using a 10% Pd/C cartridge as the catalyst. The MeOH was concentrated and the crude acid was dried under high vacuum overnight. The acid (B13) (0.162 g; 76%). was used directly in the next step $^1$H NMR (DMSO-$d_6$) δ 10.35 (s, 1H), 9.38 (s, 1H), 8.06 (dd, J=8.9, 3.3 Hz, 4H), 7.74 (d, J=8.8 Hz, 2H), 7.62 (d, J=8.4 Hz, 2H), 7.37 (s, 1H), 3.39 (s, 2H). ESIMS m/z 406 ([M+H]$^+$)

Step 3.

To a solution of the carboxylic acid from Step 2 (62 mg; 0.153 mmol) and 2,6-dimethyl aniline (20 μL; 0.153 mmol) in DMF (1.6 mL) was added HOAt (0.5 M in DMF; 0.55 mL; 0.275 mmol), EDCI HCl (53 mg; 0.275 mmol) and N-methyl morpholine (0.18 mL; 1.068 mmol). The reaction was stirred at room temperature overnight. The solution was diluted with water and extracted with EtOAc. The organic solution was washed with water (5×) and brine. The solution was then dried over MgSO$_4$, filtered and concentrated. The residue was purified via radial chromatography using a 97.5:2.5 ratio of CHCl$_3$/MeOH as the eluent (R$_f$=0.2). The fraction containing the product was contaminated with the dimethyl amide of the starting carboxylic acid. This mixture was purified via reverse phase chromatography using CH$_3$CN/H$_2$O gradient to give the pure desired diamide (9 mg; 12%). $^1$H NMR (CDCl$_3$; mixture of resonance forms, major reported) δ 10.53 (s, 1H), 9.71 (s, 1H), 8.55 (s, 1H), 8.13 (m, 3H), 7.79 (d, J=9.1 Hz, 2H), 7.71 (d, J=8.7 Hz, 1H), 7.65 (d, J=8.7 Hz, 1H), 7.37 (d, J=8.3 Hz, 2H), 7.12 (m, 1H), 3.49 (s, 2H), 3.12 (s, 3H), 3.04 (s, 3H). ESIMS m/z 509 ([M+H]$^+$)

Example 33

Preparation of (Z)-3-hydroxy-3-(4-methoxy-2-methylphenylamino)-N-(4-(1-(4-(trifluoromethoxy)phenyl)-1H-1,2,4-triazol-3-yl)phenyl)acrylamide (Molecule A33)

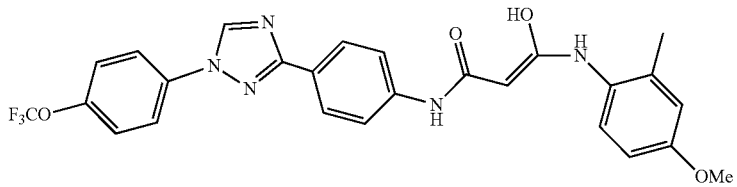 [SMILES: COc1ccc(N/C(O)=C/C(=O)Nc2ccc(-c3ncn(-c4ccc(OC(F)(F)F)cc4)n3)cc2)c(C)c1]

Using Step 3 of the above procedure, and replacing 2,6-dimethylaniline with 2-methyl-4-methoxyaniline, there was obtained 83 mg (56%) of the diamide as a tan solid, mp 168-171° C. $^1$H NMR (DMSO-$d_6$) δ 10.39 (s, 1H), 9.48 (s, 1H), 9.38 (s, 1H), 8.07 (d, J=8.9 Hz, 4H), 7.77 (d, J=8.8 Hz, 2H), 7.62 (d, J=8.3 Hz, 2H), 7.28 (d, J=8.7 Hz, 1H), 6.81 (d, J=2.8 Hz, 1H), 6.74 (dd, J=8.7, 2.9 Hz, 1H), 3.73 (s, 3H), 3.51 (s, 2H), 2.21 (s, 3H). EIMS 525 (M$^+$).

Example 34

Preparation of (Z)-3-hydroxy-3-(2-isopropyl-4-methoxyphenylamino)-N-(4-(1-(4-(trifluoromethoxy)phenyl)-1H-1,2,4-triazol-3-yl)phenyl)acrylamide (Molecule A34)

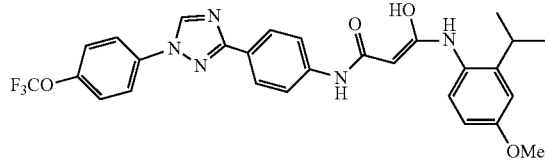 [SMILES: COc1ccc(N/C(O)=C/C(=O)Nc2ccc(-c3ncn(-c4ccc(OC(F)(F)F)cc4)n3)cc2)c(C(C)C)c1]

Using Step 3 of the above procedure, and replacing 2,6-dimethylaniline with 2-isopropyl-4-methoxyaniline, there was obtained 38 mg (36%) of the diamide. $^1$H NMR (CDCl$_3$) δ 9.81 (s, 1H), 8.92 (s, 1H), 8.58 (s, 1H), 8.12 (d, J=8.6 Hz, 2H), 7.79 (d, J=9.0 Hz, 2H), 7.69 (d, J=8.7 Hz, 2H), 7.50-7.10 (m, 3H), 6.84 (d, J=2.8 Hz, 1H), 6.72 (dd, J=8.7, 2.9 Hz, 1H), 4.02 (s, 3H), 3.80 (s, 2H), 3.08 (dt, J=13.6, 6.8 Hz, 1H), 1.20 (d, J=6.9 Hz, 6H). $^{13}$C NMR (101 MHz, CDCl$_3$) δ 166.81, 166.13, 162.98, 158.40, 144.30, 141.54, 139.02, 135.54, 127.30, 127.05, 126.87, 126.52, 126.30, 122.36, 121.13, 120.10, 111.97, 110.85, 56.04, 55.36, 44.26, 28.37, 23.06. ESIMS m/z 553 ([M+H]$^+$)

Example 35

Preparation of 4-fluoro-2-nitro-1-(prop-1-en-2-yl)benzene (B14)

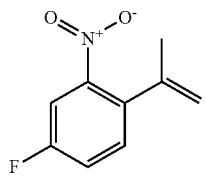

To 1-chloro-4-fluoro-2-nitrobenzene (1.03 g, 5.87 mmol) in a 100 mL round-bottomed flask equipped with a stir bar and nitrogen was added sodium carbonate (0.746 g, 7.04 mmol), dioxane (23.47 ml) and water (5.87 ml). To this was added 4,4,5,5-tetramethyl-2-(prop-1-en-2-yl)-1,3,2-dioxaborolane (1.323 ml, 7.04 mmol) followed by bis(triphenylphosphine)palladium(II)chloride (0.329 g, 0.469 mmol). The reaction mixture was evacuated and backfilled with nitrogen (3×). The reaction was heated to 80° C. overnight. The reaction was determined to be complete by TLC (10% EtOAc/Hex). The reaction was cooled, filtered through Celite, washed with EtOAc and concentrated. The residue was taken up in dichloromethane, poured through a phase separator and concentrated. Purification by flash column chromatography provided the title compound 4-fluoro-2-nitro-1-(prop-1-en-2-yl)benzene (0.837 g, 75%) as a yellow oil: IR (thin film) 3091 (w), 2979 (w), 2918 (w), 1642 (w), 1530 (s), 1350 (s) cm$^{-1}$; $^1$H NMR (400 MHz, CDCl$_3$) δ 7.60 (dd, J=8.2, 2.5 Hz, 1H), 7.37-7.21 (m, 2H), 5.19 (p, J=1.5 Hz, 1H), 4.97-4.89 (m, 1H), 2.11-2.04 (m, 3H); $^{13}$C NMR (101 MHz, CDCl$_3$) δ 160.96 (d, J$_{CF}$=250.8 Hz), 148.46, 141.88, 135.18 (d, J$_{CF}$=4.1 Hz), 132.09 (d, J$_{CF}$=7.8 Hz), 119.98 (d, J$_{CF}$=20.9 Hz), 115.99, 111.63 (d, J$_{CF}$=26.4 Hz), 23.35.

The following molecules (B15 and B16) were made in accordance with the procedures disclosed in Example 35.

1-Fluoro-3-nitro-2-(prop-1-en-2-yl)benzene (B15)

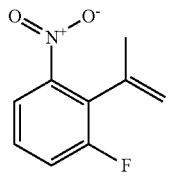

IR (thin film) 3091 (w), 2978 (w), 2922 (w), 1645 (w), 1528 (s), 1355 (s) cm$^{-1}$; $^1$H NMR (400 MHz, CDCl$_3$) δ 7.64 (dt, J=8.1, 1.2 Hz, 1H), 7.39 (td, J=8.2, 5.4 Hz, 1H), 7.31 (td, J=8.5, 1.2 Hz, 1H), 5.28 (p, J=1.5 Hz, 1H), 4.91 (p, J=1.0 Hz, 1H), 2.16 (t, J=1.3 Hz, 3H); $^{13}$C NMR (101 MHz, CDCl$_3$) δ 159.59 (d, J$_{CF}$=249.3 Hz), 149.81, 136.14, 128.57 (d, J$_{CF}$=9.0 Hz), 127.02 (d, J$_{CF}$=22.0 Hz), 119.84 (d, J$_{CF}$=23.4 Hz), 119.41 (d, J$_{CF}$=3.6 Hz), 117.25, 23.10 (d, J$_{CF}$=1.9 Hz).

4-Fluoro-1-nitro-2-(prop-1-en-2-yl)benzene (B16)

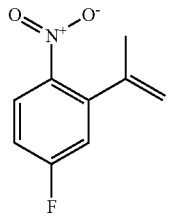

IR (thin film) 3085 (w), 2979 (w), 2919 (w), 1617 (m), 1580 (s), 1523 (s), 1344 (s) cm$^{-1}$; $^1$H NMR (400 MHz, CDCl$_3$) δ 7.96 (dd, J=9.0, 5.1 Hz, 1H), 7.08 (ddd, J=9.0, 7.4, 2.8 Hz, 1H), 7.02 (dd, J=8.7, 2.8 Hz, 1H), 5.20 (p, J=1.5 Hz, 1H), 4.96 (p, J=1.0 Hz, 1H), 2.11-2.06 (m, 3H).

Example 36

Preparation of 5-fluoro-2-isopropylaniline (B17)

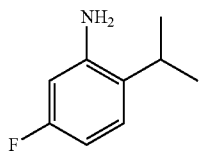

To 4-fluoro-2-nitro-1-(prop-1-en-2-yl)benzene (0.837 g, 4.62 mmol) in a 250 mL round-bottomed flask equipped with a stir bar and rubber septum was added EtOAc (46.2 ml) followed by palladium on carbon (0.983 g, 0.462 mmol). The reaction was evacuated and purged with hydrogen (balloon) (2×) and stirred under hydrogen at room temperature overnight. The reaction was determined to be complete by TLC (10% EtOAc/Hex). The mixture was filtered through Celite, washed with EtOAc and concentrated. 5-Fluoro-2-isopropylaniline (673 mg, 4.40 mmol, 95%) was obtained as a clear and yellow oil: IR (thin film) 3480 (w), 3390 (w), 2962 (m), 2872 (w), 1622 (m), 1504 (s), 1431 (m) cm$^{-1}$; $^1$H NMR (400 MHz, CDCl$_3$) δ 7.05 (dd, J=8.5, 6.4 Hz, 1H), 6.45 (td, J=8.5, 2.6 Hz, 1H), 6.37 (dd, J=10.6, 2.6 Hz, 1H), 3.74 (bs, 2H), 2.83 (hept, J=6.8 Hz, 1H), 1.24 (d, J=6.8 Hz, 6H); $^{13}$C NMR (101 MHz, CDCl$_3$) δ 161.75 (d, J$_{CF}$=241.3 Hz), 144.76 (d, J$_{CF}$=10.3 Hz), 128.11 (d, J$_{CF}$=2.8 Hz), 126.53 (d, J$_{CF}$=9.6 Hz), 105.06 (d, J$_{CF}$=20.7 Hz), 102.26 (d, J$_{CF}$=24.2 Hz), 27.27, 22.35.

The following molecules were made in accordance with the procedures disclosed in Example 36.

3-Fluoro-2-isopropylaniline (B18)

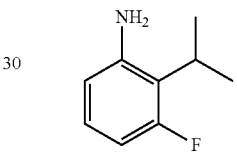

IR (thin film) 3478 (w), 3386 (w), 2963 (m), 2934 (w), 2934 (w), 1624 (s), 1466 (s), 1453 (s) cm$^{-1}$; $^1$H NMR (400 MHz, CDCl$_3$) δ 6.92 (td, J=8.1, 6.1 Hz, 1H), 6.44 (ddd, J=10.4, 8.1, 1.1 Hz, 2H), 3.72 (bs, 2H), 3.06 (heptd, J=7.1, 1.3 Hz, 1H), 1.35 (dd, J=7.1, 1.5 Hz, 6H); $^{13}$C NMR (101 MHz, CDCl$_3$) δ 162.83 (d, J$_{CF}$=243.4 Hz), 145.29 (d, J$_{CF}$=8.8 Hz), 127.08 (d, J$_{CF}$=11.2 Hz), 119.64 (d, J$_{CF}$=16.1 Hz), 111.77 (d, J$_{CF}$=2.3 Hz), 106.47 (d, J$_{CF}$=24.2 Hz), 25.65, 20.97 (d, J$_{CF}$=3.8 Hz).

4-Fluoro-2-isopropylaniline (B19)

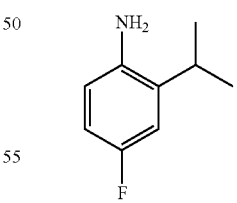

IR (thin film) 3455 (w), 3373 (w), 2962 (m), 2870 (w), 1625 (w), 1609 (w), 1497 (s), 1429 (m) cm$^{-1}$; $^1$H NMR (400 MHz, CDCl$_3$) δ 6.85 (dd, J=10.3, 2.9 Hz, 1H), 6.72 (td, J=8.3, 2.9 Hz, 1H), 6.60 (dd, J=8.6, 5.1 Hz, 1H), 3.49 (bs, 2H), 2.88 (hept, J=6.8 1H), 1.24 (d, J=6.8 Hz, 6H); $^{13}$C NMR (101 MHz, CDCl$_3$) δ 156.92 (d, J$_{CF}$=235.0 Hz), 139.17 (d, J$_{CF}$=2.1 Hz), 134.61 (d, J$_{CF}$=6.2 Hz), 116.55 (d, J$_{CF}$=7.5 Hz), 112.69 (d, J$_{CF}$=22.5 Hz), 112.17 (d, J$_{CF}$=22.4 Hz), 27.90, 22.11.

Example 37

Preparation of N-((2-cyclopropylphenyl)carbamothioyl)benzamide (B20)

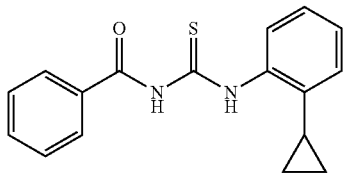 [SMILES: O=C(NC(=S)Nc1ccccc1C1CC1)c1ccccc1]

To 2-cyclopropylaniline (498 mg, 3.74 mmol) in acetone (10 mL) was added benzoyl isothiocyanate (0.53 mL, 3.93 mmol) and the mixture was heated at 50° C. for 8 hours. The reaction mixture was concentrated to provide N-((2-cyclopropylphenyl)carbamothioyDbenzamide as a orange oil (1.249 g, 100%): $^1$H NMR (400 MHz, CDCl$_3$) δ 12.59 (s, 1H), 9.14 (s, 1H), 8.07 (dd, J=7.8, 1.3 Hz, 1H), 7.92 (dd, J=8.4, 1.2 Hz, 2H), 7.69-7.63 (m, 1H), 7.59-7.52 (m, 2H), 7.31-7.26 (m, 1H), 7.23 (td, J=7.5, 1.5 Hz, 1H), 7.13 (dd, J=7.6, 1.5 Hz, 1H), 1.95 (qt, J=12.3, 4.4 Hz, 1H), 1.09-1.01 (m, 2H), 0.76-0.69 (m, 2H); $^{13}$C NMR (101 MHz, CDCl$_3$) δ 178.70, 166.72, 137.59, 137.06, 133.71, 131.72, 129.22, 127.51, 127.20, 126.93, 126.12, 125.26, 11.72, 7.03; ESIMS m/z 295 ([M−H]$^−$).

The following molecules were made in accordance with the procedures disclosed in Example 37.

N-((2-chloro-6-isopropylphenyl)carbamothioyl)benzamide (B21)

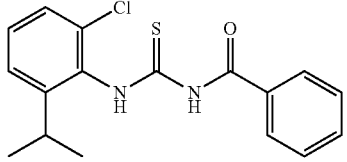 [SMILES: CC(C)c1cccc(Cl)c1NC(=S)NC(=O)c1ccccc1]

Mp 177-181° C.; $^1$H NMR (400 MHz, CDCl$_3$) δ 11.92 (s, 1H), 9.25 (s, 1H), 7.98-7.89 (m, 2H), 7.72-7.62 (m, 1H), 7.62-7.51 (m, 2H), 7.40-7.28 (m, 3H), 3.17 (hept, J=6.9 Hz, 1H), 1.33 (d, J=6.8 Hz, 3H), 1.21 (d, J=6.9 Hz, 3H); ESIMS m/z 333 ([M+H]$^+$).

N-((5-fluoro-2-isopropylphenyl)carbamothioyl)benzamide (B22)

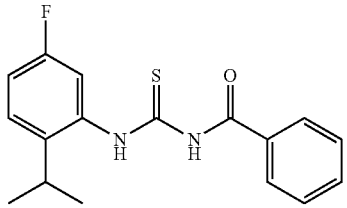 [SMILES: CC(C)c1ccc(F)cc1NC(=S)NC(=O)c1ccccc1]

Mp 134° C. (dec.); $^1$H NMR (400 MHz, CDCl$_3$) δ 12.31 (s, 1H), 9.17 (s, 1H), 7.96-7.87 (m, 2H), 7.73-7.62 (m, 1H), 7.61-7.49 (m, 3H), 7.33 (dd, J=8.8, 6.1 Hz, 1H), 7.03 (td, J=8.3, 2.8 Hz, 1H), 3.13 (hept, J=6.9 Hz, 1H), 1.27 (d, J=7.0 Hz, 6H); ESIMS m/z 315 ([M−H]$^−$).

N-((2-isopropyl-5-methylphenyl)carbamothioyl)benzamide (B23)

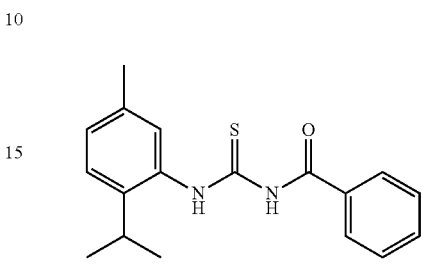

$^1$H NMR (400 MHz, CDCl$_3$) δ 12.14 (s, 1H), 9.18 (s, 1H), 7.97-7.87 (m, 2H), 7.73-7.61 (m, 1H), 7.61-7.50 (m, 2H), 7.42-7.34 (m, 1H), 7.31-7.23 (m, 1H), 7.16 (dd, J=7.9, 1.8 Hz, 1H), 3.11 (hept, J=6.9 Hz, 1H), 2.36 (s, 3H), 1.26 (d, J=6.9 Hz, 6H); $^{13}$C NMR (101 MHz, CDCl$_3$) δ 180.23, 166.97, 140.94, 136.03, 134.89, 133.75, 131.67, 129.22, 129.20, 127.71, 127.55, 126.01, 28.17, 23.38, 20.90; ESIMS m/z 311 ([M−H]$^−$).

N-((2-isopropyl-4-methylphenyl)carbamothioyl)benzamide (B24)

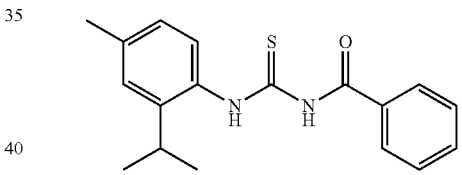

Mp 136° C. (dec.); $^1$H NMR (400 MHz, CDCl$_3$) δ 12.11 (s, 1H), 9.17 (s, 1H), 7.97-7.86 (m, 2H), 7.72-7.61 (m, 1H), 7.60-7.49 (m, 2H), 7.44 (d, J=8.0 Hz, 1H), 7.18 (d, J=1.9 Hz, 1H), 7.09 (dd, J=8.1, 2.0 Hz, 1H), 3.11 (hept, J=6.8 Hz, 1H), 2.38 (s, 3H), 1.27 (d, J=6.9 Hz, 6H); ESIMS m/z 311 ([M−H]$^−$).

N-((2-isopropyl-3-methylphenyl)carbamothioyl)benzamide (B25)

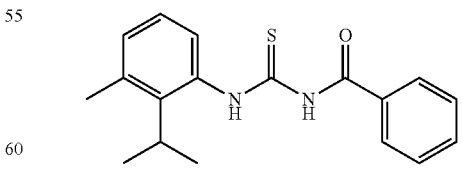

$^1$H NMR (400 MHz, CDCl$_3$) δ 12.12 (s, 1H), 9.18 (s, 1H), 7.99-7.86 (m, 2H), 7.71-7.60 (m, 1H), 7.60-7.50 (m, 2H), 7.32 (dd, J=6.6, 2.8 Hz, 1H), 7.21-7.09 (m, 2H), 3.46-3.31 (m, 1H), 2.42 (s, 3H), 1.37 (d, J=7.2 Hz, 6H); $^{13}$C NMR (101 MHz, CDCl$_3$) δ 180.41, 166.88, 141.79, 137.22, 136.15, 133.76, 131.65, 130.94, 130.53, 129.23, 127.57, 126.02, 28.69, 21.17, 21.05; ESIMS m/z 311 ([M−H]⁻).

N-((3-fluoro-2-isopropylphenyl)carbamothioyl)benzamide (B26)

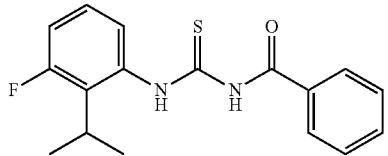 [SMILES: CC(C)c1c(F)cccc1NC(=S)NC(=O)c1ccccc1]

¹H NMR (400 MHz, CDCl₃) δ 12.11 (s, 1H), 9.20 (s, 1H), 8.00-7.85 (m, 2H), 7.73-7.62 (m, 1H), 7.62-7.50 (m, 2H), 7.32-7.18 (m, 2H), 7.11-6.98 (m, 1H), 3.27-3.14 (m, 1H), 1.38 (dd, J=7.1, 1.4 Hz, 6H); ¹³C NMR (101 MHz, CDCl₃) δ 180.87, 167.04, 162.36 (d, $J_{CF}$=247.2 Hz), 136.61 (d, $J_{CF}$=8.8 Hz), 133.88, 132.02 (d, $J_{CF}$=15.2 Hz), 131.50, 129.27, 127.57, 127.06 (d, $J_{CF}$=10.2 Hz), 123.77 (d, $J_{CF}$=3.0 Hz), 116.04 (d, $J_{CF}$=23.5 Hz), 27.36, 21.35, 21.31; ESIMS m/z 315 ([M−H]⁻).

N-((4-fluoro-2-isopropylphenyl)carbamothioyl)benzamide (B27)

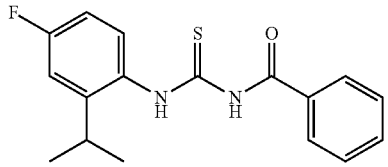 [SMILES: CC(C)c1cc(F)ccc1NC(=S)NC(=O)c1ccccc1]

Mp 96-102° C.; ¹H NMR (400 MHz, CDCl₃) δ 12.11 (s, 1H), 9.18 (s, 1H), 7.97-7.87 (m, 2H), 7.73-7.63 (m, 1H), 7.60-7.48 (m, 3H), 7.07 (dd, J=10.0, 2.9 Hz, 1H), 6.97 (ddd, J=8.7, 7.7, 2.9 Hz, 1H), 3.20-3.06 (m, 1H), 1.27 (d, J=6.8 Hz, 6H); ESIMS m/z 315 ([M−H]⁻).

N-((1-isopropyl-1H-pyrazol-5-yl)carbamothioyl)benzamide (B28)

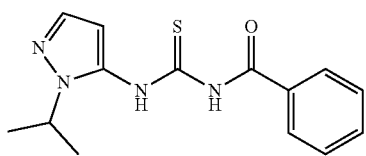 [SMILES: CC(C)n1nccc1NC(=S)NC(=O)c1ccccc1]

¹H NMR (400 MHz, CDCl₃) δ 12.37 (s, 1H), 9.24 (s, 1H), 7.97-7.85 (m, 2H), 7.75-7.63 (m, 1H), 7.58 (ddd, J=7.6, 5.9, 2.4 Hz, 3H), 6.56 (d, J=1.9 Hz, 1H), 4.49 (hept, J=6.6 Hz, 1H), 1.54 (d, J=6.7 Hz, 6H); ¹³C NMR (101 MHz, CDCl₃) δ 179.82, 167.18, 138.45, 134.40, 134.13, 131.16, 129.37, 127.58, 101.12, 49.79, 22.33; ESIMS m/z 289 ([M+H]⁺).

N-((3-isopropylphenyl)carbamothioyl)benzamide (B29)

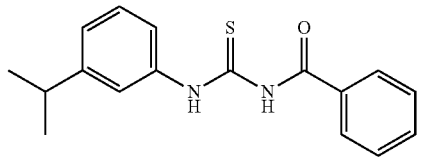 [SMILES: CC(C)c1cccc(NC(=S)NC(=O)c2ccccc2)c1]

¹H NMR (400 MHz, CDCl₃) δ 12.57 (s, 1H), 9.05 (s, 1H), 7.96-7.84 (m, 2H), 7.72-7.49 (m, 5H), 7.35 (t, J=7.8 Hz, 1H), 7.15 (dt, J=7.7, 1.3 Hz, 1H), 2.95 (hept, J=6.9 Hz, 1H), 1.28 (d, J=6.9 Hz, 6H); ¹³C NMR (101 MHz, CDCl₃) δ 178.05, 166.86, 149.90, 137.52, 133.75, 131.70, 129.25, 128.73, 127.46, 125.11, 122.10, 121.43, 34.04, 23.87; ESIMS m/z 299 ([M+H]⁺).

Example 38

Preparation of 1-(2-cyclopropylphenyl)thiourea (B30)

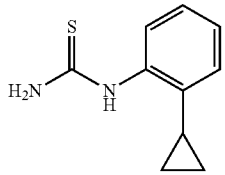 [SMILES: NC(=S)Nc1ccccc1C1CC1]

To N-((2-cyclopropylphenyl)carbamothioyl)benzamide (1.210 g, 4.08 mmol) in MeOH (10 mL) was added 2 N NaOH (4.1 mL, 8.17 mmol) and stirred at 65° C. for 3 hours. The reaction was cooled, neutralized with 2 N HCl, and half of the reaction volume was evaporated under a stream of nitrogen. A yellow precipitate formed that was filtered, rinsed with water and dried in the vacuum oven to give 1-(2-cyclopropylphenyl)thiourea as a yellow solid (444.5 mg, 56%): mp 152-154° C.; ¹H NMR (400 MHz, CDCl₃) δ 7.75 (s, 1H), 7.31-7.27 (m, 1H), 7.26-7.22 (m, 2H), 7.00 (d, J=7.4 Hz, 1H), 5.95 (s, 2H), 1.99 (tt, J=8.4, 5.3 Hz, 1H), 1.06 (ddd, J=8.4, 6.3, 4.5 Hz, 2H), 0.69 (dt, J=6.4, 4.6 Hz, 2H); ¹³C NMR (101 MHz, CDCl₃) δ 182.10, 140.33, 135.18, 128.81, 126.96, 126.45, 126.04, 10.95, 8.39; ESIMS m/z 193 ([M+H]⁺).

The following molecules were made in accordance with the procedures disclosed in Example 38.

1-(2-Chloro-6-isopropylphenyl)thiourea (B31)

¹H NMR (400 MHz, CDCl₃) δ 7.63-7.52 (m, 1H), 7.40-7.29 (m, 3H), 5.30 (bs, 2H), 3.24 (hept, J=6.9 Hz, 1H), 1.34-1.11 (m, 6H); $^{13}$C NMR (101 MHz, CDCl$_3$) δ 182.68, 149.91, 133.87, 130.66, 130.41, 128.07, 125.63, 29.11, 24.11; ESIMS m/z 227 ([M−H]$^-$).

1-(5-Fluoro-2-isopropylphenyl)thiourea (B32)

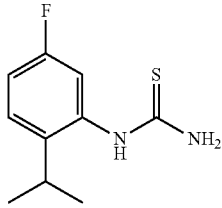

$^1$H NMR (400 MHz, CDCl$_3$) δ 7.89 (s, 1H), 7.37 (dd, J=8.8, 6.1 Hz, 1H), 7.13-7.05 (m, 1H), 6.97 (dd, J=8.8, 2.7 Hz, 1H), 5.98 (s, 2H), 3.16 (hept, J=6.9 Hz, 1H), 1.21 (d, J=6.9 Hz, 6H); $^{19}$F NMR (376 MHz, CDCl$_3$) δ −114.00; ESIMS m/z 211 ([M−H]$^-$).

1-(2-Isopropyl-5-methylphenyl)thiourea (B33)

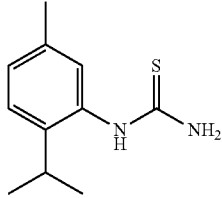

$^1$H NMR (400 MHz, CDCl$_3$) δ 7.58 (s, 1H), 7.29 (d, J=8.0 Hz, 1H), 7.18 (dd, J=8.1, 1.9 Hz, 1H), 7.05-6.99 (m, 1H), 6.33-5.36 (m, 2H), 3.13 (hept, J=6.9 Hz, 1H), 2.45-2.23 (m, 3H), 1.29-1.10 (m, 6H); $^{13}$C NMR (101 MHz, CDCl$_3$) δ 182.36, 143.05, 137.35, 132.92, 130.29, 127.99, 127.20, 27.94, 23.54, 20.74; ESIMS m/z 207 ([M−H]$^-$).

1-(2-Isopropyl-4-methylphenyl)thiourea (B34)

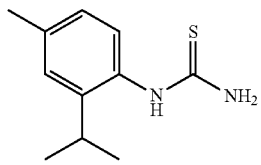

$^1$H NMR (400 MHz, CDCl$_3$) δ 7.64-7.51 (m, 1H), 7.21-7.17 (m, 1H), 7.13-7.02 (m, 2H), 6.35-5.31 (m, 2H), 3.14 (hept, J=6.9 Hz, 1H), 2.37 (s, 3H), 1.21 (d, J=6.9 Hz, 6H); $^{13}$C NMR (101 MHz, CDCl$_3$) δ 182.50, 146.05, 139.59, 130.49, 128.03, 127.94, 127.52, 28.18, 23.49, 21.37; ESIMS m/z 207 ([M−H]$^-$).

1-(2-Isopropyl-3-methylphenyl)thiourea (B35)

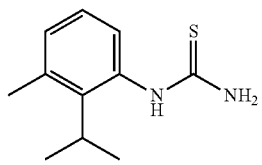

$^1$H NMR (400 MHz, CDCl$_3$) δ 7.52 (d, J=4.2 Hz, 1H), 7.20-7.12 (m, 2H), 7.05 (dd, J=6.6, 2.7 Hz, 1H), 6.34-5.05 (m, 2H), 3.40 (hept, J=7.3 Hz, 1H), 2.41 (s, 3H), 1.33 (d, J=7.2 Hz, 6H); $^{13}$C NMR (101 MHz, CDCl$_3$) δ 182.09, 143.68, 138.60, 134.25, 131.94, 127.11, 126.66, 28.66, 21.00, 20.92; ESIMS m/z 209 ([M+H]$^+$).

1-(3-Fluoro-2-isopropylphenyl)thiourea (B36)

$^1$H NMR (400 MHz, CDCl$_3$) δ 7.74-7.56 (m, 1H), 7.32-7.19 (m, 1H), 7.13-7.01 (m, 2H), 6.41-5.27 (m, 2H), 3.35-3.17 (m, 1H), 1.33 (dd, J=7.1, 1.3 Hz, 6H); $^{19}$F NMR (376 MHz, CDCl$_3$) δ −110.45; ESIMS m/z 211 ([M−H]$^+$).

1-(4-Fluoro-2-isopropylphenyl)thiourea (B37)

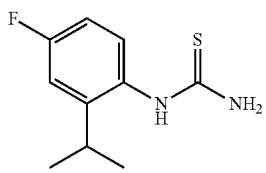

$^1$H NMR (400 MHz, CDCl$_3$) δ 7.59-7.42 (m, 1H), 7.25-7.18 (m, 1H), 7.12-7.05 (m, 1H), 7.02-6.91 (m, 1H), 6.33-5.27 (m, 2H), 3.24-3.08 (m, 1H), 1.22 (d, J=6.8 Hz, 6H); $^{19}$F NMR (376 MHz, CDCl$_3$) δ −110.29; ESIMS m/z 211 ([M−H]$^-$).

1-(1-Isopropyl-1H-pyrazol-5-yl)thiourea (B38)

$^1$H NMR (400 MHz, DMSO-d$_6$) δ 9.35 (s, 1H), 8.07 (s, 1H), 7.41 (d, J=1.9 Hz, 1H), 7.10 (s, 1H), 6.07 (d, J=1.9 Hz, 1H), 4.36 (hept, J=6.6 Hz, 1H), 1.33 (d, J=6.6 Hz, 6H); $^{13}$C NMR (101 MHz, DMSO-d$_6$) δ 183.02, 137.47, 135.00, 102.00, 48.12, 22.27; ESIMS m/z 185 ([M+H]$^+$).

1-(3-Isopropylphenyl)thiourea (B39)

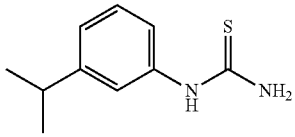

$^1$H NMR (400 MHz, CDCl$_3$) δ 7.99 (s, 1H), 7.36 (t, J=7.8 Hz, 1H), 7.20 (dt, J=7.8, 1.4 Hz, 1H), 7.12-7.02 (m, 2H), 6.11 (s, 2H), 2.92 (hept, J=6.9 Hz, 1H), 1.25 (d, J=7.0 Hz, 6H); $^{13}$C NMR (101 MHz, CDCl$_3$) δ 181.65, 151.61, 136.18, 130.11, 126.13, 123.17, 122.40, 33.98, 23.83; ESIMS m/z 195 ([M+H]$^+$).

Example 39

Preparation of N-[[(2-isopropylphenyl)amino]thioxomethyl]-N'-(4-(1-(4-(trifluoromethyl)phenyl)-1H-1,2,4-triazol-3-yl)phenyl urea. (Molecule A48)

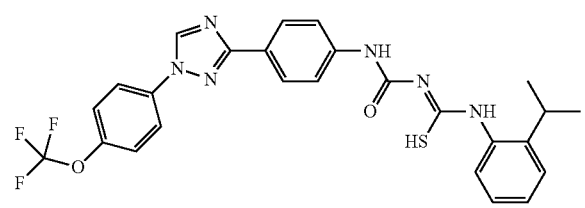 [SMILES: CC(C)c1ccccc1N/C(S)=N/C(=O)Nc1ccc(-c2ncn(-c3ccc(OC(F)(F)F)cc3)n2)cc1]

To a round bottom flask was added 4-(1-(4-(trifluoromethoxy)phenyl)-1H-1,2,4-triazol-3-yl)benzoyl azide (300 mg, 0.802 mmol). The flask was evacuated/backfilled with N$_2$, then toluene (20.0 mL) was added, followed by 1-(2-isopropylphenyl)thiourea (30 mg, 0.154 mmol). The reaction mixture was heated to 100° C. for 1 h. the reaction was then cooled to 50° C. and stirred for an additional 1 h. The reaction mixture was then cooled to 35° C. THF (1 mL) was added, followed by sodium hydride (32.1 mg, 0.802 mmol) in one portion. Vigorous bubbling occurred, and the reaction mixture turned yellow. The reaction mixture was stirred at 35° C. for an additional 15 min. The reaction mixture was cooled to room temperature, poured over ice water, extracted with Et$_2$O, dried, and concentrated onto silica. The crude residue was purified via flash chromatography (silica/EtOAc/hexanes) to yield the title compound as a white solid (57 mg, 0.104 mmol, 13%): mp 201-203° C.; $^1$H NMR (400 MHz, CDCl$_3$) δ 8.57 (s, 1H), 8.16 (m, 2H), 7.80 (m, 3H), 7.56 (d, J=8.3 Hz, 2H), 7.40 (ddt, J=8.0, 6.7, 1.7 Hz, 2H), 7.28 (dt, J=6.8, 1.8 Hz, 2H), 7.23 (m, 2H), 3.16 (dp, J=16.4, 6.9 Hz, 3H), 1.22 (d, J=6.9 Hz, 6H); $^{19}$F NMR (376 MHz, CDCl$_3$) δ −58.02; EIMS m/z 542 ([M+2]).

Molecules A46, A63, A64, A67, A68, A70-A73, A78-A84, A89, A97-A101, A106, A107, A112, A113, A116, A118 and A119 in Table 1 were made either in accordance with the procedures disclosed in Example 39 or by the procedure described in Example 53.

Example 41

Preparation of N-[[(2-methyl-4-methoxyphenyl)amino]oxomethyl]-N'-(4-(1-(4-(trifluoromethyl)phenyl)-1H-1,2,4-triazol-3-yl)phenyl urea (Molecule A53)

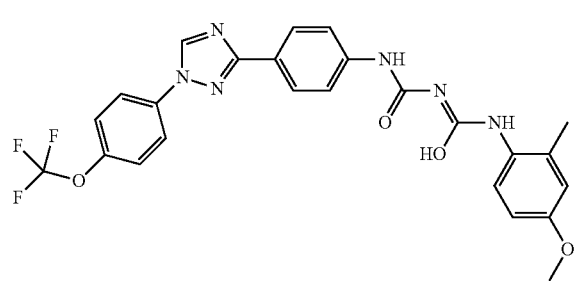 [SMILES: COc1ccc(N/C(O)=N/C(=O)Nc2ccc(-c3ncn(-c4ccc(OC(F)(F)F)cc4)n3)cc2)c(C)c1]

In a 100 mL round-bottomed flask were added 1-(4-(1-(4-(trifluoromethoxy)phenyl)-1H-1,2,4-triazol-3-yl)phenyl) urea (200 mg, 0.551 mmol) and 1-isocyanato-4-methoxy-2-methylbenzene (135 mg, 0.826 mmol) in dioxane (10 mL). The vessel was heated at 100° C. for 2 hours before the contents were cooled and the solvent removed under reduced pressure. The residue was suspended in DCM and purified via normal phase chromatography (silica gel; hexanes/EtOAc) to afford the title product as a white solid (30 mg): mp 213-233° C.; $^1$H NMR (400 MHz, DMSO-d$_6$) δ 10.71 (s, 1H), 10.34 (s, 1H), 10.13 (s, 1H), 9.39 (s, 1H), 8.08 (m, 4H), 7.70-7.57 (m, 4H), 7.26 (d, J=8.7 Hz, 1H), 6.87 (d, J=2.9 Hz, 1H), 6.81 (dd, J=8.7, 2.9 Hz, 1H), 3.75 (s, 3H), 2.20 (s, 3H); EIMS m/z 527 ([M+H]$^+$).

Example 42

Preparation of (E)-methyl 4-(3-(dimethylamino)acryloyl)benzoate (B40)

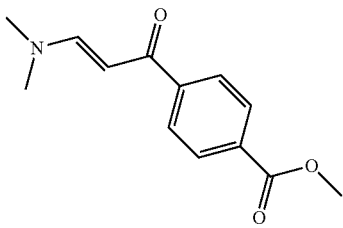

A mixture of methyl 4-acetylbenzoate (5.00 g, 28.1 mmol) in DMF-DMA (38 mL, 284 mmol) was heated at 105° C. for 20 hours. The reaction was cooled, concentrated, and used crude in the next reaction.

Example 43

Preparation of methyl 4-(1H-pyrazol-3-yl)benzoate (B41)

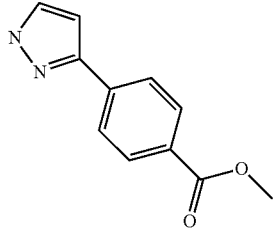

To a solution of crude (E)-methyl 4-(3-(dimethylamino)acryloyl)benzoate (28.1 mmol) in EtOH (100 mL) was added hydrazine monohydrate (1.50 mL, 30.9 mmol) and the reaction was heated at 50° C. for 24 hours. The reaction temperature was then increased to 60° C. for 24 hours. Additional hydrazine monohydrate (1.5 mL) was added, and the reaction was heated at 60° C. for an additional 6 hours. The reaction was cooled, concentrated, and dried in a vacuum oven at 45° C. overnight to yield methyl 4-(1H-pyrazol-3-yl)benzoate as an orange solid (8.15 g, quantitative): mp 106° C. (dec); $^1$H NMR (400 MHz, CDCl$_3$) δ 8.15-8.05 (m, 2H), 7.91-7.83 (m, 2H), 7.65 (d, J=2.4 Hz, 1H), 6.71 (d, J=2.3 Hz, 1H), 3.94 (s, 3H); $^{13}$C NMR (101 MHz, CDCl$_3$) δ 166.91, 136.89, 131.83, 130.13, 129.37, 125.50, 103.35, 52.14, 22.46; EIMS m/z 202.

Example 44

Preparation of 4-(1-(4-(trifluoromethoxy)phenyl)-1H-pyrazol-3-yl)benzoic acid (B42)

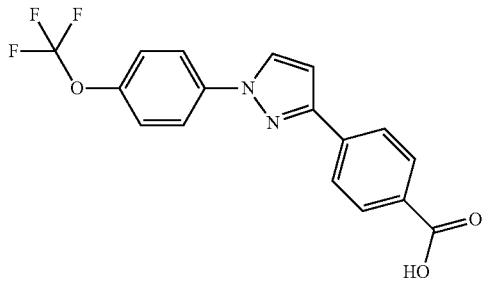 [SMILES: O=C(O)c1ccc(-c2ccn(-c3ccc(OC(F)(F)F)cc3)n2)cc1]

Methyl 4-(1H-pyrazol-3-yl)benzoate (2.00 g, 9.89 mmol), 1-bromo-4-(trifluoromethoxy)benzene (2.38 g, 9.88 mmol), copper (I) iodide (0.28 g, 1.47 mmol), 8-hydroxyquinoline (0.21 g, 1.45 mmol), and cesium carbonate (6.47 g, 19.86 mmol) in DMF/water (11:1) was heated at 120° C. for 20 hours. The reaction was cooled, diluted with water and EtOAc, and decanted from the copper solids. The mixture was extracted three times with EtOAc (3×150 mL) and the combined organic layers washed with water. The organic layers were dried over anhydrous sodium sulfate, filtered, and adsorbed onto silica gel. Purification by flash chromatography (0-10% MeOH/dichloromethane) gave 4-(1-(4-(trifluoromethoxy)phenyl)-1H-pyrazol-3-yl)benzoic acid as a brown solid (580 mg, 16%): $^1$H NMR (400 MHz, CDCl$_3$) δ 8.19 (d, J=7.7 Hz, 2H), 8.03 (d, J=7.7 Hz, 2H), 7.98 (d, J=2.5 Hz, 1H), 7.85-7.79 (m, 2H), 7.35 (d, J=8.4 Hz, 2H), 6.88 (d, J=2.5 Hz, 1H); $^{19}$F NMR (376 MHz, CDCl$_3$) δ −58.05; ESIMS m/z 349 ([M+H]$^+$).

Example 45

Preparation of 4-(1-(4-(trifluoromethoxy)phenyl)-1H-pyrazol-3-yl)benzoyl azide (B43)

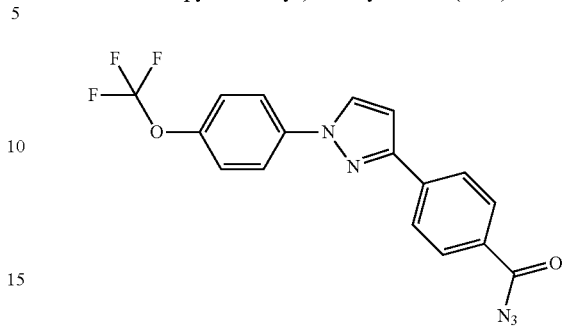

To 4-(1-(4-(trifluoromethoxy)phenyl)-1H-pyrazol-3-yl)benzoic acid (0.58 g, 1.67 mmol) in isopropanol (10.7 mL) was added triethylamine (0.30 mL, 2.17 mmol) and diphenylphosphoryl azide (0.47 mL, 2.17 mmol) and the reaction was stirred at room temperature for 16 hours. The orange precipitate that had formed was filtered through a fritted glass funnel, rinsed with isopropanol, and dried in a vacuum oven to provide 4-(1-(4-(trifluoromethoxy)phenyl)-1H-pyrazol-3-yl)benzoyl azide as an orange solid (188 mg, 30%): $^1$H NMR (400 MHz, DMSO-d$_6$) δ 8.69 (d, J=2.6 Hz, 1H), 8.17-8.11 (m, 2H), 8.09-8.04 (m, 4H), 7.57 (d, J=8.4 Hz, 2H), 7.24 (d, J=2.6 Hz, 1H); $^{19}$F NMR (376 MHz, DMSO-d$_6$) δ −56.97; ESIMS m/z 374 ([M+H]$^+$).

Example 46

Preparation of N-[[(2-isopropylphenyl)amino]thioxomethyl]-N'-((4-(1-(4-(trifluoromethoxy)phenyl)-1H-pyrazol-3-yl)phenyl))urea (Molecule A114)

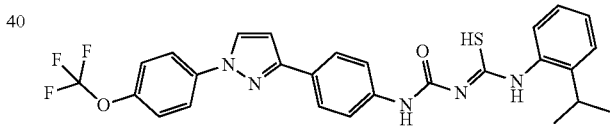

A solution of 4-(1-(4-(trifluoromethoxy)phenyl)-1H-pyrazol-3-yl)benzoyl azide (186 mg, 0.50 mmol) in DCE (2.5 mL) was heated at 80° C. for 2 hours. The reaction was cooled to room temperature and 1-(2-isopropylphenyl)thiourea (97 mg, 0.50 mmol) and cesium carbonate (170 mg, 0.52 mmol) were added. The mixture was stirred at room temperature for 3 days. The reaction was diluted with EtOAc and transferred to a separatory funnel containing water. The aqueous layer was extracted twice with EtOAc. The organic layers were dried over anhydrous sodium sulfate, filtered, and adsorbed onto silica gel. Purification by flash chromatography (0-20% EtOAc/B, where B=1:1 dichloromethane/hexanes) provided a yellow solid that contained a 10% impurity by LC/MS. Reverse-phase flash chromatography (0-100% acetonitrile/water) provided the title compound as a white solid (36.5 mg, 13%): mp 131° C. (dec); $^1$H NMR (400 MHz, CDCl$_3$) δ 11.98 (s, 1H), 10.56 (s, 1H), 8.16 (s, 1H), 7.93 (d, J=2.5 Hz, 1H), 7.86 (d, J=8.5 Hz, 2H), 7.83-7.76 (m, 2H), 7.47 (d, J=7.9 Hz, 2H), 7.43-7.35 (m, 3H), 7.35-7.27 (m, 3H), 6.76 (d, J=2.5 Hz, 1H), 3.15 (dt, J=13.7, 6.8 Hz, 1H), 1.26 (d, J=6.5 Hz, 6H); $^{19}$F NMR (376 MHz, CDCl$_3$) δ −58.06; ESIMS m/z 540 ([M+11]$^+$).

Example 47

Preparation of ethyl 4-(perfluoroethoxy)benzoate (B44)

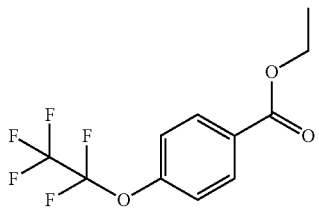 [SMILES: CCOC(=O)c1ccc(OC(F)(F)C(F)(F)F)cc1]

To an oven-dried 500-mL round bottom flask equipped with a stirring bar was added 1-bromo-4-(perfluoroethoxy)benzene (9.35 g, 32.1 mmol) and anhydrous THF (200 mL). The flask was placed under nitrogen and cooled in an ice bath for 10 min. A solution of 1.3 M isopropylmagnesium chloride-lithium chloride complex (30 mL, 38.6 mmol) was added over 15 min. The ice bath was removed after 1 hour, and the reaction was warmed to room temperature and stirred overnight. GC/MS showed the presence of starting material. The reaction was cooled in an ice bath and 1.3 M isopropylmagnesium chloride-lithium chloride complex (5 mL) was added. The ice bath was removed after 20 min and stirred at room temperature for 9 hours. Ethyl chloroformate (3.4 mL, 35.3 mmol) was added in a slow, steady stream. The reaction was warmed slightly during the addition and was stirred at room temperature overnight. The reaction was diluted with EtOAc and washed with saturated aqueous ammonium chloride. The aqueous layer was extracted three times with EtOAc. The organic layers were dried over anhydrous sodium sulfate, filtered, and concentrated to give a yellow liquid, which was purified by flash chromatography (0-0, 0-4, 4-10% EtOAc/hexanes) to provide ethyl 4-(perfluoroethoxy)benzoate as a yellow liquid (4.58 g, 50%): $^1$H NMR (400 MHz, CDCl$_3$) δ 8.10 (d, J=8.8 Hz, 2H), 7.28 (d, J=8.7 Hz, 2H), 4.39 (q, J=7.1 Hz, 2H), 1.40 (t, J=7.1 Hz, 3H); $^{19}$F NMR (376 MHz, CDCl$_3$) δ −86.05, −87.84; ESIMS m/z 284 ([M+11]$^+$).

Example 48

Preparation of 4-(perfluoroethoxy)benzohydrazide (B45)

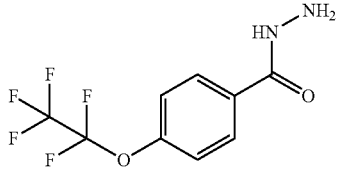 [SMILES: NNC(=O)c1ccc(OC(F)(F)C(F)(F)F)cc1]

To a solution of ethyl 4-(perfluoroethoxy)benzoate (4.58 g, 16.1 mmol) in EtOH (16 mL) was added hydrazine monohydrate (1.96 mL, 40.3 mmol) and the reaction was heated at 85° C. for 36 hours. The reaction was cooled and poured into ice water (100 mL). A white gel-solid formed and was filtered through a Büchner funnel under vacuum. The solid was dried in a vacuum oven at 45° C. overnight to provide 4-(perfluoroethoxy)benzohydrazide as an off-white solid (3.177 g, 73%): mp 117-119.5° C.; $^1$H NMR (400 MHz, CDCl$_3$) δ 7.83-7.76 (m, 2H), 7.36 (s, 1H), 7.31 (d, J=8.8 Hz, 2H), 4.13 (s, 2H); $^{19}$F NMR (376 MHz, CDCl$_3$) δ −86.01, −87.83; ESIMS m/z 269 [(M−H)$^−$].

Example 49

Preparation of 2-(4-(perfluoroethoxy)phenyl)-1,3,4-oxadiazole (B46)

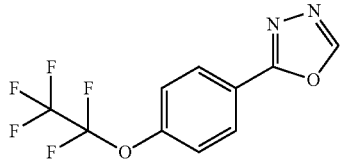 [SMILES: FC(F)(F)C(F)(F)Oc1ccc(-c2nnco2)cc1]

A mixture of 4-(perfluoroethoxy)benzohydrazide (3.17 g, 11.7 mmol) in trimethyl orthoformate (11.6 mL, 106 mmol) and acetic acid (0.13 mL, 2.35 mmol) was heated at 120° C. for 5 hours. The reaction was diluted with MeOH (15 mL) and poured into a beaker containing ice water (150 mL). The white precipitate was vacuum filtered and dried in a vacuum oven to provide 166 mg of 2-(4-(perfluoroethoxy)phenyl)-1,3,4-oxadiazole as an off-white solid. An orange precipitate had formed in the aqueous filtrate and was collected by vacuum filtration and adsorbed onto silica gel. Purification by flash chromatography (0-40% EtOAc/hexanes) provided 2.02 g of 2-(4-(perfluoroethoxy)phenyl)-1,3,4-oxadiazole as an off-white solid giving a combined yield of 2.186 g (67%): mp 87-89° C.; $^1$H NMR (400 MHz, CDCl$_3$) δ 8.49 (s, 1H), 8.28-8.05 (m, 2H), 7.40 (d, J=8.9 Hz, 2H); $^{19}$F NMR (376 MHz, CDCl$_3$) δ −85.98, −87.82; ESIMS m/z 280 ([M+H]$^+$).

Example 50

Preparation of methyl 4-(5-(4-(perfluoroethoxy)phenyl)-1,3,4-oxadiazol-2-yl)benzoate (B47)

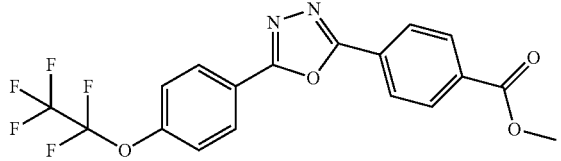 [SMILES: COC(=O)c1ccc(-c2nnc(-c3ccc(OC(F)(F)C(F)(F)F)cc3)o2)cc1]

A mixture of 2-(4-(perfluoroethoxy)phenyl)-1,3,4-oxadiazole (2.186 g, 7.80 mmol), methyl 4-iodobenzoate (3.07 g, 11.70 mmol), copper(I) iodide (0.28 g, 1.47 mmol), 1,10-phenanthroline (0.30 g, 1.67 mmol), and cesium carbonate (2.54 g, 7.80 mmol) in anhydrous DMSO (20 mL) was heated at 100° C. for 18 hours. The reaction was cooled, diluted with water, and extracted three times with EtOAc. The organic layers were dried over anhydrous sodium sulfate, filtered, and adsorbed onto silica gel. Purification by flash chromatography (0-50% EtOAc/hexanes) provided methyl 4-(5-(4-(perfluoroethoxy)phenyl)-1,3,4-oxadiazol-2-yl)benzoate as a white solid (1.08 g, 33%): mp 185-191° C.; $^1$H NMR (400 MHz, CDCl$_3$) δ 8.25-8.19 (m, 6H), 7.41 (t, J=9.4 Hz, 2H), 3.98 (s, 3H); $^{19}$F NMR (376 MHz, CDCl$_3$) δ −85.96, −85.98, −87.79; ESIMS m/z 415 ([M+H]$^+$).

Example 51

Preparation of 4-(5-(4-(perfluoroethoxy)phenyl)-1,3,4-oxadiazol-2-yl)benzoic acid (B48)

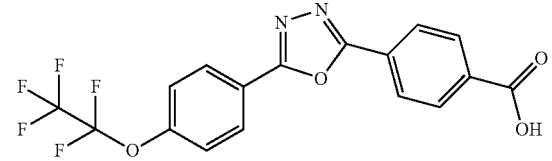 [SMILES: O=C(O)c1ccc(-c2nnc(-c3ccc(OC(F)(F)C(F)(F)F)cc3)o2)cc1]

To methyl 4-(5-(4-(perfluoroethoxy)phenyl)-1,3,4-oxadiazol-2-yl)benzoate (1.07 g, 2.58 mmol) was added MeOH (26 mL) (starting material remained partially insoluble). A solution of 2 N NaOH (5.2 mL, 10.33 mmol) was added, and the reaction was stirred at room temperature for 18 h. Stirring had become hindered overnight due to the formation of solid. LC/MS showed 25% conversion to product. The reaction mixture was diluted with MeOH and additional 2 N NaOH (20 mL) was added and the reaction was heated to 45° C. for 24 h. The reaction was cooled and neutralized with 2 N HCl (20 mL). Some of the MeOH was concentrated off in vacuo, causing the product to precipitate. The white precipitate was vacuum filtered and dried in a vacuum oven at 45° C. to provide 44544-(perfluoroethoxy)phenyl)-1,3,4-oxadiazol-2-yl)benzoic acid as a white solid (760 mg, 90% purity, 66%): mp 301-307° C.; $^1$H NMR (400 MHz, DMSO-$d_6$) δ 13.40 (s, 1H), 8.34-8.26 (m, 4H), 8.18 (d, J=8.6 Hz, 2H), 7.68 (d, J=8.8 Hz, 2H); $^{19}$F NMR (376 MHz, DMSO-$d_6$) δ −85.25, −86.89; ESIMS m/z 401 ([M+H]$^+$).

Example 52

Preparation of 4-(5-(4-(perfluoroethoxy)phenyl)-1,3,4-oxadiazol-2-yl)benzoyl azide (B49)

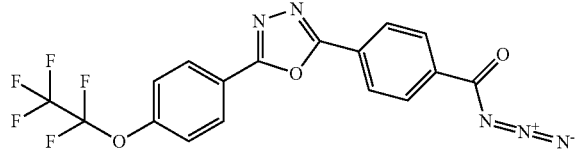 [SMILES: [N-]=[N+]=NC(=O)c1ccc(-c2nnc(-c3ccc(OC(F)(F)C(F)(F)F)cc3)o2)cc1]

To a solution of 4-(5-(4-(perfluoroethoxy)phenyl)-1,3,4-oxadiazol-2-yl)benzoic acid (217 mg, 0.54 mmol) in isopropanol (5.4 mL) was added triethylamine (0.09 mL, 0.65 mmol) and diphenyl phosphorazidate (0.13 mL, 0.60 mmol) and the reaction was stirred at room temperature for 16 hours. The white precipitate that had formed was filtered and dried in a vacuum oven to provide 4-(5-(4-(perfluoroethoxy)phenyl)-1,3,4-oxadiazol-2-yl)benzoyl azide as a white solid (145 mg, 63%): mp 140° C. (dec); $^1$H NMR (400 MHz, DMSO-$d_6$) δ 8.32 (m, 4H), 8.24-8.17 (m, 2H), 7.68 (d, J=8.9 Hz, 2H); $^{19}$F NMR (376 MHz, DMSO-$d_6$) δ −85.25, −86.89; ESIMS m/z 426 ([M+H]$^+$).

Example 53

Preparation of N-[[(2-isopropyllphenyl)amino]thioxomethyl]-N'-((4-(5-(4-(perfluoroethoxy)phenyl)-1,3,4-oxadiazol-2-yl)phenyl))urea (Molecule A96)

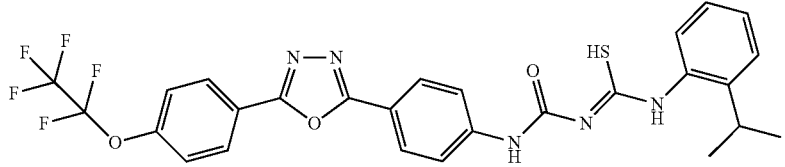 [SMILES: CC(C)c1ccccc1N/C(S)=N/C(=O)Nc1ccc(-c2nnc(-c3ccc(OC(F)(F)C(F)(F)F)cc3)o2)cc1]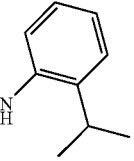

A solution of 4-(5-(4-(perfluoroethoxy)phenyl)-1,3,4-oxadiazol-2-yl)benzoyl azide (278 mg, 0.65 mmol) in DCE (3.3 mL) was heated at 80° C. for 3 hrs. The reaction was cooled to room temperature and 1-(2-isopropylphenyl)thiourea (131 mg, 0.67 mmol) followed by cesium carbonate (243 mg, 0.75 mmol) were added. The reaction mixture was stirred at room temperature for 18 hours. The reaction was diluted with EtOAc and transferred to a separatory funnel containing aqueous sodium bicarbonate. The aqueous layer was extracted twice with EtOAc. The organic layers were dried over anhydrous sodium sulfate, filtered, and adsorbed onto silica gel. Purification by flash chromatography (0-20% EtOAc/B, where B=1:1 dichloromethane/hexanes) provided the title compound as a white powder (43 mg, 11%): mp 219° C. (dec); $^1$H NMR (400 MHz, DMSO-$d_6$) δ 11.61 (s, 1H), 10.25 (s, 1H), 9.71 (s, 1H), 8.30-8.22 (m, 2H), 8.14 (d, J=8.8 Hz, 2H), 7.71 (d, J=8.8 Hz, 2H), 7.66 (d, J=8.7 Hz, 2H), 7.39 (dd, J=10.3, 3.9 Hz, 2H), 7.27 (ddd, J=13.5, 10.6, 6.1 Hz, 2H), 3.07 (heptet, J=6.8 Hz, 1H), 1.20 (d, J=6.9 Hz, 6H); $^{19}$F NMR (376 MHz, DMSO-$d_6$) δ −85.25, −86.89; ESIMS m/z 590 ([M−H]$^-$).

Example 54

Preparation of (Z)-1-(3-(2-isopropylphenyl)-4-oxothiazolidin-2-ylidene)-3-(4-(5-(4-(perfluoroethoxy)phenyl)-1,3,4-oxadiazol-2-yl)phenyl)urea (Molecule A102)

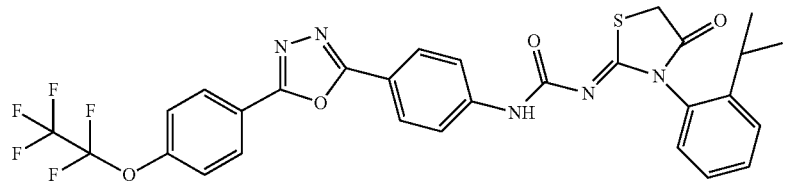 [SMILES: CC(C)c1ccccc1N1C(=O)CS/C1=N\C(=O)Nc1ccc(-c2nnc(-c3ccc(OC(F)(F)C(F)(F)F)cc3)o2)cc1]

To the thiobiuret (135.5 mg, 0.23 mmol) and sodium acetate (80 mg, 0.98 mmol) in ethanol (3 mL) was added methyl 2-bromoacetate (0.05 mL, 0.49 mmol) and the reaction was heated at 65° C. for 4 hours. The reaction was diluted with water, and the precipitate was filtered and dried in a vacuum oven. The material was purified by flash chromatography (0-20% EtOAc/B, where B=1:1 dichloromethane/hexanes) to provide (Z)-1-(3-(2-isopropylphenyl)-4-oxothiazolidin-2-ylidene)-3-(4-(5-(4-(perfluoroethoxy)phenyl)-1,3,4-oxadiazol-2-yl)phenyl)urea as a yellow solid (56 mg, 38%): mp 244-247° C.; $^1$H NMR (400 MHz, CDCl$_3$) δ 8.21-8.15 (m, 2H), 8.06 (d, J=8.8 Hz, 2H), 7.68 (d, J=8.8 Hz, 2H), 7.56-7.49 (m, 2H), 7.38 (m, 4H), 7.10 (d, J=7.5 Hz, 1H), 4.01 (d, J=2.8 Hz, 2H), 2.77-2.66 (m, 1H), 1.22 (dd, J=6.8, 3.1 Hz, 6H); $^{19}$F NMR (376 MHz, CDCl$_3$) δ −85.96, −87.77; ESIMS m/z 632 ([M+H]$^+$).

The following molecules were made in accordance with the procedures disclosed in Example 1, Step1.

(E)-((N'-(4-methoxyphenyl)carbamimidoyl)thio)methyl isobutyrate hydrobromide (B50)

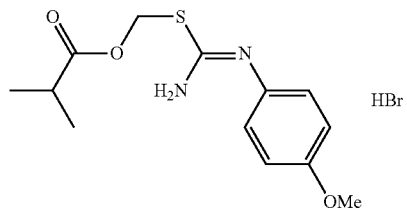 [SMILES: COc1ccc(/N=C(\N)SCOC(=O)C(C)C)cc1 ; Br]

Mp 129-130° C.; $^1$H NMR (DMSO-d$_6$) δ 9.47 (s, NH), 7.23 (s, 2H), 7.07 (d, J=8.9 Hz, 2H), 6.90 (d, J=9.0 Hz, 1H), 5.76 (s, 2H), 3.79 (s, 3H), 3.74 (s, 1H), 2.65 (dd, J=12.0, 5.1 Hz, 1H), 1.13 (d, J=7.0 Hz, 6H); ESIMS m/z 283 ([M+H]$^+$).

(E)-((N'-mesitylcarbamimidoyl)thio)methyl isobutyrate hydrobromide (B51)

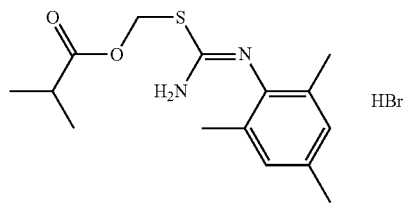 [SMILES: Cc1cc(C)c(/N=C(\N)SCOC(=O)C(C)C)c(C)c1 ; Br]

Mp 189-191° C.; $^1$H NMR (DMSO-d$_6$) δ 11.26 (s, 1H), 9.82 (s, 1H), 8.96 (s, 1H), 7.06 (s, 2H), 5.85 (s, 2H), 2.73-2.54 (m, 1H), 2.29 (s, 3H), 2.11 (d, J=18.4 Hz, 6H), 1.13 (d, J=7.0 Hz, 6H); ESIMS m/z 295 ([M+H]$^+$).

(E)-((N'-(2,6-difluorophenyl)carbamimidoyl)thio)methyl isobutyrate hydrobromide (B52)

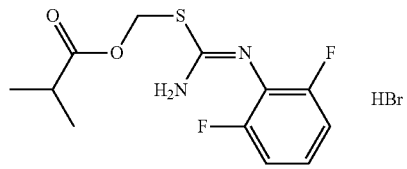

$^1$H NMR (400 MHz, CDCl$_3$) δ 11.25 (s, 1H), 10.46 (s, 1H), 9.17 (s, 1H), 7.45 (s, 1H), 7.05 (t, J=8.1 Hz, 2H), 5.78 (s, 2H), 2.76-2.64 (m, 1H), 1.29-1.14 (m, 6H).

(E)-((N'-(o-tolyl)carbamimidoyl)thio)methyl isobutyrate hydrobromide (B53)

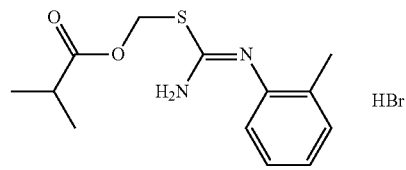 [SMILES: Cc1ccccc1/N=C(\N)SCOC(=O)C(C)C ; Br]

$^1$H NMR (DMSO-d$_6$) δ 11.50 (s, 1H), 10.28 (s, 1H), 8.48 (s, 1H), 7.43-7.07 (m, 4H), 5.65 (s, 2H), 2.69 (s, 1H), 2.37 (s, 3H), 1.22 (d, J=7.0 Hz, 6H); ESIMS m/z 295 ([M+H]$^+$).

(E)-((N'-(2-ethylphenyl)carbamimidoyl)thio)methyl isobutyrate hydrobromide (B54)

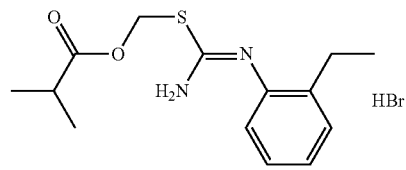 [SMILES: CCc1ccccc1/N=C(\N)SCOC(=O)C(C)C ; Br]

$^1$H NMR (DMSO-d$_6$) δ 11.51 (s, 1H), 10.30 (s, 1H), 8.49 (s, 1H), 7.43-7.31 (m, 2H), 7.27-7.15 (m, 1H), 5.66 (s, 2H), 2.81-2.61 (m, 3H), 1.27-1.21 (m, 9H); ESIMS m/z 295 ([M+H]$^+$).

(E)-((N'-(2,6-dichlorophenyl)carbamimidoyl)thio)methyl isobutyrate hydrobromide (B55)

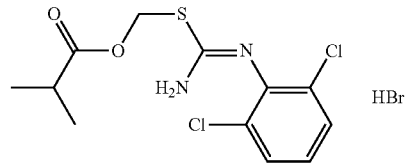 [SMILES: CC(C)C(=O)OCS/C(N)=N/c1c(Cl)cccc1Cl ; Br]

$^1$H NMR (400 MHz, CDCl$_3$) δ 11.48 (s, 1H), 10.55 (s, 1H), 9.05 (s, 1H), 7.47-7.41 (m, 2H), 7.36 (dd, J=9.2, 6.9 Hz, 1H), 5.75 (s, 2H), 2.69 (m, 1H), 1.25-1.18 (m, 6H); ESIMS m/z 322 ([M+H]$^+$).

(E)-((N'-(2-ethyl-6-methylphenyl)carbamimidoyl)thio)methyl isobutyrate hydrobromide (B56)

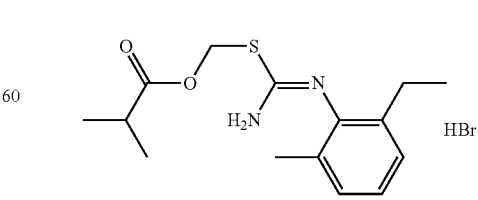

$^1$H NMR (400 MHz, CDCl$_3$) δ 11.17 (s, 1H), 10.20 (s, 1H), 8.67 (s, 1H), 7.32-7.27 (m, 1H), 7.18-7.08 (m, 2H), 5.71 (s, 2H), 2.71-2.56 (m, 3H), 2.30 (s, 3H), 1.26-1.18 (m, 9H); ESIMS m/z 295 ([M+H]⁺).

(E)-((N'-(2-(sec-butyl)phenyl)carbamimidoyl)thio)methyl isobutyrate hydrobromide (B57)

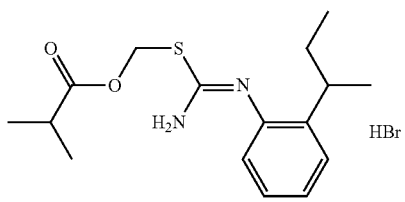 [SMILES: CCC(C)c1ccccc1/N=C(\N)SCOC(=O)C(C)C ; Br]

¹H NMR (400 MHz, CDCl₃) 7.46-7.39 (m, 1H), 7.37-7.32 (m, 1H), 7.23 (t, J=7.1 Hz, 1H), 7.17 (d, J=7.6 Hz, 1H), 5.64 (s, 2H), 2.92 (dd, J=13.9, 7.0 Hz, 1H), 2.68 (dt, J=14.0, 7.0 Hz, 1H), 1.70-1.60 (m, 2H), 1.23 (t, J=6.7 Hz, 9H), 0.84 (t, J=7.4 Hz, 3H); ESIMS m/z 332 ([M+Na]⁺).

Example 55

Preparation of 1-(4-(perfluoropropyl)phenyl)-3-(p-tolyl)-1H-1,2,4-triazole (B58)

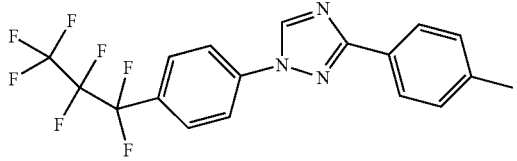 [SMILES: Cc1ccc(-c2ncn(-c3ccc(C(F)(F)C(F)(F)C(F)(F)F)cc3)n2)cc1]

Heptafluoropropyl-1-iodopropane (3.14 g, 10.6 mmol), 1-iodo-4-bromobenzene (2.0 g, 7.07 mmol), and copper (powder: 1.123 g, 17.7 mmol) were combined in 16 mL of DMSO in a 20 mL microwave tube, and the solution was stirred and heated at 175° C. for 90 min. The cooled solution was then extracted with 2×30 mL of hexanes, and the combined organic layer was washed with water, dried and concentrated to give 2.0 grams of a yellow oil. This crude material, which consisted of a mixture of 4-heptafluoropropyl-iodobenzene and 4-heptafluoropropyl-bromobenzene, was combined with 3-(p-tolyl)-1H-1,2,4-triazole (1.0 g, 6.28 mmol), cesium carbonate (6.14 g, 18.9 mmol), CuI (0.12 g, 0.63 mmol), and quinolin-8-ol (0.091 g, 0.63 mmol) in 16 mL of 90:10 DMF-water, and the solution was heated to 125° C. for 8 hrs. The cooled solution was then poured onto 60 mL of a 2N aqueous NH₄OH solution, and the resulting precipitate was filtered and air-dried. This material was heated in 50 mL of MeOH, filtered, and the filtrate diluted with 30 mL of water. The resulting solid was filtered and air-dried to give 1-(4-(perfluoropropyl)phenyl)-3-(p-tolyl)-1H-1,2,4-triazole as a white solid (1.03 g, 39%): mp 140-143° C.; ¹H NMR (400 MHz, CDCl₃) δ 8.66 (s, 1H), 8.10 (d, J=8.1 Hz, 2H), 7.94 (d, J=8.9 Hz, 2H), 7.76 (d, J=8.5 Hz, 2H), 7.30 (dt, J=8.0, 0.7 Hz, 2H), 2.43 (s, 3H); ESIMS m/z 405 ([M+H]⁺).

Example 56

Preparation of 4-(1-(4-(perfluoropropyl)phenyl)-1H-1,2,4-triazol-3-yl)benzoic acid (B59)

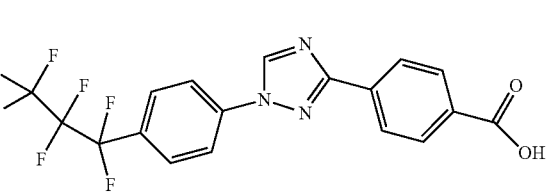

A solution of the tolyl triazole (1.0 g, 2.48 mmol) in 6 mL of AcOH was heated to 60° C., and eerie ammonium nitrate (4.50 g, 8.21 mmol) in 3 mL of water was added over 10 minutes. Heating was continued for 1 hr, then the solution was cooled and diluted with 30 mL of water. The liquid was decanted from a light yellow gummy solid which formed over 30 min. This residue was then combined with 10 mL of dioxane and 3 mL of 50% aqueous KOH, and heated at 75-80° C. for 2 hrs. The solution was cooled and diluted with 20 mL of water. The resulting solid was filtered and then re-dissolved in 15 mL of acetonitrile, and sodium bromate (1.12 g, 7.44 mmol) and sodium bisulfite (0.298 g, 2.48 mmol) were added. The solution was heated at reflux for 2 hr, then cooled and diluted with 10 mL of water. A white precipitate formed, which was filtered and air-dried to give 4-(1-(4-(perfluoropropyl)phenyl)-1H-1,2,4-triazol-3-yl)benzoic acid as a white powder (472 mg, 41%): mp 225° C.; ¹H NMR (400 MHz, DMSO-d₆) δ 9.60 (s, 1H), 8.29-8.20 (m, 4H), 8.13-8.06 (m, 2H), 7.96 (d, J=8.7 Hz, 2H); ESIMS m/z 434 ([M+H]⁺).

Example 57

Preparation of 4-(1-(4-(perfluoropropyl)phenyl)-1H-1,2,4-triazol-3-yl)benzoyl azide (B60)

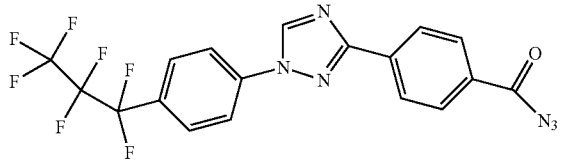 [SMILES: [N-]=[N+]=NC(=O)c1ccc(-c2ncn(-c3ccc(C(F)(F)C(F)(F)C(F)(F)F)cc3)n2)cc1]

4-(1-(4-(Perfluoropropyl)phenyl)-1H-1,2,4-triazol-3-yl)benzoic acid (400 mg, 0.92 mmol) was dissolved in 7 mL of isopropanol and treated with diphenylphosphoryl azide (0.300 g, 1.09 mmol) and triethylamine (0.200 g, 2.0 mmol). The solution was allowed to stir for 6 h, then it was cooled to 0° C. and the resulting solid was filtered, washed with a minimum amount of ⁱPrOH, and dried under high vacuum to give the azide as an off-white solid (0.120 g, 30%). This solid was not further characterized, but used directly in the subsequent Curtius rearrangement to prepare molecule A113, using conditions described in Example 39.

Example 58

Preparation of (Z)-1-(3-mesityl-4-methylthiazol-2 (3H)-ylidene)-3-(4-(1-(4-(trifluoromethoxy)phenyl)-1H-1,2,4-triazol-3-yl)phenyl)urea (Molecule A43)

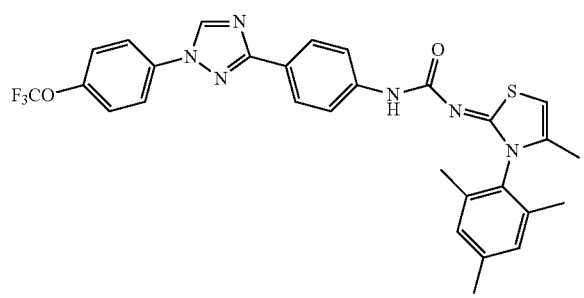 [SMILES: Cc1cc(C)c(-n2c(C)cs/c2=N\C(=O)Nc2ccc(-c3ncn(-c4ccc(OC(F)(F)F)cc4)n3)cc2)c(C)c1]

To free thiobiuret (100 mg, 0.185 mmol) in 3 mL of butanone was added triethylamine (0.052 mL, 0.370 mmol) followed by chloroacetone (0.021 mL, 0.259 mmol). The solution was heated at reflux for 20 hrs, then it was cooled, diluted with 20 mL of $CH_2Cl_2$, washed with water (10 ml), dried and concentrated in vacuo. Chromatography (silica, 0-100% EtOAc-hexanes) furnished the desired product as a viscous yellow oil (0.92 g, 84%): $^1H$ NMR (400 MHz, $CDCl_3$) δ 8.55 (s, 1H), 8.17 (d, J=8.7 Hz, 2H), 7.85-7.68 (m, 5H), 7.37 (d, J=8.3 Hz, 2H), 7.02 (s, 2H), 6.35 (d, J=0.9 Hz, 1H), 2.43 (s, 3H), 2.34 (s, 3H), 2.17 (s, 6H); $^{19}F$ NMR (376 MHz, $CDCl_3$) δ -58.01 (s); ESIMS m/z 579 ([M+H]$^+$).

Molecule A42 in Table 1 was made in accordance with the procedures disclosed in Example 58.

Example 59

Preparation of 3-bromo-1-(4-(trifluoromethoxy) phenyl)-1H-1,2,4-triazole (B61)

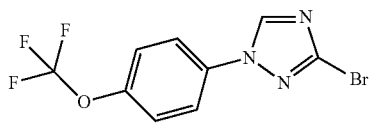 [SMILES: FC(F)(F)Oc1ccc(-n2cnc(Br)n2)cc1]

To a 250 mL reaction flask was added 3-bromo-1H-1,2,4-triazole (5 g, 33.8 mmol), copper(I) iodide (0.644 g, 3.38 mmol) and cesium carbonate (11.01 g, 33.8 mmol). The flask was evacuated/backfilled with $N_2$, then DMSO (33.8 ml) and 1-iodo-4-(trifluoromethoxy)benzene (4.87 g, 16.90 mmol) were added. The reaction mixture was heated to 100° C. for 20 h. The reaction was cooled to room temperature, diluted with EtOAc and filtered through a plug of Celite. The Celite was further washed with EtOAc. Water was added to the combined organics, and the layers were separated. The aqueous phase was neutralized to pH 7, and further extracted with EtOAc. The combined organics were concentrated in vacuo. Purification via flash chromatography (silica/EtOAc/Hex) yielded 3-bromo-1-(4-(trifluoromethoxy)phenyl)-1H-1,2,4-triazole as an off white solid (3.78 g, 12.27 mmol, 72.6%): mp 69-70° C.; $^1H$ NMR (400 MHz, $CDCl_3$) δ 8.44 (s, 1H), 7.70 (d, J=8.9 Hz, 2H), 7.38 (d, J=8.5 Hz, 2H); $^{19}F$ NMR (376 MHz, $CDCl_3$) δ -58.04; EIMS m/z 307.

Example 60

Preparation of methyl 2-methyl-4-(1-(4-(trifluoromethoxy)phenyl)-1H-1,2,4-triazol-3-yl)benzoate (B62)

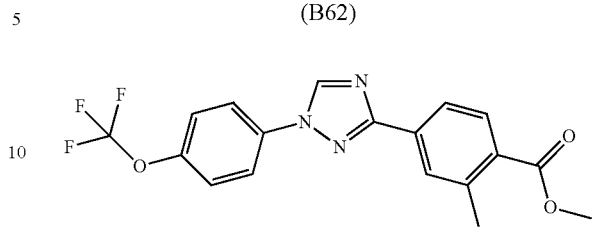

To 3-bromo-1-(4-(trifluoromethoxy)phenyl)-1H-1,2,4-triazole (0.496 g, 1.609 mmol), methyl 2-methyl-4-(4,4,5,5-tetramethyl-1,3,2-dioxaborolan-2-yl)benzoate (0.466 g, 1.689 mmol), sodium bicarbonate (0.405 g, 4.83 mmol) and tetrakis(triphenylphosphine)palladium (0.186 g, 0.161 mmol) in a 2.0 mL microwave vial was added dioxane (6 mL) and water (1.5 mL). The reaction was capped and placed on a Biotage® Initiator microwave reactor for 30 min at 140° C. The reaction mixture was then diluted with EtOAc and washed with water. The aqueous layer was extracted with EtOAc. The combined organic layers were dried over $MgSO_4$, filtered and concentrated. Purification by flash column chromatography provided the title compound as a white solid (0.376 g, 0.997 mmol, 62%): $^1H$ NMR (400 MHz, $CDCl_3$) δ 8.59 (s, 1H), 8.10 (dt, J=1.6, 0.7 Hz, 1H), 8.09-8.00 (m, 2H), 7.84-7.78 (m, 2H), 7.44-7.37 (m, 2H), 3.93 (s, 3H), 2.70 (s, 3H); $^{19}F$ NMR (376 MHz, $CDCl_3$) δ -58.02; ESIMS m/z 378 ([M+H]$^+$).

Example 61

Preparation of 2-methyl-4-(1-(4-(trifluoromethoxy) phenyl)-1H-1,2,4-triazol-3-yl)benzoic acid (B63)

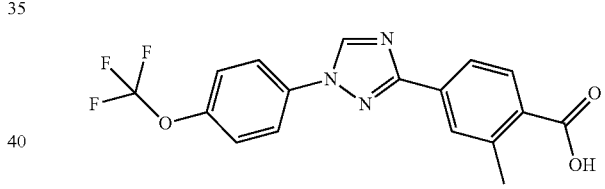

To two batches of methyl 2-methyl-4-(1-(4-(trifluoromethoxy)phenyl)-1H-1,2,4-triazol-3-yl)benzoate (0.452 g, 1.198 mmol) in a 250 mL round-bottomed flask equipped with a stir bar was added MeOH (12 ml), THF (12 ml) and 2N sodium hydroxide (5.99 ml, 11.98 mmol). The reaction was stirred overnight. The reaction mixture was diluted with water and acidified with 1N HCl. The solid was extracted with EtOAc (3×). The organic layer was dried over $MgSO_4$, filtered and concentrated providing the title compound as a yellow solid (0.412 g, 1.134 mmol, 95%): $^1H$ NMR (300 MHz, DMSO-$d_6$) δ 12.94 (s, 1H), 9.43 (s, 1H), 8.14-8.03 (m, 2H), 8.03-7.89 (m, 3H), 7.61 (d, J=8.7 Hz, 2H), 2.60 (s, 3H); $^{19}F$ NMR (376 MHz, DMSO-$d_6$) δ -56.95; ESIMS m/z 364 ([M+H]$^+$).

Example 62

Preparation of 2-methyl-4-(1-(4-(trifluoromethoxy) phenyl)-1H-1,2,4-triazol-3-yl)benzoyl azide (B64)

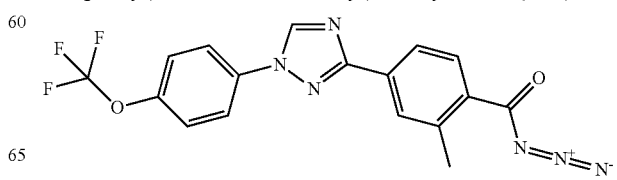

To 2-methyl-4-(1-(4-(trifluoromethoxy)phenyl)-1H-1,2,4-triazol-3-yl)benzoic acid (0.412 g, 1.134 mmol) in a 100 mL round-bottomed flask equipped with a stir bar under N₂ was added isopropyl alcohol (11 mL), triethylamine (0.205 ml, 1.474 mmol) and diphenyl phosphorazidate (0.319 ml, 1.474 mmol). The reaction was stirred at room temperature overnight. The resultant solid was filtered, washed with isopropyl alcohol followed by hexanes and dried under vacuum providing the title compound as a white solid (0.294 g, 0.757 mmol, 67%): ¹H NMR (300 MHz, CDCl₃) δ 8.60 (s, 1H), 8.13 (s, 1H), 8.11-8.02 (m, 2H), 7.84-7.77 (m, 2H), 7.40 (d, J=8.6 Hz, 2H), 2.74 (s, 3H); ¹⁹F NMR (376 MHz, CDCl₃) δ −58.02; ESIMS m/z 389 ([M+H]⁺).

Example 63

Preparation of N-[[(2-isopropyllphenyl)amino]thioxomethyl]-N'-(2-methyl(4-(1-(4-(trifluoromethoxy)phenyl)-1H-1,2,4-triazol-3-yl)phenyl))urea (Molecule A122)

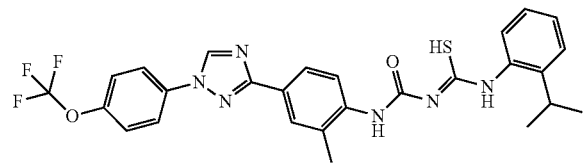 [SMILES: Cc1cc(-c2ncn(-c3ccc(OC(F)(F)F)cc3)n2)ccc1NC(=O)/N=C(\S)Nc1ccccc1C(C)C]

To 2-methyl-4-(1-(4-(trifluoromethoxy)phenyl)-1H-1,2,4-triazol-3-yl)benzoyl azide (0.294 g, 0.757 mmol) in a 25 mL vial equipped with a stir bar and a Vigreux column was added 1,2-dichloroethane (4 ml). The reaction was heated to 80° C. Following isocyanate formation the reaction was cooled to room temperature. To the reaction was added 1-(2-isopropylphenyl)thiourea (0.162 g, 0.833 mmol) and cesium carbonate (0.271 g, 0.833 mmol). The reaction was stirred overnight. The reaction mixture was diluted with EtOAc and washed with saturated sodium bicarbonate. The aqueous layer was extracted with EtOAc. The combined organic layers were dried over MgSO₄, filtered and concentrated. Purification by flash column chromatography provided the title compound as a white solid (0.243 g, 0.438 mmol, 58%): ¹H NMR (400 MHz, DMSO-d₆) δ 11.74 (s, 1H), 10.71 (s, 1H), 9.39 (s, 1H), 8.83 (s, 1H), 8.13-8.04 (m, 2H), 8.04-7.88 (m, 3H), 7.68-7.56 (m, 2H), 7.47-7.35 (m, 2H), 7.35-7.27 (m, 1H), 7.27-7.21 (m, 1H), 3.06 (hept, J=6.8 Hz, 1H), 2.37 (s, 3H), 1.19 (d, J=6.8 Hz, 6H); ¹⁹F NMR (376 MHz, DMSO-d₆) δ −56.97; ESIMS m/z 555 ([M+H]⁺).

Example 64

Preparation of (Z)-1-(3-(2-isopropylphenyl)-4-oxothiazolidin-2-ylidene)-3-(2-methyl-4-(1-(4-(trifluoromethoxy)phenyl)-1H-1,2,4-triazol-3-yl)phenyl)urea (Molecule A123)

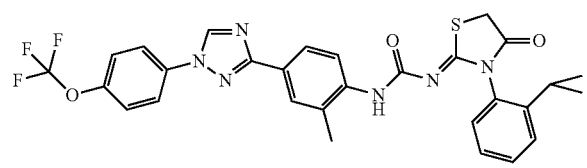 [SMILES: Cc1cc(-c2ncn(-c3ccc(OC(F)(F)F)cc3)n2)ccc1NC(=O)/N=C1\SCC(=O)N1c1ccccc1C(C)C]

To N-[[(2-isopropyllphenyl)amino]thioxomethyl]-N'-(2-methyl(4-(1-(4-(trifluoromethoxy)phen-yl)-1H-1,2,4-triazol-3-yl)phenyl))urea (0.193 g, 0.348 mmol) in a 25 mL vial equipped with a stir bar and Vigreux column was added sodium acetate (0.114 g, 1.392 mmol), EtOH (4 ml) and methyl 2-bromoacetate (0.066 ml, 0.696 mmol). The reaction was stirred at 60° C. overnight. The reaction was cooled and the solid was filtered, washed with EtOH, followed by diethyl ether and dried under vacuum providing the title compound as a white solid (0.124 g, 0.209 mmol, 60%): ¹H NMR (400 MHz, CDCl₃) δ 8.53 (s, 1H), 8.18 (d, J=8.6 Hz, 1H), 8.06-8.01 (m, 1H), 7.98 (s, 1H), 7.82-7.76 (m, 2H), 7.53-7.48 (m, 2H), 7.41-7.34 (m, 3H), 7.13-7.06 (m, 2H), 3.99 (s, 2H), 2.73 (hept, J=6.8 Hz, 1H), 2.25 (s, 3H), 1.27-1.22 (m, 6H); ¹⁹F NMR (376 MHz, CDCl₃) δ −58.03; ESIMS m/z 595 ([M+H]⁺).

Example 65

Preparation of N-((1H-benzo[d][1,2,3]triazol-1-yl)methyl)-4-(1-(4-(trifluoromethoxy)phenyl)-1H-1,2,4-triazol-3-yl)aniline (B65)

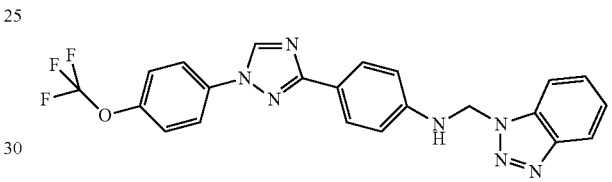

To a 100 mL flask was added benzotriazole (2.083 g, 17.5 mmol) and 4-(1-(4-(trifluoromethyl)phenyl)-1H-1,2,4-triazol-3-yl)aniline (5.6 g, 17.5 mmol), and the solids were melted with a heat gun. EtOH (26 mL) was quickly added and the mixture was stirred while formaldehyde (1.3 mL of a 37% aqueous solution, 47.2 mmol) was added via syringe. The solution was allowed to stir at ambient temperature for 30 min, then it was warmed to 40° C. for another 30 min, then allowed to cool to ambient temperature before collecting the solid product by vacuum filtration. After washing the solid with EtOH and hexanes, there was obtained crude N-((1H-benzo[d][1,2,3]triazol-1-yl)methyl)-4-(1-(4-(trifluoromethoxy)phenyl)-1H-1,2,4-triazol-3-yl)aniline, which was used directly without further purification (3.79 g, 49%): ¹H NMR (400 MHz, CDCl₃) δ 8.49 (s, 1H), 8.06 (d, J=8.4 Hz, 1H), 8.02 (d, J=8.7 Hz, 2H), 7.76 (d, J=9.0 Hz, 2H), 7.64 (d, J=8.3 Hz, 1H), 7.48 (ddd, J=8.3, 7.0, 1.0 Hz, 1H), 7.40-7.33 (m, 2H), 6.96 (d, J=8.8 Hz, 2H), 6.15 (d, J=7.2 Hz, 2H), 5.07 (t, J=7.1 Hz, 1H).

Example 66

Preparation of N-methyl-4-(1-(4-(trifluoromethyl)phenyl)-1H-1,2,4-triazol-3-yl)aniline (B66)

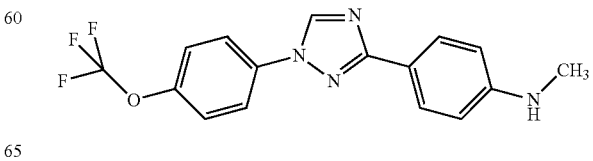

To a solution of N-((1H-benzo[d][1,2,3]triazol-1-yl)methyl)-4-(1-(4-(trifluoromethoxy)phenyl)-1H-1,2,4-triazol-3-yl)aniline (3.78 g, 8.37 mmol) in THF (25 mL) was added sodium borohydride (0.475 g, 12.56 mmol), slowly with stirring under $N_2$. The solution was allowed to stir at ambient temperature for 1 h, then it was heated to reflux for 3.5 h. After cooling to ambient temperature, the solution was poured onto water (25 mL) and extracted with 50 mL of ether (2×). Drying and concentration of the organic layer furnished N-methyl-4-(1-(4-(trifluoromethyl)phenyl)-1H-1,2,4-triazol-3-yl)aniline as an orange solid (2.49 g, 86%): mp 106-113° C.; ESIMS m/z 335 ([M+H]$^+$).

Example 67

Preparation of N-(methyl(4-(1-(4-(trifluoromethoxy)phenyl)-1H-1,2,4-triazol-3-yl)phenyl)carbamothioyl)benzamide (B67)

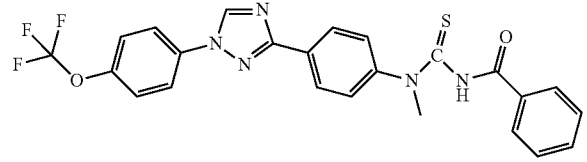 [SMILES: CN(C(=S)NC(=O)c1ccccc1)c1ccc(-c2ncn(-c3ccc(OC(F)(F)F)cc3)n2)cc1]

To a solution of N-methyl-4-(1-(4-(trifluoromethyl)phenyl)-1H-1,2,4-triazol-3-yl)aniline (2.0 g, 5.98 mmol) in acetone was added benzoyl isothiocyanate (0.847 g, 6.28 mmol) via syringe, and the solution was heated at 50° C. for 8 h, then the solution was cooled and concentrated in vacuo to give N-(methyl(4-(1-(4-(trifluoromethoxy)phenyl)-1H-1,2,4-triazol-3-yl)phenyl)carbamothioyl)benzamide as a yellow solid (2.9 g, 96%): mp 166-169° C.; $^1$H NMR (400 MHz, CDCl$_3$) δ 8.53 (s, 1H), 8.36 (s, 1H), 8.20 (d, J=8.6 Hz, 2H), 7.76 (d, J=9.0 Hz, 2H), 7.60 (d, J=7.5 Hz, 1H), 7.52-7.42 (m, 4H), 7.38 (dt, J=8.0, 1.0 Hz, 2H), 3.82 (s, 3H); ESIMS m/z 497 ([M+H]$^+$).

Example 68

Preparation of 1-methyl-1-(4-(1-(4-(trifluoromethoxy)phenyl)-1H-1,2,4-triazol-3-yl)phenyl)thiourea (B68)

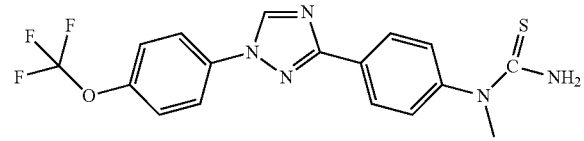 [SMILES: CN(C(N)=S)c1ccc(-c2ncn(-c3ccc(OC(F)(F)F)cc3)n2)cc1]

To a 100 mL round bottom flask containing MeOH (23 mL) was added N-(methyl(4-(1-(4-(trifluoromethoxy)phenyl)-1H-1,2,4-triazol-3-yl)phenyl)carbamothioyl)benzamide (2.8 g, 5.63 mmol) and sodium hydroxide (5.6 mL of a 2 N solution, 11.3 mmol), and the solution was heated at 65° C. for 3.5 hours. Another 20 mL (40 mmol) of 2N NaOH was then added and heating was continued for 6 hours. Upon cooling the solution was neutralized by addition of 2N HCl, and the resulting yellow solid was collected by vacuum filtration to give 1-methyl-1-(4-(1-(4-(trifluoromethoxy)phenyl)-1H-1,2,4-triazol-3-yl)phenyl)thiourea as a yellow solid (1.073 g, 47%): mp 142-152° C.; $^1$H NMR (400 MHz, CDCl$_3$) δ 8.59 (s, 1H), 8.36-8.24 (m, 2H), 7.81 (d, J=9.0 Hz, 2H), 7.46-7.33 (m, 4H), 5.62 (s, 2H), 3.73 (s, 3H); ESIMS m/z 393 ([M+H]$^+$).

Example 69

Preparation of 2-(methyl(4-(1-(4-(trifluoromethoxy)phenyl)-1H-1,2,4-triazol-3-yl)phenyl)amino)thiazole-4,5-dione (B69)

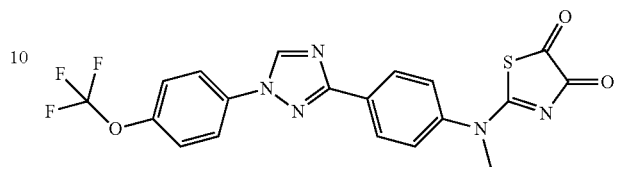

To a flask containing EtOAc (30 mL) was added 1-methyl-1-(4-(1-(4-(trifluoromethoxy)phenyl)-1H-1,2,4-triazol-3-yl)phenyl)thiourea (0.600 g, 1.52 mmol) and triethylamine (510 µl, 3.66 mmol). A solution of oxalyl chloride (467 mL, 5.34 mmol) in EtOAc (24 mL) was added and the solution was stirred at ambient temperature for 15 min Evaporation of solvent in vacuo left a white-yellow solid which was dissolved in 50 mL of dichloromethane and washed with water (3×25 mL). The organic layer was dried (MgSO$_4$) and concentrated to furnish 2-(methyl(4-(1-(4-(trifluoromethoxy)phenyl)-1H-1,2,4-triazol-3-yl)phenyl)amino)thiazole-4,5-dione as an orange solid (632 mg, 92%): mp 114-118° C.; $^1$H NMR (400 MHz, CDCl$_3$) δ 8.62 (s, 1H), 8.36 (d, J=8.7 Hz, 2H), 7.82 (d, J=9.1 Hz, 2H), 7.50-7.34 (m, 4H), 3.82 (s, 3H); ESIMS m/z 448 ([M+H]$^+$).

Example 70

Preparation N-[[(2-isopropyl]phenyl)amino]thioxomethyl]-N'-methyl-N'-(4-(1-(4-(trifluoromethoxy)phenyl)-1H-1,2,4-triazol-3-yl)phenyl))urea (A124)

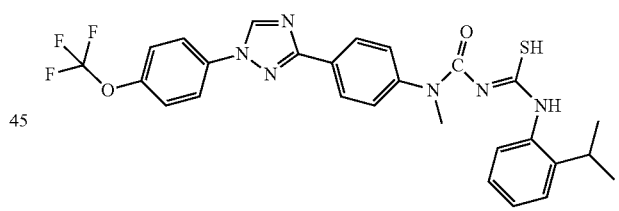

A solution of 2-(methyl(4-(1-(4-(trifluoromethoxy)phenyl)-1H-1,2,4-triazol-3-yl)phenyl)amino)thiazole-4,5-dione (615 mg, 1.38 mmol) in toluene (16 mL) was heated to 100° C. for 25 min, then cooled to 0° C. and 2-isopropylaniline (0.212 mL, 1.51 mmol) in acetone (4 mL) was added under N$_2$. After 2 h, the solution was allowed to warm to ambient temperature and then concentrated. Purification by flash column chromatography (EtOAc-hexanes) furnished N-[[(2-isopropyl]phenyl)amino]thioxomethyl]-N'-methyl-N'-(4-(1-(4-(trifluoromethoxy)phenyl)-1H-1,2,4-triazol-3-yl)phenyl))urea as a light orange oil (300 mg, 40%); $^1$H NMR (400 MHz, CDCl$_3$) δ 12.03 (s, 1H), 8.60 (s, 1H), 8.36 (d, J=8.7 Hz, 1H), 7.89 (s, 1H), 7.81 (d, J=9.1 Hz, 1H), 7.52-7.48 (m, 1H), 7.46 (d, J=8.7 Hz, 1H), 7.41 (dt, J=7.9, 1.0 Hz, 2H), 7.36 (dd, J=7.8, 1.7 Hz, 1H), 7.30 (td, J=7.5, 1.5 Hz, 1H), 7.25-7.20 (m, 1H), 3.40 (s, 3H), 1.27 (d, J=6.9 Hz, 6H); ESIMS m/z 555 ([M+H]$^+$).

Example 71

Preparation (Z)-3-(3-(2-isopropylphenyl)-4-oxothiazolidin-2-ylidene)-1-methyl-1-(4-(1-(4-(trifluoromethoxy)phenyl)-1H-1,2,4-triazol-3-yl)phenyl) urea (A125)

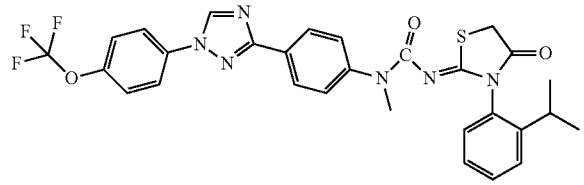 [SMILES: CC(C)c1ccccc1N1C(=O)CS/C1=N\C(=O)N(C)c1ccc(-c2ncn(-c3ccc(OC(F)(F)F)cc3)n2)cc1]

Conditions described in Example 14 were used to convert N-[[(2-isopropyllphenyl)amino]thioxomethyl]-N'-methyl-N'-(4-(1-(4-(trifluoromethoxy)phenyl)-1H-1,2,4-triazol-3-yl)phenyl))urea into (Z)-3-(3-(2-isopropylphenyl)-4-oxothiazolidin-2-ylidene)-1-methyl-1-(4-(1-(4-(trifluoromethoxy)phenyl)-1H-1,2,4-triazol-3-yl)phenyl)urea, which was isolated as a yellow oil (19 mg, 34%): δ $^1$H NMR (400 MHz, CDCl$_3$) δ 8.58 (s, 1H), 8.17 (s, 1H), 7.83 (d, J=8.9 Hz, 2H), 7.73 (d, J=8.1 Hz, 2H), 7.42 (d, J=8.8 Hz, 3H), 7.22 (d, J=7.6 Hz, 1H), 7.17-7.07 (m, 1H), 6.85 (dd, J=28.9, 8.0 Hz, 2H), 3.95 (d, J=2.5 Hz, 3H), 3.37 (s, 2H), 2.50 (d, J=7.1 Hz, 1H), 1.05 (d, J=6.9 Hz, 3H), 0.79 (d, J=6.8 Hz, 3H); ESIMS m/z 595 ([M+H]$^+$).

TABLE 1

Structure for Compounds

| No. | Structure |
|---|---|
| AA1 | 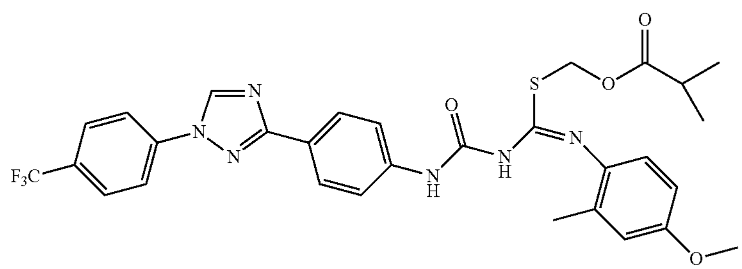 [SMILES: COc1ccc(/N=C(\NC(=O)Nc2ccc(-c3ncn(-c4ccc(C(F)(F)F)cc4)n3)cc2)SCOC(=O)C(C)C)c(C)c1] |
| AA2 | 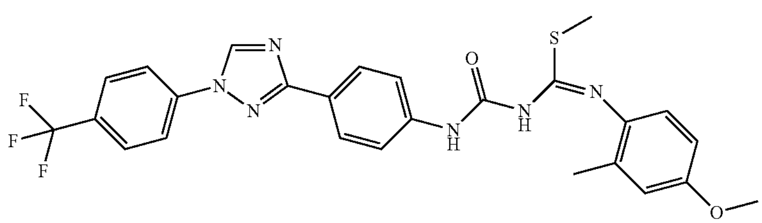 [SMILES: COc1ccc(/N=C(\NC(=O)Nc2ccc(-c3ncn(-c4ccc(C(F)(F)F)cc4)n3)cc2)SC)c(C)c1] |
| AA3 | 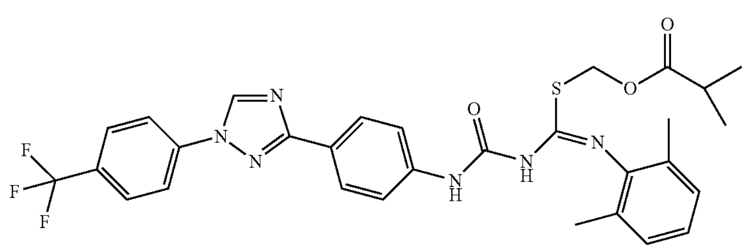 [SMILES: Cc1cccc(C)c1/N=C(\NC(=O)Nc1ccc(-c2ncn(-c3ccc(C(F)(F)F)cc3)n2)cc1)SCOC(=O)C(C)C] |
| AA4 | 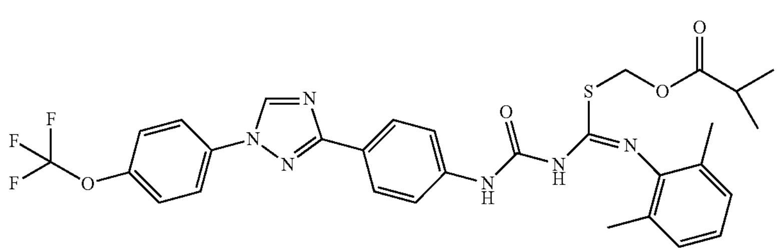 [SMILES: Cc1cccc(C)c1/N=C(\NC(=O)Nc1ccc(-c2ncn(-c3ccc(OC(F)(F)F)cc3)n2)cc1)SCOC(=O)C(C)C] |

TABLE 1-continued

Structure for Compounds

| No. | Structure |
|---|---|
| AA5 | 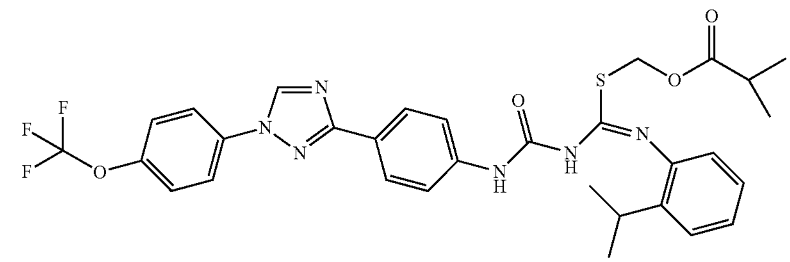 [SMILES: CC(C)C(=O)OCS/C(=N/c1ccccc1C(C)C)NC(=O)Nc1ccc(-c2ncn(-c3ccc(OC(F)(F)F)cc3)n2)cc1] |
| AA6 | 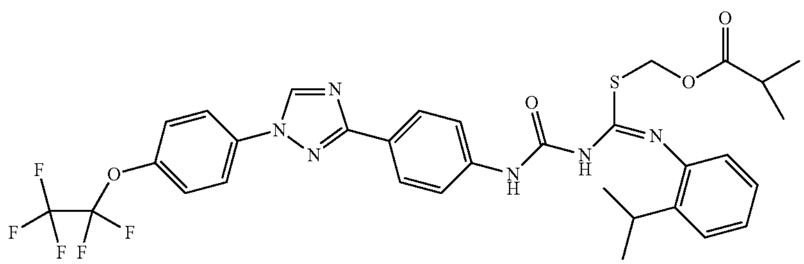 [SMILES: CC(C)C(=O)OCS/C(=N/c1ccccc1C(C)C)NC(=O)Nc1ccc(-c2ncn(-c3ccc(OC(F)(F)C(F)(F)F)cc3)n2)cc1] |
| AA7 | 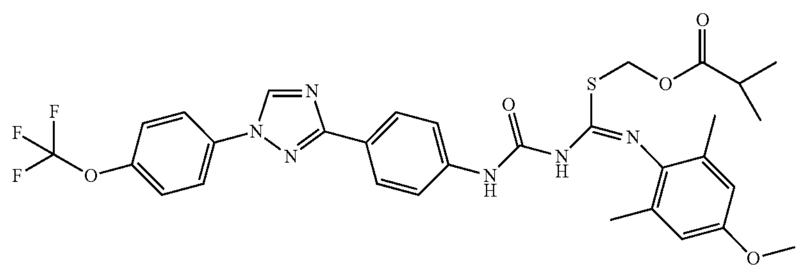 [SMILES: COc1cc(C)c(/N=C(\NC(=O)Nc2ccc(-c3ncn(-c4ccc(OC(F)(F)F)cc4)n3)cc2)SCOC(=O)C(C)C)c(C)c1] |
| AA8 | 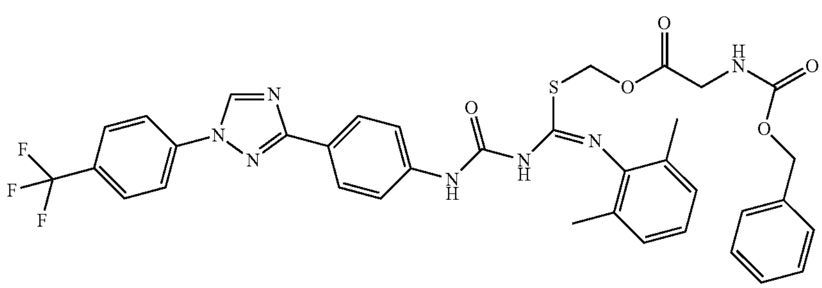 [SMILES: Cc1cccc(C)c1/N=C(\NC(=O)Nc1ccc(-c2ncn(-c3ccc(C(F)(F)F)cc3)n2)cc1)SCOC(=O)CNC(=O)OCc1ccccc1] |
| AA9 | 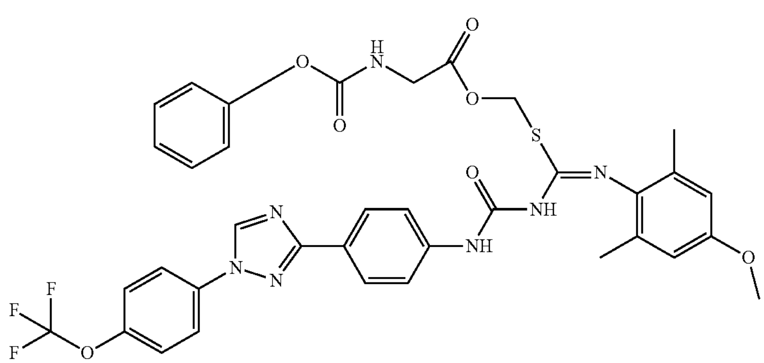 [SMILES: COc1cc(C)c(/N=C(\NC(=O)Nc2ccc(-c3ncn(-c4ccc(OC(F)(F)F)cc4)n3)cc2)SCOC(=O)CNC(=O)OCc2ccccc2)c(C)c1] |

TABLE 1-continued

Structure for Compounds

| No. | Structure |
|---|---|
| AA10 | 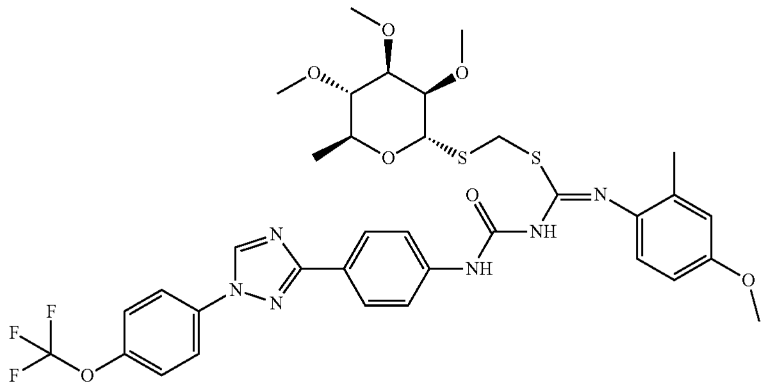 [SMILES: COc1ccc(/N=C(\NC(=O)Nc2ccc(-c3ncn(-c4ccc(OC(F)(F)F)cc4)n3)cc2)SCS[C@@H]2O[C@@H](C)[C@H](OC)[C@@H](OC)[C@H]2OC)c(C)c1] |
| A1 | 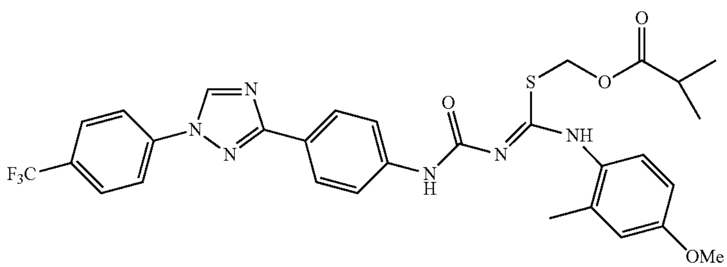 [SMILES: COc1ccc(N/C(=N/C(=O)Nc2ccc(-c3ncn(-c4ccc(C(F)(F)F)cc4)n3)cc2)SCOC(=O)C(C)C)c(C)c1] |
| A2 | 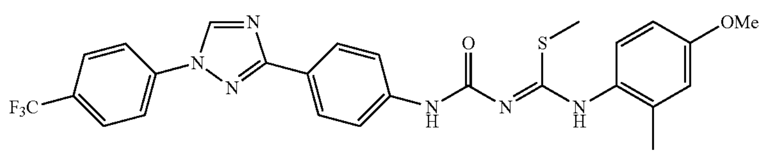 [SMILES: COc1ccc(N/C(=N/C(=O)Nc2ccc(-c3ncn(-c4ccc(C(F)(F)F)cc4)n3)cc2)SC)c(C)c1] |
| A3 | 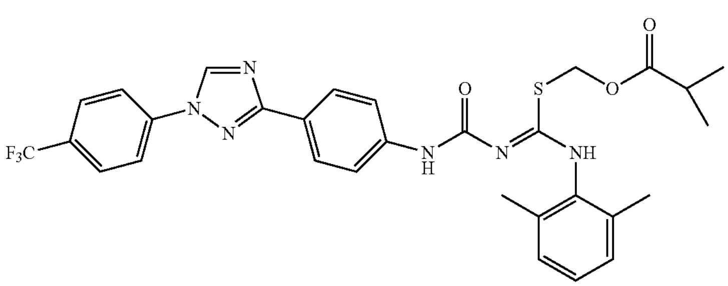 |
| A4 | 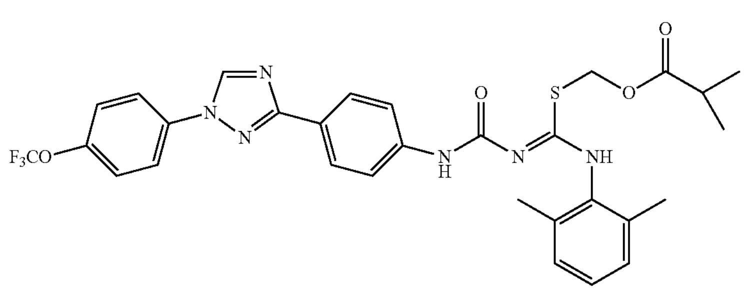 [SMILES: Cc1cccc(C)c1N/C(=N/C(=O)Nc1ccc(-c2ncn(-c3ccc(OC(F)(F)F)cc3)n2)cc1)SCOC(=O)C(C)C] |

TABLE 1-continued
Structure for Compounds
| No. | Structure |
|---|---|
| A5 | 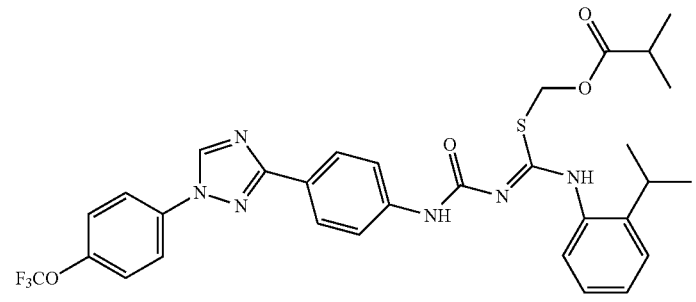 [SMILES: CC(C)C(=O)OCS/C(=N\C(=O)Nc1ccc(-c2ncn(-c3ccc(OC(F)(F)F)cc3)n2)cc1)Nc1ccccc1C(C)C] |
| A6 | 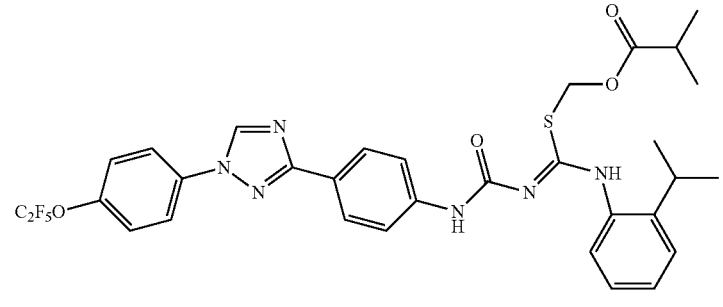 |
| A7 | 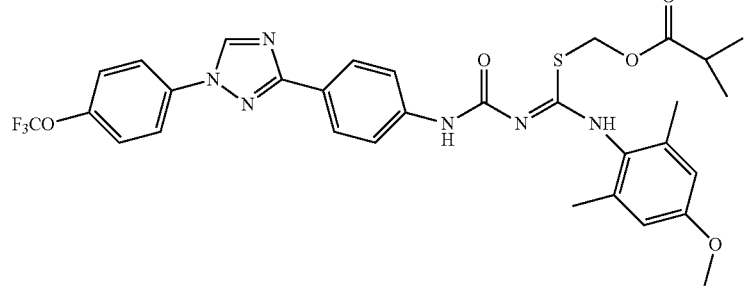 |
| A8 | 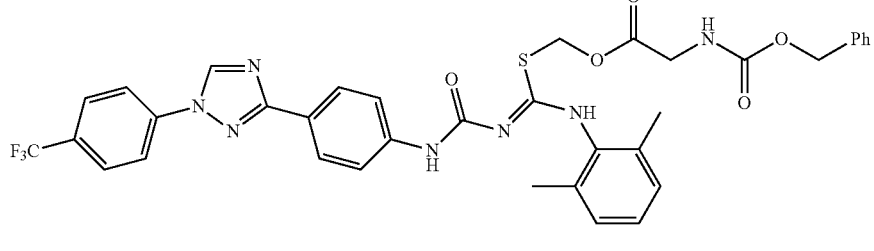 |
| A9 | 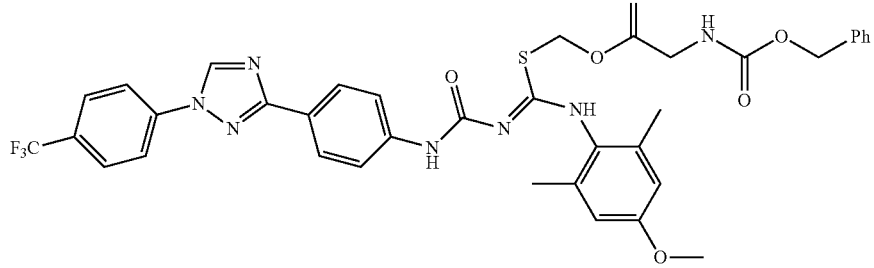 |

TABLE 1-continued

Structure for Compounds

| No. | Structure |
|---|---|
| A10 | (structure) |
| A11 | (structure) |
| A12 | (structure) |
| A13 | (structure) |
| A14 | (structure) |
| A15 | (structure) |

TABLE 1-continued
Structure for Compounds
| No. | Structure |
|---|---|
| A16 | 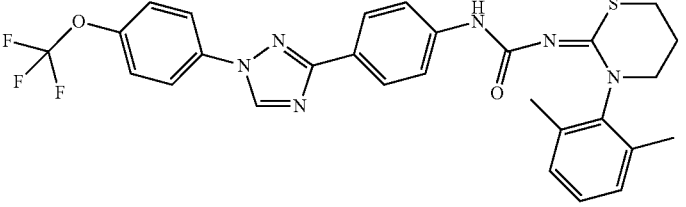 |
| A17 | 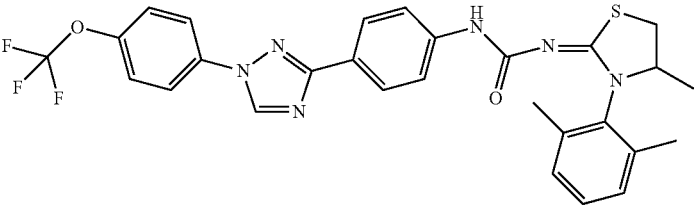 [SMILES: Cc1cccc(C)c1N1/C(=N\C(=O)Nc2ccc(-c3ncn(-c4ccc(OC(F)(F)F)cc4)n3)cc2)SCC1C] |
| A18 | 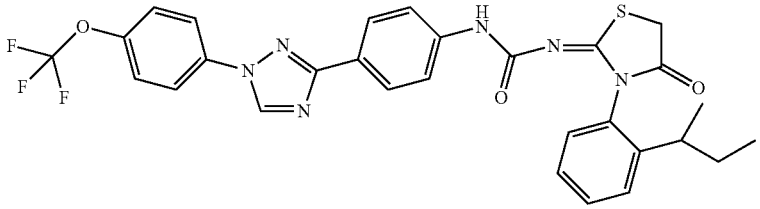 [SMILES: CCC(C)c1ccccc1N1C(=O)CS/C1=N/C(=O)Nc1ccc(-c2ncn(-c3ccc(OC(F)(F)F)cc3)n2)cc1] |
| A19 | 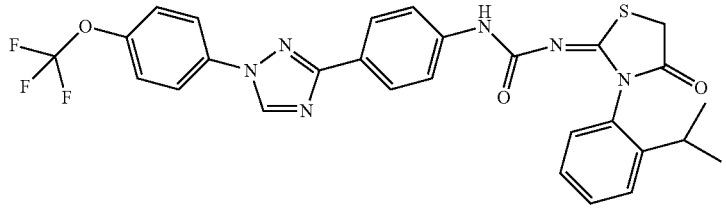 [SMILES: CC(C)c1ccccc1N1C(=O)CS/C1=N/C(=O)Nc1ccc(-c2ncn(-c3ccc(OC(F)(F)F)cc3)n2)cc1] |
| A20 | 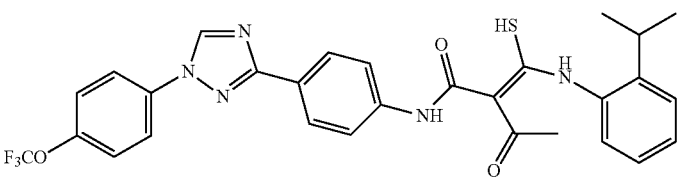 [SMILES: CC(=O)/C(C(=O)Nc1ccc(-c2ncn(-c3ccc(OC(F)(F)F)cc3)n2)cc1)=C(/S)Nc1ccccc1C(C)C] |
| A21 | 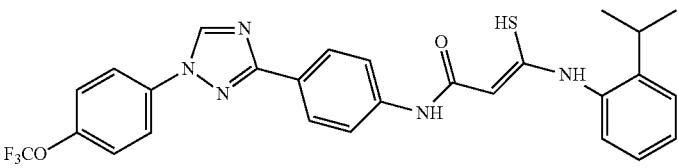 [SMILES: CC(C)c1ccccc1N/C(S)=C/C(=O)Nc1ccc(-c2ncn(-c3ccc(OC(F)(F)F)cc3)n2)cc1] |
| A22 | 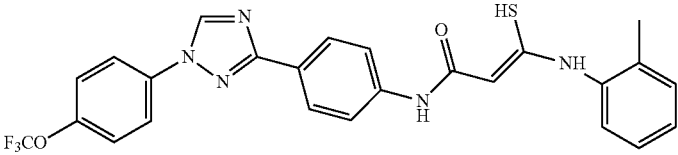 [SMILES: Cc1ccccc1N/C(S)=C/C(=O)Nc1ccc(-c2ncn(-c3ccc(OC(F)(F)F)cc3)n2)cc1] |

TABLE 1-continued

Structure for Compounds

| No. | Structure |
|---|---|
| A23 | 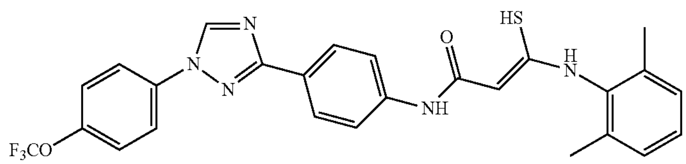 [SMILES: Cc1cccc(C)c1N/C(S)=C/C(=O)Nc1ccc(-c2ncn(-c3ccc(OC(F)(F)F)cc3)n2)cc1] |
| A24 | 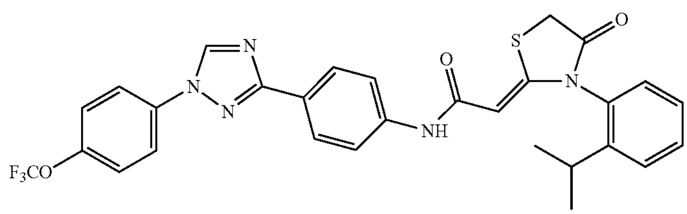 [SMILES: CC(C)c1ccccc1N1C(=O)CS/C1=C\C(=O)Nc1ccc(-c2ncn(-c3ccc(OC(F)(F)F)cc3)n2)cc1] |
| A25 | 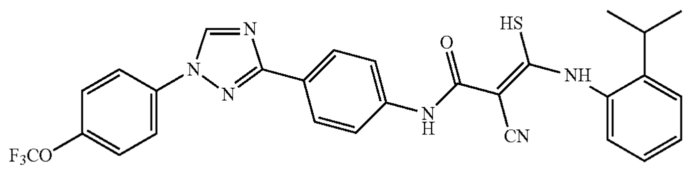 [SMILES: CC(C)c1ccccc1N/C(S)=C(\C#N)C(=O)Nc1ccc(-c2ncn(-c3ccc(OC(F)(F)F)cc3)n2)cc1] |
| A26 | 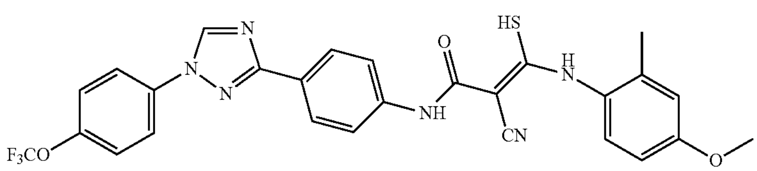 [SMILES: COc1ccc(N/C(S)=C(\C#N)C(=O)Nc2ccc(-c3ncn(-c4ccc(OC(F)(F)F)cc4)n3)cc2)c(C)c1] |
| A27 | 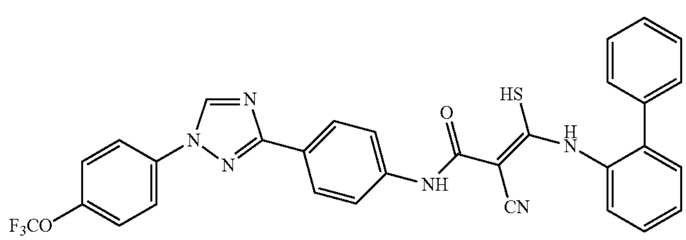 [SMILES: N#C/C(C(=O)Nc1ccc(-c2ncn(-c3ccc(OC(F)(F)F)cc3)n2)cc1)=C(/S)Nc1ccccc1-c1ccccc1] |
| A28 | 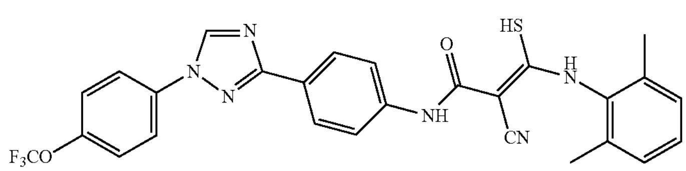 [SMILES: Cc1cccc(C)c1N/C(S)=C(\C#N)C(=O)Nc1ccc(-c2ncn(-c3ccc(OC(F)(F)F)cc3)n2)cc1] |
| A29 | 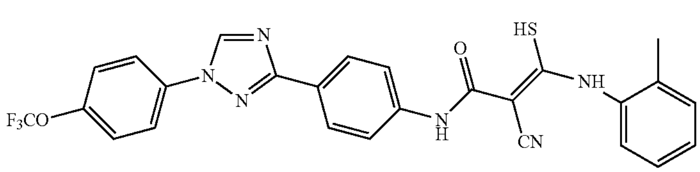 [SMILES: Cc1ccccc1N/C(S)=C(\C#N)C(=O)Nc1ccc(-c2ncn(-c3ccc(OC(F)(F)F)cc3)n2)cc1] |
| A30 | 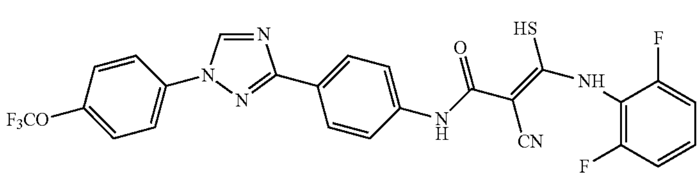 [SMILES: N#C/C(C(=O)Nc1ccc(-c2ncn(-c3ccc(OC(F)(F)F)cc3)n2)cc1)=C(/S)Nc1c(F)cccc1F] |

TABLE 1-continued

Structure for Compounds

| No. | Structure |
|---|---|
| A31 | 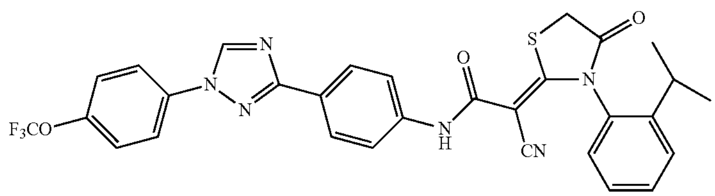 [SMILES: CC(C)c1ccccc1N1C(=O)CS/C1=C(/C#N)C(=O)Nc1ccc(-c2ncn(-c3ccc(OC(F)(F)F)cc3)n2)cc1] |
| A32 | 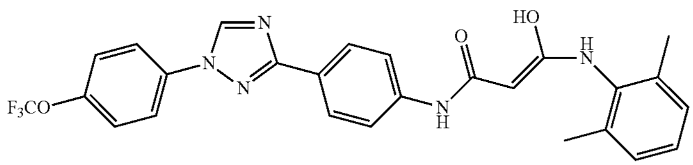 [SMILES: Cc1cccc(C)c1N/C(O)=C/C(=O)Nc1ccc(-c2ncn(-c3ccc(OC(F)(F)F)cc3)n2)cc1] |
| A33 | 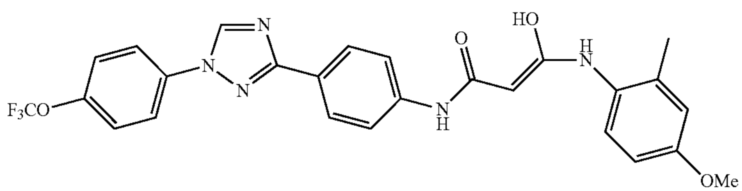 [SMILES: COc1ccc(N/C(O)=C/C(=O)Nc2ccc(-c3ncn(-c4ccc(OC(F)(F)F)cc4)n3)cc2)c(C)c1] |
| A34 | 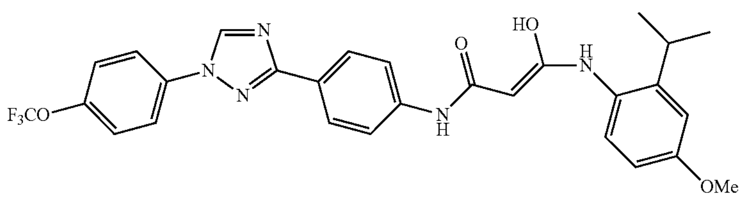 [SMILES: COc1ccc(N/C(O)=C/C(=O)Nc2ccc(-c3ncn(-c4ccc(OC(F)(F)F)cc4)n3)cc2)c(C(C)C)c1] |
| A35 | 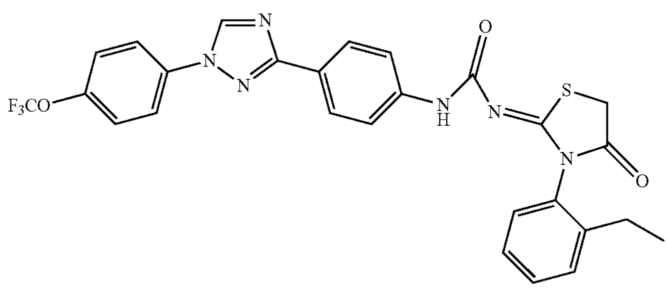 [SMILES: CCc1ccccc1N1C(=O)CS/C1=N\C(=O)Nc1ccc(-c2ncn(-c3ccc(OC(F)(F)F)cc3)n2)cc1] |
| A36 | 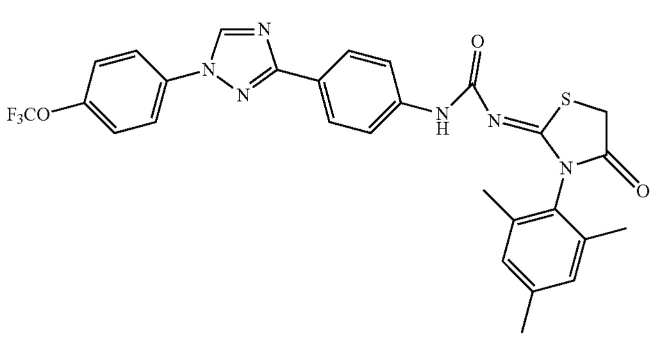 [SMILES: Cc1cc(C)c(N2C(=O)CS/C2=N\C(=O)Nc2ccc(-c3ncn(-c4ccc(OC(F)(F)F)cc4)n3)cc2)c(C)c1] |

TABLE 1-continued

Structure for Compounds

| No. | Structure |
|---|---|
| A37 | 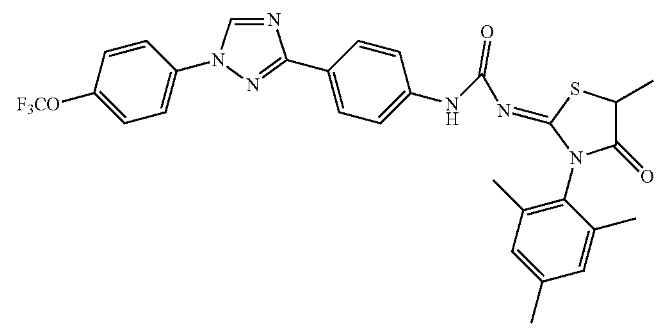 [SMILES: Cc1cc(C)c(N2C(=O)C(C)S/C2=N\C(=O)Nc2ccc(-c3ncn(-c4ccc(OC(F)(F)F)cc4)n3)cc2)c(C)c1] |
| A38 | 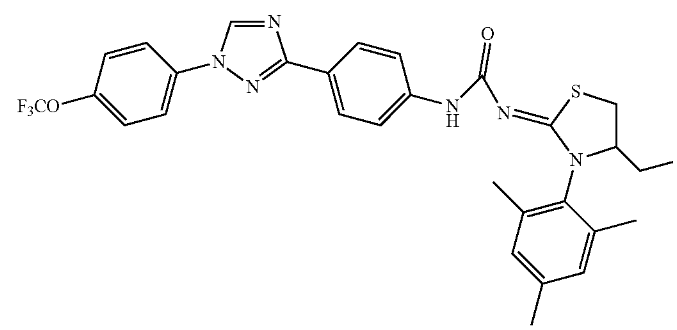 [SMILES: CCC1CS/C(=N\C(=O)Nc2ccc(-c3ncn(-c4ccc(OC(F)(F)F)cc4)n3)cc2)N1c1c(C)cc(C)cc1C] |
| A39 | 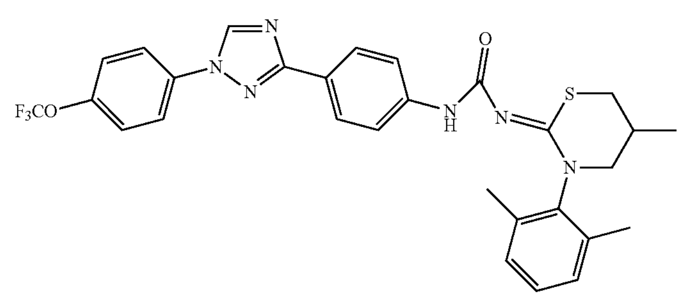 [SMILES: Cc1cccc(C)c1N1CC(C)CS/C1=N\C(=O)Nc1ccc(-c2ncn(-c3ccc(OC(F)(F)F)cc3)n2)cc1] |
| A40 | 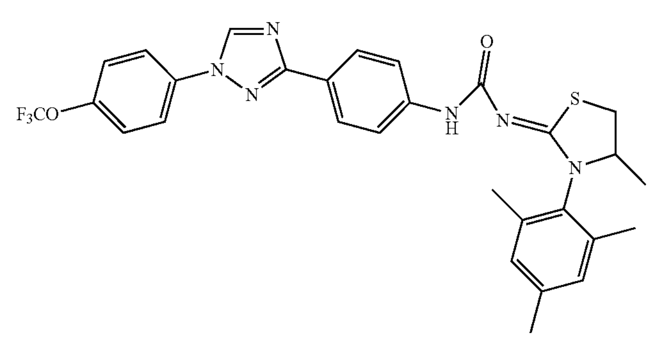 [SMILES: Cc1cc(C)c(N2/C(=N/C(=O)Nc3ccc(-c4ncn(-c5ccc(OC(F)(F)F)cc5)n4)cc3)SCC2C)c(C)c1] |

TABLE 1-continued

Structure for Compounds

| No. | Structure |
|---|---|
| A41 | 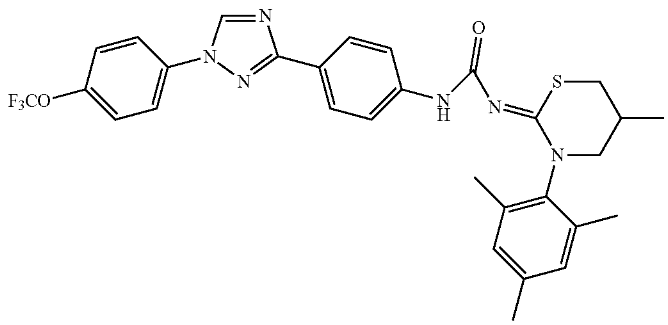 [SMILES: Cc1cc(C)c(N2CC(C)CS/C2=N\C(=O)Nc2ccc(-c3ncn(-c4ccc(OC(F)(F)F)cc4)n3)cc2)c(C)c1] |
| A42 | 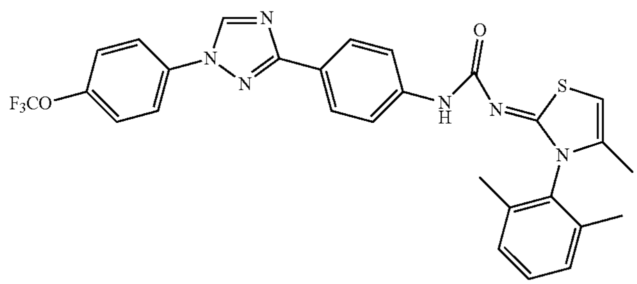 [SMILES: Cc1cccc(C)c1-n1c(C)cs/c1=N\C(=O)Nc1ccc(-c2ncn(-c3ccc(OC(F)(F)F)cc3)n2)cc1] |
| A43 | 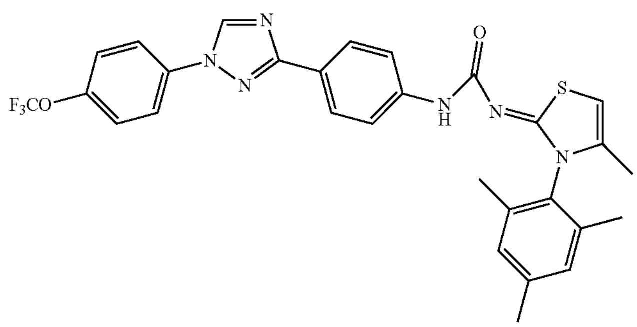 [SMILES: Cc1cc(C)c(-n2c(C)cs/c2=N\C(=O)Nc2ccc(-c3ncn(-c4ccc(OC(F)(F)F)cc4)n3)cc2)c(C)c1] |
| A44 | 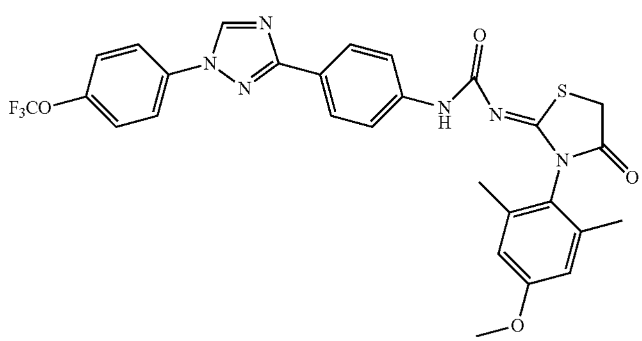 [SMILES: COc1cc(C)c(N2C(=O)CS/C2=N\C(=O)Nc2ccc(-c3ncn(-c4ccc(OC(F)(F)F)cc4)n3)cc2)c(C)c1] |
| A46 | 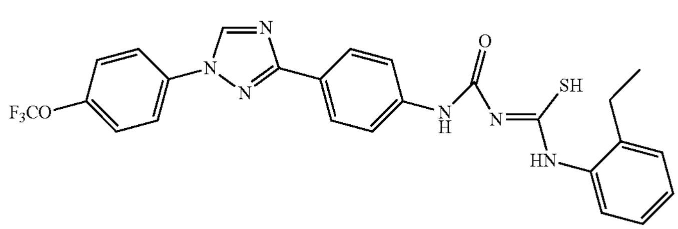 [SMILES: CCc1ccccc1N/C(S)=N/C(=O)Nc1ccc(-c2ncn(-c3ccc(OC(F)(F)F)cc3)n2)cc1] |

TABLE 1-continued

Structure for Compounds

| No. | Structure |
|---|---|
| A48 | 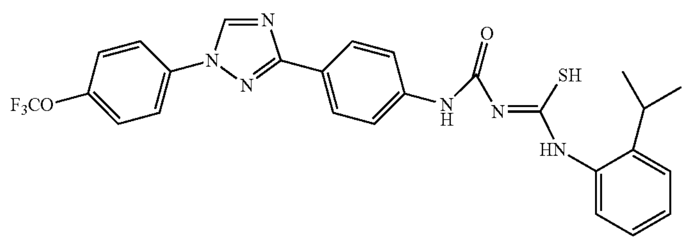 [SMILES: CC(C)c1ccccc1N/C(S)=N/C(=O)Nc1ccc(-c2ncn(-c3ccc(OC(F)(F)F)cc3)n2)cc1] |
| A49 | 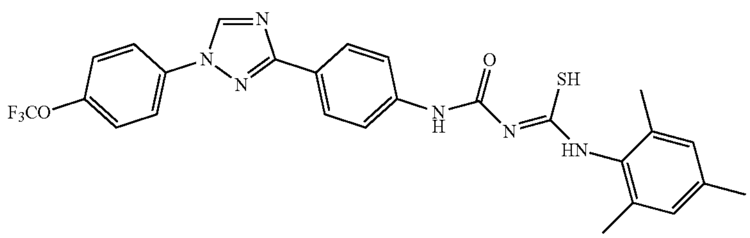 [SMILES: Cc1cc(C)c(N/C(S)=N/C(=O)Nc2ccc(-c3ncn(-c4ccc(OC(F)(F)F)cc4)n3)cc2)c(C)c1] |
| A50 | 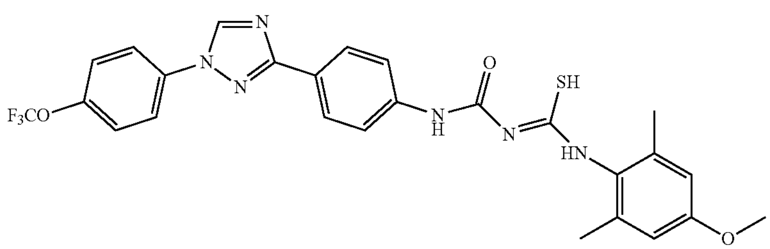 [SMILES: COc1cc(C)c(N/C(S)=N/C(=O)Nc2ccc(-c3ncn(-c4ccc(OC(F)(F)F)cc4)n3)cc2)c(C)c1] |
| A51 | 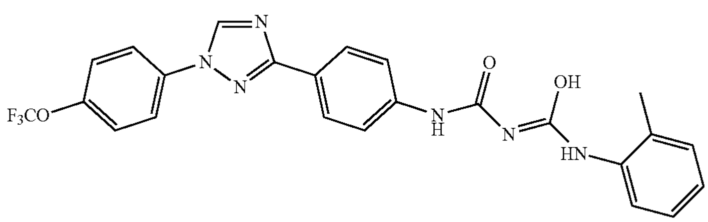 [SMILES: Cc1ccccc1N/C(O)=N/C(=O)Nc1ccc(-c2ncn(-c3ccc(OC(F)(F)F)cc3)n2)cc1] |
| A52 | 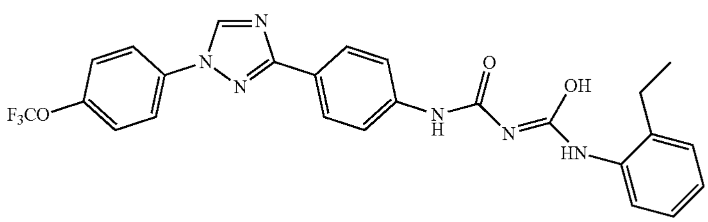 [SMILES: CCc1ccccc1N/C(O)=N/C(=O)Nc1ccc(-c2ncn(-c3ccc(OC(F)(F)F)cc3)n2)cc1] |
| A53 | 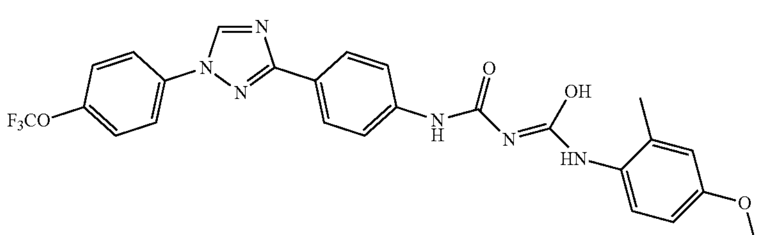 |

TABLE 1-continued

Structure for Compounds

| No. | Structure |
|---|---|
| A54 | 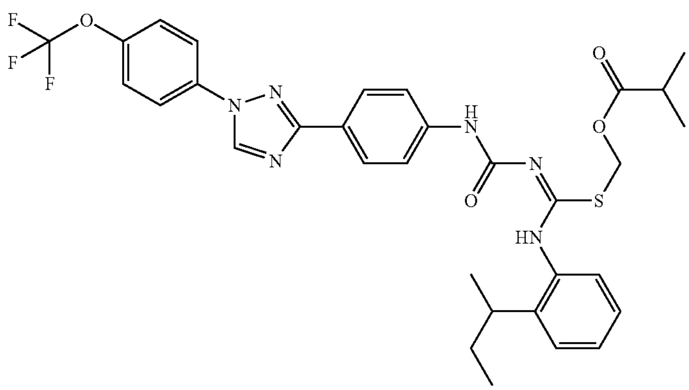 [SMILES: CCC(C)c1ccccc1N/C(=N\C(=O)Nc1ccc(-c2ncn(-c3ccc(OC(F)(F)F)cc3)n2)cc1)SCOC(=O)C(C)C] |
| A55 | 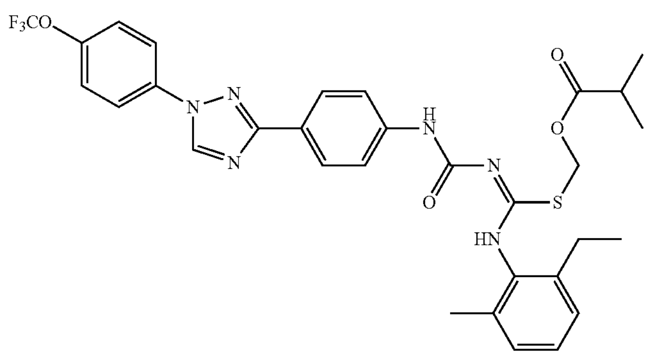 [SMILES: CCc1cccc(C)c1N/C(=N\C(=O)Nc1ccc(-c2ncn(-c3ccc(OC(F)(F)F)cc3)n2)cc1)SCOC(=O)C(C)C] |
| A56 | 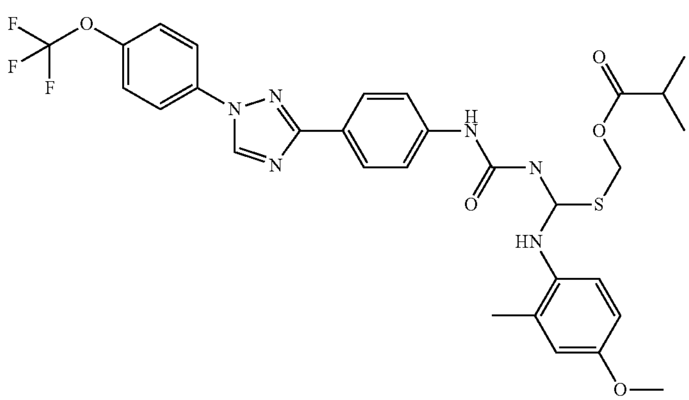 [SMILES: COc1ccc(NC(NC(=O)Nc2ccc(-c3ncn(-c4ccc(OC(F)(F)F)cc4)n3)cc2)SCOC(=O)C(C)C)c(C)c1] |
| A57 | 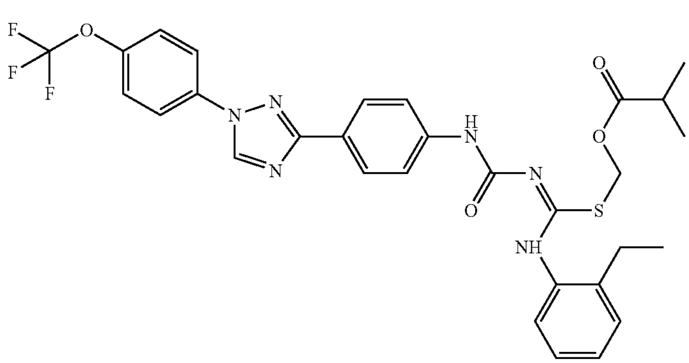 [SMILES: CCc1ccccc1N/C(=N\C(=O)Nc1ccc(-c2ncn(-c3ccc(OC(F)(F)F)cc3)n2)cc1)SCOC(=O)C(C)C] |

TABLE 1-continued
Structure for Compounds
| No. | Structure |
|---|---|
| A58 | 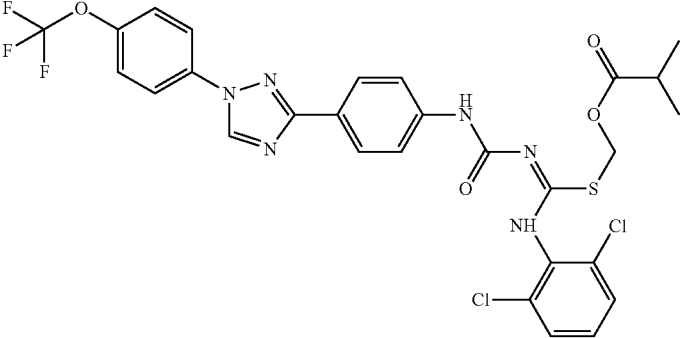 |
| A59 | 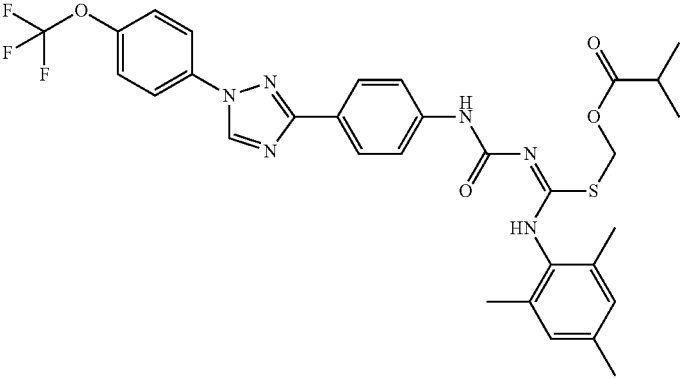 [SMILES: Cc1cc(C)c(N/C(=N\C(=O)Nc2ccc(-c3ncn(-c4ccc(OC(F)(F)F)cc4)n3)cc2)SCOC(=O)C(C)C)c(C)c1] |
| A60 | 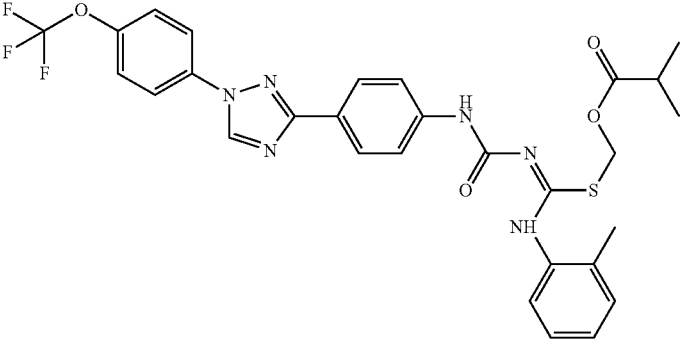 [SMILES: Cc1ccccc1N/C(=N\C(=O)Nc1ccc(-c2ncn(-c3ccc(OC(F)(F)F)cc3)n2)cc1)SCOC(=O)C(C)C] |
| A61 | 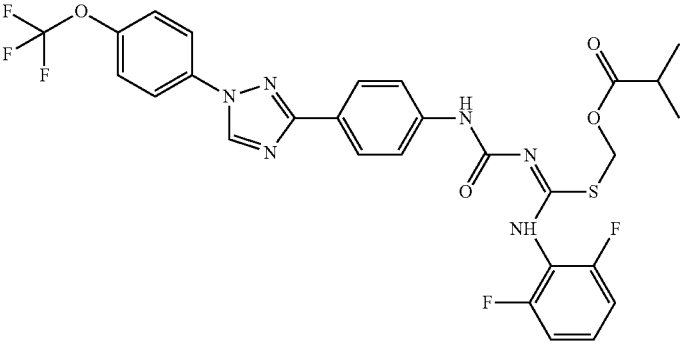 [SMILES: CC(C)C(=O)OCS/C(=N/C(=O)Nc1ccc(-c2ncn(-c3ccc(OC(F)(F)F)cc3)n2)cc1)Nc1c(F)cccc1F] |

TABLE 1-continued

Structure for Compounds

| No. | Structure |
|---|---|
| A62 | 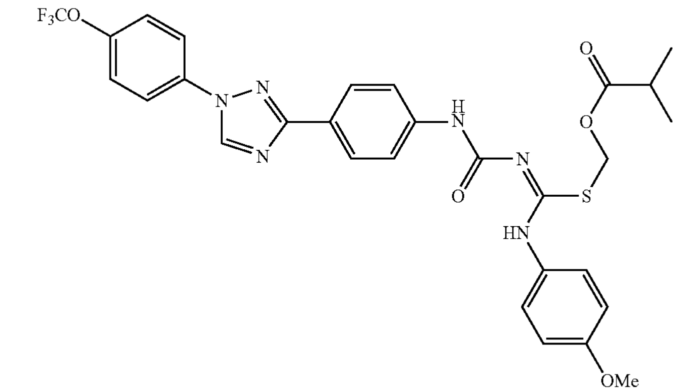 [SMILES: COc1ccc(N/C(=N\C(=O)Nc2ccc(-c3ncn(-c4ccc(OC(F)(F)F)cc4)n3)cc2)SCOC(=O)C(C)C)cc1] |
| A63 | 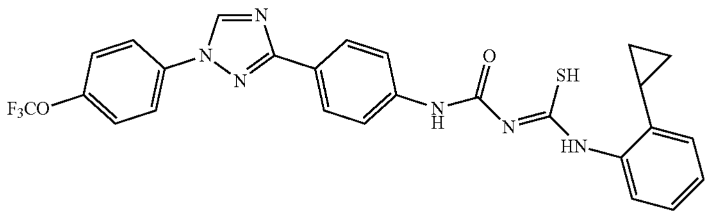 [SMILES: O=C(/N=C(\S)Nc1ccccc1C1CC1)Nc1ccc(-c2ncn(-c3ccc(OC(F)(F)F)cc3)n2)cc1] |
| A64 | 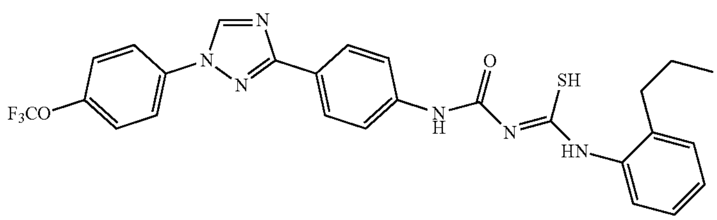 [SMILES: CCCc1ccccc1N/C(S)=N/C(=O)Nc1ccc(-c2ncn(-c3ccc(OC(F)(F)F)cc3)n2)cc1] |
| A65 | 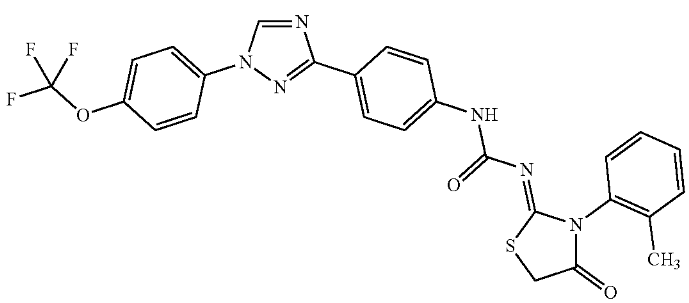 [SMILES: Cc1ccccc1N1C(=O)CS/C1=N\C(=O)Nc1ccc(-c2ncn(-c3ccc(OC(F)(F)F)cc3)n2)cc1] |
| A66 | 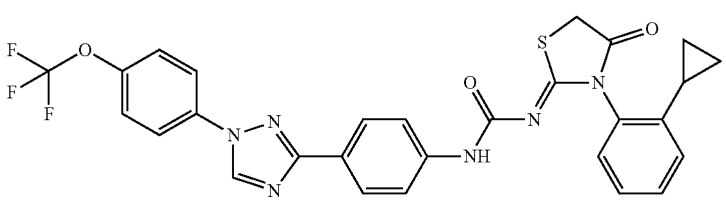 [SMILES: O=C(/N=C1\SCC(=O)N1c1ccccc1C1CC1)Nc1ccc(-c2ncn(-c3ccc(OC(F)(F)F)cc3)n2)cc1] |
| A67 | 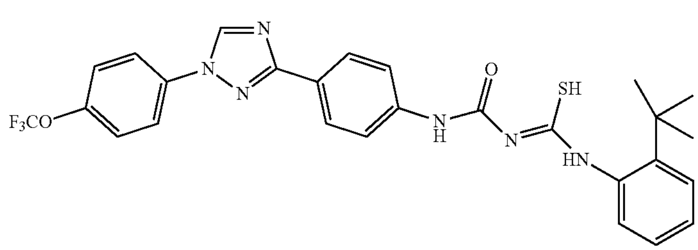 [SMILES: CC(C)(C)c1ccccc1N/C(S)=N/C(=O)Nc1ccc(-c2ncn(-c3ccc(OC(F)(F)F)cc3)n2)cc1] |

TABLE 1-continued

Structure for Compounds

| No. | Structure |
|---|---|
| A68 | 4-(1-(4-(trifluoromethoxy)phenyl)-1H-1,2,4-triazol-3-yl)phenyl-substituted N-(2,4-dimethylphenyl)carbamothioyl urea |
| A69 | 4-(1-(4-(trifluoromethoxy)phenyl)-1H-1,2,4-triazol-3-yl)phenyl urea linked to 3-(2-propylphenyl)-4-oxothiazolidin-2-ylidene |
| A70 | 4-(1-(4-(trifluoromethoxy)phenyl)-1H-1,2,4-triazol-3-yl)phenyl-substituted N-(2-chloro-6-methylphenyl)carbamothioyl urea |
| A71 | 4-(1-(4-(trifluoromethoxy)phenyl)-1H-1,2,4-triazol-3-yl)phenyl-substituted N-(2,3-dimethylphenyl)carbamothioyl urea |
| A72 | 4-(1-(4-(trifluoromethoxy)phenyl)-1H-1,2,4-triazol-3-yl)phenyl-substituted N-(5-chloro-2-methylphenyl)carbamothioyl urea |
| A73 | 4-(1-(4-(trifluoromethoxy)phenyl)-1H-1,2,4-triazol-3-yl)phenyl-substituted N-(2-chloro-4-methylphenyl)carbamothioyl urea |

TABLE 1-continued
Structure for Compounds
| No. | Structure |
|---|---|
| A74 | 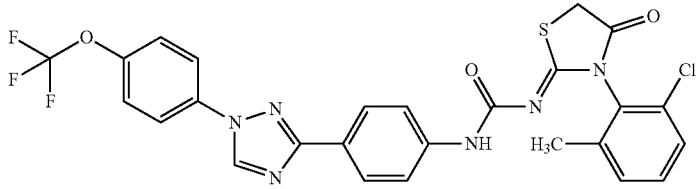 [SMILES: Cc1cccc(Cl)c1N1C(=O)CS/C1=N\C(=O)Nc1ccc(-c2ncn(-c3ccc(OC(F)(F)F)cc3)n2)cc1] |
| A75 | 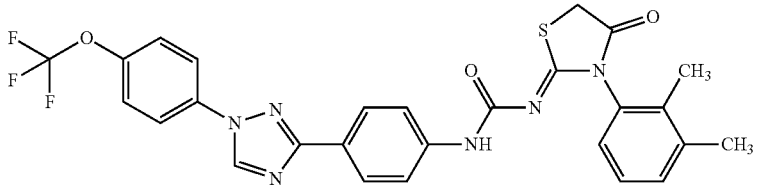 [SMILES: Cc1cccc(N2C(=O)CS/C2=N\C(=O)Nc2ccc(-c3ncn(-c4ccc(OC(F)(F)F)cc4)n3)cc2)c1C] |
| A76 | 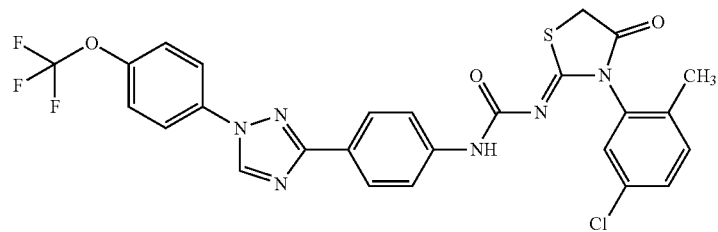 [SMILES: Cc1ccc(Cl)cc1N1C(=O)CS/C1=N\C(=O)Nc1ccc(-c2ncn(-c3ccc(OC(F)(F)F)cc3)n2)cc1] |
| A77 | 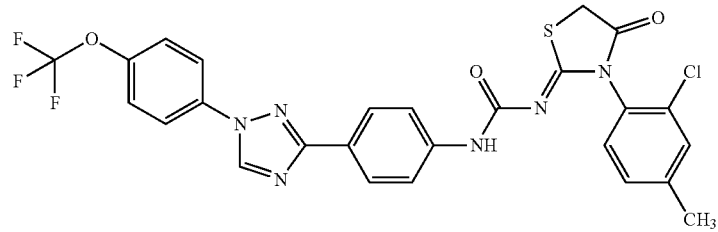 [SMILES: Cc1ccc(N2C(=O)CS/C2=N\C(=O)Nc2ccc(-c3ncn(-c4ccc(OC(F)(F)F)cc4)n3)cc2)c(Cl)c1] |
| A78 | 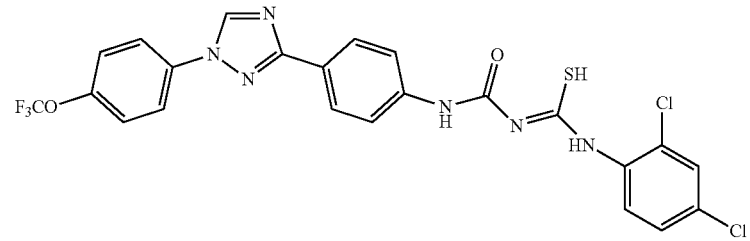 [SMILES: O=C(/N=C(\S)Nc1ccc(Cl)cc1Cl)Nc1ccc(-c2ncn(-c3ccc(OC(F)(F)F)cc3)n2)cc1] |
| A79 | 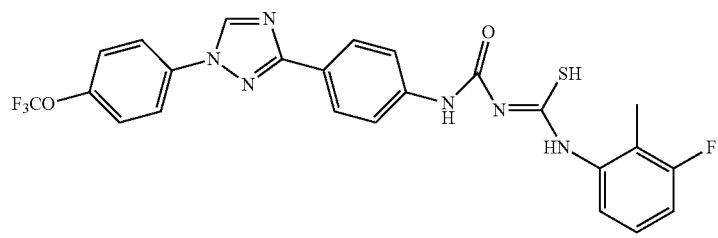 [SMILES: Cc1c(F)cccc1N/C(S)=N/C(=O)Nc1ccc(-c2ncn(-c3ccc(OC(F)(F)F)cc3)n2)cc1] |

TABLE 1-continued

Structure for Compounds

| No. | Structure |
|---|---|
| A80 | 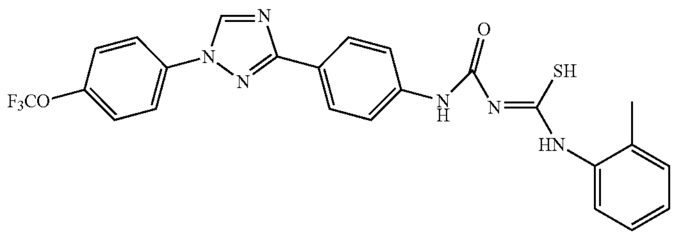 [SMILES: Cc1ccccc1N/C(S)=N/C(=O)Nc1ccc(-c2ncn(-c3ccc(OC(F)(F)F)cc3)n2)cc1] |
| A81 | 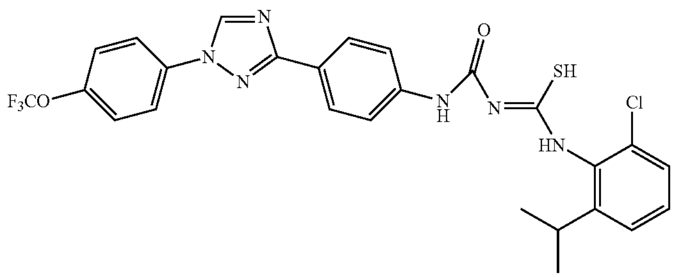 [SMILES: CC(C)c1cccc(Cl)c1N/C(S)=N/C(=O)Nc1ccc(-c2ncn(-c3ccc(OC(F)(F)F)cc3)n2)cc1] |
| A82 | 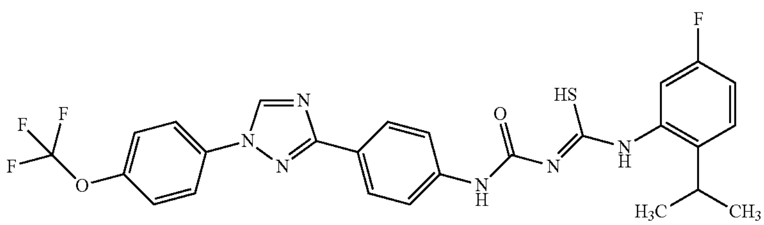 [SMILES: CC(C)c1ccc(F)cc1N/C(S)=N/C(=O)Nc1ccc(-c2ncn(-c3ccc(OC(F)(F)F)cc3)n2)cc1] |
| A83 | 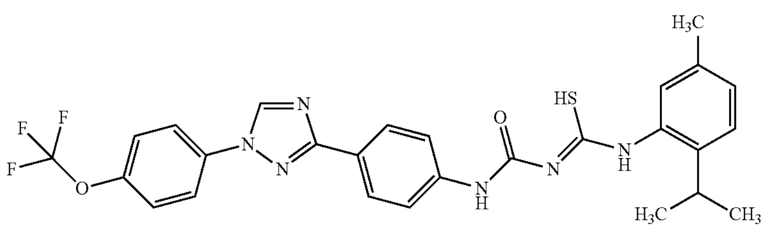 [SMILES: Cc1ccc(C(C)C)c(N/C(S)=N/C(=O)Nc2ccc(-c3ncn(-c4ccc(OC(F)(F)F)cc4)n3)cc2)c1] |
| A84 | 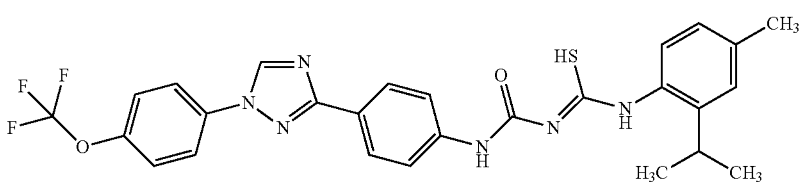 [SMILES: Cc1ccc(N/C(S)=N/C(=O)Nc2ccc(-c3ncn(-c4ccc(OC(F)(F)F)cc4)n3)cc2)c(C(C)C)c1] |
| A85 | 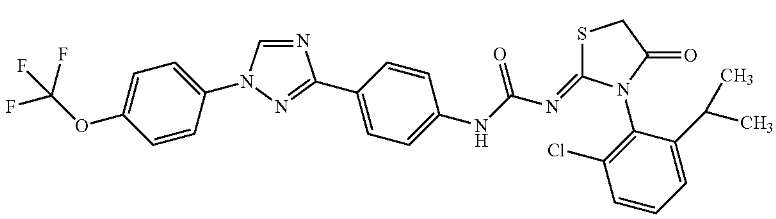 [SMILES: CC(C)c1cccc(Cl)c1N1C(=O)CS/C1=N\C(=O)Nc1ccc(-c2ncn(-c3ccc(OC(F)(F)F)cc3)n2)cc1] |

TABLE 1-continued

Structure for Compounds

| No. | Structure |
|---|---|
| A86 | 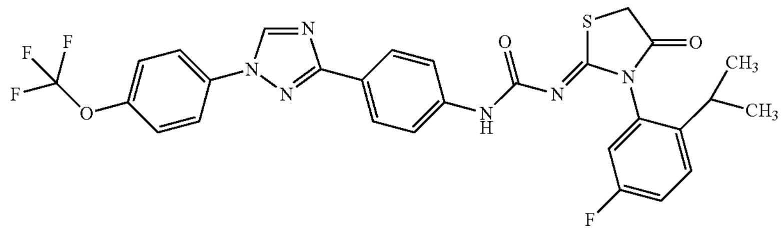 [SMILES: CC(C)c1ccc(F)cc1N1C(=O)CS/C1=N\C(=O)Nc1ccc(-c2ncn(-c3ccc(OC(F)(F)F)cc3)n2)cc1] |
| A87 | 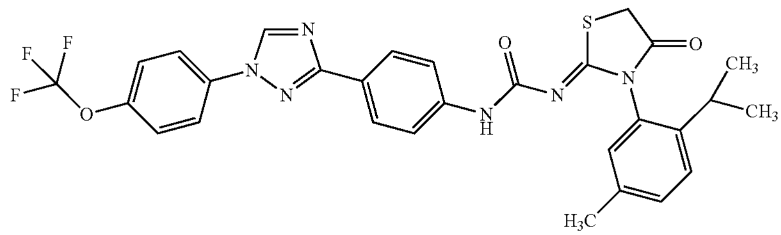 [SMILES: Cc1ccc(C(C)C)c(N2C(=O)CS/C2=N\C(=O)Nc2ccc(-c3ncn(-c4ccc(OC(F)(F)F)cc4)n3)cc2)c1] |
| A88 | 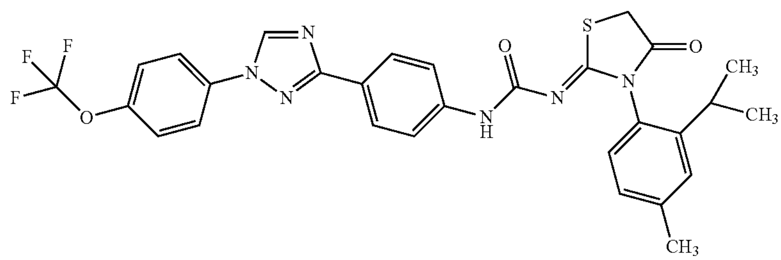 [SMILES: Cc1ccc(N2C(=O)CS/C2=N\C(=O)Nc2ccc(-c3ncn(-c4ccc(OC(F)(F)F)cc4)n3)cc2)c(C(C)C)c1] |
| A89 | 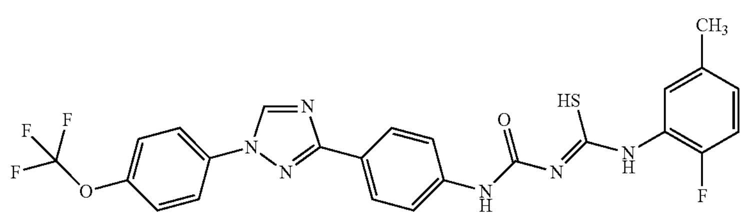 [SMILES: Cc1ccc(F)c(N/C(S)=N/C(=O)Nc2ccc(-c3ncn(-c4ccc(OC(F)(F)F)cc4)n3)cc2)c1] |
| A92 | 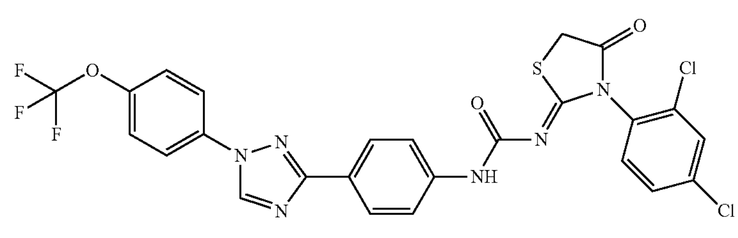 [SMILES: O=C(/N=C1\SCC(=O)N1c1ccc(Cl)cc1Cl)Nc1ccc(-c2ncn(-c3ccc(OC(F)(F)F)cc3)n2)cc1] |
| A93 | 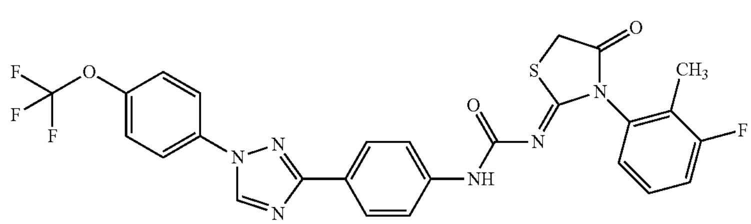 [SMILES: Cc1c(F)cccc1N1C(=O)CS/C1=N\C(=O)Nc1ccc(-c2ncn(-c3ccc(OC(F)(F)F)cc3)n2)cc1] |

TABLE 1-continued

Structure for Compounds

| No. | Structure |
|---|---|
| A94 | 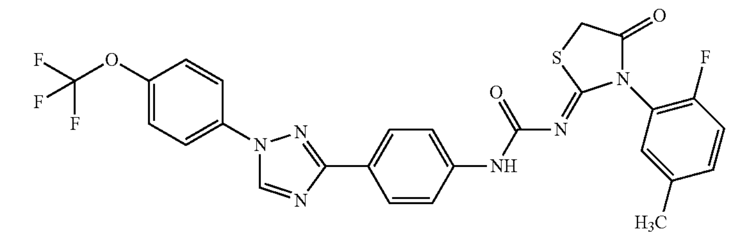 [SMILES: Cc1ccc(F)c(N2C(=O)CS/C2=N\C(=O)Nc2ccc(-c3ncn(-c4ccc(OC(F)(F)F)cc4)n3)cc2)c1] |
| A95 | 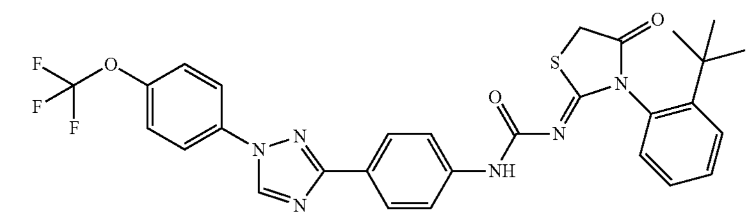 [SMILES: CC(C)(C)c1ccccc1N1C(=O)CS/C1=N\C(=O)Nc1ccc(-c2ncn(-c3ccc(OC(F)(F)F)cc3)n2)cc1] |
| A96 | 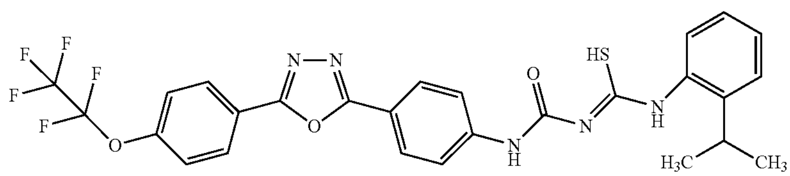 |
| A97 | 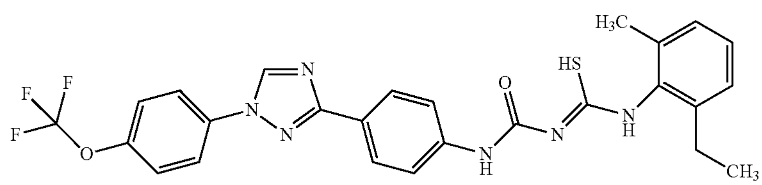 [SMILES: CCc1cccc(C)c1N/C(S)=N/C(=O)Nc1ccc(-c2ncn(-c3ccc(OC(F)(F)F)cc3)n2)cc1] |
| A98 | 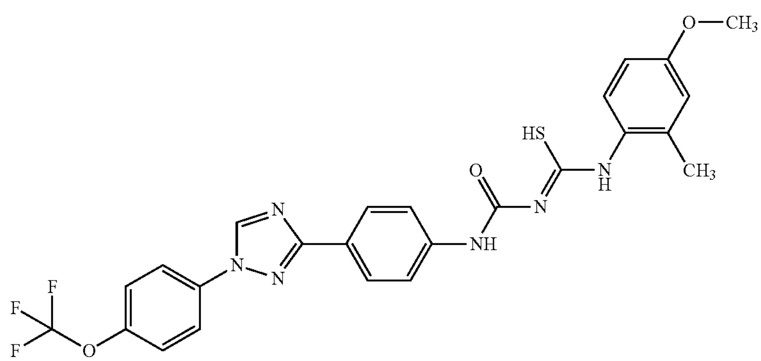 [SMILES: COc1ccc(N/C(S)=N/C(=O)Nc2ccc(-c3ncn(-c4ccc(OC(F)(F)F)cc4)n3)cc2)c(C)c1] |
| A99 | 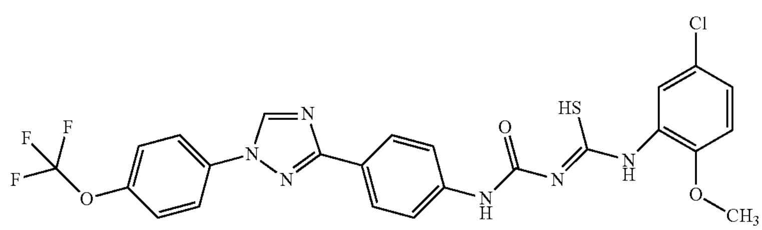 [SMILES: COc1ccc(Cl)cc1N/C(S)=N/C(=O)Nc1ccc(-c2ncn(-c3ccc(OC(F)(F)F)cc3)n2)cc1] |

TABLE 1-continued

Structure for Compounds

| No. | Structure |
|---|---|
| A100 | 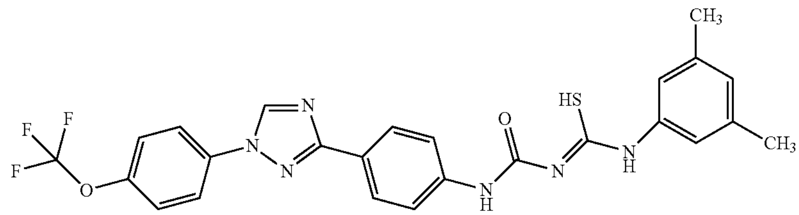 [SMILES: Cc1cc(C)cc(N/C(S)=N/C(=O)Nc2ccc(-c3ncn(-c4ccc(OC(F)(F)F)cc4)n3)cc2)c1] |
| A101 | 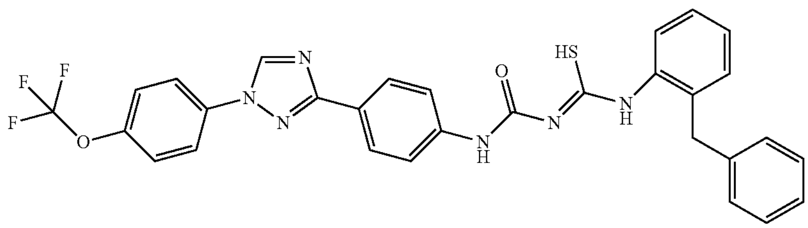 [SMILES: O=C(/N=C(\S)Nc1ccccc1Cc1ccccc1)Nc1ccc(-c2ncn(-c3ccc(OC(F)(F)F)cc3)n2)cc1] |
| A102 | 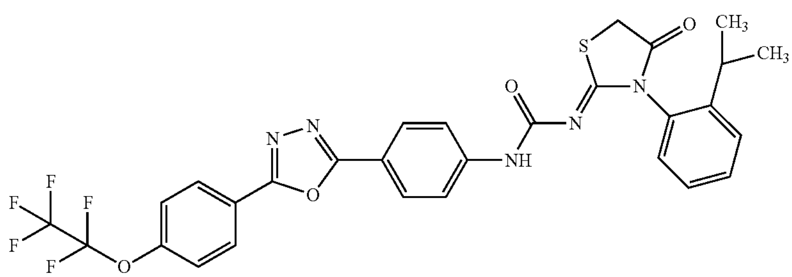 [SMILES: CC(C)c1ccccc1N1C(=O)CS/C1=N\C(=O)Nc1ccc(-c2nnc(-c3ccc(OC(F)(F)C(F)(F)F)cc3)o2)cc1] |
| A103 | 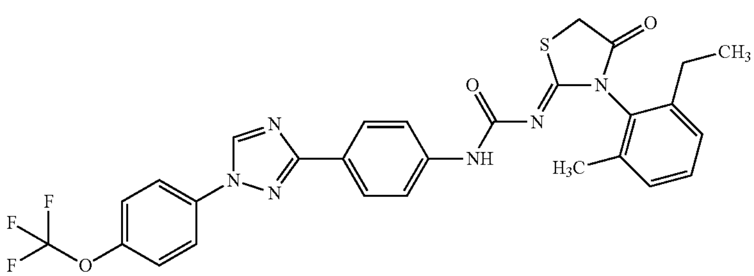 [SMILES: CCc1cccc(C)c1N1C(=O)CS/C1=N\C(=O)Nc1ccc(-c2ncn(-c3ccc(OC(F)(F)F)cc3)n2)cc1] |
| A104 | 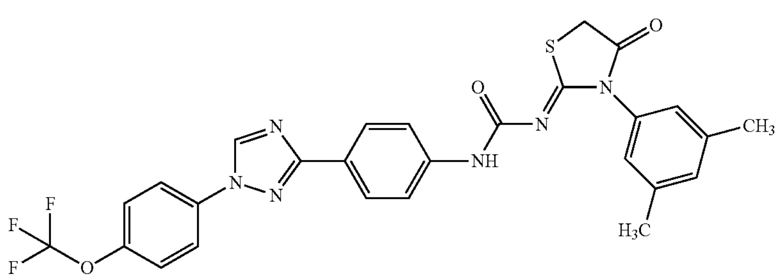 [SMILES: Cc1cc(C)cc(N2C(=O)CS/C2=N\C(=O)Nc2ccc(-c3ncn(-c4ccc(OC(F)(F)F)cc4)n3)cc2)c1] |
| A105 | 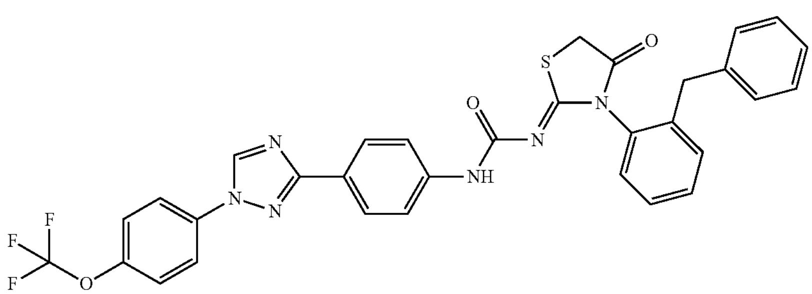 [SMILES: O=C(/N=C1\SCC(=O)N1c1ccccc1Cc1ccccc1)Nc1ccc(-c2ncn(-c3ccc(OC(F)(F)F)cc3)n2)cc1] |

TABLE 1-continued

Structure for Compounds

| No. | Structure |
|---|---|
| A106 | 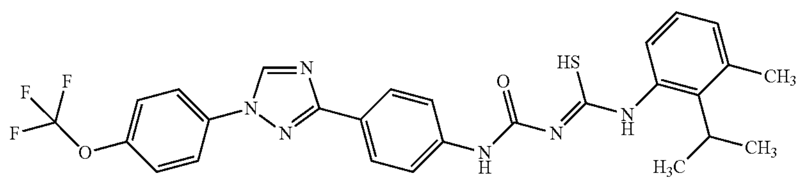 [SMILES: Cc1cccc(N/C(S)=N/C(=O)Nc2ccc(-c3ncn(-c4ccc(OC(F)(F)F)cc4)n3)cc2)c1C(C)C] |
| A107 | 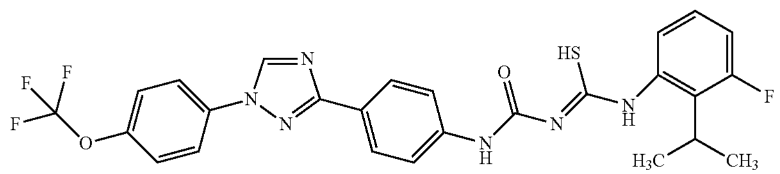 [SMILES: CC(C)c1c(F)cccc1N/C(S)=N/C(=O)Nc1ccc(-c2ncn(-c3ccc(OC(F)(F)F)cc3)n2)cc1] |
| A108 | 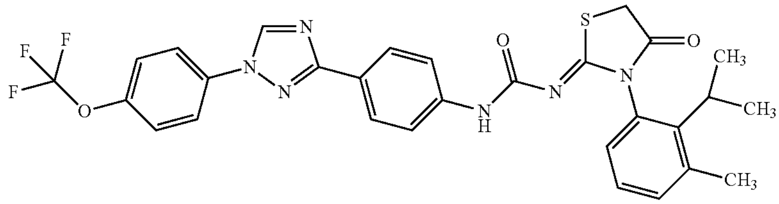 [SMILES: Cc1cccc(N2C(=O)CS/C2=N\C(=O)Nc2ccc(-c3ncn(-c4ccc(OC(F)(F)F)cc4)n3)cc2)c1C(C)C] |
| A109 | 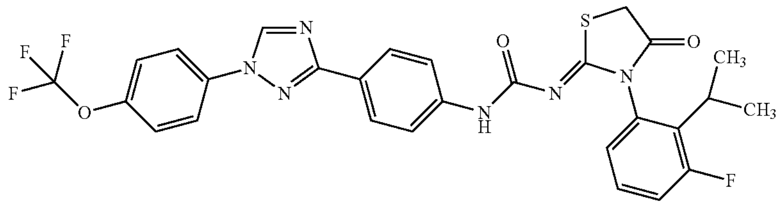 [SMILES: CC(C)c1c(F)cccc1N1C(=O)CS/C1=N\C(=O)Nc1ccc(-c2ncn(-c3ccc(OC(F)(F)F)cc3)n2)cc1] |
| A110 | 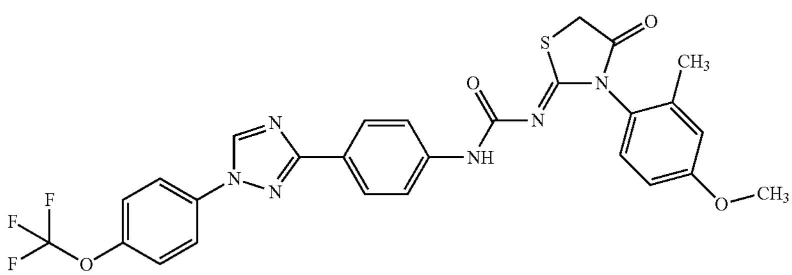 [SMILES: COc1ccc(N2C(=O)CS/C2=N\C(=O)Nc2ccc(-c3ncn(-c4ccc(OC(F)(F)F)cc4)n3)cc2)c(C)c1] |
| A111 | 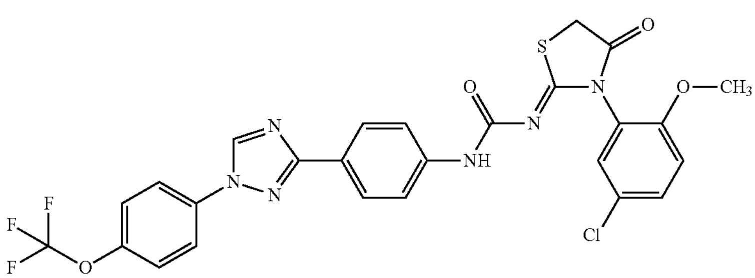 [SMILES: COc1ccc(Cl)cc1N1C(=O)CS/C1=N\C(=O)Nc1ccc(-c2ncn(-c3ccc(OC(F)(F)F)cc3)n2)cc1] |
| A112 | 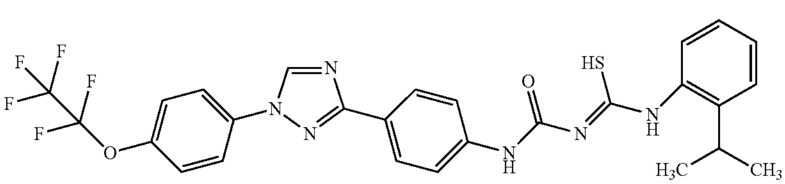 [SMILES: CC(C)c1ccccc1N/C(S)=N/C(=O)Nc1ccc(-c2ncn(-c3ccc(OC(F)(F)C(F)(F)F)cc3)n2)cc1] |

TABLE 1-continued

Structure for Compounds

| No. | Structure |
|---|---|
| A113 | 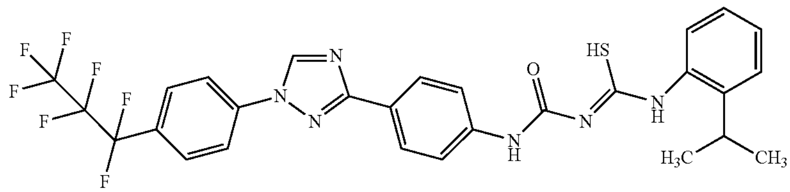 [SMILES: CC(C)c1ccccc1N/C(S)=N/C(=O)Nc1ccc(-c2ncn(-c3ccc(C(F)(F)C(F)(F)C(F)(F)F)cc3)n2)cc1] |
| A114 | 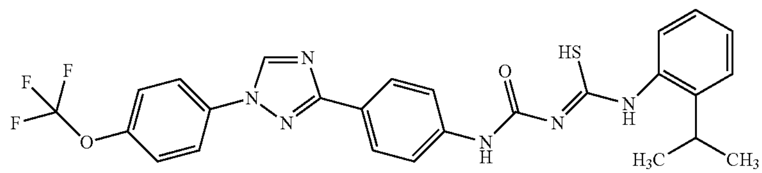 |
| A115 | 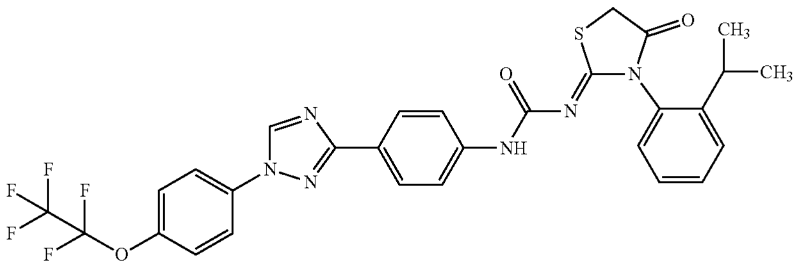 [SMILES: CC(C)c1ccccc1N1C(=O)CS/C1=N\C(=O)Nc1ccc(-c2ncn(-c3ccc(OC(F)(F)C(F)(F)F)cc3)n2)cc1] |
| A116 | 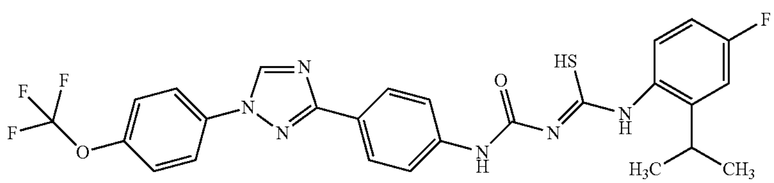 [SMILES: CC(C)c1cc(F)ccc1N/C(S)=N/C(=O)Nc1ccc(-c2ncn(-c3ccc(OC(F)(F)F)cc3)n2)cc1] |
| A117 | 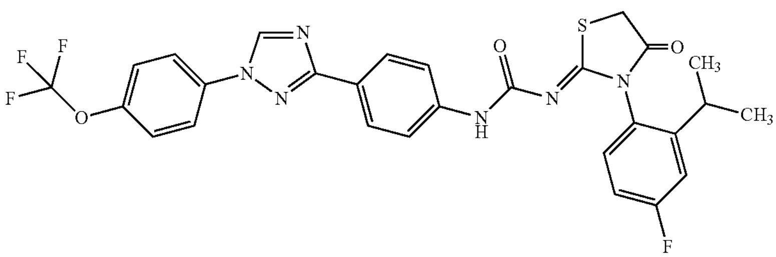 [SMILES: CC(C)c1cc(F)ccc1N1C(=O)CS/C1=N\C(=O)Nc1ccc(-c2ncn(-c3ccc(OC(F)(F)F)cc3)n2)cc1] |
| A118 | 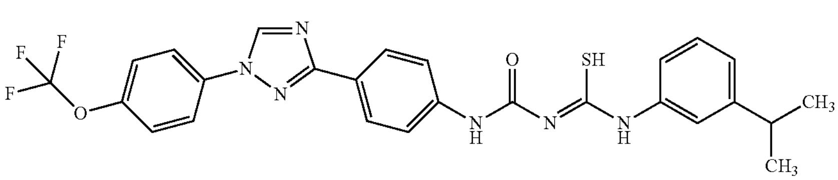 [SMILES: CC(C)c1cccc(N/C(S)=N/C(=O)Nc2ccc(-c3ncn(-c4ccc(OC(F)(F)F)cc4)n3)cc2)c1] |
| A119 | 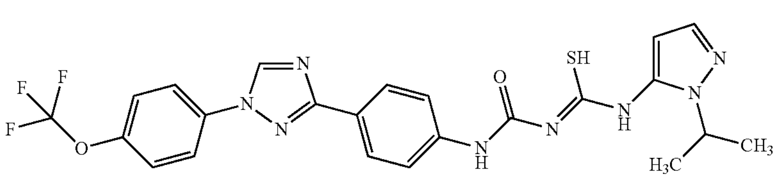 [SMILES: CC(C)n1nccc1N/C(S)=N/C(=O)Nc1ccc(-c2ncn(-c3ccc(OC(F)(F)F)cc3)n2)cc1] |

TABLE 1-continued

Structure for Compounds

| No. | Structure |
|---|---|
| A120 | 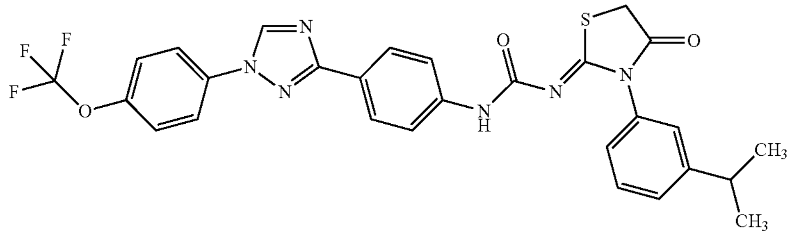 [SMILES: CC(C)c1cccc(N2C(=O)CS/C2=N\C(=O)Nc2ccc(-c3ncn(-c4ccc(OC(F)(F)F)cc4)n3)cc2)c1] |
| A121 | 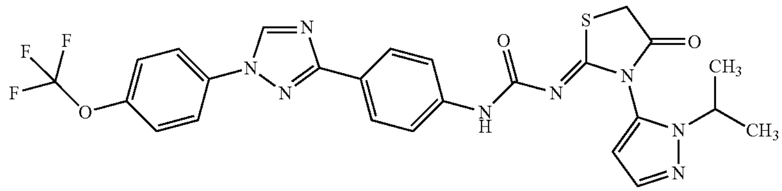 [SMILES: CC(C)n1nccc1N1C(=O)CS/C1=N\C(=O)Nc1ccc(-c2ncn(-c3ccc(OC(F)(F)F)cc3)n2)cc1] |
| A112 | 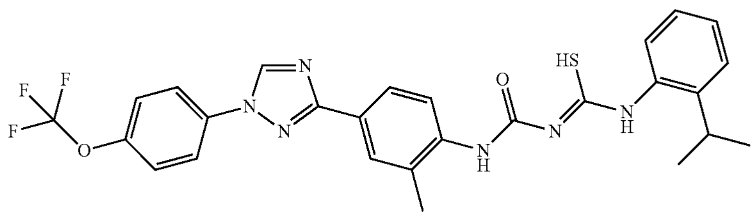 [SMILES: Cc1cc(-c2ncn(-c3ccc(OC(F)(F)F)cc3)n2)ccc1NC(=O)/N=C(\S)Nc1ccccc1C(C)C] |
| A123 | 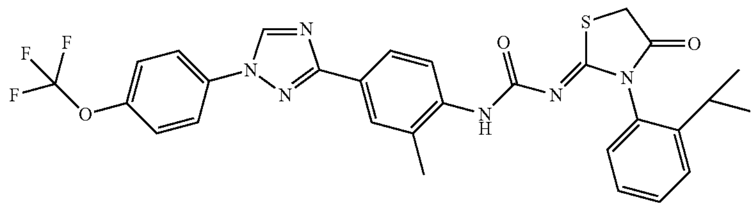 [SMILES: Cc1cc(-c2ncn(-c3ccc(OC(F)(F)F)cc3)n2)ccc1NC(=O)/N=C1\SCC(=O)N1c1ccccc1C(C)C] |
| A124 | 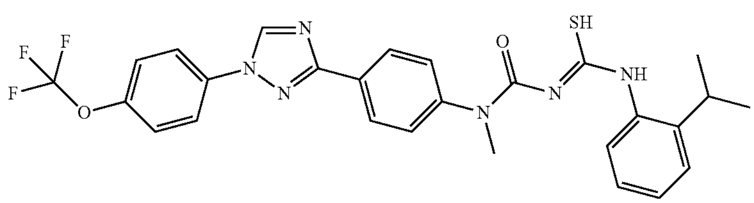 [SMILES: CC(C)c1ccccc1N/C(S)=N/C(=O)N(C)c1ccc(-c2ncn(-c3ccc(OC(F)(F)F)cc3)n2)cc1] |
| A125 | 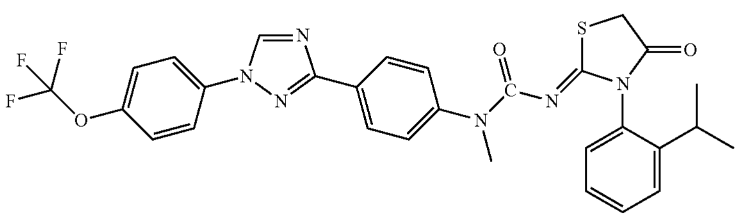 [SMILES: CC(C)c1ccccc1N1C(=O)CS/C1=N\C(=O)N(C)c1ccc(-c2ncn(-c3ccc(OC(F)(F)F)cc3)n2)cc1] |

TABLE 2

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| A1 | | 160-164 | 627 (M + H) | 11.24 (s, 1H), 8.64 (s, 1H), 8.17 (d, J = 8.7 Hz, 2H), 7.92 (d, J = 8.4 Hz, | |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|-----|------------|-----------|-----------|-------------------|----------------------------------|
|     |            |           |           | 2H), 7.80 (d, J = 8.5 Hz, 2H), 7.67 (d, J = 8.7 Hz, 2H), 7.41 (s, 1H), 7.12 (d, J = 8.6 Hz, 1H), 6.79 (d, J = 2.8 Hz, 1H), 6.74 (dd, J = 8.4, 3.1 Hz, 1H), 5.65 (s, 2H), 3.82 (s, 3H), 2.59 (heptet, J = 7.0 Hz, 1H), 2.27 (s, 3H), 1.18 (d, J = 7.0 Hz, 6H) | |
| A2 |            | 172-175   | 541 (M + 1) | 11.34 (s, 1H), 10.29 (s, 1H), 8.32 (s, 1H), 7.09 (d, J = 8.7 11.29 (s, 1H), 8.64 (s, 1H), 8.17 (d, J = 8.7 Hz, 2H), 7.92 (d, J = 8.5 Hz, 2H), 7.80 (d, J = 8.5 Hz, 2H), 7.66 (d, J = 8.7 Hz, 2H), 7.33 (s, 1H), 7.16 (d, J = 8.6 Hz, 1H), 6.80 (d, J = 2.9 Hz, 1H), 6.75 (dd, J = 8.6, 2.8 Hz, 1H), 3.82 (s, 3H), 2.38 (s, 3H), 2.30 (s, 3H) | |
| A3 |            | 173-176   | 611 (M + H) | 11.21 (s, 1H), 8.65 (s, 1H), 8.18 (d, J = 8.7 Hz, 2H), 7.92 (d, J = 8.4 Hz, 2H), 7.80 (d, J = 8.5 Hz, 2H), 7.68 (d, J = 8.7 Hz, 2H), 7.20 (m, 1H), 7.14-7.04 (m, 2H), 5.65 (s, 2H), 2.59 (heptet, J = 7.0 Hz, 1H), 2.29 (s, 6H), 1.18 (d, J = 7.0 Hz, 6H) | |
| A4 |            | 148-151   | 627 (M + 1) | 11.21 (s, 1H), 8.55 (s, 1H), 8.17 (d, J = 8.7 Hz, 2H), 7.81 (d, J = 8.7 Hz, 2H), 7.67 (d, J = 8.7 Hz, 2H), 7.42 (br s, 1H), 7.39 (d, J = 8.7 Hz, 2H), 7.21-7.10 (m, 3H), 5.65 (s, 2H), 2.67-2.52 (m, 1H), 2.29 (s, 6H), 1.18 (d, J = 7.0 Hz, 6H) | |
| A5 |            | 141-143   | 640       | 11.54 (s, 1H), 8.55 (d, J = 3.7 Hz, 1H), 8.16 (d, J = 8.6 Hz, 2H), 7.80 (d, J = 9.1 Hz, 2H), 7.67 (d, J = 8.6 Hz, 2H), 7.46-7.32 (m, 5H), 7.23-7.16 (m, 2H), 5.67 (s, 2H), 3.25-3.10 (m, 1H), 2.65-2.52 (m, 1H), 1.24 (d, J = 6.9 Hz, 6H), 1.17 (d, J = 7.0 Hz, 6H) | |
| A6 |            | 154-156   | 691 (M + 1) | 11.54 (s, 1H), 8.56 (d, J = 3.7 Hz, 1H), 8.17 (d, J = 8.7 Hz, 1H), 7.81 (d, J = 9.1 Hz, 1H), 7.67 (d, J = 8.7 Hz, 1H), 7.46-7.33 (m, 3H), 7.24-7.19 (m, 1H), 5.67 (s, 2H), 3.29-3.08 (m, 1H), 2.66-2.50 (m, 1H), 1.24 (d, J = 6.9 Hz, 3H), 1.17 (d, J = 7.0 Hz, 3H) | |
| A7 |            | 148-151   | 657 (M + 1) | 11.03 (s, 1H), 8.55 (s, 1H), 8.16 (d, J = 8.7 Hz, 2H), 7.80 (d, J = 9.1 Hz, 2H), 7.67 (d, J = 8.7 Hz, 2H), 7.39 (m, 3H), 6.64 (s, 2H), 5.64 (s, 2H), 3.80 (s, 3H), 2.59 (heptet, J = 7.0 Hz, 1H), 2.25 (s, 6H), 1.17 (d, J = 7.0 Hz, 6H) | |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| A8 | | 142-148 | 732 (M + 1) | 11.26 (s, 1H), 8.64 (s, 1H), 8.16 (d, J = 8.4 Hz, 2H), 7.91 (d, J = 8.2 Hz, 2H), 7.79 (d, J = 8.5 Hz, 2H), 7.71 (d, J = 8.1 Hz, 2H), 7.54 (s, 1H), 7.34 (m,, 5H), 7.15 (m, 3H), 5.69 (s, 2H), 5.23 (s, 1H), 5.13 (s, 2H), 4.02 (d, J = 5.7 Hz, 2H), 2.29 (s, 6H) | |
| A9 | | 142-148 | 778.5 (M + 1) | 11.07 (s, 1H), 8.55 (s, 1H), 8.15 (d, J = 8.5 Hz, 2H), 7.80 (d, J = 8.8 Hz, 2H), 7.70 (d, J = 8.4 Hz, 2H), 7.52 (d, J = 3.1 Hz, 1H), 7.44-7.31 (m, 7H), 6.64 (s, 2H), 5.67 (s, 2H), 5.23 (s, 1H), 5.12 (s, 2H), 4.02 (d, J = 5.8 Hz, 2H), 3.80 (s, 3H), 2.21 (s, 6H) | |
| A10 | | 128-132 | 777 (M + 1) | 11.19 (s, 1H), 8.56 (s, 1H), 8.15 (d, J = 8.4 Hz, 2H), 7.80 (J = 8.4 Hz, 2H), 7.66 (d, J = 8.5 Hz, 2H), 7.38 (d, J = 8.3 Hz, 2H), 7.14 (d, J = 8.6 Hz, 1H), 6.82-6.69 (m, 3H), 5.69 (s, 1H), 4.46 (d, J = 13.9 Hz, 1H), 4.05 (d, J = 13.9 Hz, 1H), 3.91 (dd, J = 9.3, 6.2 Hz, 1H), 3.81 (s, 3H), 3.67 (dd, J = 3.2, 1.5 Hz, 1H), 3.56 (s, 3H), 3.46 s, 3H), 3.44 (s, 3H), 3.38 (dd, J = 9.3, 3.3 Hz, 1H), 3.21 (t, J = 9.3 Hz, 1H), 2.29 (s, 3H), 1.32 (d, J = 6.1 Hz, 3H) | |
| A11 | | 233-235 | 527 (M + H) | 8.54 (s, 1H), 8.12 (d, J = 8.7 Hz, 2H), 7.79 (d, J = 9.1 Hz, 2H), 7.62 (d, J = 8.8 Hz, 2H), 7.44-7.29 (m, 4H), 7.22 (d, J = 7.5 Hz, 2H), 4.01 (s, 2H), 2.17 (s, 6H) | |
| A12 | | 204-212 | 511 (M + H) | 11.30 (s, 1H), 10.20 (s, 1H), 9.52 (s, 1H), 9.51 (s, 1H), 8.19 (d, J = 8.4 Hz, 2H), 8.11 (d, J = 8.7 Hz, 2H), 7.99 (d, J = 8.6 Hz, 2H), 7.62 (d, J = 8.8 Hz, 2H), 7.13 (m, 3H), 2.20 (s, 6H) | |
| A13 | | 300 (dec) | 525 (M + H) | (DMSO-d$_6$) δ 9.86 (s, 1H), 9.57 (s, 1H), 9.37 (d, J = 13.8 Hz, 2H), 8.15-7.98 (m, 4H), 7.74 (dd, J = 7.9, 1.5 Hz, 1H), 7.67-7.53 (m, 4H), 7.33 (dd, J = 7.5, 1.8 Hz, 1H), 7.24-7.06 (m, 2H), 3.20-2.99 (m, 1H), 1.22 (d, J = 6.8 Hz, 6H) | |
| A14 | | 190-196 | 567 (M + H) | 8.54 (s, 1H), 8.12 (d, J = 8.7 Hz, 2H), 7.79 (d, J = 9.1 Hz, 2H), 7.62 (d, J = 8.8 Hz, 2H), 7.44-7.29 (m, 4H), 7.22 (d, J = 7.5 Hz, 2H), 4.01 (s, 2H), 2.17 (s, 6H) | |
| A15 | | 145-150 | 553 (M + H) | 8.51 (s, 1H), 8.07 (d, J = 7.9 Hz, 2H), 7.81-7.74 (m, 2H), 7.59 (d, J = 6.8 Hz, 2H), 7.36 (d, J = 8.3 Hz, 2H), 7.19 (m, 3H), | |

TABLE 2-continued

Analytical Data for Compounds in Table 1.

| No. | Appearance | Mp (° C.) | ESIMS m/z | ¹H NMR (δ)[a] | ¹³C NMR or ¹⁹F NMR (δ) |
|---|---|---|---|---|---|
| | | | | 7.12 (s, 1H), 3.81 (t, J = 7.7 Hz, 2H), 3.37 (t, J = 7.6 Hz, 2H), 2.23 (s, 6H) | |
| A16 | | 121-125 | 567 (M + H) | 12.81 (s, 1H), 8.54 (s, 1H), 8.16-8.09 (m, 2H), 7.79 (d, J = 9.2 Hz, 2H), 7.63 (d, J = 8.8 Hz, 2H), 7.38 (d, J = 8.3 Hz, 2H), 7.18-6.96 (m, 3H), 4.22-4.09 (m, 2H), 3.00 (t, J = 6.9 Hz, 2H), 2.25-2.13 (m, 8H) | |
| A17 | | 105-115 | 567 (M + H) | 8.52 (s, 1H), 8.07 (d, J = 8.3 Hz, 2H), 7.83-7.73 (m, 2H), 7.59 (d, J = 8.2 Hz, 2H), 7.37 (d, J = 8.3 Hz, 2H), 7.20 (m, 4H), 4.24 (dd, J = 14.5, 6.6 Hz, 1H), 3.58-3.41 (m, 4H), 3.02 (dd, J = 11.0, 8.6 Hz, 1H), 2.25 (s, 3H), 2.21 (s, 3H), 1.21 (d, J = 6.4 Hz, 3H) | |
| A18 | | 169-177 | 594 (M + H) | 8.53 (s, 1H), 8.12 (d, J = 8.7 Hz, 2H), 7.81-7.74 (m, 2H), 7.63-7.56 (m, 2H), 7.52 (m, 1H), 7.45 (d, J = 7.9 Hz, 1H), 7.41-7.32 (m, 3H), 7.28 (s, 1H), 7.11 (d, J = 7.9 Hz, 1H), 4.03-3.95 (m, 2H), 2.43 (dd, J = 13.5, 6.8 Hz, 1H), 1.73-1.56 (m, 2H), 1.20 (overlapping d, J = 7.6 Hz, 3H), 0.78 (overlapping t, J = 7.4 Hz, 3H) | |
| A19 | | 180-183 | 581 (M + H) | 8.53 (s, 1H), 8.12 (d, J = 8.7 Hz, 2H), 7.80-7.74 (m, 2H), 7.60 (d, J = 8.8 Hz, 2H), 7.54-7.45 (m, 2H), 7.40-7.34 (m, 3H), 7.32 (s, 1H), 7.10 (d, J = 7.5 Hz, 1H), 3.98 (d, J = 2.5 Hz, 2H), 2.73 (heptet, J = 6.9 Hz, 1H), 1.22 (dd, J = 6.8, 5.0 Hz, 6H) | |
| A20 | | 141-144 | 582 (M + H) | 15.35-14.58 (m, 1H), 10.93 (s, 1H), 8.57 (m, 3H), 8.31-8.11 (m, 6H), 7.71 (m, 12H), 7.56-7.30 (m, 15H), 5.35 (s, 1H), 3.02 (heptet, J = 6.9 Hz, 1H), 2.52 (s, 3H), 1.35-1.11 (m, 6H) | |
| A21 | | 173-178 | 540 (M + H) | 10.46 (s, 1H), 8.57 (s, 1H), 8.38 (s, 1H), 8.19 (d, J = 8.7 Hz, 2H), 7.80 (d, J = 9.1 Hz, 2H), 7.67 (d, J = 8.8 Hz, 2H), 7.47-7.31 (m, 6H), 4.10 (s, 2H), 3.04 (heptet, J = 6.7 Hz, 1H), 1.22 (d, J = 6.9 Hz, 6H) | |
| A22 | | | 511 (M + H) | 10.76 (s, 1H), 8.84 (s, 1H), 8.56 (s, 1H), 8.15-8.13 (d, J = 8.4 Hz, 2H), 7.81-7.74 (m, 3H), 7.66-7.33 (d, J = 8.4 Hz, 2H), 7.58-7.50 (m, 1H), 7.43-7.20 (m, 4H), 4.10 (s, 2H), 2.28 (s, 3H) | |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| A23 | | 178-182 | 526 (M + H) | 10.41 (s, 1H), 8.88 (s, 1H), 8.58 (s, 1H), 8.15 (d, J = 8.7 Hz, 2H), 7.85-7.76 (m, 2H), 7.65 (d, J = 8.7 Hz, 2H), 7.38 (d, J = 8.4 Hz, 2H), 7.22-6.99 (m, 3H), 4.14 (s, 2H), 2.22 (s, 6H) | |
| A24 | | 250 (dec) | 580 (M + H) | 8.53 (s, 1H), 8.13-8.07 (m, 2H), 7.81-7.76 (m, 2H), 7.61 (d, J = 8.6 Hz, 2H), 7.53 (d, J = 3.9 Hz, 2H), 7.42-7.33 (m, 2H), 7.23-7.16 (m, 1H), 7.13 (d, J = 7.7 Hz, 1H), 6.97 (s, 1H), 5.01 (s, 1H), 3.91 (s, 2H), 2.83-2.68 (m, 1H), 1.31-1.16 (m, 6H) | |
| A25 | | 159-162 | 565 (M + H) | 12.56 (s, 1H), 8.56 (s, 1H), 8.18 (d, J = 8.7 Hz, 2H), 7.85-7.77 (m, 2H), 7.68-7.60 (m, 3H), 7.45-7.36 (m, 4H), 7.32-7.27 (m, 1H), 7.20 (d, J = 7.7 Hz, 1H), 4.42 (s, 1H), 3.11 (heptet, J = 6.9 Hz, 1H), 1.26 (d, J = 6.9 Hz, 6H) | |
| A26 | | 174-177 | 567 (M + H) | 12.27 (s, 1H), 8.56 (s, 1H), 8.18 (d, J = 8.7 Hz, 2H), 7.80 (d, J = 9.1 Hz, 2H), 7.63 (d, J = 8.9 Hz, 2H), 7.61 (s, 1H), 7.39 (d, J = 8.3 Hz, 2H), 7.12 (d, J = 8.6 Hz, 1H), 6.92-6.73 (m, 2H), 4.40 (s, 1H), 3.83 (s, 3H), 2.28 (s, 3H) | |
| A27 | | 162-166 | 599 (M + H) | 12.52 (s, 1H), 8.55 (s, 1H), 8.15 (d, J = 8.6 Hz, 2H), 7.80 (m, 3H), 7.57-7.28 (m, 13H), 4.29 (s, 1H) | |
| A28 | | 196-199 | 551 (M + H) | 12.24 (s, 1H), 8.56 (s, 1H), 8.18 (d, J = 8.8 Hz, 2H), 7.80 (d, J = 9.1 Hz, 2H), 7.64 (d, J = 8.7 Hz, 2H), 7.42-7.33 (m, 2H), 7.23 (m, 1H), 7.17 (d, J = 7.7 Hz, 2H), 4.30 (s, 1H), 2.28 (s, 6H) | |
| A29 | | 157-160 | 537 (M + H) | 12.51 (s, 1H), 8.56 (2, 1H), 8.18 (d, J = 8.8 Hz, 2H), 7.84-7.73 (m, 2H), 7.67-7.60 (m, 3H), 7.39 (d, J = 8.3 Hz, 2H), 7.32 (m, 3H), 7.23 (m, 1H), 4.42 (s, 1H), 2.33 (s, 3H) | |
| A30 | | 135-142 | 559 (M + H) | 12.31 (s, 1H), 8.64-8.50 (m, 1H), 8.19 (dd, J = 13.9, 7.1 Hz, 2H), 7.80 (m, 2H), 7.65 (m, 2H), 7.39 (m, 3H), 7.14-6.86 (m, 3H), 4.97-4.11 (m, 1H) | |
| A31 | | 250-255 | 605 (M + H) | 8.55 (s, 1H), 8.16 (d, J = 8.8 Hz, 2H), 7.95 (s, 1H), 7.79 (d, J = 9.1 Hz, 2H), 7.62 (d, J = 8.8 Hz, 3H), 7.53 (dd, J = 7.8, 1.2 Hz, 1H), 7.42-7.34 (m, 3H), 7.18 (dd, J = 7.9, 1.2 Hz, 1H), 3.92 (d, J = 1.3 Hz, 2H), 2.71 (heptet, J = 6.8 Hz, 1H), 1.33 (d, J = 6.9 | |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| A32 | | | 509 (M + H) | Hz, 3H), 1.23 (d, J = 6.8 Hz, 3H)<br>10.53 (s, 1H), 9.71 (s, 1H), 8.55 (s, 1H), 8.13 (m, 3H), 7.79 (d, J = 9.1 Hz, 2H), 7.71 (d, J = 8.7 Hz, 1H), 7.65 (d, J = 8.7 Hz, 1H), 7.37 (d, J = 8.3 Hz, 2H), 7.12 (m, 1H), 3.49 (s, 2H), 3.12 (s, 3H), 3.04 (s, 3H) | |
| A33 | | 168-171 | 525 (M + H) | 10.39 (s, 1H), 9.48 (s, 1H), 9.38 (s, 1H), 8.07 (d, J = 8.9 Hz, 4H), 7.77 (d, J = 8.8 Hz, 2H), 7.62 (d, J = 8.3 Hz, 2H), 7.28 (d, J = 8.7 Hz, 1H), 6.81 (d, J = 2.8 Hz, 1H), 6.74 (dd, J = 8.7, 2.9 Hz, 1H), 3.73 (s, 3H), 3.51 (s, 2H), 2.21 (s, 3H) | |
| A34 | | | 553 (M + H) | 9.81 (s, 1H), 8.92 (s, 1H), 8.58 (s, 1H), 8.12 (d, J = 8.6 Hz, 2H), 7.79 (d, J = 9.0 Hz, 2H), 7.69 (d, J = 8.7 Hz, 2H), 7.50-7.10 (m, 3H), 6.84 (d, J = 2.8 Hz, 1H), 6.72 (dd, J = 8.7, 2.9 Hz, 1H), 4.02 (s, 3H), 3.80 (s, 2H), 3.08 (dt, J = 13.6, 6.8 Hz, 1H), 1.20 (d, J = 6.9 Hz, 6H) | $^{13}$C NMR (101 MHz, CDCl3) δ 166.81, 166.13, 162.98, 158.40, 144.30, 141.54, 139.02, 135.54, 127.30, 127.05, 126.87, 126.52, 126.30, 122.36, 121.13, 120.10, 111.97, 110.85 56.04, 55.36, 44.26, 28.37, 23.06 |
| A35 | | | 567 (M + 1) | 8.53 (s, 1H), 8.13-8.07 (m, 2H), 7.80-7.74 (m, 2H), 7.63-7.55 (m, 2H), 7.49 (d, J = 4.5 Hz, 1H), 7.48-7.41 (m, 2H), 7.38-7.35 (m, 3H), 7.12 (dd, J = 7.8, 1.2 Hz, 1H), 3.97 (d, J = 2.0 Hz, 2H), 2.49 (q, J = 7.6 Hz, 2H), 1.20 (t, J = 7.6 Hz, 3H) | $^{19}$F NMR (376 MHz, CDCl$_3$) δ −58.02 (s) |
| A36 | | 262-266 | 581 (M + 1) | 8.53 (s, 1H), 8.12 (d, J = 8.7 Hz, 2H), 7.78 (d, J = 9.1 Hz, 2H), 7.61 (d, J = 8.8 Hz, 2H), 7.47 (s, 1H), 7.37 (d, J = 8.4 Hz, 2H), 7.02 (s, 2H), 3.98 (s, 2H), 2.35 (s, 3H), 2.12 (s, 6H) | |
| A37 | | | 595 (M + 1) | 8.53 (s, 1H), 8.14-8.09 (m, 2H), 7.80-7.76 (m, 2H), 7.64-7.58 (m, 2H), 7.45 (s, 1H), 7.37 (d, J = 8.3 Hz, 2H), 7.01 (s, 2H), 4.15 (q, J = 7.3 Hz, 1H), 2.36 (s, 3H), 2.12 (s, 3H), 2.10 (s, 3H), 1.77 (d, J = 7.3 Hz, 3H) | $^{19}$F NMR (376 MHz, CDCl$_3$) δ −58.02 (s) |
| A38 | | | 595 (M + 1) | 8.51 (s, 1H), 8.06 (d, J = 8.1 Hz, 2H), 7.79-7.75 (m, 2H), 7.60 (t, J = 8.4 Hz, 2H), 7.36 (d, J = 8.4 Hz, 2H), 7.19 (s, 1H), 6.97 (d, J = 7.4 Hz, 2H), 3.95 (m, 1H), 3.45 (dd, J = 11.0, 7.3 Hz, 1H), 3.10-2.97 (m, 1H), 2.33 (s, 3H), 2.21 (s, 3H), 2.18 (s, 3H), 1.63-1.44 (m, 2H), 0.89 (m, 3H) | $^{19}$F NMR (376 MHz, CDCl$_3$) δ −58.03 (s) |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| A39 | | | 581 (M + 1) | 8.51 (s, 1H), 8.03 (s, 2H), 7.80-7.75 (m, 2H), 7.55 (s, 2H), 7.36 (d, J = 8.6 Hz, 2H), 7.15 (m, 3H), 6.86 (br s, 1H, NH), 3.33 (d, J = 9.7 Hz, 2H), 3.03-2.80 (m, 2H), 2.54 (dd, J = 10.1, 4.2 Hz, 1H), 2.24 (s, 6H), 1.17 (d, J = 6.6 Hz, 3H) | $^{19}$F NMR (376 MHz, CDCl3) δ −58.03 (s) |
| A40 | | | 581 (M + 1) | 12.37 (s, 1H), 8.54 (s, 1H), 8.13 (d, J = 4.8 Hz, 2H), 7.79 (d, J = 4.7 Hz, 2H), 7.64 (d, J = 4.8 Hz, 2H), 7.37 (dd, J = 4.6, 1.1 Hz, 2H), 6.93-6.92 (m, 2H), 5.26 (t, J = 6.5 Hz, 2H), 3.46 (d, J = 3.8 Hz, 1H), 2.30 (s, 3H), 1.26 (t, J = 7.1 Hz, 6H), 2.16-2.16 (m, 3H) | $^{19}$F NMR (376 MHz, CDCl3) δ −58.02 (s) |
| A41 | | | 595 (M + 1) | 8.51 (s, 1H), 8.02 (m, 2H), 7.81-7.74 (m, 3H), 7.56 (s, 1H), 7.36 (m, 3H), 6.94 (br s, 2H), 3.32 (m, 2H), 2.95 (dd, J = 3.7, 1.8 Hz, 1H), 2.87 (dd, J = 12.3, 10.4 Hz, 1H), 2.58-2.44 (m, 1H), 2.33 (s, 3H), 2.19 (s, 6H), 1.16 (d, J = 6.6 Hz, 3H) | $^{19}$F NMR (376 MHz, CDCl3) δ −58.03 (s) |
| A42 | | 190-200 | 565 (M + 1) | 8.55 (s, 1H), 8.21-8.12 (m, 2H), 7.88-7.66 (m, 4H), 7.41-7.35 (m, 2H), 7.30 (dd, J = 8.3, 6.7 Hz, 1H), 7.22 (d, J = 7.6 Hz, 2H), 6.36 (d, J = 1.0 Hz, 1H), 2.44 (s, 3H), 2.22 (s, 6H) | |
| A43 | | | 579 (M + 1) | 8.55 (s, 1H), 8.17 (d, J = 8.7 Hz, 2H), 7.85-7.68 (m, 4H), 7.37 (d, J = 8.3 Hz, 2H), 7.02 (s, 2H), 6.35 (d, J = 0.9 Hz, 1H), 2.43 (s, 3H), 2.34 (s, 3H), 2.17 (s, 6H) | $^{19}$F NMR (376 MHz, CDCl3) δ −58.01 (s) |
| A44 | | 239-246 | 597 (M + 1) | 8.57 (s, 1H), 8.55 (s, 1H), 8.14 (d, J = 8.8 Hz, 2H), 7.80 (d, J = 9.0 Hz, 2H), 7.63 (d, J = 8.8 Hz, 2H), 7.43-7.35 (m, 2H), 6.75 (s, 2H), 4.00 (s, 2H), 3.85 (s, 3H), 2.14 (s, 6H) | |
| A46 | white solid | 188-190 | 527 [(M + H)$^+$] | 8.57 (s, 1H), 8.17 (m, 1H), 7.81 (m, 2H), 7.61 (d, J = 30.5 Hz, 3H), 7.34 (m, 6H), 7.24 (m, 3H), 2.67 (qd, J = 7.5, 4.1 Hz, 2H), 1.23 (td, J = 7.5, 6.5 Hz, 3H) | $^{19}$F NMR (376 MHz, CDCl3) δ −58.03 |
| A48 | White Solid | 201-203 | | 8.57 (s, 1H), 8.16 (m, 2H), 7.80 (m, 3H), 7.56 (d, J = 8.3 Hz, 2H), 7.40 (ddt, J = 8.0, 6.7, 1.7 Hz, 2H), 7.28 (dt, J = 6.8, 1.8 Hz, 2H), 7.23 (m, 2H), 3.16 (dp, J = 16.4, 6.9 Hz, 3H), 1.22 (d, J = 6.9 Hz, 6H). | $^{19}$F NMR (376 MHz, CDCl3) δ −58.02 |
| A49 | | 190-193 | 541 (M + 1) | (DMSO-d$_6$) δ 11.23 (s, 1H), 10.18 (s, 1H), 9.57 (s, 1H), 9.39 (s, 1H), 8.15-7.95 (m, 4H), 7.62 (dd, J = 8.1, 6.0 Hz, 4H), 6.92 | |

TABLE 2-continued

Analytical Data for Compounds in Table 1.

| No. | Appearance | Mp (° C.) | ESIMS m/z | ¹H NMR (δ)ᵃ | ¹³C NMR or ¹⁹F NMR (δ) |
|---|---|---|---|---|---|
| | | | | (s, 2H), 2.25 (s, 3H), 2.15 (s, 6H) | |
| A50 | | 260 (dec) | 557 (M + 1) | 8.57 (s, 1H), 8.15 (d, J = 8.6 Hz, 2H), 7.85-7.76 (m, 2H), 7.52 (d, J = 8.4 Hz, 2H), 7.39 (d, J = 8.3 Hz, 2H), 6.69 (s, 2H), 3.82 (s, 3H), 2.26 (s, 6H) | |
| A51 | | 210-212 | 497 (M + 1) | (DMSO-d₆) δ 9.85 (s, 1H), 9.66 (s, 1H), 9.39 (s, 1H), 9.39 (s, 1H), 8.08 (t, J = 2.5 Hz, 2H), 8.06 (d, J = 3.0 Hz, 2H), 7.90 (d, J = 7.9 Hz, 1H), 7.65-7.59 (m, 4H), 7.26-7.14 (m, 2H), 7.03 (t, J = 7.4 Hz, 1H), 2.28 (s, 3H) | |
| A52 | | 245-255 | 511 (M + 1) | (DMSO-d₆) δ 9.82 (s, 1H), 9.63 (s, 1H), 9.44-9.35 (m, 2H), 8.18-8.06 (m, 5H), 7.86 (d, J = 7.0 Hz, 1H), 7.64-7.60 (m, 3H), 7.22 (dd, J = 19.2, 7.7 Hz, 2H), 7.10 (dd, J = 7.4, 1.2 Hz, 1H), 2.63 (d, J = 7.5 Hz, 2H), 1.19 (t, J = 7.5 Hz, 3H). | |
| A53 | | 231-233 | 527 (M + 1) | (DMSO-d₆) δ 10.71 (s, 1H), 10.34 (s, 1H), 10.13 (s, 1H), 9.39 (s, 1H), 8.08 (m, 4H), 7.70-7.57 (m, 4H), 7.26 (d, J = 8.7 Hz, 1H), 6.87 (d, J = 2.9 Hz, 1H), 6.81 (dd, J = 8.7, 2.9 Hz, 1H), 3.75 (s, 3H), 2.20 (s, 3H) | |
| A54 | | | 655 (M + 1) | 11.57 (s, 1H), 8.55 (s, 1H), 8.16 (d, J = 8.6 Hz, 2H), 7.82-7.78 (m, 2H), 7.70-7.64 (m, 2H), 7.46 (s, 1H), 7.42-7.35 (m, 4H), 7.30 (d, J = 7.3 Hz, 1H), 7.22 (d, J = 3.0 Hz, 1H), 5.67 (d, J = 4.1 Hz, 2H), 2.92 (d, J = 7.0 Hz, 1H), 2.69-2.50 (m, 1H), 1.63-1.55 (m, 2H), 1.26-1.16 (m, 9H), 0.83 (d, J = 7.4 Hz, 3H) | ¹⁹F NMR (376 MHz, CDCl3) δ −58.02 (s) |
| A55 | | | 641 (M + 1) | 8.56 (s, 1H), 8.16 (d, J = 8.9 Hz, 2H), 7.82-7.79 (m, 2H), 7.67 (d, J = 8.5 Hz, 2H), 7.43 (s, 1H), 7.39 (d, J = 8.4 Hz, 2H), 7.24 (d, J = 7.5 Hz, 1H), 7.16-7.10 (m, 3H), 5.65 (s, 2H), 2.62 (m, 3H), 2.29 (s, 3H), 1.22-1.15 (m, 9H) | |
| A56 | | 106-109 | 643 (M + 1) | 11.22 (s, 1H), 8.57 (s, 1H), 8.17-8.15 (m, 2H), 7.84-7.79 (m, 2H), 7.66 (d, J = 8.5 Hz, 2H), 7.41-7.37 (m, 2H), 7.12 (d, J = 8.6 Hz, 1H), 6.92-6.88 (m, 2H), 6.77 (d, J = 12.5 Hz, 1H), 5.65 (s, 2H), 3.82 (s, 3H), 2.58 (dq, J = 14.0, 7.0 Hz, 1H), 2.27 (s, 3H), 1.18 (d, J = 7.0 Hz, 6H) | |
| A57 | | 132-137 | 627 (M + 1) | 8.59 (s, 1H), 8.20-8.09 (m, 4H), 7.86-7.80 (d, J = 8.4 Hz, 2H), 7.65 (d, J = 8.6 Hz, 2H), 7.48 (s, | |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | 1H), 7.39 (d, J = 8.4 Hz, 2H), 7.30 (s, 1H), 7.23 (s, 1H), 6.97-6.84 (m, 2H), 5.67 (s, 2H), 2.63 (m, 2H), 1.24-1.17 (m, 9H) | |
| A58 | | | 668 (M + 1) | 11.23 (s, 1H), 8.56 (s, 1H), 8.46 (s, 1H), 8.17-8.13 (m, 3H), 7.80 (q, J = 3.7 Hz, 2H), 7.68-7.60 (m, 2H), 7.39-7.36 (m, 4H), 7.07 (t, J = 8.1 Hz, 1H), 5.48 (s, 2H), 2.77-2.62 (m, 1H), 1.27-1.24 (m, 6H) | |
| A59 | | 125-129 | 641 (M + 1) | (DMSO-d$_6$) 10.92 (s, 1H), 9.82 (s, 1H), 9.37 (s, 1H), 8.13-8.10 (m, 2H), 7.84 (s, 2H), 7.62 (d, J = 8.6 Hz, 2H), 6.97 (s, 2H), 6.91 (d, J = 8.8 Hz, 3H), 5.74 (s, 2H), 2.62-2.56 (m, 1H), 2.26 (s, 3H), 2.15 (s, 6H), 1.08-1.06 (m, 6H) | |
| A60 | | 120-125 | 613 (M + 1) | 8.57 (s, 1H), 8.14 (d, J = 8.6 Hz, 2H), 7.82-7.78 (m, 2H), 7.66 (d, J = 8.6 Hz, 2H), 7.54 (s, 1H), 7.38 (d, J = 8.5 Hz, 2H), 7.29 (t, J = 4.0 Hz, 1H), 7.23 (d, J = 2.6 Hz, 2H), 5.67 (s, 2H), 2.67-2.47 (m, 1H), 2.31 (s, 3H), 1.22-1.11 (m, 6H) | |
| A61 | | 165-170 | 635 (M + 1) | (DMSO-d$_6$) 9.37 (s, 1H), 8.06 (d, J = 9.1 Hz, 6H), 7.62 (d, J = 8.4 Hz, 4H), 7.19 (s, 3H), 5.78-5.66 (m, 1H), 5.62 (s, 2H), 2.67 (s, 1H), 1.06 (d, J = 7.0 Hz, 6H) | |
| A62 | | 155-157 | 629 (M + 1) | 8.55 (s, 1H), 8.16 (d, J = 8.7 Hz, 2H), 7.80 (d, J = 9.1 Hz, 2H), 7.66 (d, J = 8.6 Hz, 2H), 7.40 (s, 3H), 7.18 (d, J = 8.8 Hz, 2H), 6.90 (d, J = 8.9 Hz, 2H), 5.66 (s, 2H), 3.83 (s, 3H), 2.67-2.51 (m, 1H), 1.19 (d, J = 7.0 Hz, 6H) | |
| A63 | White Solid | 197 (dec) | 539 ([M + H]$^+$) | (DMSO-d$_6$) δ 12.03 (s, 1H), 10.21 (s, 1H), 9.56 (s, 1H), 9.39 (s, 1H), 8.13-8.03 (m, 4H), 7.79 (d, J = 7.1 Hz, 1H), 7.62 (t, J = 7.9 Hz, 4H), 7.28-7.16 (m, 2H), 7.09 (d, J = 7.0 Hz, 1H), 1.97-1.81 (m, 1H), 1.02-0.91 (m, 2H), 0.72-0.62 (m, 2H) | $^{19}$F NMR (376 MHz, DMSO-d$_6$) δ −56.96 |
| A64 | White Solid | 185 (dec) | 541 ([M + H]$^+$) | (DMSO-d$_6$) δ 11.78 (s, 1H), 10.21 (s, 1H), 9.54 (s, 1H), 9.39 (s, 1H), 8.16-7.98 (m, 4H), 7.68-7.52 (m, 5H), 7.36-7.17 (m, 3H), 2.59-2.52 (m, 2H), 1.67-1.43 (m, 2H), 0.91 (t, J = 7.3 Hz, 3H) | $^{19}$F NMR (376 MHz, DMSO-d$_6$) δ −56.96 |
| A65 | White Solid | 175-178 | 553 ([M + H]$^+$) | 8.53 (s, 1H), 8.12 (d, J = 8.6 Hz, 2H), 7.78 (d, J = 8.9 Hz, 2H), 7.61 (d, J = 8.6 Hz, 2H), 7.43-7.39 (m, 6H), 7.15 (d, J = 7.4 | $^{19}$F NMR (376 MHz, CDCl$_3$) δ −58.03 |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | Hz, 1H), 3.99 (s, 2H), 2.20 (s, 3H) | |
| A66 | White Solid | 178-181 | 579 ([M + H]$^+$) | 8.54 (s, 1H), 8.13 (d, J = 8.7 Hz, 2H), 7.81-7.75 (m, 2H), 7.61 (d, J = 8.8 Hz, 2H), 7.45 (t, J = 7.0 Hz, 1H), 7.36 (dd, J = 14.3, 6.6 Hz, 4H), 7.24-7.13 (m, 2H), 4.00 (s, 2H), 1.73 (dd, J = 11.3, 5.8 Hz, 1H), 0.91-0.85 (m, 2H), 0.74-0.59 (m, 2H) | $^{19}$F NMR (376 MHz, CDCl$_3$) δ −58.03 |
| A67 | Off-White Sticky Solid | | 555 ([M + H]$^+$) | (DMSO-d$_6$) δ 11.77 (s, 1H), 10.25 (s, 1H), 9.56 (s, 1H), 9.39 (s, 1H), 8.18-7.97 (m, 4H), 7.61 (dd, J = 11.2, 8.7 Hz, 4H), 7.53-7.38 (m, 1H), 7.38-7.21 (m, 3H), 1.36 (s, 9H) | $^{19}$F NMR (376 MHz, DMSO-d$_6$) δ −56.96 |
| A68 | White Solid | 201 (dec) | 525 ([M − H]$^−$) | (DMSO-d$_6$) δ 11.64 (s, 1H), 10.16 (s, 1H), 9.53 (s, 1H), 9.39 (s, 1H), 8.14-8.01 (m, 4H), 7.61 (dd, J = 12.1, 5.2 Hz, 4H), 7.44 (d, J = 8.0 Hz, 1H), 7.10 (s, 1H), 7.04 (d, J = 8.0 Hz, 1H), 2.29 (s, 3H), 2.21 (s, 3H) | $^{19}$F NMR (376 MHz, DMSO-d$_6$) δ −56.96 |
| A69 | White Solid | 144-147 | 581 ([M + H]$^+$) | 8.54 (s, 1H), 8.12 (d, J = 8.7 Hz, 2H), 7.79 (d, J = 9.0 Hz, 2H), 7.61 (d, J = 8.7 Hz, 2H), 7.42 (ddd, J = 24.5, 14.6, 6.9 Hz, 6H), 7.13 (d, J = 7.8 Hz, 1H), 3.99 (d, J = 2.5 Hz, 2H), 2.48-2.39 (m, 2H), 1.62 (dt, J = 15.4, 7.6 Hz, 2H), 0.94 (t, J = 7.3 Hz, 3H) | $^{19}$F NMR (376 MHz, CDCl$_3$) δ −58.03 |
| A70 | White Solid | 203 (dec) | 545 ([M − H]$^−$) | (DMSO-d$_6$) δ 11.42 (s, 1H), 10.32 (s, 1H), 9.51 (s, 1H), 9.39 (s, 1H), 8.08 (ddd, J = 10.2, 7.2, 5.0 Hz, 4H), 7.66-7.58 (m, 4H), 7.39 (t, J = 4.7 Hz, 1H), 7.27 (d, J = 5.4 Hz, 2H), 2.27 (s, 3H) | $^{19}$F NMR (376 MHz, DMSO-d$_6$) δ −56.96 |
| A71 | White Solid | 217 (dec) | 525 ([M − H]$^−$) | (DMSO-d$_6$) δ 11.64 (s, 1H), 10.17 (s, 1H), 9.54 (s, 1H), 9.39 (s, 1H), 8.14-8.03 (m, 4H), 7.62 (t, J = 7.7 Hz, 4H), 7.30 (t, J = 4.6 Hz, 1H), 7.13 (d, J = 4.8 Hz, 2H), 2.29 (s, 3H), 2.13 (s, 3H) | $^{19}$F NMR (376 MHz, DMSO-d$_6$) δ −56.96 |
| A72 | White Solid | 205 (dec) | 545 ([M − H]$^−$) | (DMSO-d$_6$) δ 11.81 (s, 1H), 10.28 (s, 1H), 9.53 (s, 1H), 9.38 (d, J = 4.6 Hz, 1H), 8.17-7.95 (m, 5H), 7.61 (dd, J = 11.2, 4.4 Hz, 4H), 7.38-7.21 (m, 2H), 2.24 (s, 3H) | $^{19}$F NMR (376 MHz, DMSO-d$_6$) δ −56.96 |
| A73 | White Solid | 195 (dec) | 545 ([M − H]$^−$) | (DMSO-d$_6$) δ 12.00 (s, 1H), 10.32 (s, 1H), 9.54 (s, 1H), 9.39 (s, 1H), 8.12-8.03 (m, 4H), 7.89 (d, J = 8.2 Hz, 1H), 7.61 (dd, J = 11.6, 4.7 Hz, 4H), 7.41 (d, J = 1.2 Hz, 1H), 7.21 (d, J = 8.3 Hz, 1H), 2.33 (s, 3H) | $^{19}$F NMR (376 MHz, DMSO-d$_6$) δ −56.96 |
| A74 | Tan Solid | 134 (dec) | 587 ([M + H]$^+$) | 8.54 (s, 1H), 8.13 (d, J = 8.7 Hz, 2H), 7.82-7.76 (m, 2H), 7.62 (d, J = 8.7 | $^{19}$F NMR (376 MHz, CDCl$_3$) δ −58.03 |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | Hz, 2H), 7.45-7.28 (m, 6H), 4.02 (d, J = 8.0 Hz, 2H), 2.24 (s, 3H) | |
| A75 | Pale Yellow Solid | 188-191 | 567 ([M + H]$^+$) | 8.54 (s, 1H), 8.12 (d, J = 8.7 Hz, 2H), 7.79 (d, J = 9.0 Hz, 2H), 7.61 (d, J = 8.7 Hz, 2H), 7.41-7.27 (m, 5H), 7.01 (d, J = 7.3 Hz, 1H), 3.99 (d, J = 1.3 Hz, 2H), 2.38 (s, 3H), 2.07 (s, 3H) | $^{19}$F NMR (376 MHz, CDCl$_3$) δ −58.03 |
| A76 | Yellow Powder | 134 (dec) | 587 ([M + H]$^+$) | 8.54 (s, 1H), 8.14 (d, J = 8.7 Hz, 2H), 7.79 (d, J = 9.0 Hz, 2H), 7.63 (d, J = 8.8 Hz, 2H), 7.37 (m, 5H), 7.18 (d, J = 2.1 Hz, 1H), 3.99 (s, 2H), 2.16 (s, 3H). | $^{19}$F NMR (376 MHz, CDCl$_3$) δ −58.03 |
| A77 | Yellow Solid | 184-186 | 587 ([M + H]$^+$) | 8.54 (s, 1H), 8.13 (d, J = 8.7 Hz, 2H), 7.79 (d, J = 9.0 Hz, 2H), 7.61 (d, J = 8.8 Hz, 2H), 7.46-7.35 (m, 3H), 7.32 (s, 1H), 7.25 (s, 1H), 7.18 (d, J = 8.0 Hz, 1H), 3.99 (q, J = 18.1 Hz, 2H), 2.45 (s, 3H) | $^{19}$F NMR (376 MHz, CDCl$_3$) δ −58.03 |
| A78 | White Solid | 211 (dec) | 565 ([M − H]$^−$) | (DMSO-d$_6$) δ 12.07 (s, 1H), 10.41 (s, 1H), 9.54 (s, 1H), 9.39 (s, 1H), 8.15-8.01 (m, 5H), 7.77 (d, J = 2.4 Hz, 1H), 7.62 (dd, J = 8.6, 6.9 Hz, 4H), 7.50 (dd, J = 8.7, 2.4 Hz, 1H) | $^{19}$F NMR (376 MHz, DMSO-d$_6$) δ −56.96 |
| A79 | White Solid | 225 (dec) | 531 ([M + H]$^+$) | (DMSO-d$_6$) δ 11.72 (s, 1H), 10.26 (s, 1H), 9.53 (s, 1H), 9.39 (s, 1H), 8.14-8.04 (m, 4H), 7.62 (dd, J = 8.4, 6.1 Hz, 4H), 7.41 (d, J = 8.0 Hz, 1H), 7.35-7.22 (m, 1H), 7.14 (t, J = 8.7 Hz, 1H), 2.15 (s, 3H) | $^{19}$F NMR (376 MHz, DMSO-d$_6$) δ −56.96, −115.93 |
| A80 | White Solid | 222 (dec) | 513 ([M + H]$^+$) | (DMSO-d$_6$) δ 11.71 (s, 1H), 10.17 (s, 1H), 9.52 (s, 1H), 9.37 (d, J = 0.9 Hz, 1H), 8.13-7.98 (m, 4H), 7.59 (dd, J = 8.4, 5.4 Hz, 5H), 7.33-7.14 (m, 3H), 2.24 (s, 3H) | |
| A81 | White Solid | 283 (dec) | 575 ([M]$^+$) | (DMSO-d$_6$) δ 11.42 (s, 1H), 10.34 (s, 1H), 9.52 (s, 1H), 9.39 (s, 1H), 8.13-8.03 (m, 4H), 7.67-7.57 (m, 4H), 7.43-7.33 (m, 3H), 3.06 (hept, J = 6.8 Hz, 1H), 1.24 (d, J = 6.9 Hz, 3H), 1.15 (d, J = 6.9 Hz, 3H) | |
| A82 | White Solid | | 559 ([M + H]$^+$) | (DMSO-d$_6$) δ 11.76 (s, 1H), 10.29 (s, 1H), 9.54 (s, 1H), 9.39 (s, 1H), 8.15-8.03 (m, 4H), 7.61 (ddt, J = 9.3, 6.9, 1.8 Hz, 4H), 7.45-7.35 (m, 2H), 7.15 (td, J = 8.5, 2.8 Hz, 1H), 3.04 (hept, J = 7.0 Hz, 1H), 1.23-1.16 (m, 6H) | $^{19}$F NMR (376 MHz, DMSO-d$_6$) δ −56.96, −116.95 |
| A83 | White Solid | | 555 ([M + H]$^+$) | (DMSO-d$_6$) δ 11.62 (s, 1H), 10.20 (s, 1H), 9.53 (s, 1H), 9.39 (s, 1H), 8.13-8.03 (m, 4H), 7.67-7.56 (m, 4H), 7.26 (d, J = 8.0 Hz, 1H), 7.21 (d, J = 1.8 Hz, 1H), 7.15-7.08 | $^{19}$F NMR (376 MHz, DMSO-d$_6$) δ −56.96 |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| A84 | White Solid | | 555 ([M + H]$^+$) | (m, 1H), 3.07-2.95 (m, 1H), 2.28 (s, 3H), 1.17 (d, J = 6.9 Hz, 6H) (DMSO-d$_6$) δ 11.58 (s, 1H), 10.18 (s, 1H), 9.53 (s, 1H), 9.39 (s, 1H), 8.13-8.02 (m, 4H), 7.67-7.55 (m, 4H), 7.26 (d, J = 8.0 Hz, 1H), 7.17 (d, J = 2.0 Hz, 1H), 7.09-7.01 (m, 1H), 3.01 (hept, J = 6.9 Hz, 1H), 2.32 (s, 3H), 1.18 (d, J = 6.9 Hz, 6H) | $^{19}$F NMR (376 MHz, DMSO-d$_6$) δ −56.96 |
| A85 | Light Yellow Solid | 179 (dec) | 616 ([M + H]$^+$) | 8.54 (s, 1H), 8.16-8.10 (m, 2H), 7.82-7.75 (m, 2H), 7.65-7.59 (m, 2H), 7.49-7.42 (m, 2H), 7.39 (ddd, J = 8.2, 5.4, 1.8 Hz, 3H), 7.31 (s, 1H), 4.05 (d, J = 18.1 Hz, 1H), 3.99 (d, J = 18.1 Hz, 1H), 2.77 (hept, J = 6.9 Hz, 1H), 1.22 (t, J = 6.8 Hz, 6H) | |
| A86 | Yellow Solid | 206-208 | 599 ([M + H]$^+$) | 8.54 (s, 1H), 8.17-8.09 (m, 2H), 7.82-7.75 (m, 2H), 7.66-7.57 (m, 2H), 7.46 (dd, J = 8.9, 5.9 Hz, 1H), 7.41-7.34 (m, 2H), 7.31 (s, 1H), 7.25-7.18 (m, 1H), 6.86 (dd, J = 8.6, 2.7 Hz, 1H), 4.05-3.99 (m, 1H), 3.99-3.94 (m, 1H), 2.68 (hept, J = 6.8 Hz, 1H), 1.20 (d, J = 6.8 Hz, 6H) | |
| A87 | Grey Solid | | 595 ([M + H]$^+$) | 8.54 (d, J = 1.1 Hz, 1H), 8.13 (d, J = 8.3 Hz, 2H), 7.82-7.76 (m, 2H), 7.61 (d, J = 8.3 Hz, 2H), 7.43-7.30 (m, 5H), 6.92 (s, 1H), 3.98 (d, J = 3.2 Hz, 2H), 2.75-2.61 (m, 1H), 2.39 (s, 3H), 1.20 (t, J = 6.6 Hz, 6H) | $^{19}$F NMR (376 MHz, CDCl$_3$) δ −58.03 |
| A88 | Light Yellow Solid | | 595 ([M + H]$^+$) | 8.53 (s, 1H), 8.15-8.09 (m, 2H), 7.81-7.75 (m, 2H), 7.63-7.57 (m, 2H), 7.41-7.32 (m, 3H), 7.29 (d, J = 1.9 Hz, 1H), 7.17 (dd, J = 8.3, 1.9 Hz, 1H), 6.99 (d, J = 8.0 Hz, 1H), 4.04-3.90 (m, 2H), 2.68 (hept, J = 6.9 Hz, 1H), 2.45 (s, 3H), 1.24-1.15 (m, 6H) | $^{19}$F NMR (376 MHz, CDCl$_3$) δ −58.03 |
| A89 | White Solid | 292 (dec) | 531 ([M + H]$^+$) | (DMSO-d$_6$) δ 11.96 (s, 1H), 10.31 (s, 1H), 9.53 (s, 1H), 9.39 (s, 1H), 8.18-8.00 (m, 4H), 7.87 (d, J = 5.7 Hz, 1H), 7.61 (dd, J = 11.6, 4.8 Hz, 4H), 7.21 (dd, J = 10.4, 8.5 Hz, 1H), 7.13 (d, J = 5.3 Hz, 1H), 2.31 (s, 3H) | $^{19}$F NMR (376 MHz, DMSO-d$_6$) δ −56.96, −128.73 |
| A92 | Pink Solid | 121 (dec) | 607 ([M])$^+$ | 8.54 (s, 1H), 8.14 (d, J = 8.7 Hz, 2H), 7.82-7.77 (m, 2H), 7.64-7.60 (m, 3H), 7.44 (dd, J = 8.5, 2.3 Hz, 1H), 7.38 (d, J = 8.4 Hz, 2H), 7.31 (s, 1H), 7.26-7.24 (s, 1H), 4.09-3.91 (m, 2H) | $^{19}$F NMR (376 MHz, CDCl$_3$) δ −58.03 |
| A93 | Off-White Solid | 138 (dec) | 571 ([M + H]$^+$) | 8.54 (s, 1H), 8.13 (d, J = 8.7 Hz, 2H), 7.81-7.76 (m, 2H), 7.62 (d, J = 8.8 | $^{19}$F NMR (376 MHz, CDCl$_3$) δ −58.03, −113.60 |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| | | | | Hz, 2H), 7.41-7.30 (m, 4H), 7.21 (t, J = 8.8 Hz, 1H), 7.01-6.96 (m, 1H), 4.00 (d, J = 1.1 Hz, 2H), 2.11 (d, J = 1.8 Hz, 3H) | |
| A94 | Off-White Powder | 168-172 | 571 ([M + H]$^+$) | 8.54 (s, 1H), 8.15-8.10 (m, 2H), 7.81-7.76 (m, 2H), 7.64-7.59 (m, 2H), 7.41-7.33 (m, 3H), 7.32-7.27 (m, 1H), 7.20-7.12 (m, 1H), 7.09 (dd, J = 6.8, 1.7 Hz, 1H), 4.08-3.90 (m, 2H), 2.41 (s, 3H) | $^{19}$F NMR (376 MHz, CDCl$_3$) δ −58.03, −124.58 |
| A95 | Off-White Oil | | 595 ([M + H]$^+$) | 8.54 (s, 1H), 8.12 (d, J = 8.7 Hz, 2H), 7.79 (d, J = 9.1 Hz, 2H), 7.64 (dd, J = 19.6, 8.5 Hz, 3H), 7.49 (dd, J = 15.0, 7.6 Hz, 1H), 7.41-7.32 (m, 4H), 7.01-6.91 (m, 1H), 3.93 (s, 2H), 1.35 (s, 9H) | $^{19}$F NMR (376 MHz, CDCl$_3$) δ −58.03 |
| A96 | White Powder | 219 (dec) | 590 ([M − H]$^−$) | (DMSO-d$_6$) δ 11.61 (s, 1H), 10.25 (s, 1H), 9.71 (s, 1H), 8.30-8.22 (m, 2H), 8.14 (d, J = 8.8 Hz, 2H), 7.71 (d, J = 8.8 Hz, 2H), 7.66 (d, J = 8.7 Hz, 2H), 7.39 (dd, J = 10.3, 3.9 Hz, 2H), 7.27 (ddd, J = 13.5, 10.6, 6.1 Hz, 2H), 3.07 (dt, J = 13.8, 6.8 Hz, 1H), 1.20 (d, J = 6.9 Hz, 6H) | $^{19}$F NMR (376 MHz, DMSO-d$_6$) δ −85.25, −86.89 |
| A97 | White Solid | 288 (dec) | 541 ([M + H]$^+$) | (DMSO-d$_6$) δ 11.35 (s, 1H), 10.21 (s, 1H), 9.52 (s, 1H), 9.39 (s, 1H), 8.17-7.98 (m, 4H), 7.62 (dd, J = 8.4, 5.5 Hz, 4H), 7.26-7.08 (m, 3H), 2.58-2.52 (m, 2H), 2.21 (s, 3H), 1.16 (t, J = 7.6 Hz, 3H) | $^{19}$F NMR (376 MHz, DMSO-d$_6$) δ −56.96 |
| A98 | White Solid | 275-280 | 541 ([M − H]$^−$) | (DMSO-d$_6$) δ 11.55 (s, 1H), 10.17 (s, 1H), 9.55 (s, 1H), 9.41 (s, 1H), 8.14-8.06 (m, 4H), 7.63 (dd, J = 12.3, 5.4 Hz, 4H), 7.41 (d, J = 8.7 Hz, 1H), 6.89 (d, J = 2.8 Hz, 1H), 6.82 (dd, J = 8.7, 2.9 Hz, 1H), 3.79 (s, 3H), 2.24 (s, 3H) | $^{19}$F NMR (376 MHz, DMSO-d$_6$) δ −56.96 |
| A99 | White Solid | 198 (dec) | 561 ([M − H]$^−$) | (DMSO-d$_6$) δ 12.46 (s, 1H), 10.25 (s, 1H), 9.52 (s, 1H), 9.39 (s, 1H), 8.75 (d, J = 2.6 Hz, 1H), 8.16-7.97 (m, 4H), 7.71-7.44 (m, 4H), 7.27 (dd, J = 8.8, 2.6 Hz, 1H), 7.16 (d, J = 8.9 Hz, 1H), 3.90 (s, 3H) | $^{19}$F NMR (376 MHz, DMSO-d$_6$) δ −56.96 |
| A100 | White Solid | 200 (dec) | 525 ([M − H]$^−$) | (DMSO-d$_6$) δ 12.05 (s, 1H), 10.11 (s, 1H), 9.54 (s, 1H), 9.39 (s, 1H), 8.14-8.01 (m, 4H), 7.61 (dd, J = 11.8, 5.0 Hz, 4H), 7.31 (s, 2H), 6.90 (s, 1H), 2.29 (s, 6H) | $^{19}$F NMR (376 MHz, DMSO-d$_6$) δ −56.96 |
| A101 | White Solid | 251 (dec) | 587 ([M − H]$^−$) | (DMSO-d$_6$) δ 11.68 (s, 1H), 10.19 (s, 1H), 9.51 (s, 1H), 9.39 (s, 1H), 8.14-8.01 (m, 4H), 7.60 (dd, J = 16.8, 8.6 Hz, 4H), 7.55-7.49 (m, 1H), 7.33- | $^{19}$F NMR (376 MHz, DMSO-d$_6$) δ −56.96 |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| A102 | Yellow Solid | 244-247 | 632 ([M + H]$^+$) | 7.15 (m, 8H), 3.97 (s, 2H) (DMSO-d$_6$) δ 8.21-8.15 (m, 2H), 8.06 (d, J = 8.8 Hz, 2H), 7.68 (d, J = 8.8 Hz, 2H), 7.56-7.49 (m, 2H), 7.38 (ddd, J = 10.0, 8.8, 3.9 Hz, 4H), 7.10 (d, J = 7.5 Hz, 1H), 4.01 (d, J = 2.8 Hz, 2H), 2.77-2.66 (m, 1H), 1.22 (dd, J = 6.8, 3.1 Hz, 6H) | $^{19}$F NMR (376 MHz, CDCl$_3$) δ −85.96, −87.77 |
| A103 | Off-White Solid | 145 (dec) | 581 ([M + H]$^+$) | (DMSO-d$_6$) δ 8.54 (s, 1H), 8.13 (d, J = 8.7 Hz, 2H), 7.82-7.76 (m, 2H), 7.62 (d, J = 8.7 Hz, 2H), 7.44 (dd, J = 8.9, 2.6 Hz, 1H), 7.40-7.34 (m, 3H), 7.22 (d, J = 2.6 Hz, 1H), 7.00 (d, J = 8.9 Hz, 1H), 3.96 (q, J = 18.0 Hz, 2H), 3.82 (s, 3H), 3.79-3.66 (m, 2H), 1.25 (t, J = 7.0 Hz, 3H) | $^{19}$F NMR (376 MHz, CDCl$_3$) δ −58.03 |
| A104 | Off-White Solid | 192 (dec) | 567 ([M + H]$^+$) | 8.54 (s, 1H), 8.13 (d, J = 8.7 Hz, 2H), 7.81-7.76 (m, 2H), 7.62 (d, J = 8.8 Hz, 2H), 7.38 (d, J = 8.2 Hz, 3H), 7.14 (s, 1H), 6.88 (s, 2H), 3.95 (s, 2H), 2.40 (s, 6H) | $^{19}$F NMR (376 MHz, CDCl$_3$) δ −58.03 |
| A105 | Off-White Solid | 140 (dec) | 629 ([M + H]$^+$) | 8.54 (s, 1H), 8.14 (d, J = 8.7 Hz, 2H), 7.82-7.76 (m, 2H), 7.61 (d, J = 8.8 Hz, 2H), 7.52-7.36 (m, 5H), 7.26-7.23 (m, 3H), 7.21-7.09 (m, 4H), 3.91 (d, J = 4.2 Hz, 2H), 3.75 (d, J = 17.9 Hz, 1H), 3.52 (d, J = 18.0 Hz, 1H) | $^{19}$F NMR (376 MHz, CDCl$_3$) δ −58.02 |
| A106 | White Solid | | 555 ([M + H]$^+$) | (DMSO-d$_6$) δ 11.62 (s, 1H), 10.21 (s, 1H), 9.55 (s, 1H), 9.38 (s, 1H), 8.14-7.96 (m, 4H), 7.61 (t, J = 9.3 Hz, 4H), 7.21-6.87 (m, 3H), 3.31-3.27 (m, 1H), 2.37 (s, 3H), 1.27 (d, J = 7.1 Hz, 6H) | $^{19}$F NMR (376 MHz, DMSO-d$_6$) δ −56.96. |
| A107 | White Solid | | 559 ([M + H]$^+$) | (DMSO-d$_6$) δ 11.56 (s, 1H), 10.27 (s, 1H), 9.52 (s, 1H), 9.39 (s, 1H), 8.14-8.02 (m, 4H), 7.67-7.56 (m, 4H), 7.28 (td, J = 8.1, 6.0 Hz, 1H), 7.18-7.08 (m, 2H), 3.13 (hept, J = 7.0 Hz, 1H), 1.30 (dd, J = 7.0, 1.3 Hz, 6H) | $^{19}$F NMR (376 MHz, DMSO-d$_6$) δ −56.96, −114.66 |
| A108 | Light Yellow Solid | | 595 ([M + H]$^+$) | 8.54 (s, 1H), 8.17-8.07 (m, 2H), 7.82-7.75 (m, 2H), 7.64-7.58 (m, 2H), 7.42-7.38 (m, 1H), 7.38-7.34 (m, 2H), 7.30 (dd, J = 7.4, 5.7 Hz, 2H), 6.94-6.86 (m, 1H), 4.03-3.92 (m, 2H), 3.08-2.95 (m, 1H), 2.53 (s, 3H), 1.32-1.27 (m, 6H) | $^{19}$F NMR (376 MHz, CDCl$_3$) δ −58.03 |
| A109 | White Solid | | 599 ([M + H]$^+$) | δ 8.54 (s, 1H), 8.17-8.10 (m, 2H), 7.82-7.75 (m, 2H), 7.66-7.58 (m, 2H), 7.41-7.36 (m, 2H), 7.36-7.30 (m, 2H), 7.24-7.16 (m, 1H), 6.91 (dd, J = 7.8, 1.1 Hz, 1H), 4.06-3.93 (m, 2H), 2.68 (hept, | $^{19}$F NMR (376 MHz, CDCl$_3$) δ −58.03, −111.63 |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| A110 | Yellow Solid | 138 (dec) | 581 ([M + H]$^+$) | J = 6.9 Hz, 1H), 1.37-1.28 (m, 6H) 8.54 (s, 1H), 8.13 (d, J = 8.7 Hz, 2H), 7.81-7.76 (m, 2H), 7.61 (d, J = 8.8 Hz, 2H), 7.38 (d, J = 9.2 Hz, 3H), 7.06 (d, J = 8.3 Hz, 1H), 6.92-6.85 (m, 2H), 3.97 (s, 2H), 3.86 (s, 3H), 2.16 (s, 3H). | $^{19}$F NMR (376 MHz, CDCl$_3$) δ −58.03 |
| A111 | Off-White Solid | 146 (dec) | 603 ([M]$^+$) | δ 8.54 (s, 1H), 8.13 (d, J = 8.7 Hz, 2H), 7.79 (d, J = 9.0 Hz, 2H), 7.63 (d, J = 8.8 Hz, 2H), 7.44 (dd, J = 8.9, 2.6 Hz, 1H), 7.42-7.32 (m, 3H), 7.22 (d, J = 2.6 Hz, 1H), 7.00 (d, J = 8.9 Hz, 1H), 3.96 (q, J = 18.0 Hz, 2H), 3.82 (s, 3H) | $^{19}$F NMR (376 MHz, CDCl$_3$) δ −58.03 |
| A112 | White Solid | 197 (dec) | 591 ([M + H]$^+$) | (DMSO-d$_6$) δ 11.67 (s, 1H), 10.22 (s, 1H), 9.54 (s, 1H), 9.40 (s, 1H), 8.13-8.05 (m, 4H), 7.62 (t, J = 8.6 Hz, 4H), 7.39 (t, J = 8.6 Hz, 2H), 7.31 (t, J = 6.9 Hz, 1H), 7.25 (dd, J = 10.5, 4.5 Hz, 1H), 3.13-2.96 (m, 1H), 1.20 (d, J = 6.9 Hz, 6H) | $^{19}$F NMR (376 MHz, DMSO-d$_6$) δ −85.18, −86.91 |
| A113 | Off-white Solid | 192 (dec) | 625 ([M + H]$^+$) | (DMSO-d$_6$) δ 11.67 (s, 1H), 10.22 (s, 1H), 9.55 (s, 1H), 9.53 (s, 1H), 8.22 (d, J = 8.8 Hz, 2H), 8.12 (d, J = 8.8 Hz, 2H), 7.94 (d, J = 8.8 Hz, 2H), 7.62 (d, J = 8.8 Hz, 2H), 7.39 (dd, J = 12.6, 4.7 Hz, 2H), 7.31 (t, J = 6.8 Hz, 1H), 7.27-7.21 (m, 1H), 3.06 (dt, J = 13.7, 6.8 Hz, 1H), 1.20 (d, J = 6.9 Hz, 6H) | $^{19}$F NMR (376 MHz, DMSO-d$_6$) δ −79.37, −79.40, −79.42, −110.35, −110.37, −125.95 |
| A114 | White Solid | 131 (dec) | 540 ([M + H]$^+$) | δ 11.98 (s, 1H), 10.56 (s, 1H), 8.16 (s, 1H), 7.93 (d, J = 2.5 Hz, 1H), 7.86 (d, J = 8.5 Hz, 2H), 7.83-7.76 (m, 2H), 7.47 (d, J = 7.9 Hz, 2H), 7.43-7.35 (m, 3H), 7.35-7.27 (m, 3H), 6.76 (d, J = 2.5 Hz, 1H), 3.15 (dt, J = 13.7, 6.8 Hz, 1H), 1.26 (d, J = 6.5 Hz, 6H) | $^{19}$F NMR (376 MHz, CDCl$_3$) δ −58.06 |
| A115 | Off-white Solid | 193-199 | 631 ([M + H]$^+$) | δ 8.55 (d, J = 3.8 Hz, 1H), 8.13 (d, J = 8.7 Hz, 2H), 7.83-7.77 (m, 2H), 7.61 (d, J = 8.8 Hz, 2H), 7.53-7.50 (m, 2H), 7.41-7.31 (m, 4H), 7.10 (d, J = 7.5 Hz, 1H), 4.00 (d, J = 2.5 Hz, 2H), 2.78-2.65 (m, 1H), 1.22 (dd, J = 6.8, 4.6 Hz, 6H) | $^{19}$F NMR (376 MHz, CDCl$_3$) δ −85.90, −87.85 |
| A116 | White Solid | | 559 ([M + H]$^+$) | (DMSO-d$_6$) δ 11.56 (s, 1H), 10.24 (s, 1H), 9.53 (s, 1H), 9.39 (s, 1H), 8.12-8.04 (m, 4H), 7.65-7.58 (m, 4H), 7.39 (dd, J = 8.8, 5.6 Hz, 1H), 7.19 (dd, J = 10.4, 3.0 Hz, 1H), 7.07 (td, J = 8.4, 3.0 Hz, 1H), 3.03 (hept, J = 7.1 Hz, 1H), 1.19 (d, J = 6.9 Hz, 6H) | $^{19}$F NMR (376 MHz, DMSO-d$_6$) δ −56.96, −114.07 |

TABLE 2-continued

Analytical Data for Compounds in Table 1.

| No. | Appearance | Mp (° C.) | ESIMS m/z | $^1$H NMR (δ)$^a$ | $^{13}$C NMR or $^{19}$F NMR (δ) |
|---|---|---|---|---|---|
| A117 | White Solid | | 599 ([M + H]$^+$) | 8.54 (s, 1H), 8.16-8.10 (m, 2H), 7.82-7.76 (m, 2H), 7.65-7.58 (m, 2H), 7.42-7.35 (m, 2H), 7.31 (s, 1H), 7.17 (dd, J = 9.9, 2.6 Hz, 1H), 7.12-7.01 (m, 2H), 4.05-3.91 (m, 2H), 2.76-2.61 (m, 1H), 1.24-1.17 (m, 6H) | $^{19}$F NMR (376 MHz, CDCl$_3$) δ −58.03, −110.25 |
| A118 | White Solid | | 541 ([M + H]$^+$) | (DMSO-d$_6$) δ 12.09 (s, 1H), 10.15 (s, 1H), 9.55 (s, 1H), 9.39 (s, 1H), 8.13-8.01 (m, 4H), 7.69-7.58 (m, 4H), 7.58-7.47 (m, 2H), 7.32 (t, J = 7.8 Hz, 1H), 7.14 (d, J = 7.7 Hz, 1H), 2.91 (hept, J = 6.9 Hz, 1H), 1.22 (d, J = 7.0 Hz, 6H) | $^{19}$F NMR (376 MHz, DMSO-d$_6$) δ −56.96 |
| A119 | White Solid | | 531 ([M + H]$^+$) | (DMSO-d$_6$) δ 11.58 (s, 1H), 10.46 (s, 1H), 9.52 (s, 1H), 9.39 (s, 1H), 8.14-8.03 (m, 4H), 7.67-7.56 (m, 4H), 7.45 (d, J = 1.9 Hz, 1H), 6.29 (d, J = 1.9 Hz, 1H), 4.39 (hept, J = 6.5 Hz, 1H), 1.39 (d, J = 6.6 Hz, 6H) | $^{19}$F NMR (376 MHz, DMSO-d$_6$) δ −56.96 |
| A120 | White Solid | | 581 ([M + H]$^+$) | 8.54 (d, J = 0.9 Hz, 1H), 8.13 (d, J = 8.5 Hz, 2H), 7.83-7.74 (m, 2H), 7.62 (d, J = 8.5 Hz, 2H), 7.47 (t, J = 7.7 Hz, 1H), 7.37 (dd, J = 10.6, 3.8 Hz, 4H), 7.14-7.06 (m, 2H), 3.97 (s, 2H), 3.00 (hept, J = 7.0 Hz, 1H), 1.31 (d, J = 6.9 Hz, 6H) | $^{19}$F NMR (376 MHz, CDCl$_3$) δ −58.03 |
| A121 | White Solid | | 571 ([M + H]$^+$) | 8.54 (s, 1H), 8.21-8.11 (m, 2H), 7.84-7.75 (m, 2H), 7.71 (d, J = 2.0 Hz, 1H), 7.68-7.59 (m, 2H), 7.38 (d, J = 7.8 Hz, 3H), 6.26 (d, J = 2.0 Hz, 1H), 4.00 (s, 2H), 3.78-3.67 (m, 1H), 1.52 (d, J = 6.6 Hz, 3H), 1.47 (d, J = 6.6 Hz, 3H) | $^{19}$F NMR (376 MHz, CDCl$_3$) δ −58.03 |
| A122 | White Solid | | 555 ([M + H]$^+$) | (DMSO-d$_6$) δ 11.74 (s, 1H), 10.71 (s, 1H), 9.39 (s, 1H), 8.83 (s, 1H), 8.13-8.04 (m, 2H), 8.04-7.88 (m, 3H), 7.68-7.56 (m, 2H), 7.47-7.35 (m, 2H), 7.35-7.27 (m, 1H), 7.27-7.21 (m, 1H), 3.06 (hept, J = 6.8 Hz, 1H), 2.37 (s, 3H), 1.19 (d, J = 6.8 Hz, 6H) | $^{19}$F NMR (376 MHz, DMSO-d$_6$) δ −56.97 |
| A123 | White Solid | | 595 ([M + H]$^+$) | 8.53 (s, 1H), 8.18 (d, J = 8.6 Hz, 1H), 8.06-8.01 (m, 1H), 7.98 (s, 1H), 7.82-7.76 (m, 2H), 7.53-7.48 (m, 2H), 7.41-7.34 (m, 3H), 7.13-7.06 (m, 2H), 3.99 (s, 2H), 2.73 (hept, J = 6.8 Hz, 1H), 2.25 (s, 3H), 1.27-1.22 (m, 6H) | $^{19}$F NMR (376 MHz, CDCl$_3$) δ −58.03 |
| A124 | Orange gummy oil | | 555 ([M + H]$^+$) | 12.03 (s, 1H), 8.60 (s, 1H), 8.36 (d, J = 8.7 Hz, 1H), 7.89 (s, 1H), 7.81 (d, J = 9.1 Hz, 1H), 7.52-7.48 (m, 1H), 7.46 (d, J = 8.7 Hz, 1H), 7.41 (dt, J = | |

TABLE 2-continued

Analytical Data for Compounds in Table 1.

| No. | Appearance | Mp (° C.) | ESIMS m/z | $^1$H NMR (δ)[a] | $^{13}$C NMR or $^{19}$F NMR (δ) |
|---|---|---|---|---|---|
| | | | | 7.9, 1.0 Hz, 2H), 7.36 (dd, J = 7.8, 1.7 Hz, 1H), 7.30 (td, J = 7.5, 1.5 Hz, 1H), 7.25-7.20 (m, 1H), 3.40 (s, 3H), 1.27 (d, J = 6.9 Hz, 6H) | |
| A125 | Yellow oil | | 595 ([M + H]$^+$) | 8.58 (s, 1H), 8.17 (s, 1H), 7.83 (d, J = 8.9 Hz, 2H), 7.73 (d, J = 8.1 Hz, 2H), 7.42 (d, J = 8.8 Hz, 3H), 7.22 (d, J = 7.6 Hz, 1H), 7.17-7.07 (m, 1H), 6.85 (dd, J = 28.9, 8.0 Hz, 2H), 3.95 (d, J = 2.5 Hz, 3H), 3.37 (s, 2H), 2.50 (d, J = 7.1 Hz, 1H), 1.05 (d, J = 6.9 Hz, 3H), 0.79 (d, J = 6.8 Hz, 3H | |

[a]All $^1$H NMR data measured in CDCl$_3$ at 400 MHz unless otherwise noted

Example A

Bioassays on Beet Armyworm ("BAW") and Corn Earworm ("CEW")

BAW has few effective parasites, diseases, or predators to lower its population. BAW infests many weeds, trees, grasses, legumes, and field crops. In various places, it is of economic concern upon asparagus, cotton, corn, soybeans, tobacco, alfalfa, sugar beets, peppers, tomatoes, potatoes, onions, peas, sunflowers, and citrus, among other plants. CEW is known to attack corn and tomatoes, but it also attacks artichoke, asparagus, cabbage, cantaloupe, collards, cowpeas, cucumbers, eggplant, lettuce, lima beans, melon, okra, peas, peppers, potatoes, pumpkin, snap beans, spinach, squash, sweet potatoes, and watermelon, among other plants. CEW is also known to be resistant to certain insecticides. Consequently, because of the above factors control of these pests is important. Furthermore, molecules that control these pests (BAW and CEW), which are known as chewing pests, are useful in controlling other pests that chew on plants.

Certain molecules disclosed in this document were tested against BAW and CEW using procedures described in the following examples. In the reporting of the results, the "BAW & CEW Rating Table" was used (See Table Section).
Bioassays on BAW (*Spodoptera exigua*)

Bioassays on BAW were conducted using a 128-well diet tray assay. one to five second instar BAW larvae were placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).
Bioassays on CEW (*Helicoverpa zea*)

Bioassays on CEW were conducted using a 128-well diet tray assay. one to five second instar CEW larvae were placed in each well (3 mL) of the diet tray that had been previously filled with 1 mL of artificial diet to which 50 μg/cm$^2$ of the test compound (dissolved in 50 μL of 90:10 acetone-water mixture) had been applied (to each of eight wells) and then allowed to dry. Trays were covered with a clear self-adhesive cover and held at 25° C., 14:10 light-dark for five to seven days. Percent mortality was recorded for the larvae in each well; activity in the eight wells was then averaged. The results are indicated in the table entitled "Table ABC: Biological Results" (See Table Section).

Example B

Bioassays on Green Peach Aphid ("GPA") (*Myzus persica*)

GPA is the most significant aphid pest of peach trees, causing decreased growth, shriveling of the leaves, and the death of various tissues. It is also hazardous because it acts as a vector for the transport of plant viruses, such as potato virus Y and potato leafroll virus to members of the night-shade/potato family Solanaceae, and various mosaic viruses to many other food crops. GPA attacks such plants as broccoli, burdock, cabbage, carrot, cauliflower, daikon, eggplant, green beans, lettuce, macadamia, *papaya*, peppers, sweet potatoes, tomatoes, watercress, and zucchini, among other plants. GPA also attacks many ornamental crops such as carnation, *chrysanthemum*, flowering white cabbage, poinsettia, and roses. GPA has developed resistance to many pesticides. Consequently, because of the above factors control of this pest is important. Furthermore, molecules that control this pest (GPA), which is known as a sucking pest, are useful in controlling other pests that suck on plants.

Certain molecules disclosed in this document were tested against GPA using procedures described in the following example. In the reporting of the results, the "GPA Rating Table" was used (See Table Section).

Cabbage seedlings grown in 3-inch pots, with 2-3 small (3-5 cm) true leaves, were used as test substrate. The seedlings were infested with 20-50 GPA (wingless adult and nymph stages) one day prior to chemical application. Four pots with individual seedlings were used for each treatment. Test compounds (2 mg) were dissolved in 2 mL of acetone/MeOH (1:1) solvent, forming stock solutions of 1000 ppm test compound. The stock solutions were diluted 5× with 0.025% Tween 20 in $H_2O$ to obtain the solution at 200 ppm test compound. A hand-held aspirator-type sprayer was used for spraying a solution to both sides of cabbage leaves until runoff. Reference plants (solvent check) were sprayed with the diluent only containing 20% by volume of acetone/ MeOH (1:1) solvent. Treated plants were held in a holding room for three days at approximately 25° C. and ambient relative humidity (RH) prior to grading. Evaluation was conducted by counting the number of live aphids per plant under a microscope. Percent Control was measured by using Abbott's correction formula (W. S. Abbott, "A Method of Computing the Effectiveness of an Insecticide" J. Econ. Entomol. 18 (1925), pp. 265-267) as follows.

Corrected % Control=$100*(X-Y)/X$ where

X=No. of live aphids on solvent check plants and
Y=No. of live aphids on treated plants
The results are indicated in the table entitled "Table ABC: Biological Results" (See Table Section).

Example C

Bioassays on Yellow Fever Mosquito "YFM"
(*Aedes aegypti*)

YFM prefers to feed on humans during the daytime and is most frequently found in or near human habitations. YFM is a vector for transmitting several diseases. It is a mosquito that can spread the dengue fever and yellow fever viruses. Yellow fever is the second most dangerous mosquito-borne disease after malaria. Yellow fever is an acute viral hemorrhagic disease and up to 50% of severely affected persons without treatment will die from yellow fever. There are an estimated 200,000 cases of yellow fever, causing 30,000 deaths, worldwide each year. Dengue fever is a nasty, viral disease; it is sometimes called "breakbone fever" or "breakheart fever" because of the intense pain it can produce. Dengue fever kills about 20,000 people annually. Consequently, because of the above factors control of this pest is important. Furthermore, molecules that control this pest (YFM), which is known as a sucking pest, are useful in controlling other pests that cause human and animal suffering.

Certain molecules disclosed in this document were tested against YFM using procedures described in the following paragraph. In the reporting of the results, the "YFM Rating Table" was used (See Table Section).

Master plates containing 400 µg of a molecule dissolved in 100 µL of dimethyl sulfoxide (DMSO) (equivalent to a 4000 ppm solution) are used. A master plate of assembled molecules contains 15 µL per well. To this plate, 135 µL of a 90:10 water:acetone mixture is added to each well. A robot (Biomek® NXP Laboratory Automation Workstation) is programmed to dispense 15 µL aspirations from the master plate into an empty 96-well shallow plate ("daughter" plate). There are 6 reps ("daughter" plates) created per master. The created daughter plates are then immediately infested with YFM larvae.

The day before plates are to be treated, mosquito eggs are placed in Millipore water containing liver powder to begin hatching (4 g. into 400 ml). After the daughter plates are created using the robot, they are infested with 220 µL of the liver powder/larval mosquito mixture (about 1 day-old larvae). After plates are infested with mosquito larvae, a non-evaporative lid is used to cover the plate to reduce drying. Plates are held at room temperature for 3 days prior to grading. After 3 days, each well is observed and scored based on mortality.

The results are indicated in the table entitled "Table ABC: Biological Results" (See Table Section).

Pesticidally Acceptable Acid Addition Salts, Salt Derivatives, Solvates, Ester Derivatives, Polymorphs, Isotopes and Radionuclides Molecules of Formula One may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, and magnesium.

Molecules of Formula One may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Molecules of Formula One may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula One may be made into ester derivatives. These ester derivatives can then be applied in the same manner as the molecules disclosed in this document is applied.

Molecules of Formula One may be made as various crystal polymorphs. Polymorphism is important in the development of agrochemicals since different crystal polymorphs or structures of the same molecule can have vastly different physical properties and biological performances.

Molecules of Formula One may be made with different isotopes. Of particular importance are molecules having $^2H$ (also known as deuterium) in place of $^1H$.

Molecules of Formula One may be made with different radionuclides. Of particular importance are molecules having $^{14}C$.

Stereoisomers

Molecules of Formula One may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures. Certain molecules disclosed in this document can exist as two or more isomers. The various isomers include geometric isomers, diastereomers, and enantiomers. Thus, the molecules disclosed in this document include geometric isomers, racemic mixtures, individual stereoisomers, and optically active mixtures. It will be appreciated by those skilled in the art that one isomer may be more active than the others. The structures disclosed in the present disclosure are drawn in only one geometric form for clarity, but are intended to represent all geometric forms of the molecule.

Combinations

Molecules of Formula One may also be used in combination (such as, in a compositional mixture, or a simultaneous or sequential application) with one or more compounds having acaricidal, algicidal, avicidal, bactericidal, fungicidal, herbicidal, insecticidal, molluscicidal, nematicidal, rodenticidal, or virucidal properties. Additionally, the molecules of Formula One may also be used in combination (such as, in a compositional mixture, or a simultaneous or sequential application) with compounds that are antifeedants, bird repellents, chemosterilants, herbicide safeners, insect attractants, insect repellents, mammal repellents, mating disrupters, plant activators, plant growth regulators, or synergists. Examples of such compounds in the above groups that may be used with the Molecules of Formula One are -(3-ethoxypropyl)mercury bromide, 1,2-dichloropropane, 1,3-dichloropropene, 1-methylcyclopropene, 1-naphthol, 2-(octylthio)ethanol, 2,3,5-tri-iodobenzoic acid, 2,3,6-TBA, 2,3,6-TBA-dimethylammonium, 2,3,6-TBA-lithium, 2,3,6-TBA-potassium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butometyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 2iP, 2-methoxyethylmercury chloride, 2-phenylphenol, 3,4-DA, 3,4-DB, 3,4-DP, 4-aminopyridine, 4-CPA, 4-CPA-potassium, 4-CPA-sodium, 4-CPB, 4-CPP, 4-hydroxyphenethyl alcohol, 8-hydroxyquinoline sulfate, 8-phenylmercurioxyquinoline, abamectin, abscisic acid, ACC, acephate, acequinocyl, acetamiprid, acethion, acetochlor, acetophos, acetoprole, acibenzolar, acibenzolar-S-methyl, acifluorfen, acifluorfen-methyl, acifluorfen-sodium, aclonifen, acrep, acrinathrin, acrolein, acrylonitrile, acypetacs, acypetacs-copper, acypetacs-zinc, alachlor, alanycarb, albendazole, aldicarb, aldimorph, aldoxycarb, aldrin, allethrin, allicin, allidochlor, allosamidin, alloxydim, alloxydim-sodium, allyl alcohol, allyxycarb, alorac, alpha-cypermethrin, alpha-endosulfan, ametoctradin, ametridione, ametryn, amibuzin, amicarbazone, amicarthiazol, amidithion, amidoflumet, amidosulfuron, aminocarb, aminocyclopyrachlor, aminocyclopyrachlor-methyl, aminocyclopyrachlor-potassium, aminopyralid, aminopyralid-potassium, aminopyralid-tris (2-hydroxypropyl)ammonium, amiprofos-methyl, amiprophos, amisulbrom, amiton, amiton oxalate, amitraz, amitrole, ammonium sulfamate, ammonium α-naphthaleneacetate, amobam, ampropylfos, anabasine, ancymidol, anilazine, anilofos, anisuron, anthraquinone, antu, apholate, aramite, arsenous oxide, asomate, aspirin, asulam, asulam-potassium, asulam-sodium, athidathion, atraton, atrazine, aureofungin, aviglycine, aviglycine hydrochloride, azaconazole, azadirachtin, azafenidin, azamethiphos, azimsulfuron, azinphos-ethyl, azinphos-methyl, aziprotryne, azithiram, azobenzene, azocyclotin, azothoate, azoxystrobin, bachmedesh, barban, barium hexafluorosilicate, barium polysulfide, barthrin, BCPC, beflubutamid, benalaxyl, benalaxyl-M, benazolin, benazolin-dimethylammonium, benazolin-ethyl, benazolin-potassium, bencarbazone, benclothiaz, bendiocarb, benfluralin, benfuracarb, benfuresate, benodanil, benomyl, benoxacor, benoxafos, benquinox, bensulfuron, bensulfuron-methyl, bensulide, bensultap, bentaluron, bentazone, bentazone-sodium, benthiavalicarb, benthiavalicarb-isopropyl, benthiazole, bentranil, benzadox, benzadox-ammonium, benzalkonium chloride, benzamacril, benzamacril-isobutyl, benzamorf, benzfendizone, benzipram, benzobicyclon, benzofenap, benzofluor, benzohydroxamic acid, benzoximate, benzoylprop, benzoylprop-ethyl, benzthiazuron, benzyl benzoate, benzyladenine, berberine, berberine chloride, beta-cyfluthrin, beta-cypermethrin, bethoxazin, bicyclopyrone, bifenazate, bifenox, bifenthrin, bifujunzhi, bilanafos, bilanafos-sodium, binapacryl, bingqingxiao, bioallethrin, bioethanomethrin, biopermethrin, bioresmethrin, biphenyl, bisazir, bismerthiazol, bispyribac, bispyribac-sodium, bistrifluron, bitertanol, bithionol, bixafen, blasticidin-S, borax, Bordeaux mixture, boric acid, boscalid, brassinolide, brassinolide-ethyl, brevicomin, brodifacoum, brofenvalerate, brofluthrinate, bromacil, bromacil-lithium, bromacil-sodium, bromadiolone, bromethalin, bromethrin, bromfenvinfos, bromoacetamide, bromobonil, bromobutide, bromocyclen, bromo-DDT, bromofenoxim, bromophos, bromophos-ethyl, bromopropylate, bromothalonil, bromoxynil, bromoxynil butyrate, bromoxynil heptanoate, bromoxynil octanoate, bromoxynil-potassium, brompyrazon, bromuconazole, bronopol, bucarpolate, bufencarb, buminafos, bupirimate, buprofezin, Burgundy mixture, busulfan, butacarb, butachlor, butafenacil, butamifos, butathiofos, butenachlor, butethrin, buthidazole, buthiobate, buthiuron, butocarboxim, butonate, butopyronoxyl, butoxycarboxim, butralin, butroxydim, buturon, butylamine, butylate, cacodylic acid, cadusafos, cafenstrole, calcium arsenate, calcium chlorate, calcium cyanamide, calcium polysulfide, calvinphos, cambendichlor, camphechlor, camphor, captafol, captan, carbamorph, carbanolate, carbaryl, carbasulam, carbendazim, carbendazim benzenesulfonate, carbendazim sulfite, carbetamide, carbofuran, carbon disulfide, carbon tetrachloride, carbophenothion, carbosulfan, carboxazole, carboxide, carboxin, carfentrazone, carfentrazone-ethyl, carpropamid, cartap, cartap hydrochloride, carvacrol, carvone, CDEA, cellocidin, CEPC, ceralure, Cheshunt mixture, chinomethionat, chitosan, chlobenthiazone, chlomethoxyfen, chloralose, chloramben, chloramben-ammonium, chloramben-diolamine, chloramben-methyl, chloramben-methylammonium, chloramben-sodium, chloramine phosphorus, chloramphenicol, chloraniformethan, chloranil, chloranocryl, chlorantraniliprole, chlorazifop, chlorazifop-propargyl, chlorazine, chlorbenside, chlorbenzuron, chlorbicyclen, chlorbromuron, chlorbufam, chlordane, chlordecone, chlordimeform, chlordimeform hydrochloride, chlorempenthrin, chlorethoxyfos, chloreturon, chlorfenac, chlorfenac-ammonium, chlorfenac-sodium, chlorfenapyr, chlorfenazole, chlorfenethol, chlorfenprop, chlorfenson, chlorfensulphide, chlorfenvinphos, chlorfluazuron, chlorflurazole, chlorfluren, chlorfluren-methyl, chlorflurenol, chlorflurenol-methyl, chloridazon, chlorimuron, chlorimuron-ethyl, chlormephos, chlormequat, chlormequat chloride, chlomidine, chlomitrofen, chlorobenzilate, chlorodinitronaphthalenes, chloroform, chloromebuform, chloromethiuron, chloroneb, chlorophacinone, chlorophacinone-sodium, chloropicrin, chloropon, chloropropylate, chlorothalonil, chlorotoluron, chloroxuron, chloroxynil, chlorphonium, chlorphonium chloride, chlorphoxim, chlorprazophos, chlorprocarb, chlorpropham, chlorpyrifos, chlorpyrifos-methyl, chlorquinox, chlorsulfuron, chlorthal, chlorthal-dimethyl, chlorthal-monomethyl, chlorthiamid, chlorthiophos, chlozolinate, choline chloride, chromafenozide, cinerin I, cinerin II, cinerins, cinidon-ethyl, cinmethylin, cinosulfuron, ciobutide, cisanilide, cismethrin, clethodim, climbazole, cliodinate, clodinafop, clodinafop-propargyl, cloethocarb, clofencet, clofencet-potassium, clofentezine, clofibric acid, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloquintocet, cloquintocet-mexyl, cloransulam, cloransulam-methyl, closantel, clothianidin, clotrimazole, cloxyfonac, cloxyfonac-sodium, CMA, codlelure, colophonate, copper acetate, copper acetoarsenite, copper arsenate, copper carbonate, basic, copper hydroxide, copper naphthenate, copper oleate, copper oxychloride, copper silicate, copper sulfate, copper zinc chromate, coumachlor, coumafuryl, coumaphos, coumatetralyl, coumithoate, coumoxystrobin, CPMC, CPMF, CPPC, credazine, cresol, crimidine, crotamiton, crotoxyphos, crufomate, cryolite, cue-lure, cufraneb, cumyluron, cuprobam, cuprous oxide, curcumenol, cyanamide, cyanatryn, cyanazine, cyanofenphos, cyanophos, cyanthoate, cyantraniliprole, cyazofamid, cybutryne, cyclafuramid, cyclanilide, cyclethrin, cycloate, cycloheximide, cycloprate, cycloprothrin, cyclosulfamuron, cycloxydim, cycluron, cyenopyrafen, cyflufenamid, cyflumetofen, cyfluthrin, cyhalofop, cyhalofop-butyl, cyhalothrin, cyhexatin, cymiazole, cymiazole hydrochloride, cymoxanil, cyometrinil, cypendazole, cypermethrin, cyperquat, cyperquat chloride, cyphenothrin, cyprazine, cyprazole, cyproconazole, cyprodinil, cyprofuram, cypromid, cyprosulfamide, cyromazine, cythioate, daimuron, dalapon, dalapon-calcium, dalapon-magnesium, dalapon-sodium, daminozide, dayoutong, dazomet, dazomet-sodium, DBCP, d-camphor, DCIP, DCPTA, DDT, debacarb, decafentin, decarbofuran, dehydroacetic acid, delachlor, deltamethrin, demephion, demephion-O, demephion-S, demeton, demeton-methyl, demeton-O, demeton-O-methyl, demeton-S, demeton-S-methyl, demeton-S-methylsulphon, desmedipham, desmetryn, d-fanshiluquebingjuzhi, diafenthiuron, dialifos, di-allate, diamidafos, diatomaceous earth, diazinon, dibutyl phthalate, dibutyl succinate, dicamba, dicamba-diglycolamine, dicamba-dimethylammonium, dicamba-diolamine, dicamba-isopropylammonium, dicamba-methyl, dicamba-olamine, dicamba-potassium, dicamba-sodium, dicamba-trolamine, dicapthon, dichlobenil, dichlofenthion, dichlofluanid, dichlone, dichloralurea, dichlorbenzuron, dichlorflurenol, dichlorflurenol-methyl, dichlormate, dichlormid, dichlorophen, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-2-ethylhexyl, dichlorprop-P-dimethylammonium, dichlorprop-potassium, dichlorprop-sodium, dichlorvos, dichlozoline, diclobutrazol, diclocymet, diclofop, diclofop-methyl, diclomezine, diclomezine-sodium, dicloran, diclosulam, dicofol, dicoumarol, dicresyl, dicrotophos, dicyclanil, dicyclonon, dieldrin, dienochlor, diethamquat, diethamquat dichloride, diethatyl, diethatyl-ethyl, diethofencarb, dietholate, diethyl pyrocarbonate, diethyltoluamide, difenacoum, difenoconazole, difenopenten, difenopenten-ethyl, difenoxuron, difenzoquat, difenzoquat metilsulfate, difethialone, diflovidazin, diflubenzuron, diflufenican, diflufenzopyr, diflufenzopyr-sodium, diflumetorim, dikegulac, dikegulac-sodium, dilor, dimatif, dimefluthrin, dimefox, dimefuron, dimepiperate, dimetachlone, dimetan, dimethacarb, dimethachlor, dimethametryn, dimethenamid, dimethenamid-P, dimethipin, dimethirimol, dimethoate, dimethomorph, dimethrin, dimethyl carbate, dimethyl phthalate, dimethylvinphos, dimetilan, dimexano, dimidazon, dimoxystrobin, dinex, dinex-diclexine, dingjunezuo, diniconazole, diniconazole-M, dinitramine, dinobuton, dinocap, dinocap-4, dinocap-6, dinocton, dinofenate, dinopenton, dinoprop, dinosam, dinoseb, dinoseb acetate, dinoseb-ammonium, dinoseb-diolamine, dinoseb-sodium, dinoseb-trolamine, dinosulfon, dinotefuran, dinoterb, dinoterb acetate, dinoterbon, diofenolan, dioxabenzofos, dioxacarb, dioxathion, diphacinone, diphacinone-sodium, diphenamid, diphenyl sulfone, diphenylamine, dipropalin, dipropetryn, dipyrithione, diquat, diquat dibromide, disparlure, disul, disulfiram, disulfoton, disul-sodium, ditalimfos, dithianon, dithicrofos, dithioether, dithiopyr, diuron, d-limonene, DMPA, DNOC, DNOC-ammonium, DNOC-potassium, DNOC-sodium, dodemorph, dodemorph acetate, dodemorph benzoate, dodicin, dodicin hydrochloride, dodicin-sodium, dodine, dofenapyn, dominicalure, doramectin, drazoxolon, DSMA, dufulin, EBEP, EBP, ecdysterone, edifenphos, eglinazine, eglinazine-ethyl, emamectin, emamectin benzoate, EMPC, empenthrin, endosulfan, endothal, endothal-diammonium, endothal-dipotassium, endothal-disodium, endothion, endrin, enestroburin, EPN, epocholeone, epofenonane, epoxiconazole, eprinomectin, epronaz, EPTC, erbon, ergocalciferol, erlujixiancaoan, esdépalléthrine, esfenvalerate, esprocarb, etacelasil, etaconazole, etaphos, etem, ethaboxam, ethachlor, ethalfluralin, ethametsulfuron, ethametsulfuron-methyl, ethaprochlor, ethephon, ethidimuron, ethiofencarb, ethiolate, ethion, ethiozin, ethiprole, ethirimol, ethoate-methyl, ethofumesate, ethohexadiol, ethoprophos, ethoxyfen, ethoxyfen-ethyl, ethoxyquin, ethoxysulfuron, ethychlozate, ethyl formate, ethyl α-naphthaleneacetate, ethyl-DDD, ethylene, ethylene dibromide, ethylene dichloride, ethylene oxide, ethylicin, ethylmercury 2,3-dihydroxypropyl mercaptide, ethylmercury acetate, ethylmercury bromide, ethylmercury chloride, ethylmercury phosphate, etinofen, etnipromid, etobenzanid, etofenprox, etoxazole, etridiazole, etrimfos, eugenol, EXD, famoxadone, famphur, fenamidone, fenaminosulf, fenamiphos, fenapanil, fenarimol, fenasulam, fenazaflor, fenazaquin, fenbuconazole, fenbutatin oxide, fenchlorazole, fenchlorazole-ethyl, fenchlorphos, fenclorim, fenethacarb, fenfluthrin, fenfuram, fenhexamid, fenitropan, fenitrothion, fenjuntong, fenobucarb, fenoprop, fenoprop-3-butoxypropyl, fenoprop-butometyl, fenoprop-butotyl, fenoprop-butyl, fenoprop-isoctyl, fenoprop-methyl, fenoprop-potassium, fenothiocarb, fenoxacrim, fenoxanil, fenoxaprop, fenoxaprop-ethyl, fenoxaprop-P, fenoxaprop-P-ethyl, fenoxasulfone, fenoxycarb, fenpiclonil, fenpirithrin, fenpropathrin, fenpropidin, fenpropimorph, fenpyrazamine, fenpyroximate, fenridazon, fenridazon-potassium, fenridazon-propyl, fenson, fensulfothion, fenteracol, fenthiaprop, fenthiaprop-ethyl, fenthion, fenthion-ethyl, fentin, fentin acetate, fentin chloride, fentin hydroxide, fentrazamide, fentrifanil, fenuron, fenuron TCA, fenvalerate, ferbam, ferimzone, ferrous sulfate, fipronil, flamprop, flamprop-isopropyl, flamprop-M, flamprop-methyl, flamprop-M-isopropyl, flamprop-M-methyl, flazasulfuron, flocoumafen, flonicamid, florasulam, fluacrypyrim, fluazifop, fluazifop-butyl, fluazifop-methyl, fluazifop-P, fluazifop-P-butyl, fluazinam, fluazolate, fluazuron, flubendiamide, flubenzimine, flucarbazone, flucarbazone-sodium, flucetosulfuron, fluchloralin, flucofuron, flucycloxuron, flucythrinate, fludioxonil, fluenetil, fluensulfone, flufenacet, flufenerim, flufenican, flufenoxuron, flufenprox, flufenpyr, flufenpyr-ethyl, flufiprole, flumethrin, flumetover, flumetralin, flumetsulam, flumezin, flumiclorac, flumiclorac-pentyl, flumioxazin, flumipropyn, flumorph, fluometuron, fluopicolide, fluopyram, fluorbenside, fluoridamid, fluoroacetamide, fluorodifen, fluoroglycofen, fluoroglycofen-ethyl, fluoroimide, fluoromidine, fluoronitrofen, fluothiuron, fluotrimazole, fluoxastrobin, flupoxam, flupropacil, flupropadine, flupropanate, flupropanate-sodium, flupyrsulfuron, flupyrsulfuron-methyl, flupyrsulfuron-methyl-sodium, fluquinconazole, flurazole, flurenol, flurenol-butyl, flurenol-methyl, fluridone, flurochloridone, fluroxypyr, fluroxypyr-butometyl, fluroxypyr-meptyl, flurprimidol, flursulamid, flurtamone, flusilazole, flusulfamide, fluthiacet, fluthiacet-methyl, flutianil, flutolanil, flutriafol, fluvalinate, fluxapyroxad, fluxofenim, folpet, fomesafen, fomesafen-sodium, fonofos, foramsulfuron, forchlorfenuron, formaldehyde, formetanate, formetanate hydrochloride, formothion, formparanate, formparanate hydrochloride, fosamine, fosamine-ammonium, fosetyl, fosetyl-aluminium, fosmethilan, fospirate, fosthiazate, fosthietan, frontalin, fuberidazole, fucaojing, fucaomi, funaihecaoling, fuphenthiourea, furalane, furalaxyl, furamethrin, furametpyr, furathiocarb, furcarbanil, furconazole, furconazole-cis, furethrin, furfural, furilazole, furmecyclox, furophanate, furyloxyfen, gamma-cyhalothrin, gamma-HCH, genit, gibberellic acid, gibberellins, gliftor, glufosinate, glufosinate-ammonium, glufosinate-P, glufosinate-P-ammonium, glufosinate-P-sodium, glyodin, glyoxime, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, glyphosine, gossyplure, grandlure, griseofulvin, guazatine, guazatine acetates, halacrinate, halfenprox, halofenozide, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, HCH, hemel, hempa, HEOD, heptachlor, heptenophos, heptopargil, heterophos, hexachloroacetone, hexachlorobenzene, hexachlorobutadiene, hexachlorophene, hexaconazole, hexaflumuron, hexaflurate, hexalure, hexamide, hexazinone, hexylthiofos, hexythiazox, HHDN, holosulf, huancaiwo, huangcaoling, huanjunzuo, hydramethylnon, hydrargaphen, hydrated lime, hydrogen cyanide, hydroprene, hymexazol, hyquincarb, IAA, IBA, icaridin, imazalil, imazalil nitrate, imazalil sulfate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, imibenconazole, imicyafos, imidacloprid, imidaclothiz, iminoctadine, iminoctadine triacetate, iminoctadine trialbesilate, imiprothrin, inabenfide, indanofan, indaziflam, indoxacarb, inezin, iodobonil, iodocarb, iodomethane, iodosulfuron, iodosulfuron-methyl, iodosulfuron-methyl-sodium, ioxynil, ioxynil octanoate, ioxynil-lithium, ioxynil-sodium, ipazine, ipconazole, ipfencarbazone, iprobenfos, iprodione, iprovalicarb, iprymidam, ipsdienol, ipsenol, IPSP, isamidofos, isazofos, isobenzan, isocarbamid, isocarbophos, isocil, isodrin, isofenphos, isofenphos-methyl, isolan, isomethiozin, isonoruron, isopolinate, isoprocarb, isopropalin, isoprothiolane, isoproturon, isopyrazam, isopyrimol, isothioate, isotianil, isouron, isovaledione, isoxaben, isoxachlortole, isoxadifen, isoxadifen-ethyl, isoxaflutole, isoxapyrifop, isoxathion, ivermectin, izopamfos, japonilure, japothrins, jasmolin I, jasmolin II, jasmonic acid, jiahuangchongzong, jiajizengxiaolin, jiaxiangjunzhi, jiecaowan, jiecaoxi, jodfenphos, juvenile hormone I, juvenile hormone II, juvenile hormone III, kadethrin, karbutilate, karetazan, karetazan-potassium, kasugamycin, kasugamycin hydrochloride, kejunlin, kelevan, ketospiradox, ketospiradox-potassium, kinetin, kinoprene, kresoxim-methyl, kuicaoxi, lactofen, lambda-cyhalothrin, latilure, lead arsenate, lenacil, lepimectin, leptophos, lindane, lineatin, linuron, lirimfos, litlure, looplure, lufenuron, lvdingjunzhi, lvxiancaolin, lythidathion, MAA, malathion, maleic hydrazide, malonoben, maltodextrin, MAMA, mancopper, mancozeb, mandipropamid, maneb, matrine, mazidox, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mebenil, mecarbam, mecarbinzid, mecarphon, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-2-ethylhexyl, mecoprop-P-dimethylammonium, mecoprop-P-isobutyl, mecoprop-potassium, mecoprop-P-potassium, mecoprop-sodium, mecoprop-trolamine, medimeform, medinoterb, medinoterb acetate, medlure, mefenacet, mefenpyr, mefenpyr-diethyl, mefluidide, mefluidide-diolamine, mefluidide-potassium, megatomoic acid, menazon, mepanipyrim, meperfluthrin, mephenate, mephosfolan, mepiquat, mepiquat chloride, mepiquat pentaborate, mepronil, meptyldinocap, mercuric chloride, mercuric oxide, mercurous chloride, merphos, mesoprazine, mesosulfuron, mesosulfuron-methyl, mesotrione, mesulfen, mesulfenfos, metaflumizone, metalaxyl, metalaxyl-M, metaldehyde, metam, metam-ammonium, metamifop, metamitron, metam-potassium, metam-sodium, metazachlor, metazosulfuron, metazoxolon, metconazole, metepa, metflurazon, methabenzthiazuron, methacrifos, methalpropalin, methamidophos, methasulfocarb, methazole, methfuroxam, methidathion, methiobencarb, methiocarb, methiopyrisulfuron, methiotepa, methiozolin, methiuron, methocrotophos, methometon, methomyl, methoprene, methoprotryne, methoquin-butyl, methothrin, methoxychlor, methoxyfenozide, methoxyphenone, methyl apholate, methyl bromide, methyl eugenol, methyl iodide, methyl isothiocyanate, methylacetophos, methylchloroform, methyldymron, methylene chloride, methylmercury benzoate, methylmercury dicyandiamide, methylmercury pentachlorophenoxide, methylneodecanamide, metiram, metobenzuron, metobromuron, metofluthrin, metolachlor, metolcarb, metominostrobin, metosulam, metoxadiazone, metoxuron, metrafenone, metribuzin, metsulfovax, metsulfuron, metsulfuron-methyl, mevinphos, mexacarbate, mieshuan, milbemectin, milbemycin oxime, milneb, mipafox, mirex, MNAF, moguchun, molinate, molosultap, monalide, monisouron, monochloroacetic acid, monocrotophos, monolinuron, monosulfuron, monosulfuron-ester, monuron, monuron TCA, morfamquat, morfamquat dichloride, moroxydine, moroxydine hydrochloride, morphothion, morzid, moxidectin, MSMA, muscalure, myclobutanil, myclozolin, N-(ethylmercury)-p-toluenesulphonanilide, nabam, naftalofos, naled, naphthalene, naphthaleneacetamide, naphthalic anhydride, naphthoxyacetic acids, naproanilide, napropamide, naptalam, naptalam-sodium, natamycin, neburon, niclosamide, niclosamide-olamine, nicosulfuron, nicotine, niflurididе, nipyraclofen, nitenpyram, nithiazine, nitralin, nitrapyrin, nitrilacarb, nitrofen, nitrofluorfen, nitrostyrene, nitrothal-isopropyl, norbormide, norflurazon, nornicotine, noruron, novaluron, noviflumuron, nuarimol, OCH, octachlorodipropyl ether, octhilinone, ofurace, omethoate, orbencarb, orfralure, ortho-dichlorobenzene, orthosulfamuron, oryctalure, orysastrobin, oryzalin, osthol, ostramone, oxabetrinil, oxadiargyl, oxadiazon, oxadixyl, oxamate, oxamyl, oxapyrazon, oxapyrazon-dimolamine, oxapyrazon-sodium, oxasulfuron, oxaziclomefone, oxine-copper, oxolinic acid, oxpoconazole, oxpoconazole fumarate, oxycarboxin, oxydemeton-methyl, oxydeprofos, oxydisulfoton, oxyfluorfen, oxymatrine, oxytetracycline, oxytetracycline hydrochloride, paclobutrazol, paichongding, para-dichlorobenzene, parafluron, paraquat, paraquat dichloride, paraquat dimetilsulfate, parathion, parathion-methyl, parinol, pebulate, pefurazoate, pelargonic acid, penconazole, pencycuron, pendimethalin, penflufen, penfluron, penoxsulam, pentachlorophenol, pentanochlor, penthiopyrad, pentmethrin, pentoxazone, perfluidone, permethrin, pethoxamid, phenamacril, phenazine oxide, phenisopham, phenkapton, phenmedipham, phenmedipham-ethyl, phenobenzuron, phenothrin, phenproxide, phenthoate, phenylmercuriurea, phenylmercury acetate, phenylmercury chloride, phenylmercury derivative of pyrocatechol, phenylmercury nitrate, phenylmercury salicylate, phorate, phosacetim, phosalone, phosdiphen, phosfolan, phosfolan-methyl, phosglycin, phosmet, phosnichlor, phosphamidon, phosphine, phosphocarb, phosphorus, phostin, phoxim, phoxim-methyl, phthalide, picloram, picloram-2-ethylhexyl, picloram-isoctyl, picloram-methyl, picloram-olamine, picloram-potassium, picloram-triethylammonium, picloram-tris(2-hydroxypropyl)ammonium, picolinafen, picoxystrobin, pindone, pindone-sodium, pinoxaden, piperalin, piperonyl butoxide, piperonyl cyclonene, piperophos, piproctanyl, piproctanyl bromide, piprotal, pirimetaphos, pirimicarb, pirimioxyphos, pirimiphos-ethyl, pirimiphos-methyl, plifenate, polycarbamate, polyoxins, polyoxorim, polyoxorim-zinc, polythialan, potassium arsenite, potassium azide, potassium cyanate, potassium gibberellate, potassium naphthenate, potassium polysulfide, potassium thiocyanate, potassium a-naphthaleneacetate, pp'-DDT, prallethrin, precocene I, precocene II, precocene III, pretilachlor, primidophos, primisulfuron, primisulfuron-methyl, probenazole, prochloraz, prochloraz-manganese, proclonol, procyazine, procymidone, prodiamine, profenofos, profluazol, profluralin, profluthrin, profoxydim, proglinazine, proglinazine-ethyl, prohexadione, prohexadione-calcium, prohydrojasmon, promacyl, promecarb, prometon, prometryn, promurit, propachlor, propamidine, propamidine dihydrochloride, propamocarb, propamocarb hydrochloride, propanil, propaphos, propaquizafop, propargite, proparthrin, propazine, propetamphos, propham, propiconazole, propineb, propisochlor, propoxur, propoxycarbazone, propoxycarbazone-sodium, propyl isome, propyrisulfuron, propyzamide, proquinazid, prosuler, prosulfalin, prosulfocarb, prosulfuron, prothidathion, prothiocarb, prothiocarb hydrochloride, prothioconazole, prothiofos, prothoate, protrifenbute, proxan, proxan-sodium, prynachlor, pydanon, pymetrozine, pyracarbolid, pyraclofos, pyraclonil, pyraclostrobin, pyraflufen, pyraflufen-ethyl, pyrafluprole, pyramat, pyrametostrobin, pyraoxystrobin, pyrasulfotole, pyrazolynate, pyrazophos, pyrazosulfuron, pyrazosulfuron-ethyl, pyrazothion, pyrazoxyfen, pyresmethrin, pyrethrin I, pyrethrin II, pyrethrins, pyribambenz-isopropyl, pyribambenz-propyl, pyribencarb, pyribenzoxim, pyributicarb, pyriclor, pyridaben, pyridafol, pyridalyl, pyridaphenthion, pyridate, pyridinitril, pyrifenox, pyrifluquinazon, pyriftalid, pyrimethanil, pyrimidifen, pyriminobac, pyriminobac-methyl, pyrimisulfan, pyrimitate, pyrinuron, pyriofenone, pyriprole, pyripropanol, pyriproxyfen, pyrithiobac, pyrithiobac-sodium, pyrolan, pyroquilon, pyroxasulfone, pyroxsulam, pyroxychlor, pyroxyfur, quassia, quinacetol, quinacetol sulfate, quinalphos, quinalphos-methyl, quinazamid, quinclorac, quinconazole, quinmerac, quinoclamine, quinonamid, quinothion, quinoxyfen, quintiofos, quintozene, quizalofop, quizalofop-ethyl, quizalofop-P, quizalofop-P-ethyl, quizalofop-P-tefuryl, quwenzhi, quyingding, rabenzazole, rafoxanide, rebemide, resmethrin, rhodethanil, rhodojaponin-III, ribavirin, rimsulfuron, rotenone, ryania, saflufenacil, saijunmao, saisentong, salicylanilide, sanguinarine, santonin, schradan, scilliroside, sebuthylazine, secbumeton, sedaxane, selamectin, semiamitraz, semiamitraz chloride, sesamex, sesamolin, sethoxydim, shuangjiaancaolin, siduron, siglure, silafluofen, silatrane, silica gel, silthiofam, simazine, simeconazole, simeton, simetryn, sintofen, SMA, S-metolachlor, sodium arsenite, sodium azide, sodium chlorate, sodium fluoride, sodium fluoroacetate, sodium hexafluorosilicate, sodium naphthenate, sodium orthophenylphenoxide, sodium pentachlorophenoxide, sodium polysulfide, sodium thiocyanate, sodium a-naphthaleneacetate, sophamide, spinetoram, spinosad, spirodiclofen, spiromesifen, spirotetramat, spiroxamine, streptomycin, streptomycin sesquisulfate, strychnine, sulcatol, sulcofuron, sulcofuron-sodium, sulcotrione, sulfallate, sulfentrazone, sulfiram, sulfluramid, sulfometuron, sulfometuron-methyl, sulfosulfuron, sulfotep, sulfoxaflor, sulfoxide, sulfoxime, sulfur, sulfuric acid, sulfuryl fluoride, sulglycapin, sulprofos, sultropen, swep, tau-fluvalinate, tavron, tazimcarb, TCA, TCA-ammonium, TCA-calcium, TCA-ethadyl, TCA-magnesium, TCA-sodium, TDE, tebuconazole, tebufenozide, tebufenpyrad, tebufloquin, tebupirimfos, tebutam, tebuthiuron, tecloftalam, tecnazene, tecoram, teflubenzuron, tefluthrin, tefuryltrione, tembotrione, temephos, tepa, TEPP, tepraloxydim, terallethrin, terbacil, terbucarb, terbuchlor, terbufos, terbumeton, terbuthylazine, terbutryn, tetcyclacis, tetrachloroethane, tetrachlorvinphos, tetraconazole, tetradifon, tetrafluron, tetramethrin, tetramethylfluthrin, tetramine, tetranactin, tetrasul, thallium sulfate, thenylchlor, theta-cypermethrin, thiabendazole, thiacloprid, thiadifluor, thiamethoxam, thiapronil, thiazafluron, thiazopyr, thicrofos, thicyofen, thidiazimin, thidiazuron, thiencarbazone, thiencarbazone-methyl, thifensulfuron, thifensulfuron-methyl, thifluzamide, thiobencarb, thiocarboxime, thiochlorfenphim, thiocyclam, thiocyclam hydrochloride, thiocyclam oxalate, thiodiazole-copper, thiodicarb, thiofanox, thiofluoximate, thiohempa, thiomersal, thiometon, thionazin, thiophanate, thiophanate-methyl, thioquinox, thiosemicarbazide, thiosultap, thiosultap-diammonium, thiosultap-disodium, thiosultap-monosodium, thiotepa, thiram, thuringiensin, tiadinil, tiaojiean, tiocarbazil, tioclorim, tioxymid, tirpate, tolclofos-methyl, tolfenpyrad, tolylfluanid, tolylmercury acetate, topramezone, tralkoxydim, tralocythrin, tralomethrin, tralopyril, transfluthrin, transpermethrin, tretamine, triacontanol, triadimefon, triadimenol, triafamone, tri-allate, triamiphos, triapenthenol, triarathene, triarimol, triasulfuron, triazamate, triazbutil, triaziflam, triazophos, triazoxide, tribenuron, tribenuron-methyl, tribufos, tributyltin oxide, tricamba, trichlamide, trichlorfon, trichlormetaphos-3, trichloronat, triclopyr, triclopyr-butotyl, triclopyr-ethyl, triclopyr-triethylammonium, tricyclazole, tridemorph, tridiphane, trietazine, trifenmorph, trifenofos, trifloxystrobin, trifloxysulfuron, trifloxysulfuron-sodium, triflumizole, triflumuron, trifluralin, triflusulfuron, triflusulfuron-methyl, trifop, trifop-methyl, tripopsime, triforine, trihydroxytriazine, trimedlure, trimethacarb, trimeturon, trinexapac, trinexapac-ethyl, triprene, tripropindan, triptolide, tritac, triticonazole, tritosulfuron, trunc-call, uniconazole, uniconazole-P, urbacide, uredepa, valerate, validamycin, valifenalate, valone, vamidothion, vangard, vaniliprole, vernolate, vinclozolin, warfarin, warfarin-potassium, warfarin-sodium, xiaochongliulin, xinjunan, xiwojunan, XMC, xylachlor, xylenols, xylylcarb, yishijing, zarilamid, zeatin, zengxiaoan, zeta-cypermethrin, zinc naphthenate, zinc phosphide, zinc thiazole, zineb, ziram, zolaprofos, zoxamide, zuomihuanglong, α-chlorohydrin, α-ecdysone, α-multistriatin, and α-naphthaleneacetic acid. For more information consult the "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council, or its prior or more recent editions.

Biopesticides

Molecules of Formula One may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinernema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula One may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

Molecules of Formula One may also be used in combination (such as in a compositional mixture, or a simultaneous or sequential application) with one or more of the following:
1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl) hydrazone;
15. N-ethyl-2,2-dichloro-1-methylcyclopropane-carboxamide-2-(2,6-dichloro-α,α,α-trifluoro-p-tolyl) hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)]phenyl mesylate; and
20. N-Ethyl-2,2-dichloro-1-methylcyclopropanecarboxamide-2-(2,6-dichloro-alpha,alpha,alpha-trifluoro-p-tolyl) hydrazone.

Synergistic Mixtures

Molecules of Formula One may be used with certain active compounds to form synergistic mixtures where the mode of action of such compounds compared to the mode of action of the molecules of Formula One are the same, similar, or different. Examples of modes of action include, but are not limited to: acetylcholinesterase inhibitor; sodium channel modulator; chitin biosynthesis inhibitor; GABA and glutamate-gated chloride channel antagonist; GABA and glutamate-gated chloride channel agonist; acetylcholine receptor agonist; acetylcholine receptor antagonist; MET I inhibitor; Mg-stimulated ATPase inhibitor; nicotinic acetylcholine receptor; Midgut membrane disrupter; oxidative phosphorylation disrupter, and ryanodine receptor (RyRs). Generally, weight ratios of the molecules of Formula One in a synergistic mixture with another compound are from about 10:1 to about 1:10, in another embodiment from about 5:1 to about 1:5, and in another embodiment from about 3:1, and in another embodiment about 1:1.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph no 2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually selected from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula One are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula One may be used to control pests e.g. beetles, earwigs, cockroaches, flies, aphids, scales, whiteflies, leafhoppers, ants, wasps, termites, moths, butterflies, lice, grasshoppers, locusts, crickets, fleas, *thrips*, bristletails, mites, ticks, nematodes, and symphylans.

In another embodiment, the molecules of Formula One may be used to control pests in the Phyla Nematoda and/or Arthropoda.

In another embodiment, the molecules of Formula One may be used to control pests in the Subphyla Chelicerata, Myriapoda, and/or Hexapoda.

In another embodiment, the molecules of Formula One may be used to control pests in the Classes of Arachnida, Symphyla, and/or Insecta.

In another embodiment, the molecules of Formula One may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In another embodiment, the molecules of Formula One may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In another embodiment, the molecules of Formula One may be used to control pests of the Order Dermaptera.

In another embodiment, the molecules of Formula One may be used to control pests of the Order *Blattaria*. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*.

In another embodiment, the molecules of Formula One may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

In another embodiment, the molecules of Formula One may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus disperses, Aleurothrixus floccosus, Amrasca biguttula biguttula, Aonidiella aurantii, Aphis gossypii,*

*Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servos, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relatives, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis*, and *Zulia entrerriana*.

In another embodiment, the molecules of Formula One may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richteri, Solenopsis xyloni*, and *Tapinoma sessile*.

In another embodiment, the molecules of Formula One may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisitermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

In another embodiment, the molecules of Formula One may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectinophora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae*, and *Zeuzera pyrina*.

In another embodiment, the molecules of Formula One may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae*, and *Trichodectes canis*.

In another embodiment, the molecules of Formula One may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria*, and *Scudderia furcata*.

In another embodiment, the molecules of Formula One may be used to control pests of the Order Siphonaptera. A non-exhaustive list of particular species includes, but is not limited to, *Ceratophyllus gallinae, Ceratophyllus niger, Ctenocephalides canis, Ctenocephalides felis*, and *Pulex irritans*.

In another embodiment, the molecules of Formula One may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Franklin-*

*iella occidentalis, Frankliniella schultzei, Frankliniella williamsi, Heliothrips haemorrhoidalis, Rhipiphorothrips cruentatus, Scirtothrips citri, Scirtothrips dorsalis*, and *Taeniothrips rhopalantennalis, Thrips hawaiiensis, Thrips nigropilosus, Thrips orientalis, Thrips tabaci.*

In another embodiment, the molecules of Formula One may be used to control pests of the Order Thysanura. A non-exhaustive list of particular genera includes, but is not limited to, *Lepisma* spp. and *Thermobia* spp.

In another embodiment, the molecules of Formula One may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae*, and *Varroa destructor.*

In another embodiment, the molecules of Formula One may be used to control pest of the Order Symphyla. A non-exhaustive list of particular sp. includes, but is not limited to, *Scutigerella immaculata.*

In another embodiment, the molecules of Formula One may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis*, and *Rotylenchulus reniformis.*

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Molecules of Formula One are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred.

The area to which a molecule of Formula One is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula One include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use ammonium sulfate with a molecule of Formula One when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The molecules of Formula One may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also known as 1-MCP). Furthermore, such molecules may be used during times when pest activity is low, such as before the plants that are growing begin to produce valuable agricultural commodities. Such times include the early planting season when pest pressure is usually low.

The molecules of Formula One can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula One can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula One.

The molecules of Formula One can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula One may be desirable to control newly emerged larvae.

Systemic movement of pesticides in plants may be utilized to control pests on one portion of the plant by applying (for example by spraying an area) the molecules of Formula One to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula One may further enhance the ability of a plant to better withstand stressful growing conditions. This results in a healthier, more vigorous plant, which can lead to higher yields at harvest time. Generally, about 1 gram of the molecules of Formula One to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula One may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula One may be used for controlling endoparasites and ectoparasites in the veterinary medicine sector or in the field of non-human animal keeping. The molecules of Formula One are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula One may also be employed advantageously in livestock keeping, for example, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula One may also be used for controlling parasitic worms, especially of the intestine, in the animals listed above.

The molecules of Formula One may also be employed in therapeutic methods for human health care. Such methods include, but are limited to, oral administration in the form of, for example, tablets, capsules, drinks, granules, and by dermal application.

Pests around the world have been migrating to new environments (for such pest) and thereafter becoming a new invasive species in such new environment. The molecules of Formula One may also be used on such new invasive species to control them in such new environment.

The molecules of Formula One may also be used in an area where plants, such as crops, are growing (e.g. pre-planting, planting, pre-harvesting) and where there are low levels (even no actual presence) of pests that can commercially damage such plants. The use of such molecules in such area is to benefit the plants being grown in the area. Such benefits, may include, but are not limited to, improving the health of a plant, improving the yield of a plant (e.g. increased biomass and/or increased content of valuable ingredients), improving the vigor of a plant (e.g. improved plant growth and/or greener leaves), improving the quality of a plant (e.g. improved content or composition of certain ingredients), and improving the tolerance to abiotic and/or biotic stress of the plant.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

A molecule according to Formula One can be tested to determine its efficacy against pests. Furthermore, mode of action studies can be conducted to determine if said molecule has a different mode of action than other pesticides. Thereafter, such acquired data can be disseminated, such as by the internet, to third parties.

| TABLE SECTION | |
|---|---|
| % Control (or Mortality) | Rating |
| BAW & CEW Rating Table | |
| 50-100 | A |
| More than 0-Less than 50 | B |
| Not Tested | C |
| No activity noticed in this bioassay | D |
| GPA Rating Table | |
| 80-100 | A |
| More than 0-Less than 80 | B |
| Not Tested | C |
| No activity noticed in this bioassay | D |
| YFM Rating Table | |
| 80-100 | A |
| More than 0-Less than 80 | B |
| Not Tested | C |
| No activity noticed in this bioassay | D |

TABLE ABC

| Biological Results | | | | |
|---|---|---|---|---|
| Molecule # | Rating YFM | Rating CEW | Rating BAW | Rating GPA |
| A1 | C | A | A | D |
| A2 | C | A | A | D |
| A3 | A | A | A | D |
| A4 | A | A | A | B |
| A5 | C | A | A | C |
| A6 | C | A | A | D |
| A7 | C | A | A | B |
| A8 | C | A | A | C |
| A9 | C | A | A | B |
| A10 | C | A | A | C |
| A11 | C | A | A | B |
| A12 | C | A | A | D |
| A13 | C | A | A | C |
| A14 | A | A | A | B |
| A15 | A | A | A | D |
| A16 | C | C | C | C |
| A17 | C | C | C | C |
| A18 | A | A | A | C |
| A19 | C | A | A | C |
| A20 | C | A | A | D |
| A21 | C | A | A | C |
| A22 | C | A | A | D |
| A23 | C | A | A | C |
| A24 | C | A | A | C |
| A25 | C | B | D | C |
| A26 | C | D | D | C |
| A27 | C | B | D | C |

TABLE ABC-continued

Biological Results

| Molecule # | Rating YFM | Rating CEW | Rating BAW | Rating GPA |
|---|---|---|---|---|
| A28 | D | A | D | C |
| A29 | C | A | B | C |
| A30 | C | D | D | C |
| A31 | C | A | A | C |
| A32 | C | A | A | D |
| A33 | C | A | A | B |
| A34 | A | A | A | D |
| A35 | A | A | A | D |
| A36 | C | A | A | C |
| A37 | C | A | A | C |
| A38 | C | A | A | C |
| A39 | C | A | A | C |
| A40 | C | A** | A** | C |
| A41 | C | A | A | C |
| A42 | C | D | B | C |
| A43 | C | A | D | C |
| A44 | A | A | A | B |
| A46 | A | A | A | B |
| A48 | C | A | A | C |
| A49 | C | A | A | C |
| A50 | C | A | A | C |
| A51 | C | A | A | C |
| A52 | C | A | A | C |
| A53 | C | D | D | C |
| A54 | C | A | A | C |
| A55 | C | A | A | C |
| A56 | C | A | A | C |
| A57 | C | A | A | C |
| A58 | C | A | A | C |
| A59 | C | A | A | C |
| A60 | C | A | A | C |
| A61 | C | A | A | C |
| A62 | A | A | A | D |
| A63 | C | A* | A | C |
| A64 | C | A* | A | C |
| A65 | A | A* | A | C |
| A66 | C | C | A | C |
| A67 | C | A* | A | C |
| A68 | C | A* | A | C |
| A69 | A | A* | A | C |
| A70 | C | A* | A | C |
| A71 | C | C | A | C |
| A72 | C | A* | A | C |
| A73 | C | A* | A | C |
| A74 | C | A* | A | C |
| A75 | C | A* | A | C |
| A76 | C | A* | A | C |
| A77 | B | A* | A | C |
| A78 | C | C | D | C |
| A79 | C | A* | A | C |
| A80 | B | A | A | C |
| A81 | C | A | A | C |
| A82 | C | A* | A | C |
| A83 | C | C | A | C |
| A84 | C | A* | A | C |
| A85 | A | A* | A | C |
| A86 | C | A* | A | C |
| A87 | C | A* | A | C |
| A88 | C | A* | A | C |
| A89 | C | A* | A | C |
| A92 | C | A* | A | C |
| A93 | C | A* | A | C |
| A94 | C | A* | A | C |
| A95 | C | A* | C | C |
| A96 | C | D | A | C |
| A97 | C | A* | A | C |
| A98 | C | A* | A | C |
| A99 | C | C | D | C |
| A100 | C | A* | A | C |
| A101 | C | A* | A | C |
| A102 | C | A* | C | C |
| A103 | C | A* | A | C |
| A104 | C | A* | D | C |
| A105 | C | A* | A | C |
| A106 | C | A* | A | C |
| A107 | C | A* | A | C |
| A108 | C | A* | A | C |
| A109 | C | A* | A | C |
| A110 | A | A* | A | D |
| A111 | C | A* | A | C |
| A112 | C | C | A | C |
| A113 | C | D | A | C |
| A114 | C | A* | A | C |
| A115 | C | A* | A | C |
| A116 | C | A* | A | C |
| A117 | C | A* | A | C |
| A118 | C | D | D | C |
| A119 | C | B* | A | C |
| A120 | C | D | D | C |
| A121 | C | A* | A | C |
| A122 | A | A* | A | C |
| A123 | A | A* | A | C |
| A124 | C | C | C | C |
| A125 | C | C | C | C |

**Tested at 12.5 μg/cm²
*Tested at 0.5 μg/cm²

We claim:

1. A composition comprising a molecule having the following formula

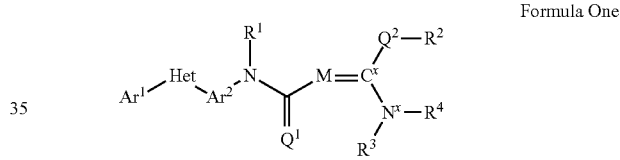

Formula One wherein:
(A) $Ar^1$ is a substituted phenyl having one or more substituents independently selected from $C_1$-$C_6$ haloalkyl and $C_1$-$C_6$ haloalkoxy;
(B) Het is a triazolyl, oxadiazolyl, or pyrazolyl;
(C) $Ar^2$ is phenyl or substituted phenyl having one or more substituents independently selected from $C_1$-$C_6$ alkyl;
(D) $R^1$ is H or $CH_3$;
(E) $R^2$ is selected from (K), H, $C_1$-$C_6$ alkyl, C alkyl-O—C(=O)$C_1$-$C_6$ alkyl, $CH_2OC(=O)N(H)(C(=O)OCH_2Ph)$, and $CH_2S(3,4,5\text{-trimethoxy-2-tetrahydropyran})$;
(F) $R^3$ is a substituted phenyl having one or more substituents independently selected from F, Cl, $CH_3$, 2-CH$(CH_3)_2$, $CH(CH_3)(C_2H_5)$, $OCH_3$, and phenyl;
(G) $R^4$ is (K) or H;
(H) M is N or C—$R^5$,
wherein $R^5$ is selected from H, CN, and C(=O)($C_1$-$C_6$ alkyl);
(I) $Q^1$ is O, and $Q^2$ is O or S;
(K) $R^2$ and $R^4$ along with $C^x(Q^2)(N^x)$, optionally as an alternative from sections (E) for $R^2$ and (G) for $R^4$, form a 4- to 7-membered saturated or unsaturated, hydrocarbyl cyclic group,
wherein said hydrocarbyl cyclic group may optionally be substituted with $C_1$-$C_6$ alkyl or oxo.

2. A composition according to claim 1 wherein $Ar^1$ is a substituted phenyl that has one or more substituents selected from $CF_3$, $OCF_3$, and $OC_2F_5$.

3. A composition according to claim 1 wherein Het is triazolyl.

4. A composition according to claim 1 wherein Het is 1,2,4 triazolyl.

5. A composition according to claim 1 wherein $Ar^2$ is phenyl.

6. A composition according to claim 1 wherein $R^1$ is H.

7. A composition according to claim 1 wherein $R^3$ is substituted phenyl wherein said substituted phenyl has more than one substituent and at least one pair of said substituents are not ortho to each other.

8. A composition according to claim 1 wherein $R^4$ is H.

9. A composition according to claim 1 wherein $Q^2$ is S.

10. A composition comprising a molecule having a structure from compounds listed below:

| No. | Structure |
|---|---|
| AA1 | 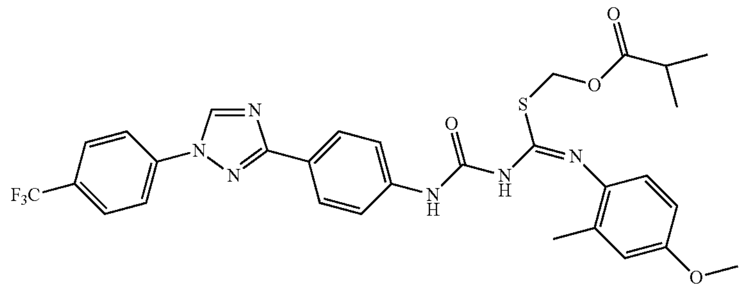 [SMILES: COc1ccc(/N=C(\NC(=O)Nc2ccc(-c3ncn(-c4ccc(C(F)(F)F)cc4)n3)cc2)SCOC(=O)C(C)C)c(C)c1] |
| AA2 | 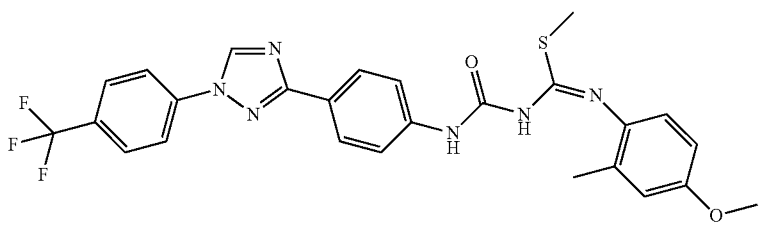 [SMILES: COc1ccc(/N=C(\NC(=O)Nc2ccc(-c3ncn(-c4ccc(C(F)(F)F)cc4)n3)cc2)SC)c(C)c1] |
| AA3 | 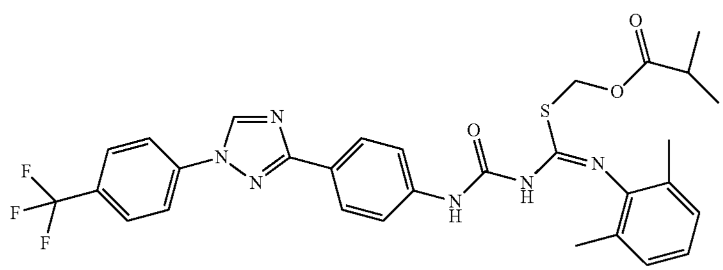 [SMILES: Cc1cccc(C)c1/N=C(\NC(=O)Nc1ccc(-c2ncn(-c3ccc(C(F)(F)F)cc3)n2)cc1)SCOC(=O)C(C)C] |
| AA4 | 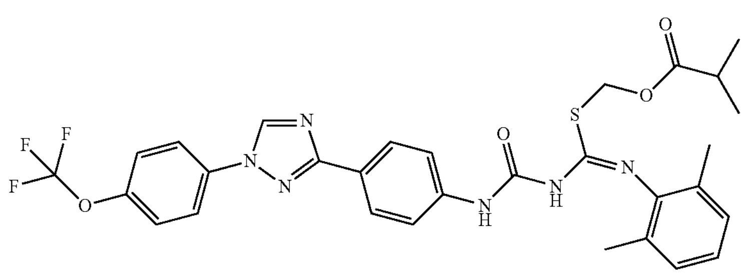 [SMILES: Cc1cccc(C)c1/N=C(\NC(=O)Nc1ccc(-c2ncn(-c3ccc(OC(F)(F)F)cc3)n2)cc1)SCOC(=O)C(C)C] |
| AA5 | 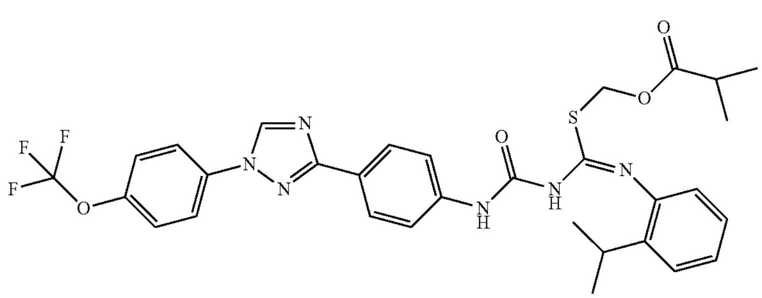 [SMILES: CC(C)C(=O)OCS/C(=N/c1ccccc1C(C)C)NC(=O)Nc1ccc(-c2ncn(-c3ccc(OC(F)(F)F)cc3)n2)cc1] |

-continued
| No. | Structure |
|---|---|
| AA6 | 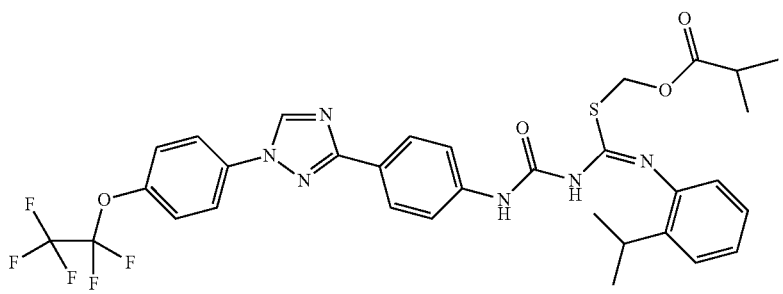 [SMILES: CC(C)C(=O)OCS/C(=N/c1ccccc1C(C)C)NC(=O)Nc1ccc(-c2ncn(-c3ccc(OC(F)(F)C(F)(F)F)cc3)n2)cc1] |
| AA7 | 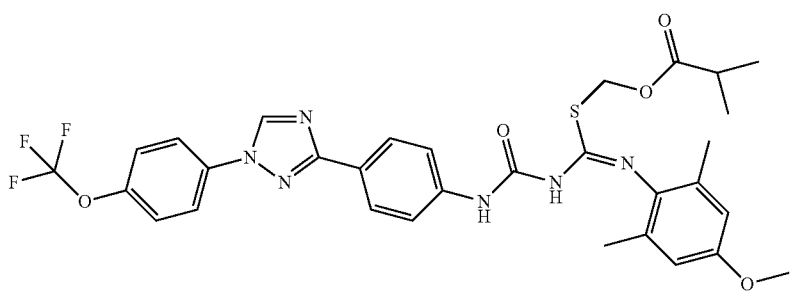 [SMILES: COc1cc(C)c(/N=C(\NC(=O)Nc2ccc(-c3ncn(-c4ccc(OC(F)(F)F)cc4)n3)cc2)SCOC(=O)C(C)C)c(C)c1] |
| AA8 | 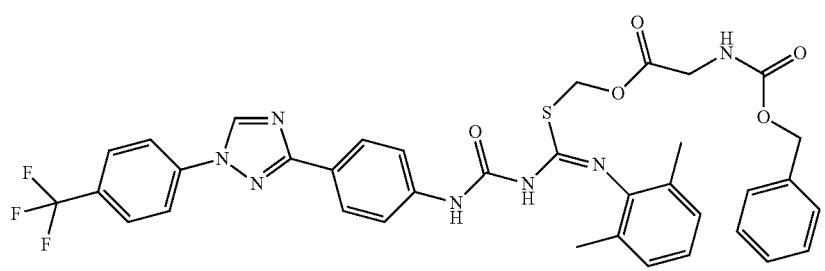 [SMILES: Cc1cccc(C)c1/N=C(\NC(=O)Nc1ccc(-c2ncn(-c3ccc(C(F)(F)F)cc3)n2)cc1)SCOC(=O)CNC(=O)OCc1ccccc1] |
| AA9 | 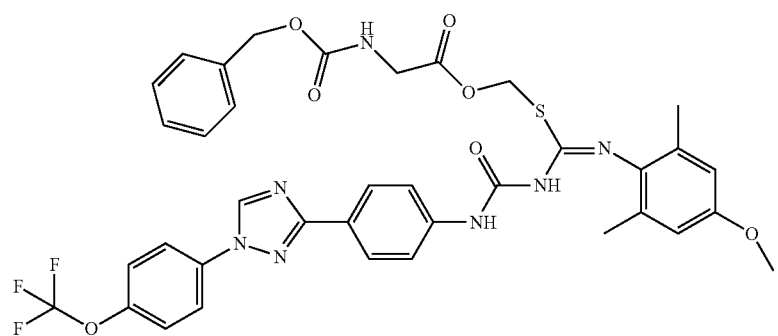 [SMILES: COc1cc(C)c(/N=C(\NC(=O)Nc2ccc(-c3ncn(-c4ccc(OC(F)(F)F)cc4)n3)cc2)SCOC(=O)CNC(=O)OCc2ccccc2)c(C)c1] |
| AA10 | 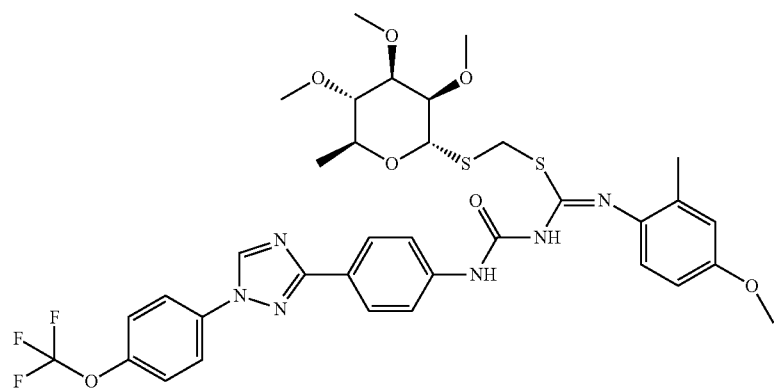 [SMILES: COc1ccc(/N=C(\NC(=O)Nc2ccc(-c3ncn(-c4ccc(OC(F)(F)F)cc4)n3)cc2)SCS[C@@H]2O[C@@H](C)[C@H](OC)[C@@H](OC)[C@H]2OC)c(C)c1] |

-continued
| No. | Structure |
|---|---|
| A1 | 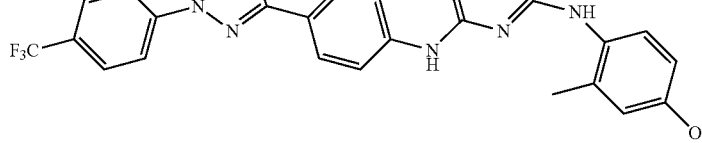 |
| A2 | 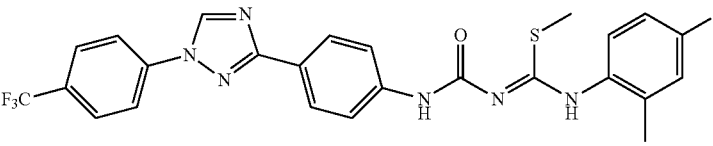 |
| A3 | 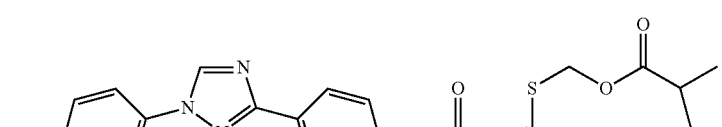 |
| A4 | 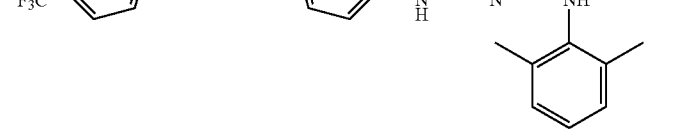 |
| A5 | 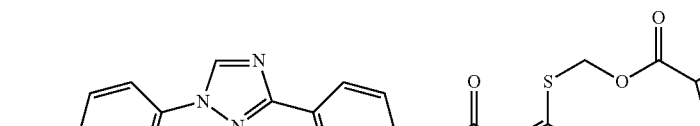 |
| A6 | 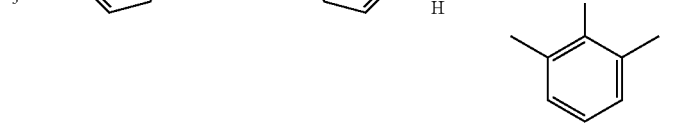 |

-continued
| No. | Structure |
|---|---|
| A7 | 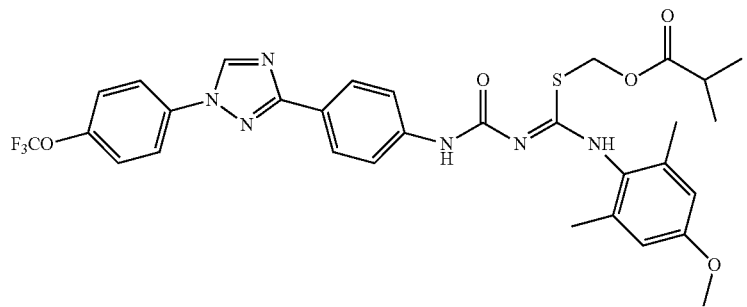 |
| A8 | 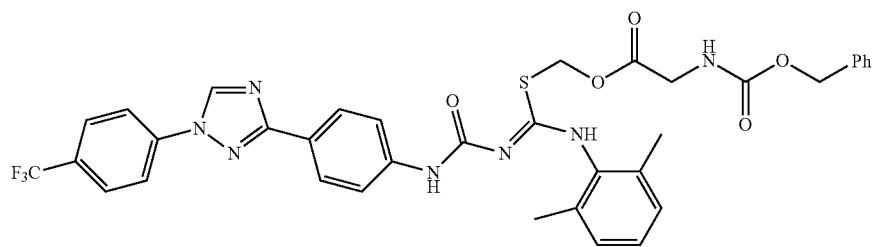 [SMILES: Cc1cccc(C)c1N/C(=N/C(=O)Nc1ccc(-c2ncn(-c3ccc(C(F)(F)F)cc3)n2)cc1)SCOC(=O)CNC(=O)OCc1ccccc1] |
| A9 | 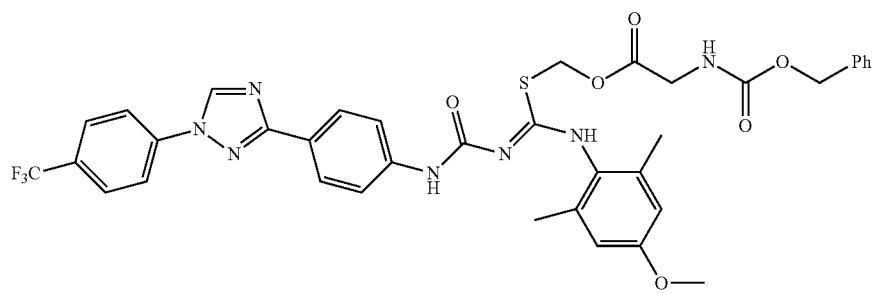 |
| A10 | 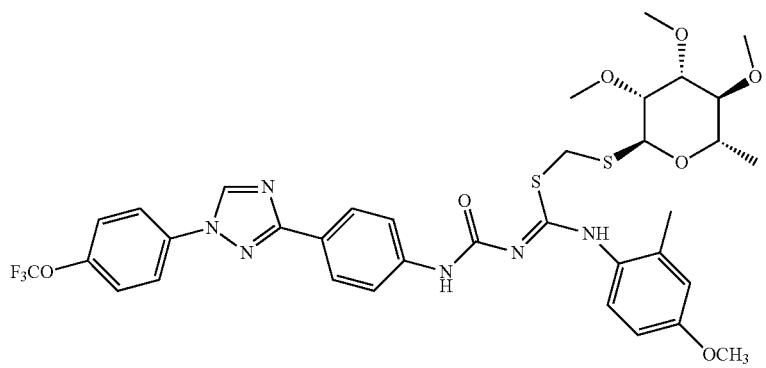 [SMILES: COc1ccc(N/C(=N/C(=O)Nc2ccc(-c3ncn(-c4ccc(OC(F)(F)F)cc4)n3)cc2)SCS[C@@H]2O[C@@H](C)[C@H](OC)[C@@H](OC)[C@H]2OC)c(C)c1] |
| A11 | 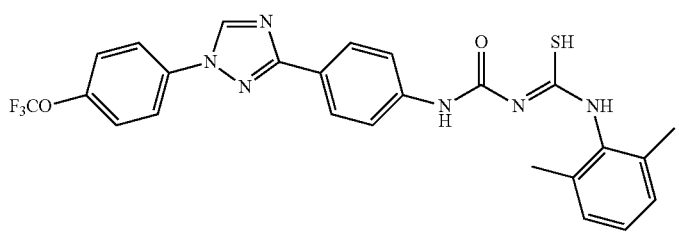 [SMILES: Cc1cccc(C)c1N/C(S)=N/C(=O)Nc1ccc(-c2ncn(-c3ccc(OC(F)(F)F)cc3)n2)cc1] |

| No. | Structure |
|---|---|
| A12 | 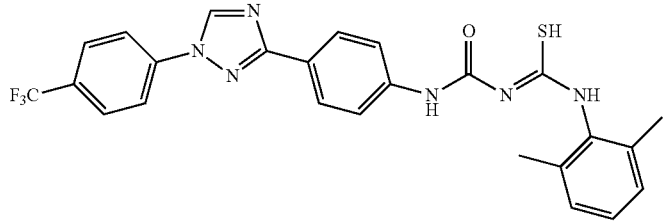 [SMILES: Cc1cccc(C)c1N/C(S)=N/C(=O)Nc1ccc(-c2ncn(-c3ccc(C(F)(F)F)cc3)n2)cc1] |
| A13 | 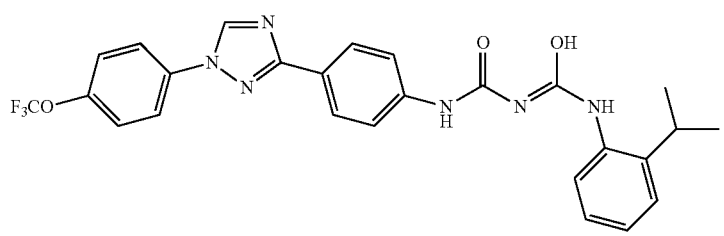 |
| A14 | 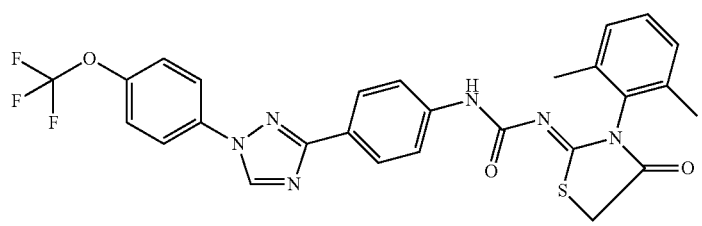 [SMILES: Cc1cccc(C)c1N1C(=O)CS/C1=N\C(=O)Nc1ccc(-c2ncn(-c3ccc(OC(F)(F)F)cc3)n2)cc1] |
| A15 | 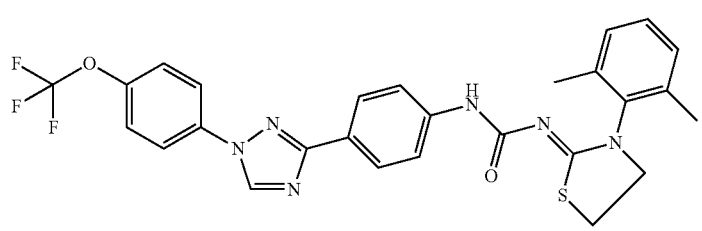 [SMILES: Cc1cccc(C)c1N1CCS/C1=N\C(=O)Nc1ccc(-c2ncn(-c3ccc(OC(F)(F)F)cc3)n2)cc1] |
| A16 | 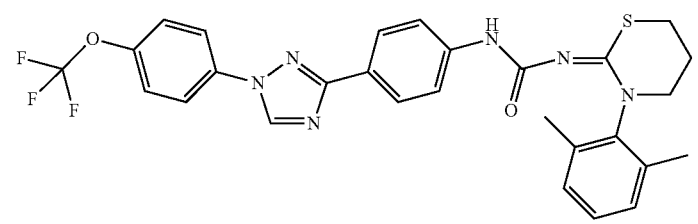 [SMILES: Cc1cccc(C)c1N1CCCS/C1=N/C(=O)Nc1ccc(-c2ncn(-c3ccc(OC(F)(F)F)cc3)n2)cc1] |
| A17 | 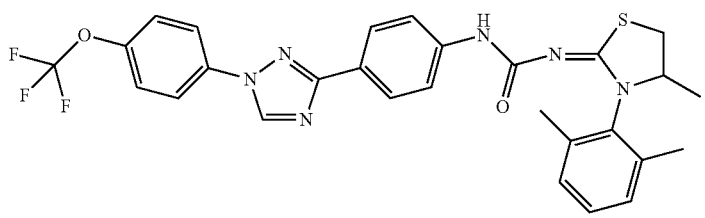 [SMILES: Cc1cccc(C)c1N1/C(=N\C(=O)Nc2ccc(-c3ncn(-c4ccc(OC(F)(F)F)cc4)n3)cc2)SCC1C] |
| A18 | 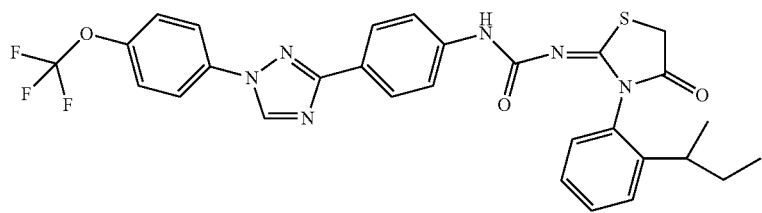 [SMILES: CCC(C)c1ccccc1N1C(=O)CS/C1=N/C(=O)Nc1ccc(-c2ncn(-c3ccc(OC(F)(F)F)cc3)n2)cc1] |

-continued
| No. | Structure |
|---|---|
| A19 | 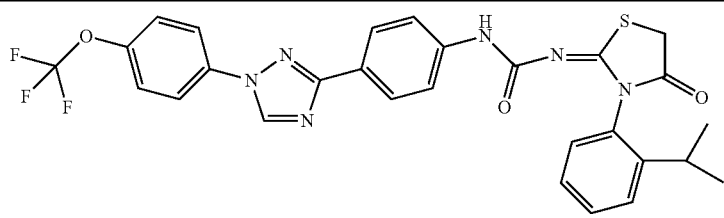 |
| A20 | 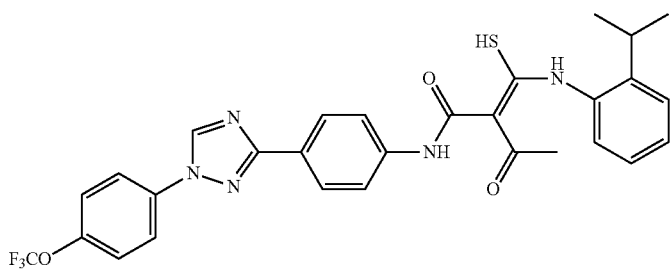 [SMILES: CC(=O)/C(C(=O)Nc1ccc(-c2ncn(-c3ccc(OC(F)(F)F)cc3)n2)cc1)=C(/S)Nc1ccccc1C(C)C] |
| A21 | 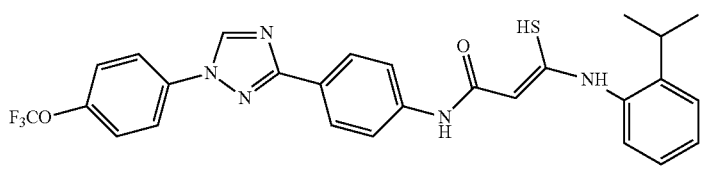 [SMILES: CC(C)c1ccccc1N/C(S)=C/C(=O)Nc1ccc(-c2ncn(-c3ccc(OC(F)(F)F)cc3)n2)cc1] |
| A22 | 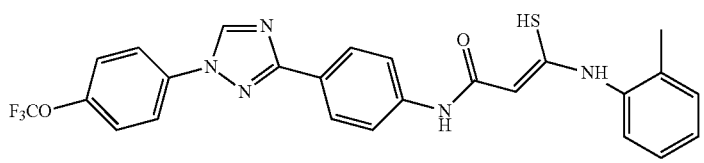 [SMILES: Cc1ccccc1N/C(S)=C/C(=O)Nc1ccc(-c2ncn(-c3ccc(OC(F)(F)F)cc3)n2)cc1] |
| A23 | 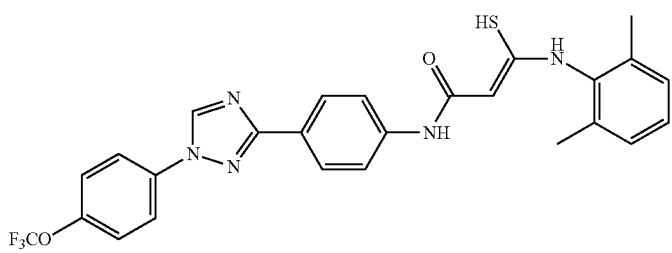 [SMILES: Cc1cccc(C)c1N/C(S)=C/C(=O)Nc1ccc(-c2ncn(-c3ccc(OC(F)(F)F)cc3)n2)cc1] |
| A24 | 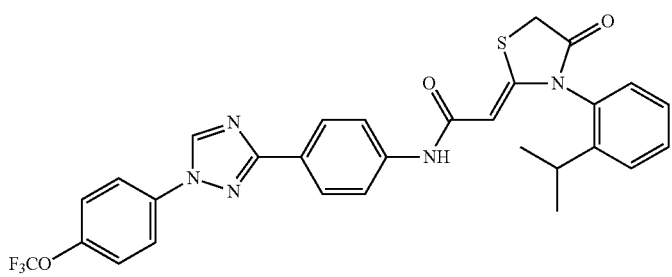 [SMILES: CC(C)c1ccccc1N1C(=O)CS/C1=C\C(=O)Nc1ccc(-c2ncn(-c3ccc(OC(F)(F)F)cc3)n2)cc1] |
| A25 | 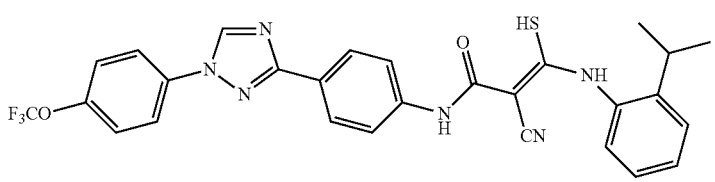 [SMILES: CC(C)c1ccccc1N/C(S)=C(\C#N)C(=O)Nc1ccc(-c2ncn(-c3ccc(OC(F)(F)F)cc3)n2)cc1] |

-continued
| No. | Structure |
|---|---|
| A26 | 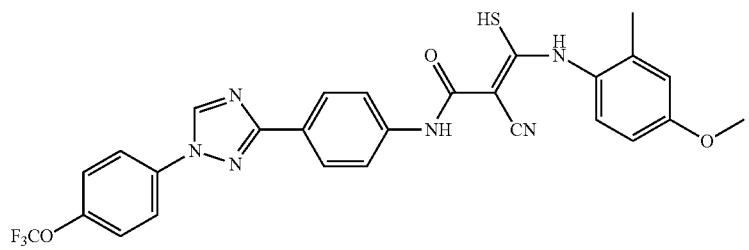 [SMILES: COc1ccc(N/C(S)=C(\C#N)C(=O)Nc2ccc(-c3ncn(-c4ccc(OC(F)(F)F)cc4)n3)cc2)c(C)c1] |
| A27 | 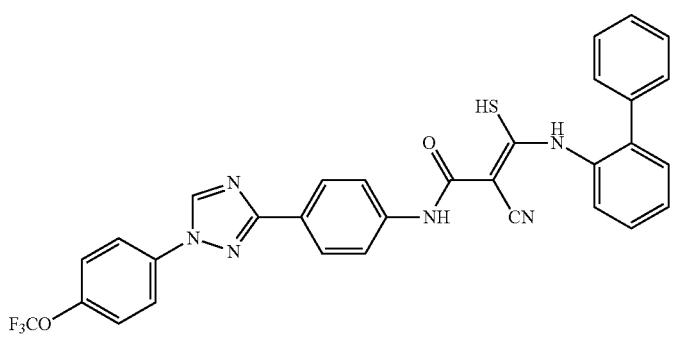 [SMILES: N#C/C(C(=O)Nc1ccc(-c2ncn(-c3ccc(OC(F)(F)F)cc3)n2)cc1)=C(/S)Nc1ccccc1-c1ccccc1] |
| A28 | 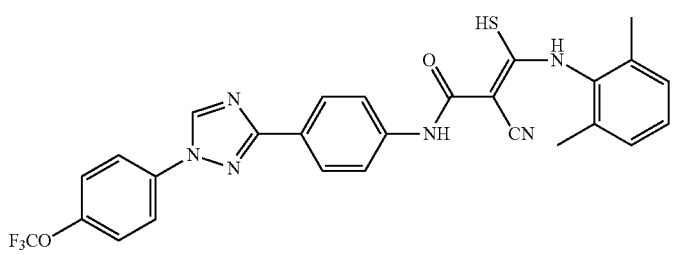 [SMILES: Cc1cccc(C)c1N/C(S)=C(\C#N)C(=O)Nc1ccc(-c2ncn(-c3ccc(OC(F)(F)F)cc3)n2)cc1] |
| A29 | 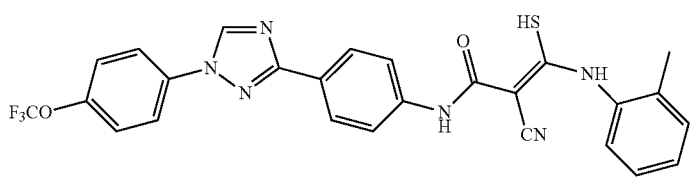 [SMILES: Cc1ccccc1N/C(S)=C(\C#N)C(=O)Nc1ccc(-c2ncn(-c3ccc(OC(F)(F)F)cc3)n2)cc1] |
| A30 | 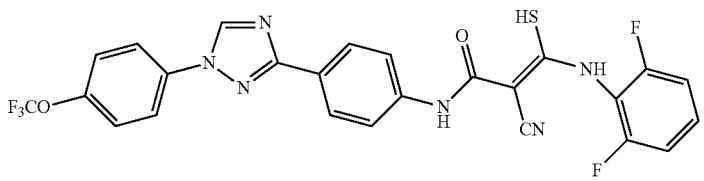 [SMILES: N#C/C(C(=O)Nc1ccc(-c2ncn(-c3ccc(OC(F)(F)F)cc3)n2)cc1)=C(/S)Nc1c(F)cccc1F] |
| A31 | 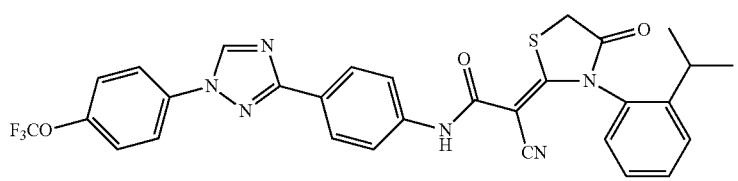 [SMILES: CC(C)c1ccccc1N1C(=O)CS/C1=C(/C#N)C(=O)Nc1ccc(-c2ncn(-c3ccc(OC(F)(F)F)cc3)n2)cc1] |
| A32 | 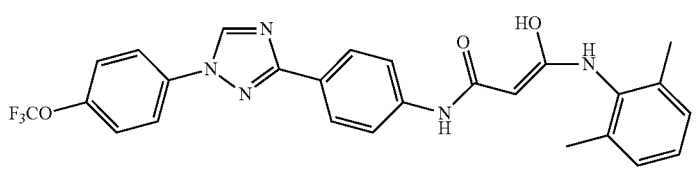 [SMILES: Cc1cccc(C)c1N/C(O)=C/C(=O)Nc1ccc(-c2ncn(-c3ccc(OC(F)(F)F)cc3)n2)cc1] |

-continued
| No. | Structure |
|---|---|
| A33 | 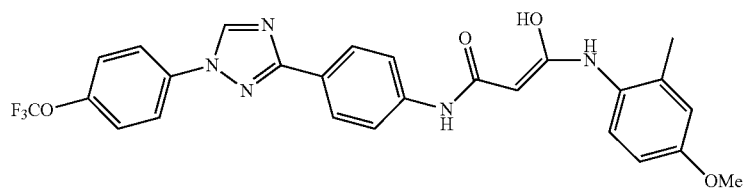 [SMILES: COc1ccc(N/C(O)=C/C(=O)Nc2ccc(-c3ncn(-c4ccc(OC(F)(F)F)cc4)n3)cc2)c(C)c1] |
| A34 | 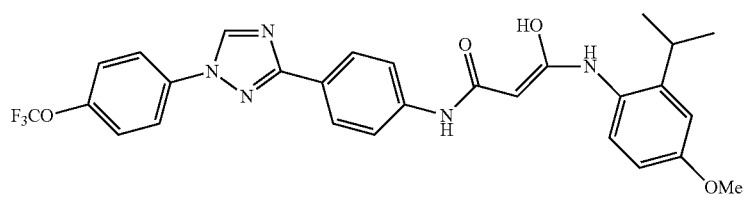 [SMILES: COc1ccc(N/C(O)=C/C(=O)Nc2ccc(-c3ncn(-c4ccc(OC(F)(F)F)cc4)n3)cc2)c(C(C)C)c1] |
| A35 | 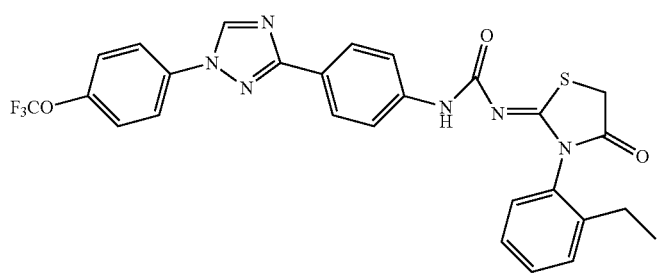 [SMILES: CCc1ccccc1N1C(=O)CS/C1=N\C(=O)Nc1ccc(-c2ncn(-c3ccc(OC(F)(F)F)cc3)n2)cc1] |
| A36 | 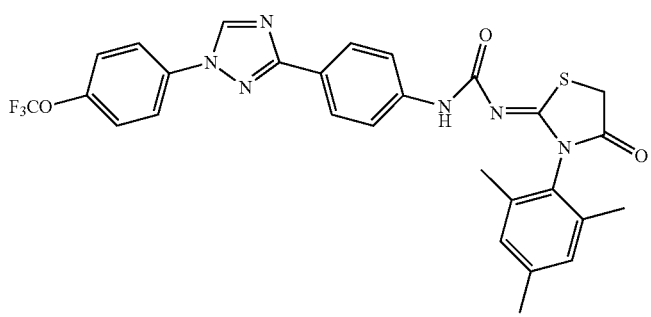 [SMILES: Cc1cc(C)c(N2C(=O)CS/C2=N\C(=O)Nc2ccc(-c3ncn(-c4ccc(OC(F)(F)F)cc4)n3)cc2)c(C)c1] |
| A37 | 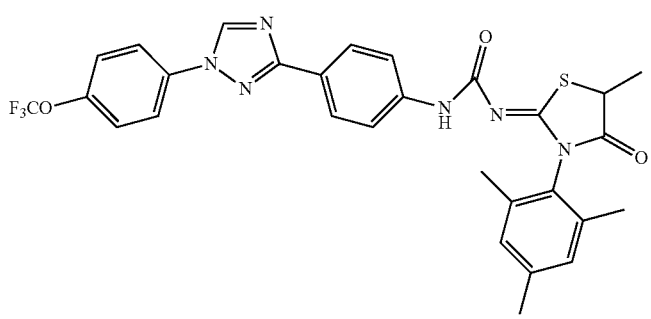 [SMILES: Cc1cc(C)c(N2C(=O)C(C)S/C2=N\C(=O)Nc2ccc(-c3ncn(-c4ccc(OC(F)(F)F)cc4)n3)cc2)c(C)c1] |

| No. | Structure |
|---|---|
| A38 | 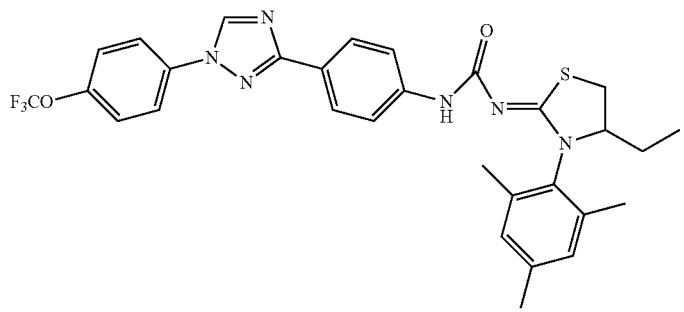 [SMILES: CCC1CS/C(=N\C(=O)Nc2ccc(-c3ncn(-c4ccc(OC(F)(F)F)cc4)n3)cc2)N1c1c(C)cc(C)cc1C] |
| A39 | 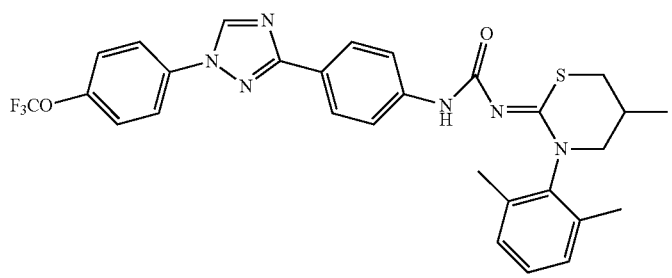 [SMILES: Cc1cccc(C)c1N1CC(C)CS/C1=N\C(=O)Nc1ccc(-c2ncn(-c3ccc(OC(F)(F)F)cc3)n2)cc1] |
| A40 | 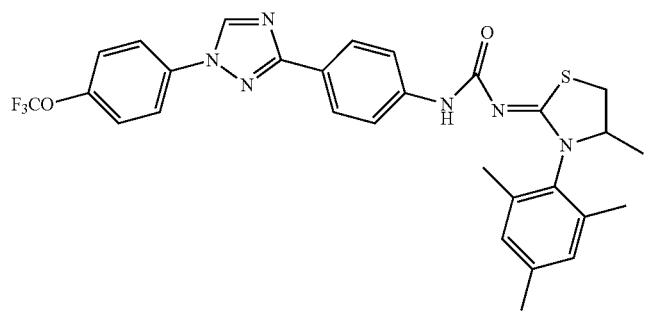 [SMILES: Cc1cc(C)c(N2/C(=N/C(=O)Nc3ccc(-c4ncn(-c5ccc(OC(F)(F)F)cc5)n4)cc3)SCC2C)c(C)c1] |
| A41 | 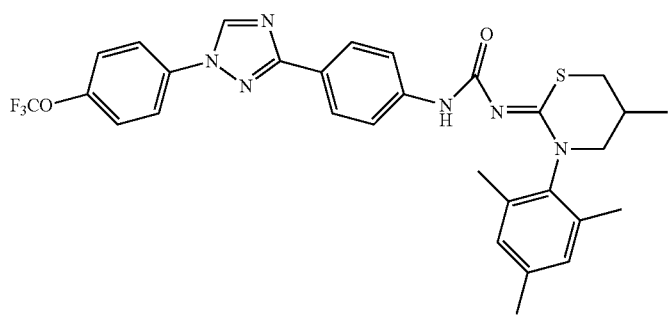 [SMILES: Cc1cc(C)c(N2CC(C)CS/C2=N\C(=O)Nc2ccc(-c3ncn(-c4ccc(OC(F)(F)F)cc4)n3)cc2)c(C)c1] |
| A42 | 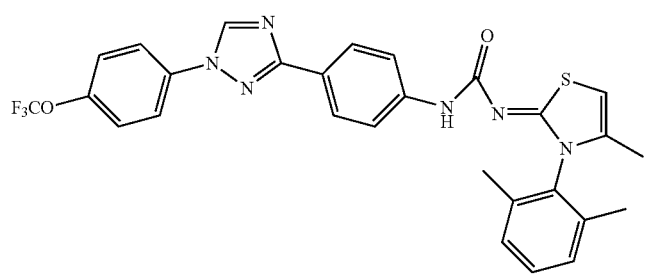 [SMILES: Cc1cccc(C)c1-n1c(C)cs/c1=N\C(=O)Nc1ccc(-c2ncn(-c3ccc(OC(F)(F)F)cc3)n2)cc1] |

| No. | Structure |
|---|---|
| A43 | 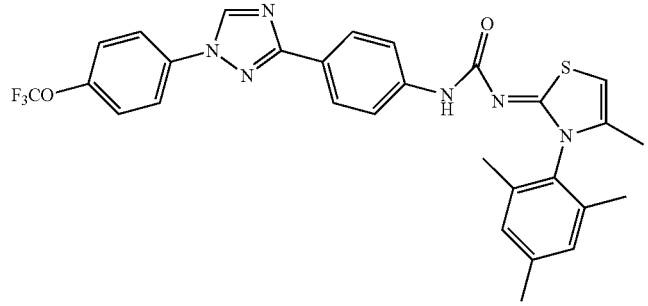 [SMILES: Cc1cc(C)c(-n2c(C)cs/c2=N\C(=O)Nc2ccc(-c3ncn(-c4ccc(OC(F)(F)F)cc4)n3)cc2)c(C)c1] |
| A44 | 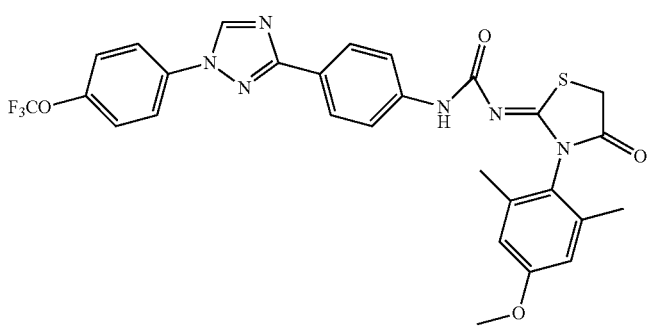 [SMILES: COc1cc(C)c(N2C(=O)CS/C2=N\C(=O)Nc2ccc(-c3ncn(-c4ccc(OC(F)(F)F)cc4)n3)cc2)c(C)c1] |
| A46 | 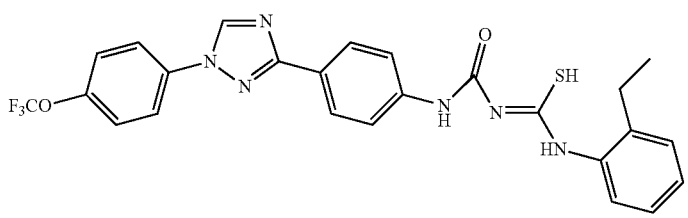 |
| A48 | 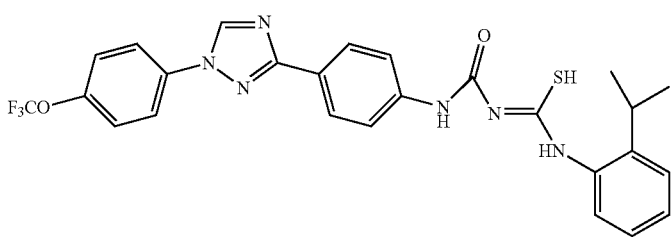 [SMILES: CC(C)c1ccccc1N/C(S)=N/C(=O)Nc1ccc(-c2ncn(-c3ccc(OC(F)(F)F)cc3)n2)cc1] |
| A49 | 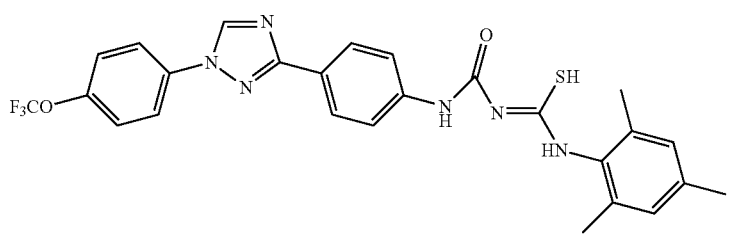 [SMILES: Cc1cc(C)c(N/C(S)=N/C(=O)Nc2ccc(-c3ncn(-c4ccc(OC(F)(F)F)cc4)n3)cc2)c(C)c1] |
| A50 | 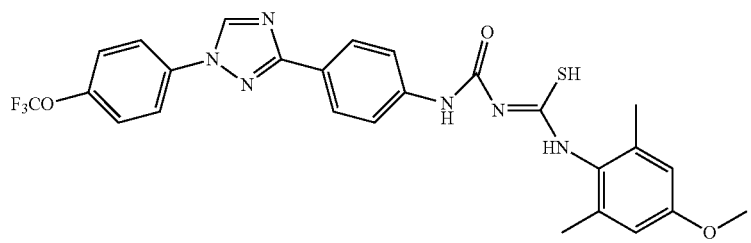 [SMILES: COc1cc(C)c(N/C(S)=N/C(=O)Nc2ccc(-c3ncn(-c4ccc(OC(F)(F)F)cc4)n3)cc2)c(C)c1] |

-continued
| No. | Structure |
|---|---|
| A51 | 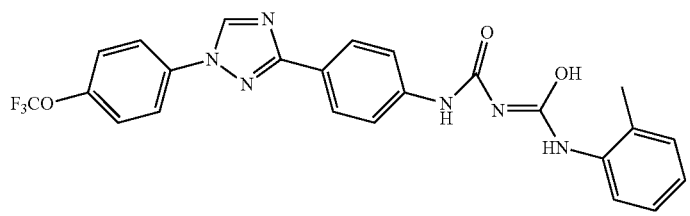 [SMILES: Cc1ccccc1N/C(O)=N/C(=O)Nc1ccc(-c2ncn(-c3ccc(OC(F)(F)F)cc3)n2)cc1] |
| A52 | 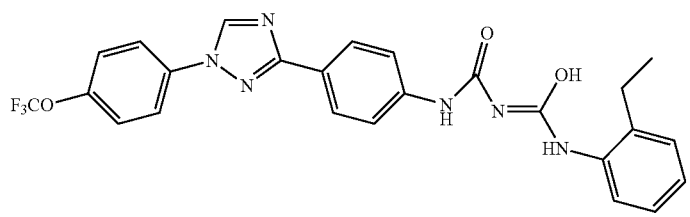 [SMILES: CCc1ccccc1N/C(O)=N/C(=O)Nc1ccc(-c2ncn(-c3ccc(OC(F)(F)F)cc3)n2)cc1] |
| A53 | 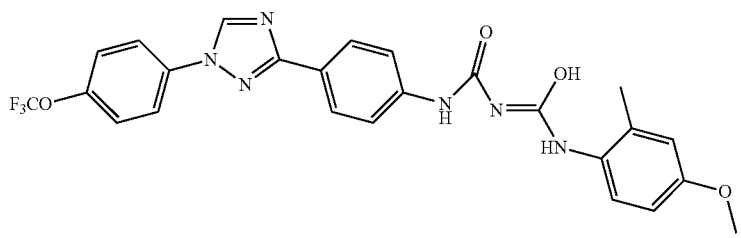 [SMILES: COc1ccc(N/C(O)=N/C(=O)Nc2ccc(-c3ncn(-c4ccc(OC(F)(F)F)cc4)n3)cc2)c(C)c1] |
| A54 | 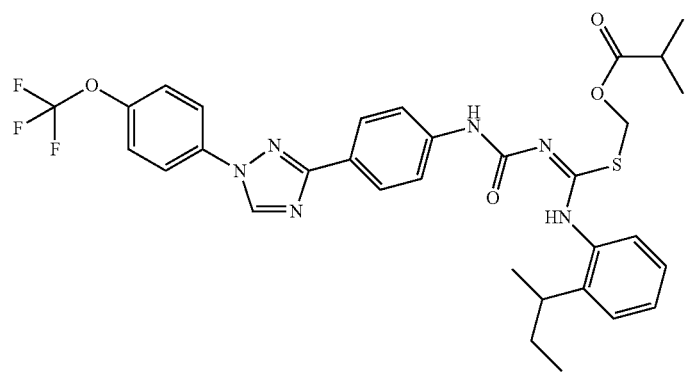 [SMILES: CCC(C)c1ccccc1N/C(=N\C(=O)Nc1ccc(-c2ncn(-c3ccc(OC(F)(F)F)cc3)n2)cc1)SCOC(=O)C(C)C] |
| A55 | 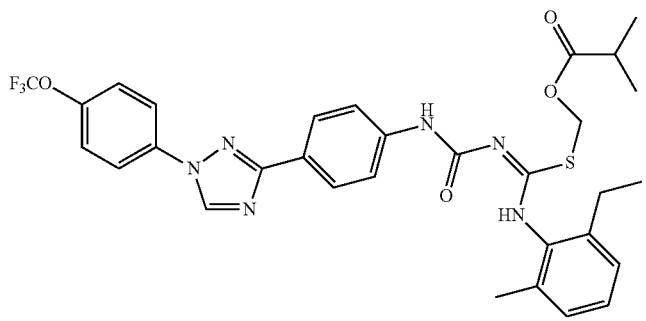 [SMILES: CCc1cccc(C)c1N/C(=N\C(=O)Nc1ccc(-c2ncn(-c3ccc(OC(F)(F)F)cc3)n2)cc1)SCOC(=O)C(C)C] |

| No. | Structure |
|---|---|
| A56 | 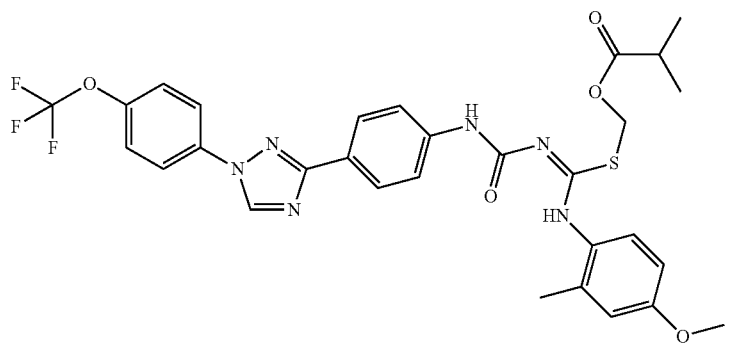 [SMILES: COc1ccc(N/C(=N\C(=O)Nc2ccc(-c3ncn(-c4ccc(OC(F)(F)F)cc4)n3)cc2)SCOC(=O)C(C)C)c(C)c1] |
| A57 | 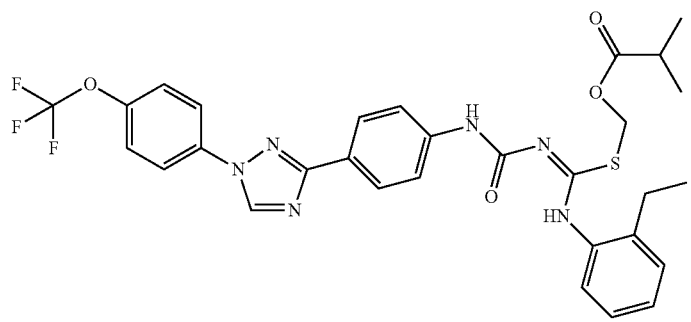 [SMILES: CCc1ccccc1N/C(=N\C(=O)Nc1ccc(-c2ncn(-c3ccc(OC(F)(F)F)cc3)n2)cc1)SCOC(=O)C(C)C] |
| A58 | 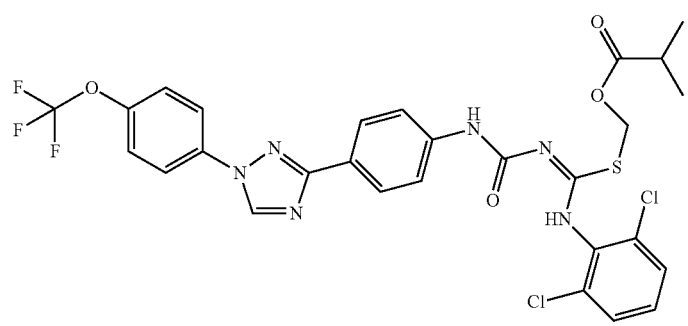 [SMILES: CC(C)C(=O)OCS/C(=N/C(=O)Nc1ccc(-c2ncn(-c3ccc(OC(F)(F)F)cc3)n2)cc1)Nc1c(Cl)cccc1Cl] |
| A59 | 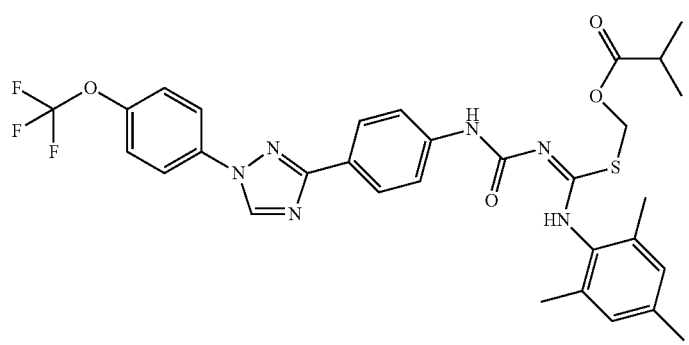 [SMILES: Cc1cc(C)c(N/C(=N\C(=O)Nc2ccc(-c3ncn(-c4ccc(OC(F)(F)F)cc4)n3)cc2)SCOC(=O)C(C)C)c(C)c1] |

| No. | Structure |
|---|---|
| A60 | 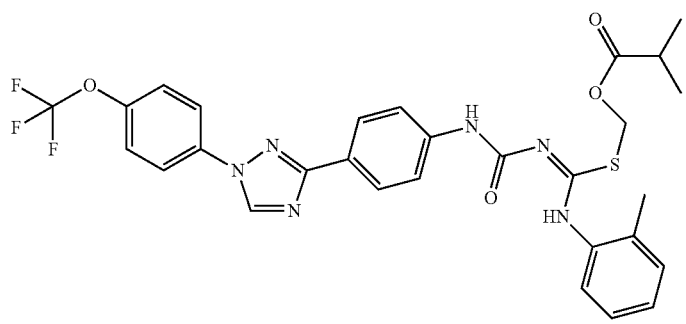 [SMILES: Cc1ccccc1N/C(=N\C(=O)Nc1ccc(-c2ncn(-c3ccc(OC(F)(F)F)cc3)n2)cc1)SCOC(=O)C(C)C] |
| A61 | 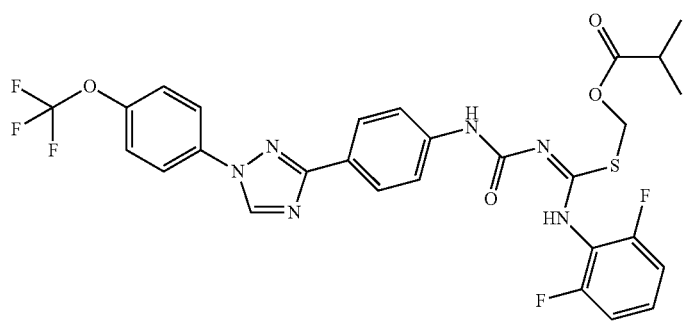 [SMILES: CC(C)C(=O)OCS/C(=N/C(=O)Nc1ccc(-c2ncn(-c3ccc(OC(F)(F)F)cc3)n2)cc1)Nc1c(F)cccc1F] |
| A62 | 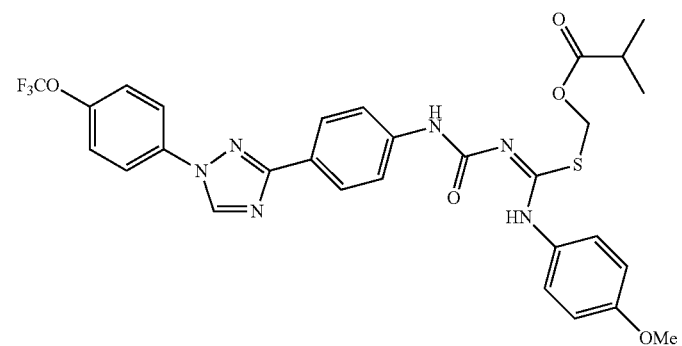 [SMILES: COc1ccc(N/C(=N\C(=O)Nc2ccc(-c3ncn(-c4ccc(OC(F)(F)F)cc4)n3)cc2)SCOC(=O)C(C)C)cc1] |
| A63 | 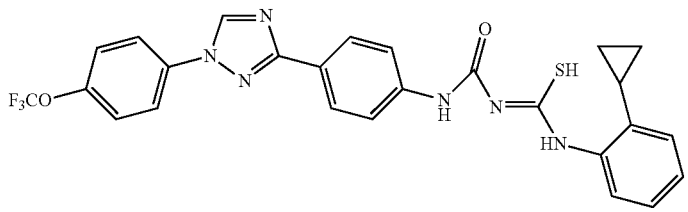 [SMILES: O=C(/N=C(\S)Nc1ccccc1C1CC1)Nc1ccc(-c2ncn(-c3ccc(OC(F)(F)F)cc3)n2)cc1] |
| A64 | 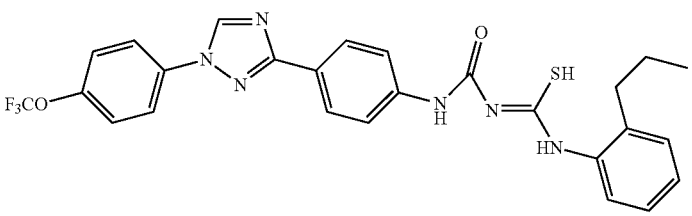 [SMILES: CCCc1ccccc1N/C(S)=N/C(=O)Nc1ccc(-c2ncn(-c3ccc(OC(F)(F)F)cc3)n2)cc1] |

| No. | Structure |
|---|---|
| A65 | 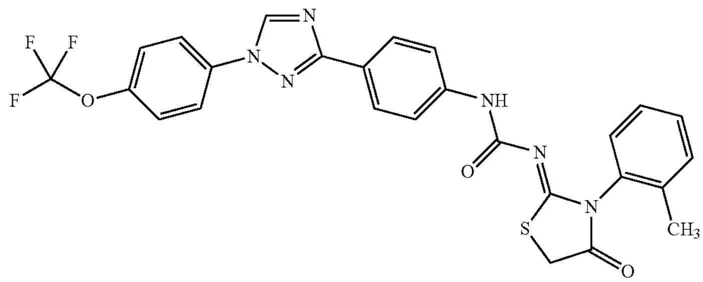 [SMILES: Cc1ccccc1N1C(=O)CS/C1=N\C(=O)Nc1ccc(-c2ncn(-c3ccc(OC(F)(F)F)cc3)n2)cc1] |
| A66 | 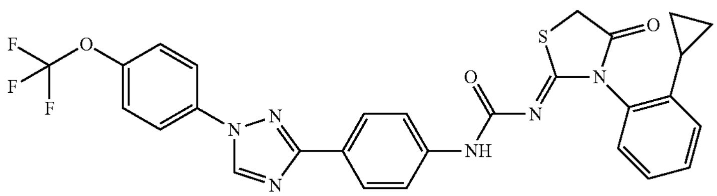 [SMILES: O=C(/N=C1\SCC(=O)N1c1ccccc1C1CC1)Nc1ccc(-c2ncn(-c3ccc(OC(F)(F)F)cc3)n2)cc1] |
| A67 | 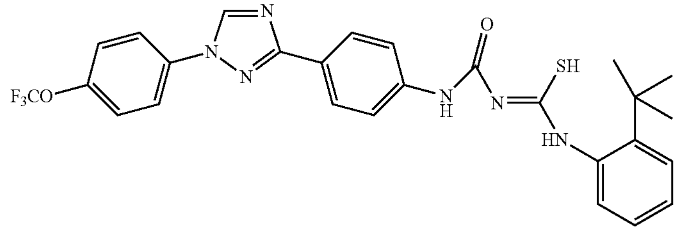 [SMILES: CC(C)(C)c1ccccc1N/C(S)=N/C(=O)Nc1ccc(-c2ncn(-c3ccc(OC(F)(F)F)cc3)n2)cc1] |
| A68 | 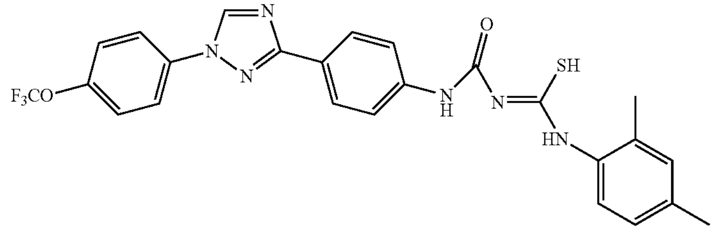 [SMILES: Cc1ccc(N/C(S)=N/C(=O)Nc2ccc(-c3ncn(-c4ccc(OC(F)(F)F)cc4)n3)cc2)c(C)c1] |
| A69 | 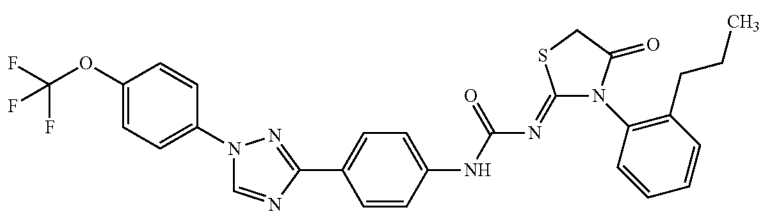 [SMILES: CCCc1ccccc1N1C(=O)CS/C1=N\C(=O)Nc1ccc(-c2ncn(-c3ccc(OC(F)(F)F)cc3)n2)cc1] |
| A70 | 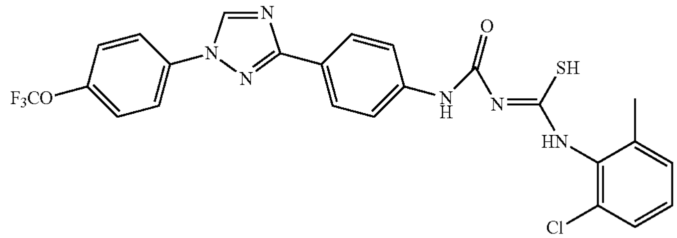 [SMILES: Cc1cccc(Cl)c1N/C(S)=N/C(=O)Nc1ccc(-c2ncn(-c3ccc(OC(F)(F)F)cc3)n2)cc1] |

| No. | Structure |
|---|---|
| A71 | 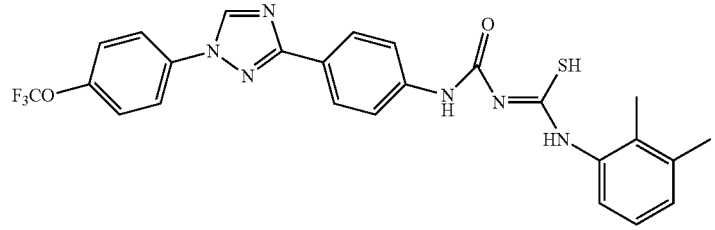 [SMILES: Cc1cccc(N/C(S)=N/C(=O)Nc2ccc(-c3ncn(-c4ccc(OC(F)(F)F)cc4)n3)cc2)c1C] |
| A72 | 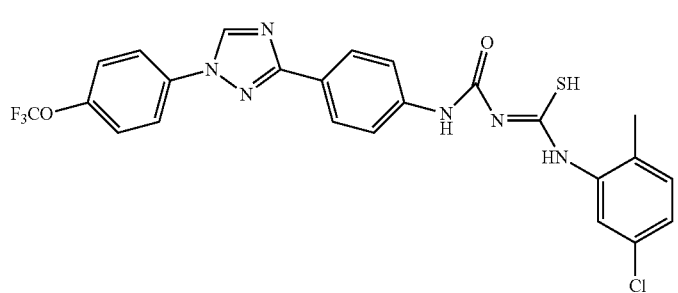 [SMILES: Cc1ccc(Cl)cc1N/C(S)=N/C(=O)Nc1ccc(-c2ncn(-c3ccc(OC(F)(F)F)cc3)n2)cc1] |
| A73 | 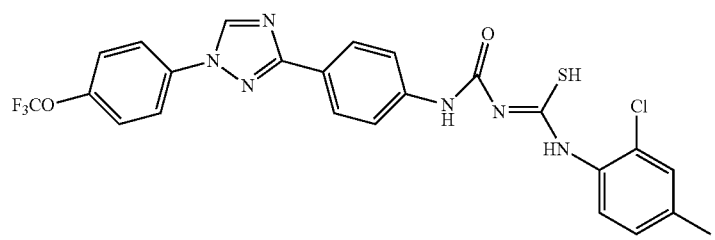 |
| A74 | 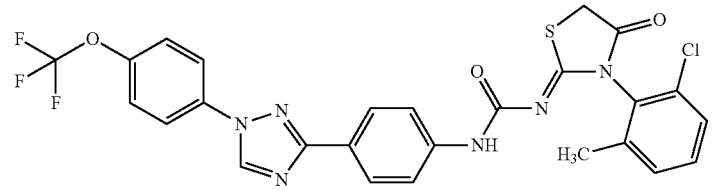 [SMILES: Cc1cccc(Cl)c1N1C(=O)CS/C1=N\C(=O)Nc1ccc(-c2ncn(-c3ccc(OC(F)(F)F)cc3)n2)cc1] |
| A75 | 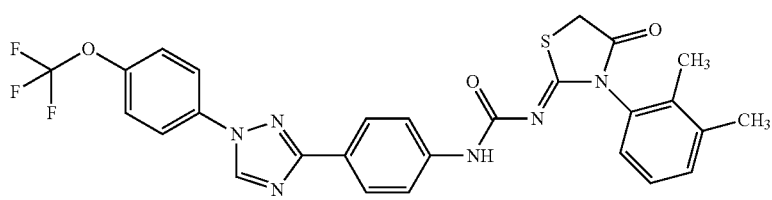 [SMILES: Cc1cccc(N2C(=O)CS/C2=N\C(=O)Nc2ccc(-c3ncn(-c4ccc(OC(F)(F)F)cc4)n3)cc2)c1C] |
| A76 | 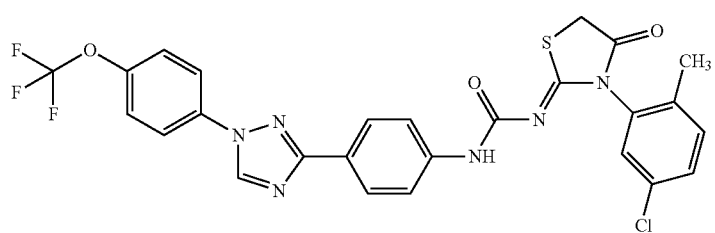 [SMILES: Cc1ccc(Cl)cc1N1C(=O)CS/C1=N\C(=O)Nc1ccc(-c2ncn(-c3ccc(OC(F)(F)F)cc3)n2)cc1] |

| No. | Structure |
|---|---|
| A77 | 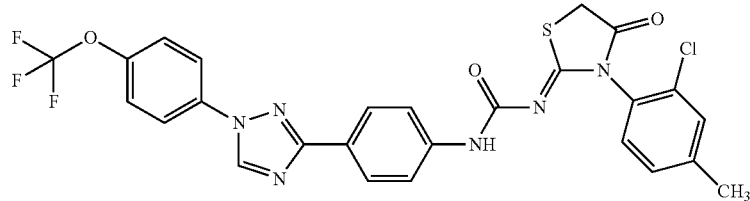 [SMILES: Cc1ccc(N2C(=O)CS/C2=N\C(=O)Nc2ccc(-c3ncn(-c4ccc(OC(F)(F)F)cc4)n3)cc2)c(Cl)c1] |
| A78 | 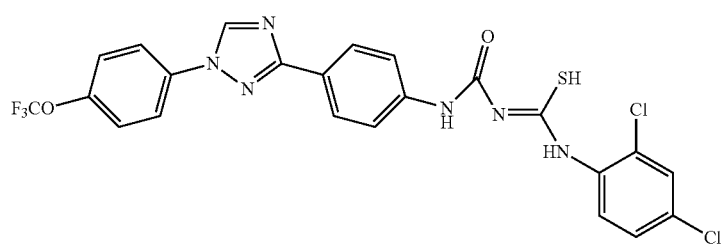 [SMILES: O=C(/N=C(\S)Nc1ccc(Cl)cc1Cl)Nc1ccc(-c2ncn(-c3ccc(OC(F)(F)F)cc3)n2)cc1] |
| A79 | 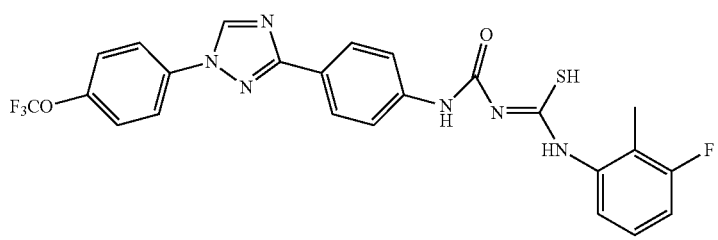 [SMILES: Cc1c(F)cccc1N/C(S)=N/C(=O)Nc1ccc(-c2ncn(-c3ccc(OC(F)(F)F)cc3)n2)cc1] |
| A80 | 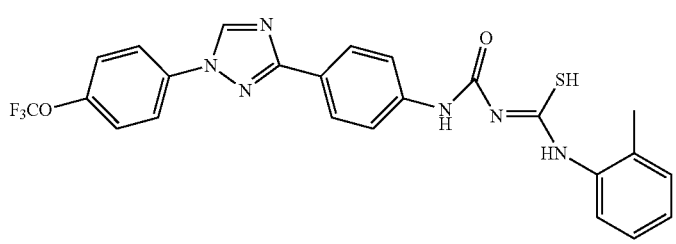 [SMILES: Cc1ccccc1N/C(S)=N/C(=O)Nc1ccc(-c2ncn(-c3ccc(OC(F)(F)F)cc3)n2)cc1] |
| A81 | 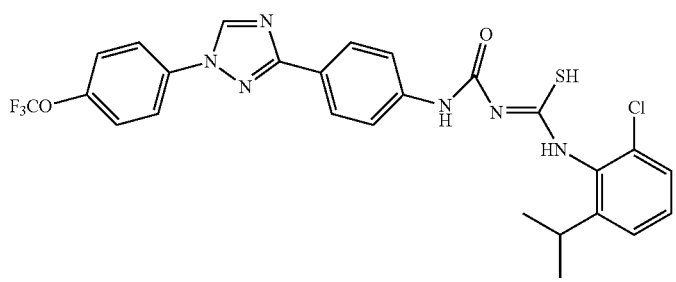 [SMILES: CC(C)c1cccc(Cl)c1N/C(S)=N/C(=O)Nc1ccc(-c2ncn(-c3ccc(OC(F)(F)F)cc3)n2)cc1] |
| A82 | 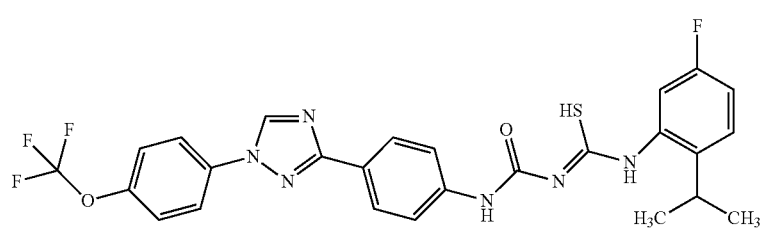 |

-continued

| No. | Structure |
|---|---|
| A83 | 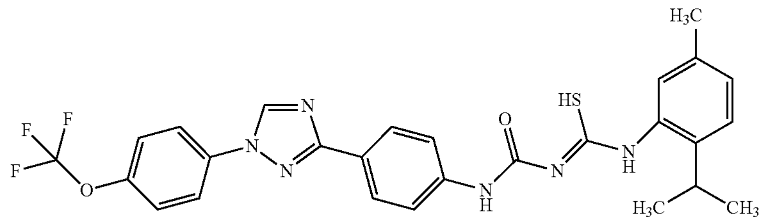 |
| A84 | 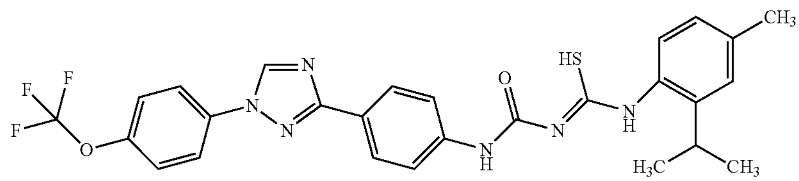 [SMILES: Cc1ccc(N/C(S)=N/C(=O)Nc2ccc(-c3ncn(-c4ccc(OC(F)(F)F)cc4)n3)cc2)c(C(C)C)c1] |
| A85 | 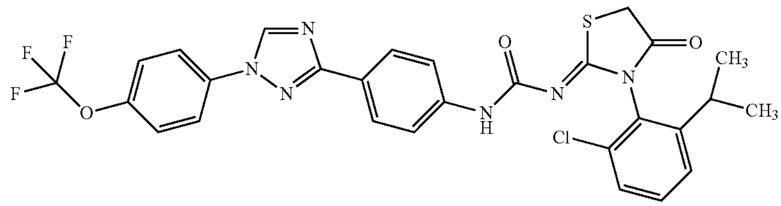 [SMILES: CC(C)c1cccc(Cl)c1N1C(=O)CS/C1=N\C(=O)Nc1ccc(-c2ncn(-c3ccc(OC(F)(F)F)cc3)n2)cc1] |
| A86 | 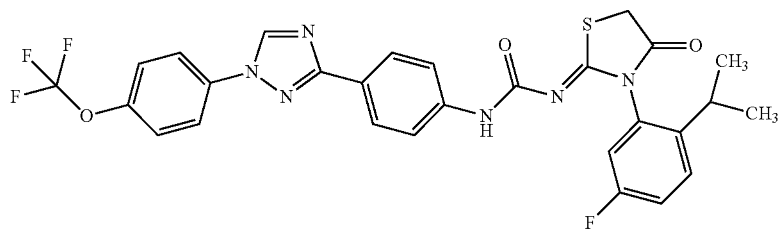 [SMILES: CC(C)c1ccc(F)cc1N1C(=O)CS/C1=N\C(=O)Nc1ccc(-c2ncn(-c3ccc(OC(F)(F)F)cc3)n2)cc1] |
| A87 | 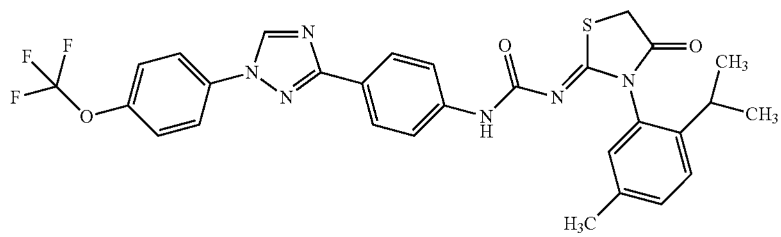 |
| A88 | 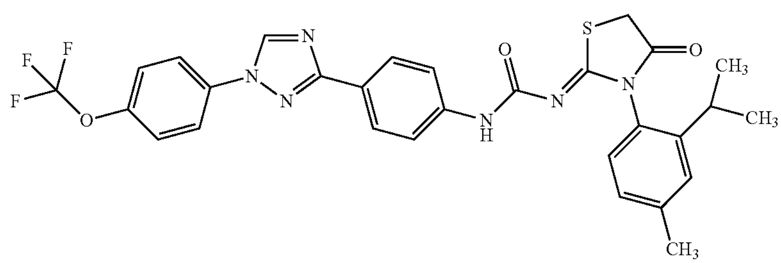 [SMILES: Cc1ccc(N2C(=O)CS/C2=N\C(=O)Nc2ccc(-c3ncn(-c4ccc(OC(F)(F)F)cc4)n3)cc2)c(C(C)C)c1] |
| A89 | 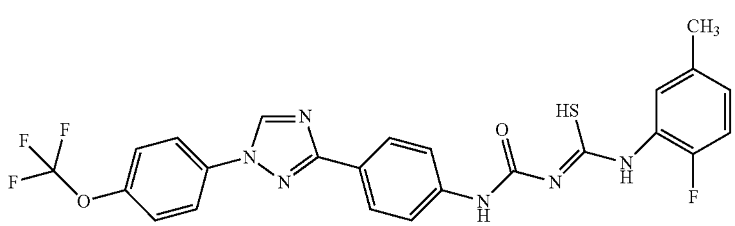 [SMILES: Cc1ccc(F)c(N/C(S)=N/C(=O)Nc2ccc(-c3ncn(-c4ccc(OC(F)(F)F)cc4)n3)cc2)c1] |

| No. | Structure |
|---|---|
| A92 | 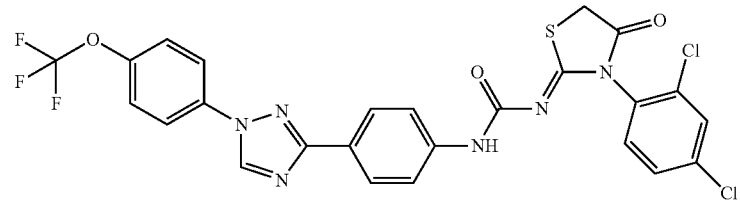 [SMILES: O=C(/N=C1\SCC(=O)N1c1ccc(Cl)cc1Cl)Nc1ccc(-c2ncn(-c3ccc(OC(F)(F)F)cc3)n2)cc1] |
| A93 | 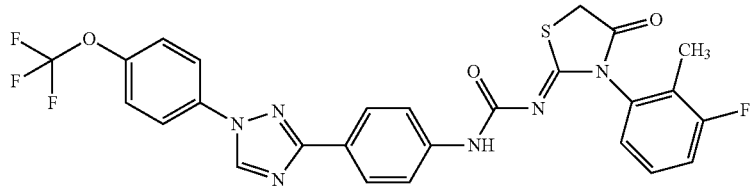 [SMILES: Cc1c(F)cccc1N1C(=O)CS/C1=N\C(=O)Nc1ccc(-c2ncn(-c3ccc(OC(F)(F)F)cc3)n2)cc1] |
| A94 | 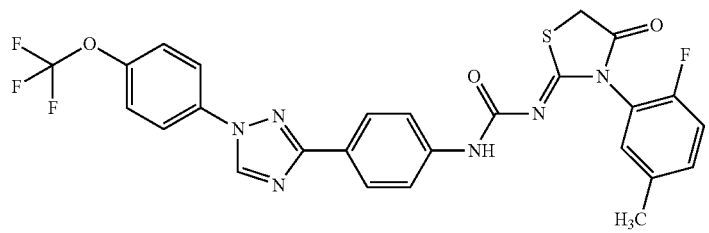 [SMILES: Cc1ccc(F)c(N2C(=O)CS/C2=N\C(=O)Nc2ccc(-c3ncn(-c4ccc(OC(F)(F)F)cc4)n3)cc2)c1] |
| A95 | 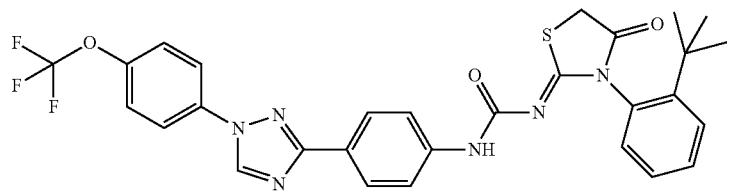 [SMILES: CC(C)(C)c1ccccc1N1C(=O)CS/C1=N\C(=O)Nc1ccc(-c2ncn(-c3ccc(OC(F)(F)F)cc3)n2)cc1] |
| A96 | 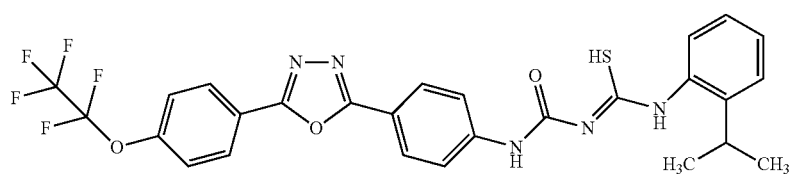 [SMILES: CC(C)c1ccccc1N/C(S)=N/C(=O)Nc1ccc(-c2nnc(-c3ccc(OC(F)(F)C(F)(F)F)cc3)o2)cc1] |
| A97 | 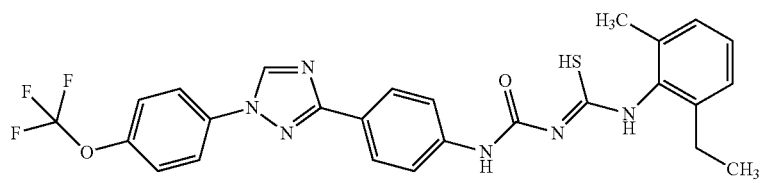 [SMILES: CCc1cccc(C)c1N/C(S)=N/C(=O)Nc1ccc(-c2ncn(-c3ccc(OC(F)(F)F)cc3)n2)cc1] |
| A98 | 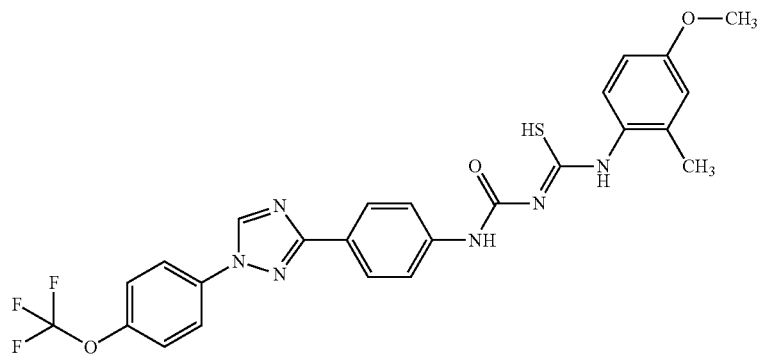 [SMILES: COc1ccc(N/C(S)=N/C(=O)Nc2ccc(-c3ncn(-c4ccc(OC(F)(F)F)cc4)n3)cc2)c(C)c1] |

| No. | Structure |
|---|---|
| A99 | 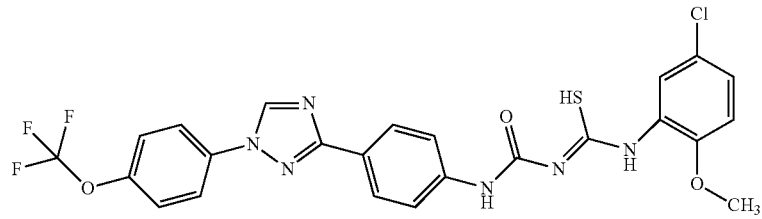 [SMILES: COc1ccc(Cl)cc1N/C(S)=N/C(=O)Nc1ccc(-c2ncn(-c3ccc(OC(F)(F)F)cc3)n2)cc1] |
| A100 | 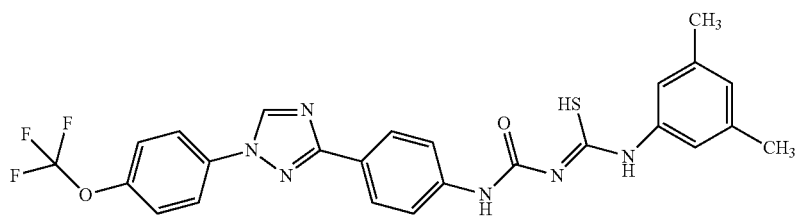 [SMILES: Cc1cc(C)cc(N/C(S)=N/C(=O)Nc2ccc(-c3ncn(-c4ccc(OC(F)(F)F)cc4)n3)cc2)c1] |
| A101 | 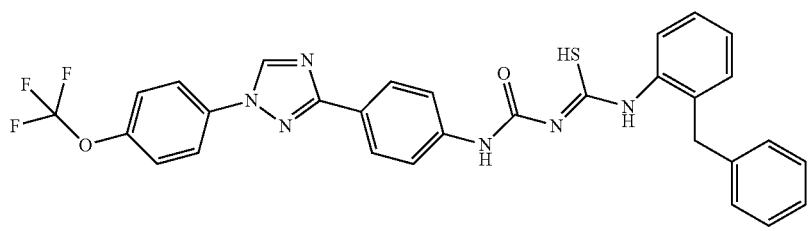 [SMILES: O=C(/N=C(\S)Nc1ccccc1Cc1ccccc1)Nc1ccc(-c2ncn(-c3ccc(OC(F)(F)F)cc3)n2)cc1] |
| A102 | 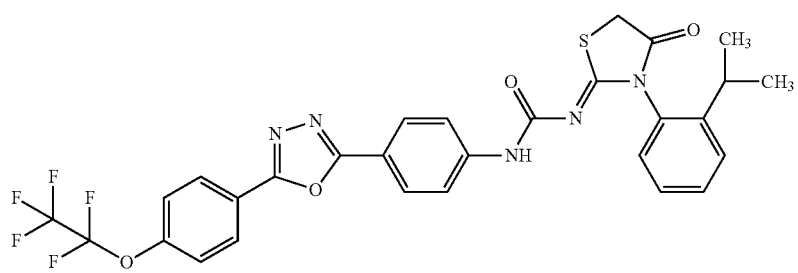 [SMILES: CC(C)c1ccccc1N1C(=O)CS/C1=N\C(=O)Nc1ccc(-c2nnc(-c3ccc(OC(F)(F)C(F)(F)F)cc3)o2)cc1] |
| A103 | 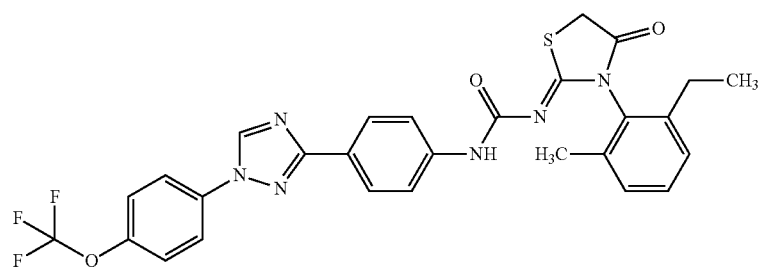 [SMILES: CCc1cccc(C)c1N1C(=O)CS/C1=N\C(=O)Nc1ccc(-c2ncn(-c3ccc(OC(F)(F)F)cc3)n2)cc1] |
| A104 | 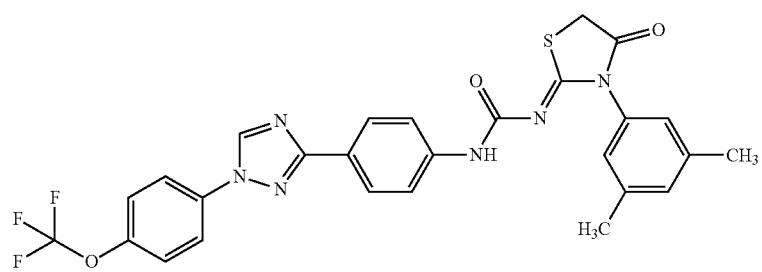 [SMILES: Cc1cc(C)cc(N2C(=O)CS/C2=N\C(=O)Nc2ccc(-c3ncn(-c4ccc(OC(F)(F)F)cc4)n3)cc2)c1] |

| No. | Structure |
|---|---|
| A105 | 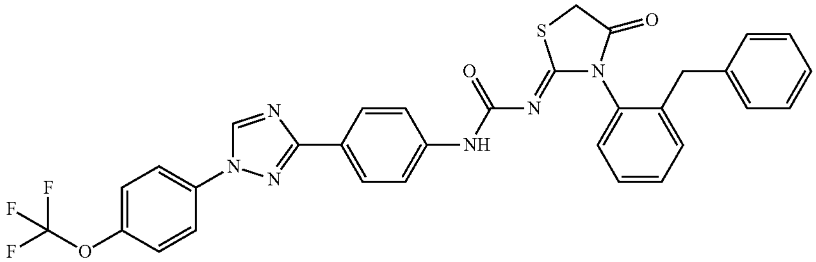 [SMILES: O=C(/N=C1\SCC(=O)N1c1ccccc1Cc1ccccc1)Nc1ccc(-c2ncn(-c3ccc(OC(F)(F)F)cc3)n2)cc1] |
| A106 | 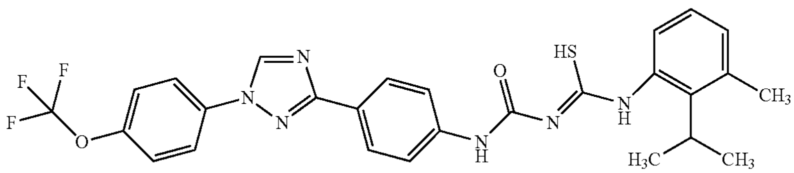 [SMILES: Cc1cccc(N/C(S)=N/C(=O)Nc2ccc(-c3ncn(-c4ccc(OC(F)(F)F)cc4)n3)cc2)c1C(C)C] |
| A107 | 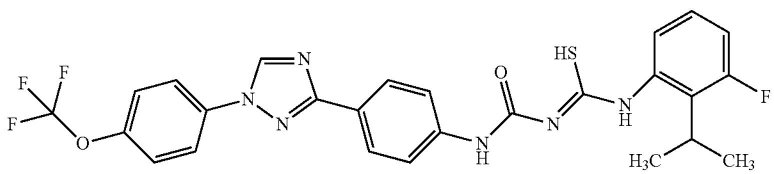 [SMILES: CC(C)c1c(F)cccc1N/C(S)=N/C(=O)Nc1ccc(-c2ncn(-c3ccc(OC(F)(F)F)cc3)n2)cc1] |
| A108 | 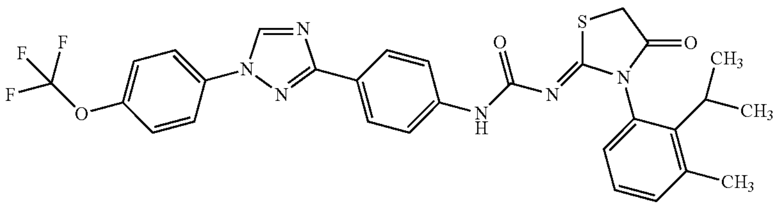 [SMILES: Cc1cccc(N2C(=O)CS/C2=N\C(=O)Nc2ccc(-c3ncn(-c4ccc(OC(F)(F)F)cc4)n3)cc2)c1C(C)C] |
| A109 | 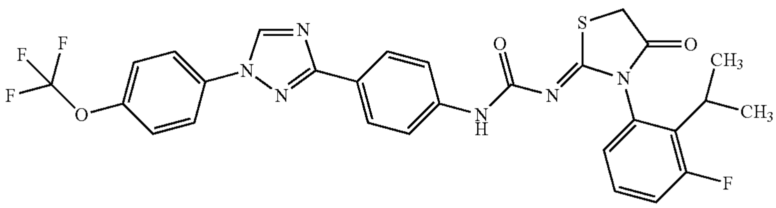 [SMILES: CC(C)c1c(F)cccc1N1C(=O)CS/C1=N\C(=O)Nc1ccc(-c2ncn(-c3ccc(OC(F)(F)F)cc3)n2)cc1] |
| A110 | 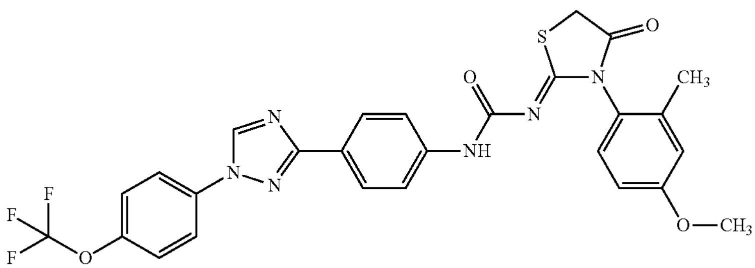 [SMILES: COc1ccc(N2C(=O)CS/C2=N\C(=O)Nc2ccc(-c3ncn(-c4ccc(OC(F)(F)F)cc4)n3)cc2)c(C)c1] |
| A111 | 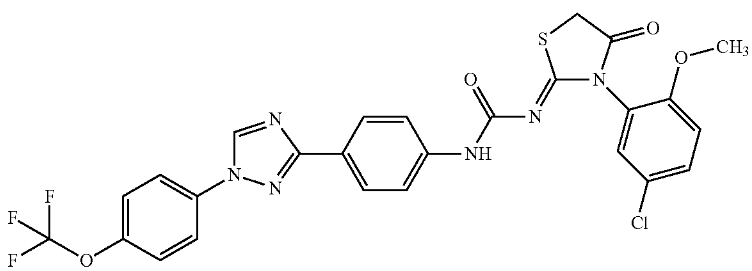 [SMILES: COc1ccc(Cl)cc1N1C(=O)CS/C1=N\C(=O)Nc1ccc(-c2ncn(-c3ccc(OC(F)(F)F)cc3)n2)cc1] |

-continued
| No. | Structure |
|---|---|
| A112 | 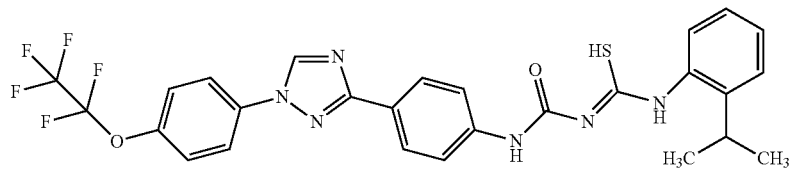 [SMILES: CC(C)c1ccccc1N/C(S)=N/C(=O)Nc1ccc(-c2ncn(-c3ccc(OC(F)(F)C(F)(F)F)cc3)n2)cc1] |
| A113 | 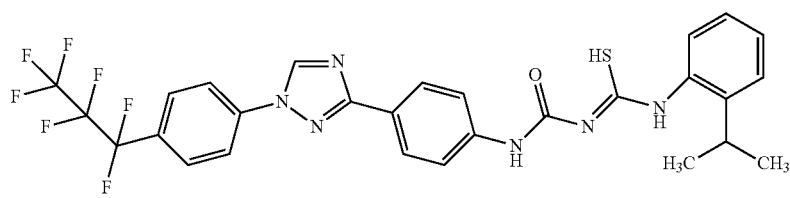 [SMILES: CC(C)c1ccccc1N/C(S)=N/C(=O)Nc1ccc(-c2ncn(-c3ccc(C(F)(F)C(F)(F)C(F)(F)F)cc3)n2)cc1] |
| A114 | 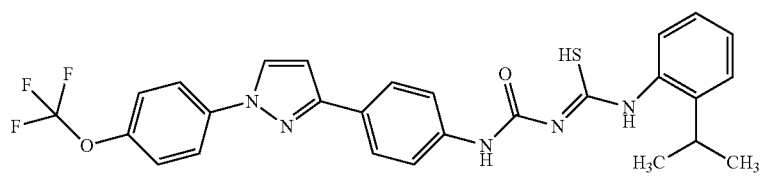 |
| A115 | 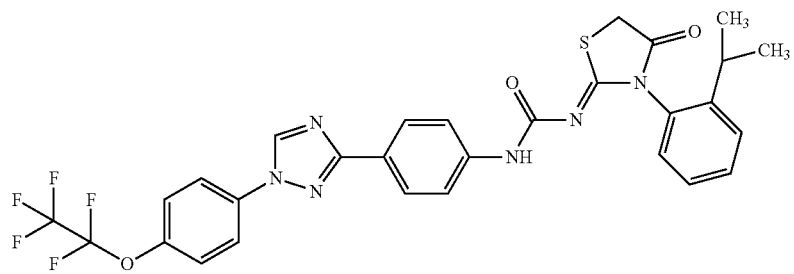 [SMILES: CC(C)c1ccccc1N1C(=O)CS/C1=N\C(=O)Nc1ccc(-c2ncn(-c3ccc(OC(F)(F)C(F)(F)F)cc3)n2)cc1] |
| A116 | 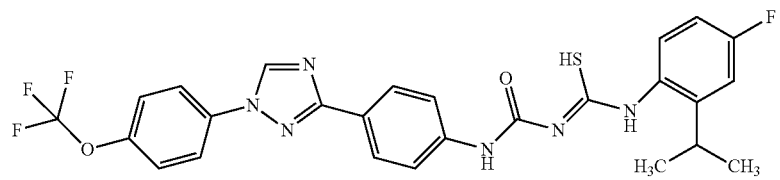 [SMILES: CC(C)c1cc(F)ccc1N/C(S)=N/C(=O)Nc1ccc(-c2ncn(-c3ccc(OC(F)(F)F)cc3)n2)cc1] |
| A117 | 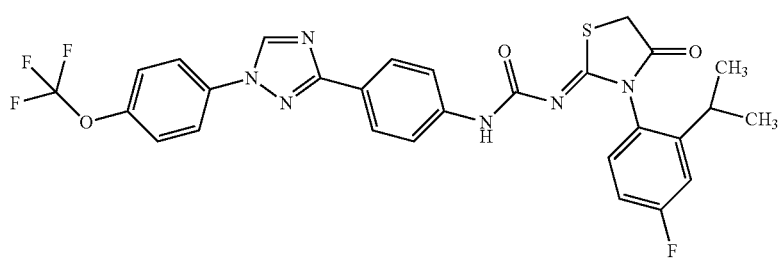 [SMILES: CC(C)c1cc(F)ccc1N1C(=O)CS/C1=N\C(=O)Nc1ccc(-c2ncn(-c3ccc(OC(F)(F)F)cc3)n2)cc1] |
| A118 | 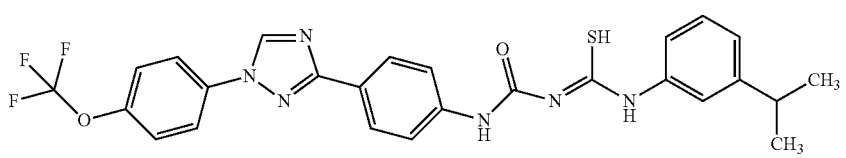 [SMILES: CC(C)c1cccc(N/C(S)=N/C(=O)Nc2ccc(-c3ncn(-c4ccc(OC(F)(F)F)cc4)n3)cc2)c1] |

-continued
| No. | Structure |
|---|---|
| A119 | 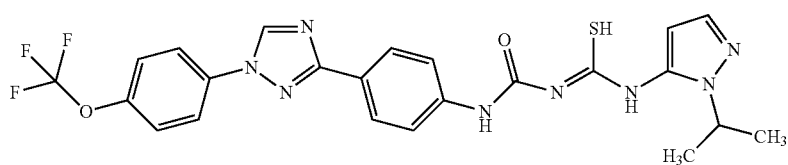 [SMILES: CC(C)n1nccc1N/C(S)=N/C(=O)Nc1ccc(-c2ncn(-c3ccc(OC(F)(F)F)cc3)n2)cc1] |
| A120 | 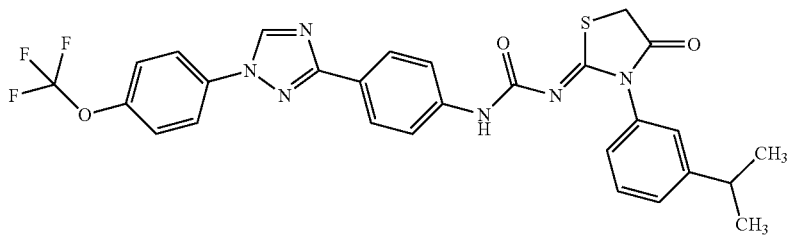 [SMILES: CC(C)c1cccc(N2C(=O)CS/C2=N\C(=O)Nc2ccc(-c3ncn(-c4ccc(OC(F)(F)F)cc4)n3)cc2)c1] |
| A121 | 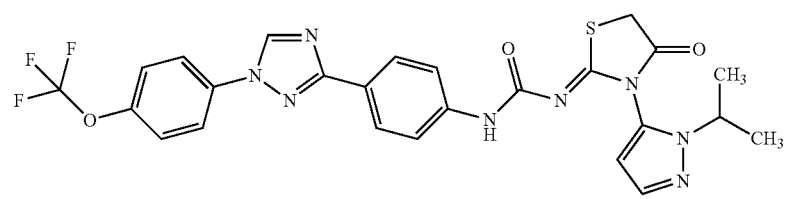 [SMILES: CC(C)n1nccc1N1C(=O)CS/C1=N\C(=O)Nc1ccc(-c2ncn(-c3ccc(OC(F)(F)F)cc3)n2)cc1] |
| A122 | 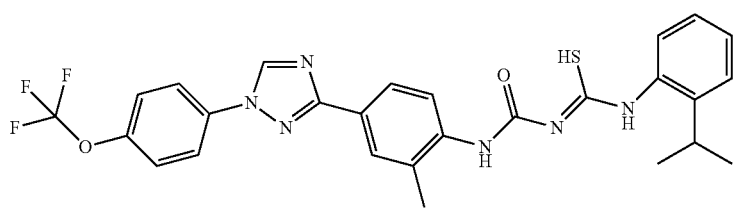 [SMILES: Cc1cc(-c2ncn(-c3ccc(OC(F)(F)F)cc3)n2)ccc1NC(=O)/N=C(\S)Nc1ccccc1C(C)C] |
| A123 | 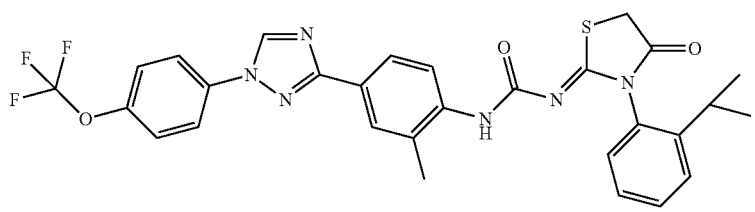 [SMILES: Cc1cc(-c2ncn(-c3ccc(OC(F)(F)F)cc3)n2)ccc1NC(=O)/N=C1\SCC(=O)N1c1ccccc1C(C)C] |
| A124 | 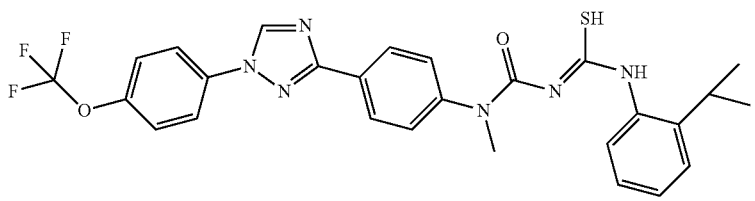 [SMILES: CC(C)c1ccccc1N/C(S)=N/C(=O)N(C)c1ccc(-c2ncn(-c3ccc(OC(F)(F)F)cc3)n2)cc1] |
| A125 | 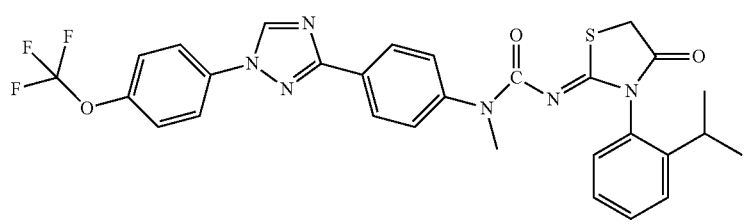 [SMILES: CC(C)c1ccccc1N1C(=O)CS/C1=N\C(=O)N(C)c1ccc(-c2ncn(-c3ccc(OC(F)(F)F)cc3)n2)cc1] |

11. The composition of claim 10, wherein the molecule has a structure selected from compounds listed below:

| No. | Structure |
|---|---|
| A1 | 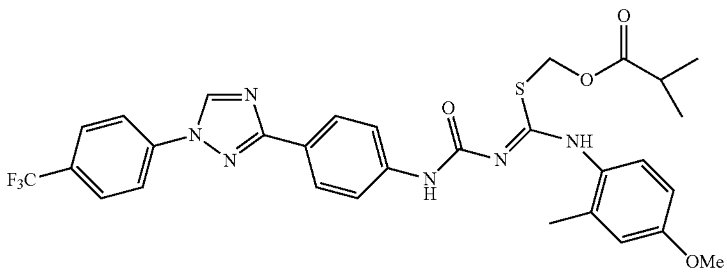 [SMILES: COc1ccc(N/C(=N/C(=O)Nc2ccc(-c3ncn(-c4ccc(C(F)(F)F)cc4)n3)cc2)SCOC(=O)C(C)C)c(C)c1] |
| A2 | 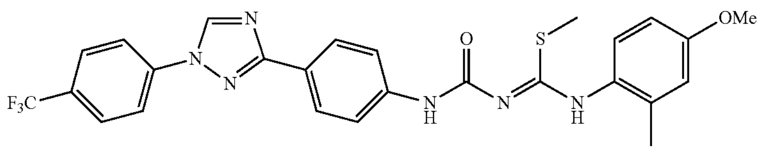 [SMILES: COc1ccc(N/C(=N/C(=O)Nc2ccc(-c3ncn(-c4ccc(C(F)(F)F)cc4)n3)cc2)SC)c(C)c1] |
| A3 | 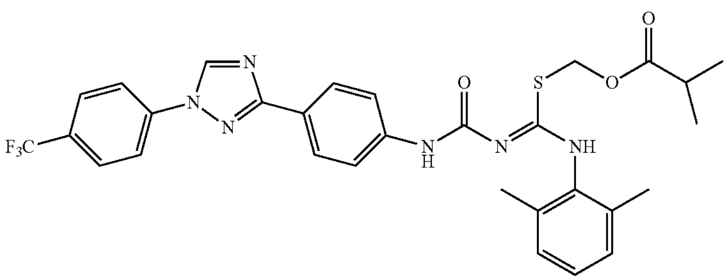 |
| A4 | 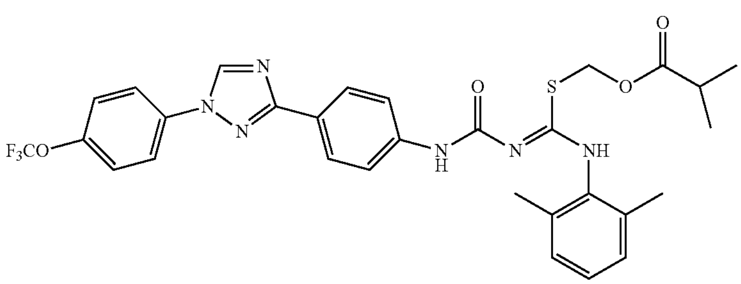 |
| A5 | 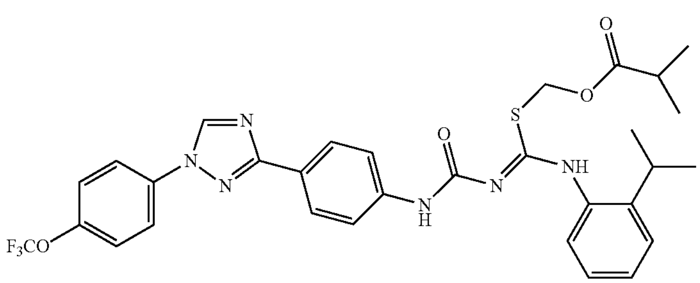 |

-continued
| No. | Structure |
|---|---|
| A6 | 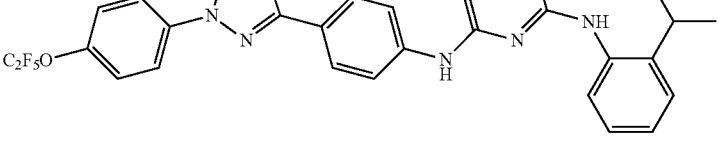 |
| A7 | 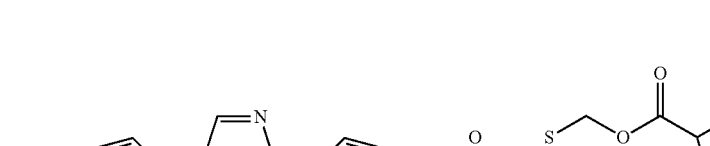 |
| A8 | 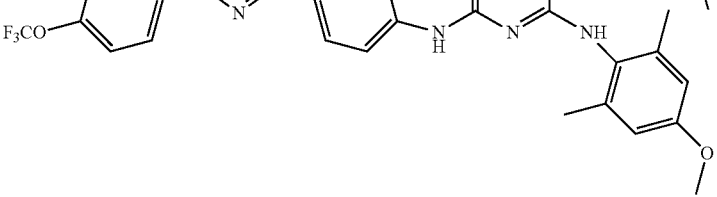 |
| A9 | 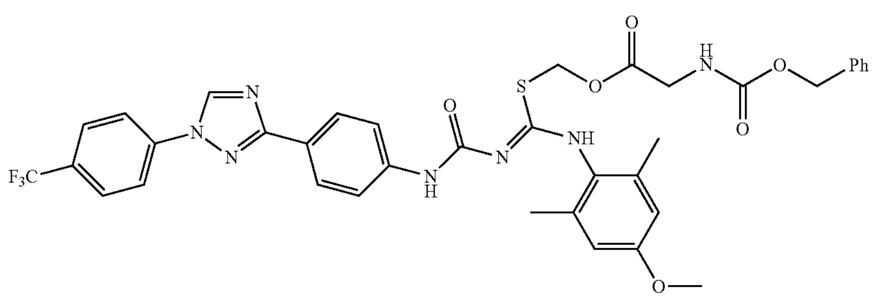 |
| A10 | 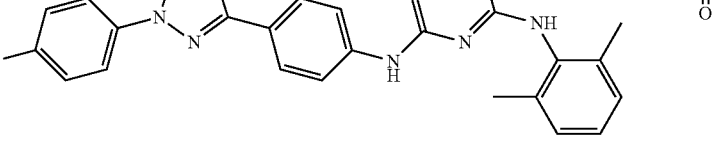 |

| No. | Structure |
|---|---|
| A11 | 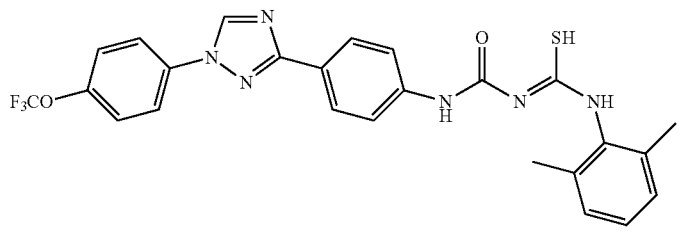 |
| A12 | 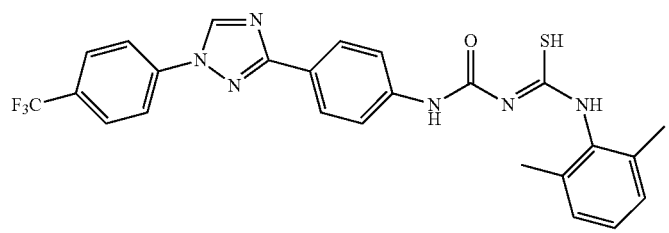 |
| A13 | 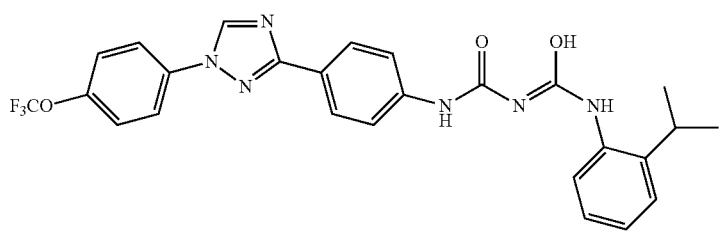 |
| A14 | 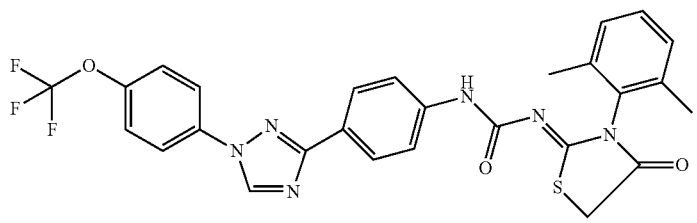 |
| A15 | 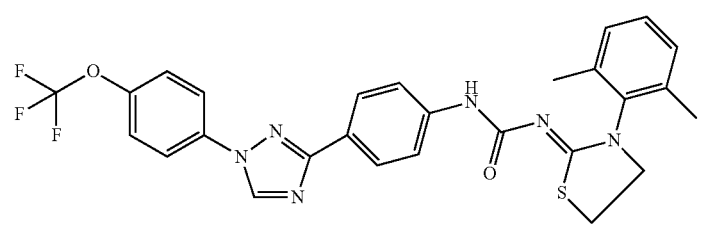 |

-continued
| No. | Structure |
|---|---|
| A16 | 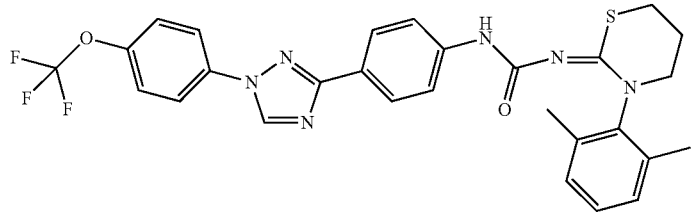 |
| A17 | 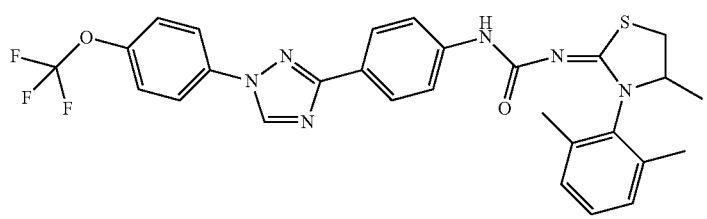 |
| A18 | 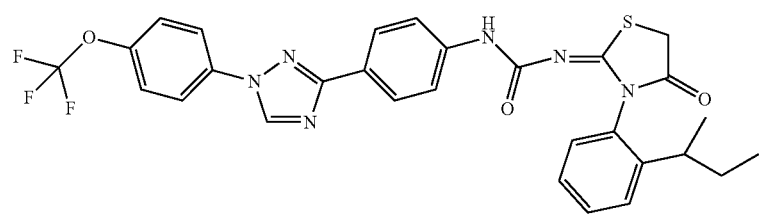 [SMILES: CCC(C)c1ccccc1N1C(=O)CS/C1=N/C(=O)Nc1ccc(-c2ncn(-c3ccc(OC(F)(F)F)cc3)n2)cc1] |
| A19 | 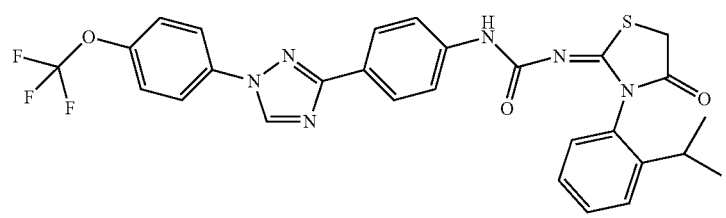 [SMILES: CC(C)c1ccccc1N1C(=O)CS/C1=N/C(=O)Nc1ccc(-c2ncn(-c3ccc(OC(F)(F)F)cc3)n2)cc1] |
| A20 | 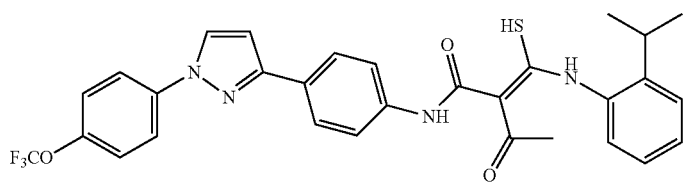 [SMILES: CC(=O)/C(C(=O)Nc1ccc(-c2ccn(-c3ccc(OC(F)(F)F)cc3)n2)cc1)=C(/S)Nc1ccccc1C(C)C] |
| A21 | 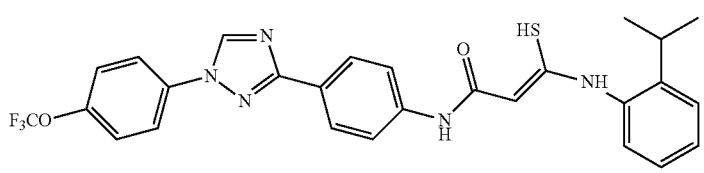 [SMILES: CC(C)c1ccccc1N/C(S)=C/C(=O)Nc1ccc(-c2ncn(-c3ccc(OC(F)(F)F)cc3)n2)cc1] |
| A22 | 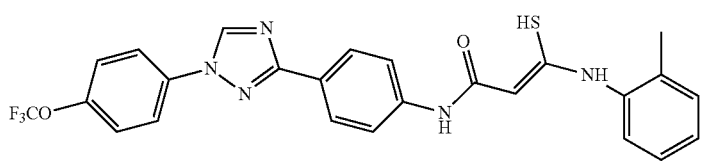 [SMILES: Cc1ccccc1N/C(S)=C/C(=O)Nc1ccc(-c2ncn(-c3ccc(OC(F)(F)F)cc3)n2)cc1] |

-continued
| No. | Structure |
|---|---|
| A23 | 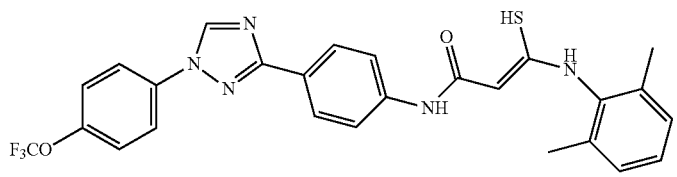 [SMILES: Cc1cccc(C)c1N/C(S)=C/C(=O)Nc1ccc(-c2ncn(-c3ccc(OC(F)(F)F)cc3)n2)cc1] |
| A24 | 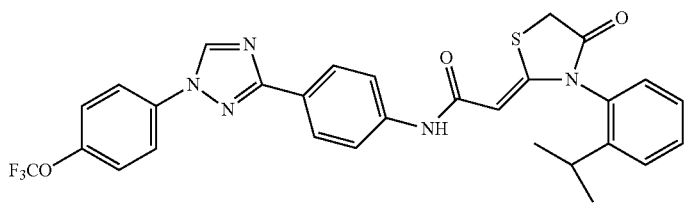 [SMILES: CC(C)c1ccccc1N1C(=O)CS/C1=C\C(=O)Nc1ccc(-c2ncn(-c3ccc(OC(F)(F)F)cc3)n2)cc1] |
| A25 | 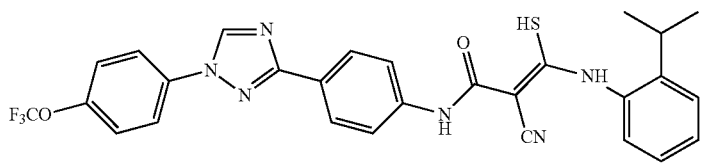 [SMILES: CC(C)c1ccccc1N/C(S)=C(\C#N)C(=O)Nc1ccc(-c2ncn(-c3ccc(OC(F)(F)F)cc3)n2)cc1] |
| A26 | 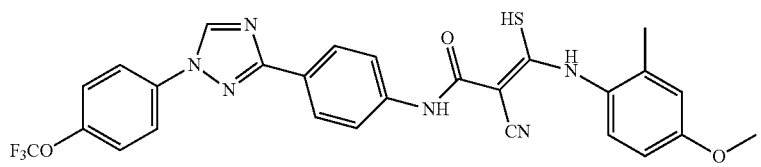 [SMILES: COc1ccc(N/C(S)=C(\C#N)C(=O)Nc2ccc(-c3ncn(-c4ccc(OC(F)(F)F)cc4)n3)cc2)c(C)c1] |
| A27 | 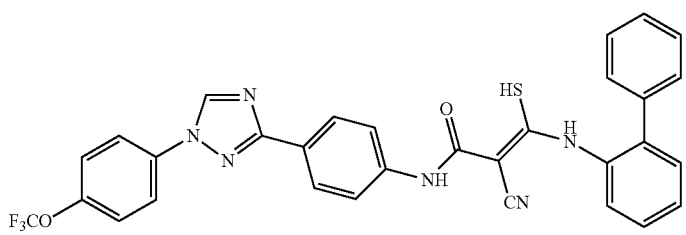 [SMILES: N#C/C(C(=O)Nc1ccc(-c2ncn(-c3ccc(OC(F)(F)F)cc3)n2)cc1)=C(/S)Nc1ccccc1-c1ccccc1] |
| A28 | 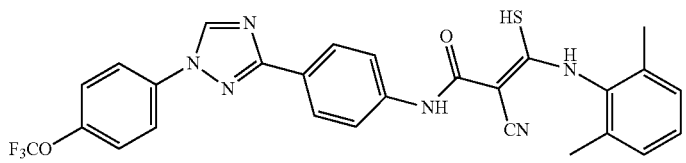 |
| A29 | 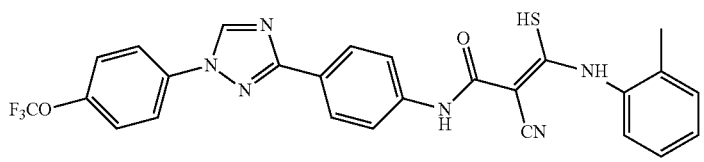 [SMILES: Cc1ccccc1N/C(S)=C(\C#N)C(=O)Nc1ccc(-c2ncn(-c3ccc(OC(F)(F)F)cc3)n2)cc1] |
| A30 | 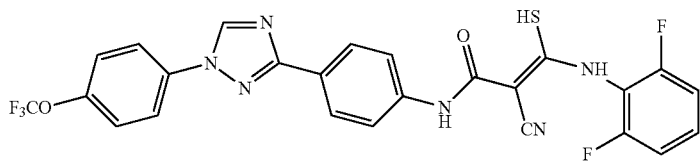 [SMILES: N#C/C(C(=O)Nc1ccc(-c2ncn(-c3ccc(OC(F)(F)F)cc3)n2)cc1)=C(/S)Nc1c(F)cccc1F] |

-continued
| No. | Structure |
|---|---|
| A31 | 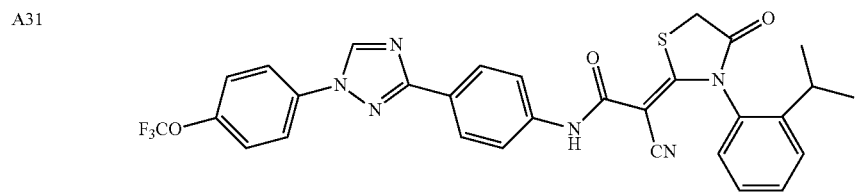 |
| A32 | 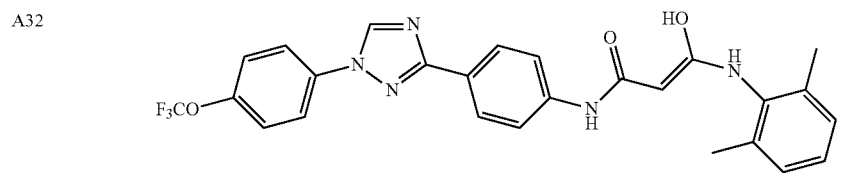 |
| A33 | 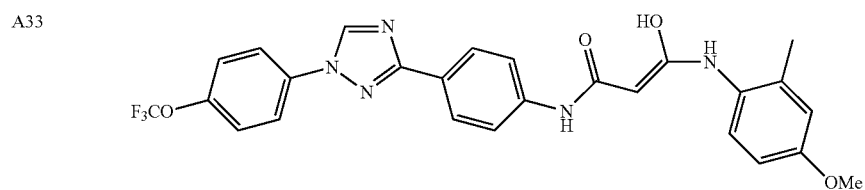 |
| A34 | 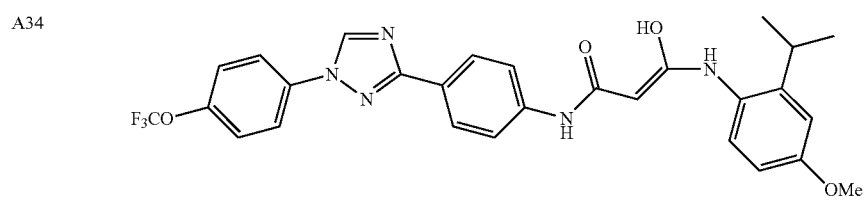 |
| A35 | 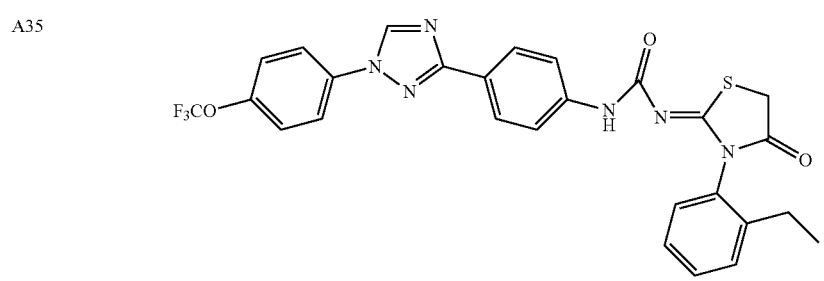 |
| A36 | 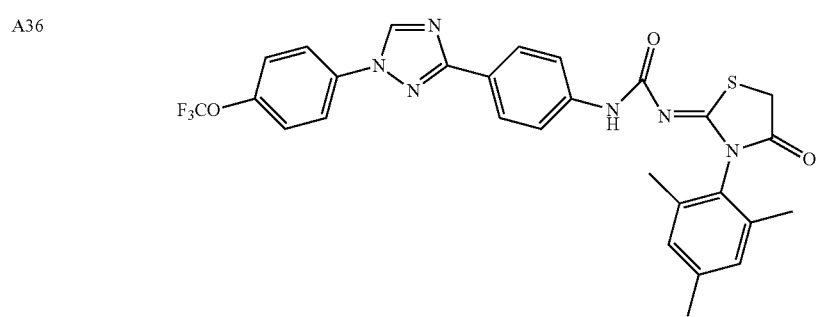 |

| No. | Structure |
|---|---|
| A37 | 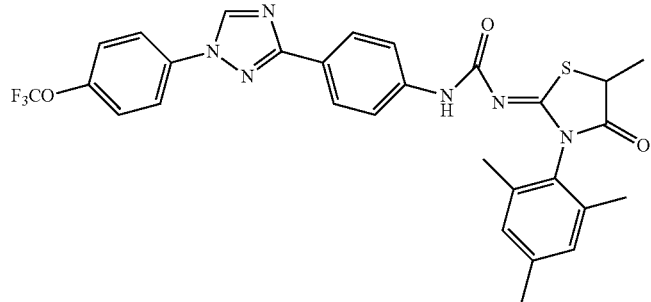 [SMILES: Cc1cc(C)c(N2C(=O)C(C)S/C2=N\C(=O)Nc2ccc(-c3ncn(-c4ccc(OC(F)(F)F)cc4)n3)cc2)c(C)c1] |
| A38 | 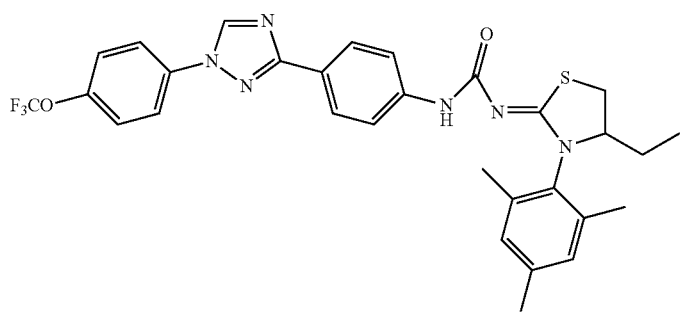 [SMILES: CCC1CS/C(=N\C(=O)Nc2ccc(-c3ncn(-c4ccc(OC(F)(F)F)cc4)n3)cc2)N1c1c(C)cc(C)cc1C] |
| A39 | 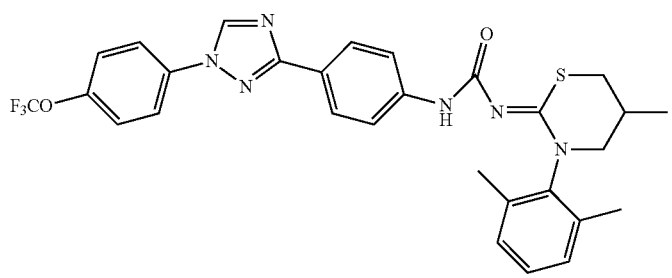 [SMILES: Cc1cccc(C)c1N1CC(C)CS/C1=N\C(=O)Nc1ccc(-c2ncn(-c3ccc(OC(F)(F)F)cc3)n2)cc1] |
| A40 | 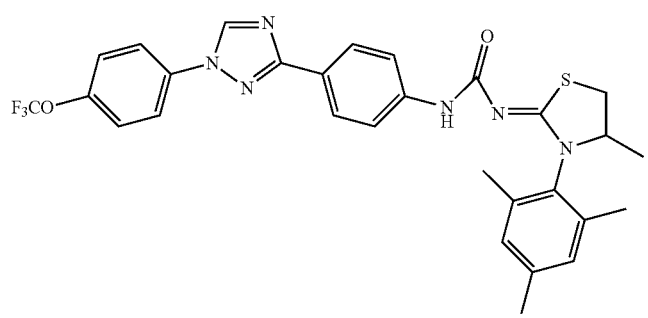 [SMILES: Cc1cc(C)c(N2/C(=N/C(=O)Nc3ccc(-c4ncn(-c5ccc(OC(F)(F)F)cc5)n4)cc3)SCC2C)c(C)c1] |
| A41 | 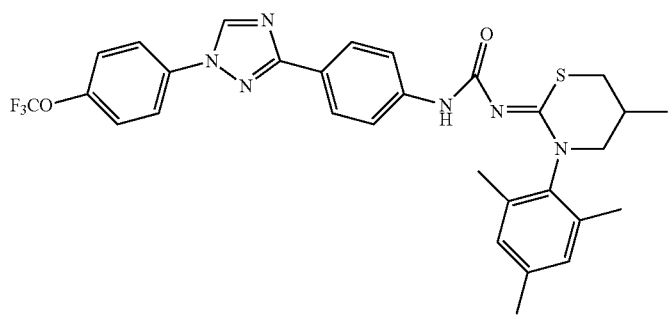 [SMILES: Cc1cc(C)c(N2CC(C)CS/C2=N\C(=O)Nc2ccc(-c3ncn(-c4ccc(OC(F)(F)F)cc4)n3)cc2)c(C)c1] |

-continued
| No. | Structure |
|---|---|
| A42 | 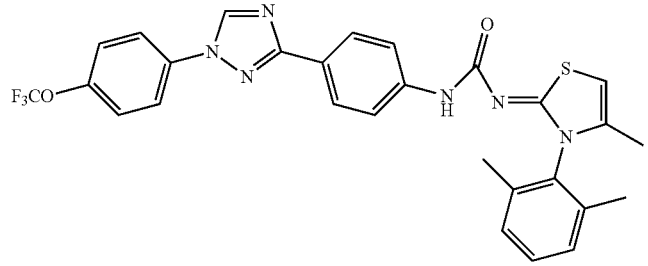 [SMILES: Cc1cccc(C)c1-n1c(C)cs/c1=N\C(=O)Nc1ccc(-c2ncn(-c3ccc(OC(F)(F)F)cc3)n2)cc1] |
| A43 | 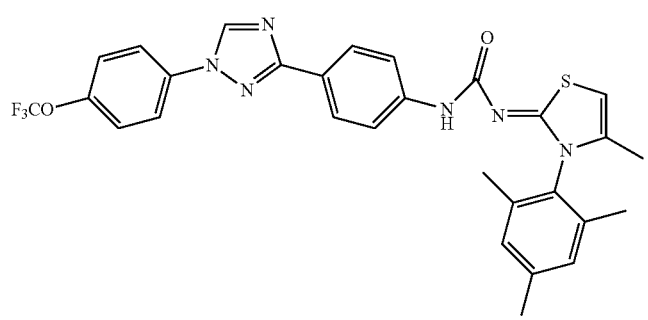 [SMILES: Cc1cc(C)c(-n2c(C)cs/c2=N\C(=O)Nc2ccc(-c3ncn(-c4ccc(OC(F)(F)F)cc4)n3)cc2)c(C)c1] |
| A44 | 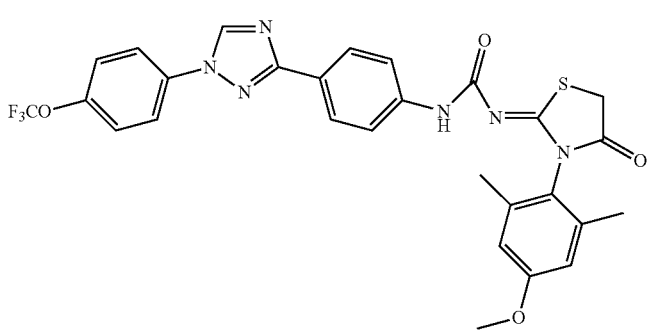 [SMILES: COc1cc(C)c(N2C(=O)CS/C2=N\C(=O)Nc2ccc(-c3ncn(-c4ccc(OC(F)(F)F)cc4)n3)cc2)c(C)c1] |
| A46 | 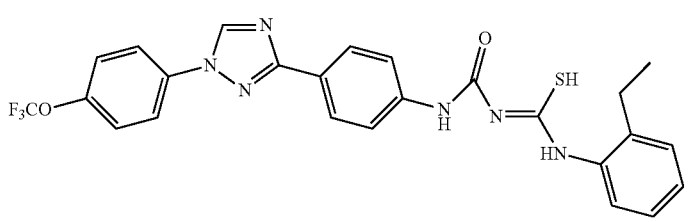 |
| A48 | 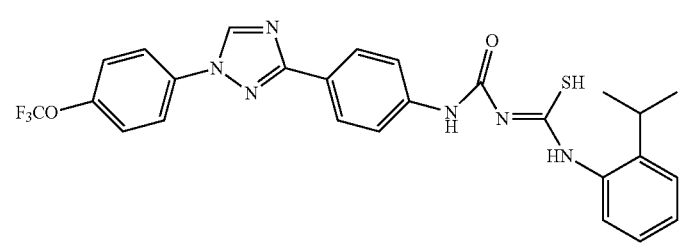 [SMILES: CC(C)c1ccccc1N/C(S)=N/C(=O)Nc1ccc(-c2ncn(-c3ccc(OC(F)(F)F)cc3)n2)cc1] |
| A49 | 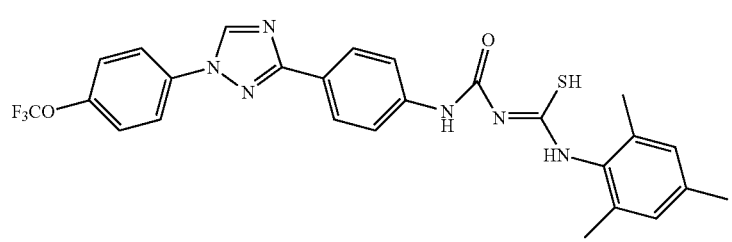 [SMILES: Cc1cc(C)c(N/C(S)=N/C(=O)Nc2ccc(-c3ncn(-c4ccc(OC(F)(F)F)cc4)n3)cc2)c(C)c1] |

| No. | Structure |
|---|---|
| A92 | 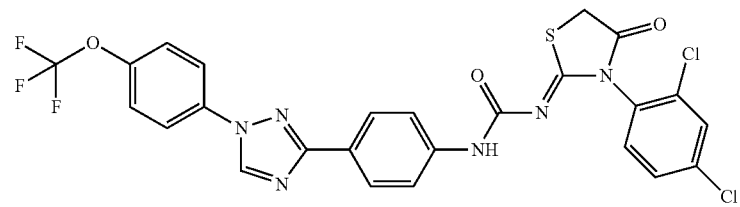 [SMILES: O=C(/N=C1\SCC(=O)N1c1ccc(Cl)cc1Cl)Nc1ccc(-c2ncn(-c3ccc(OC(F)(F)F)cc3)n2)cc1] |
| A93 | 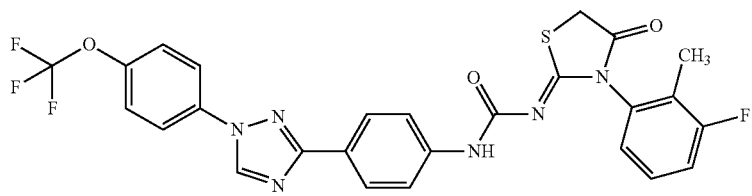 [SMILES: Cc1c(F)cccc1N1C(=O)CS/C1=N\C(=O)Nc1ccc(-c2ncn(-c3ccc(OC(F)(F)F)cc3)n2)cc1] |
| A94 | 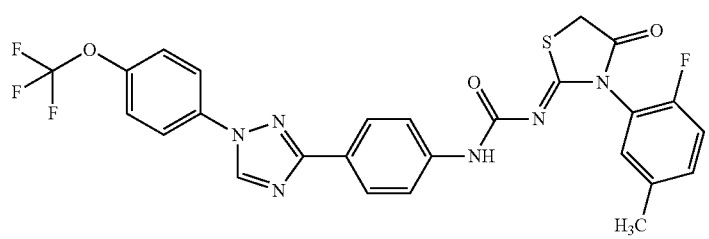 [SMILES: Cc1ccc(F)c(N2C(=O)CS/C2=N\C(=O)Nc2ccc(-c3ncn(-c4ccc(OC(F)(F)F)cc4)n3)cc2)c1] |
| A95 | 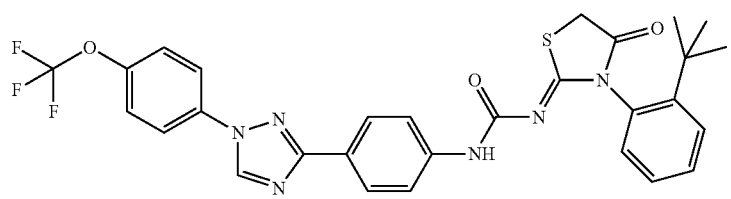 [SMILES: CC(C)(C)c1ccccc1N1C(=O)CS/C1=N\C(=O)Nc1ccc(-c2ncn(-c3ccc(OC(F)(F)F)cc3)n2)cc1] |
| A96 | 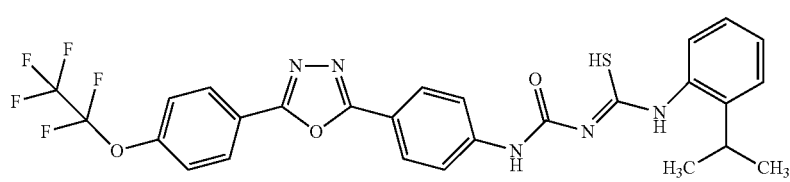 [SMILES: CC(C)c1ccccc1N/C(S)=N/C(=O)Nc1ccc(-c2nnc(-c3ccc(OC(F)(F)C(F)(F)F)cc3)o2)cc1] |
| A97 | 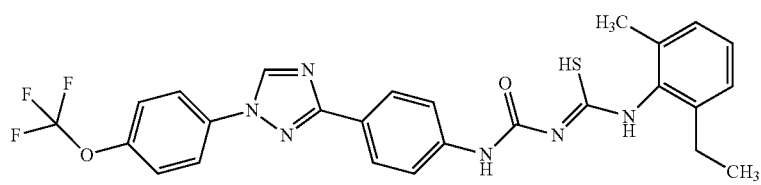 |
| A98 | 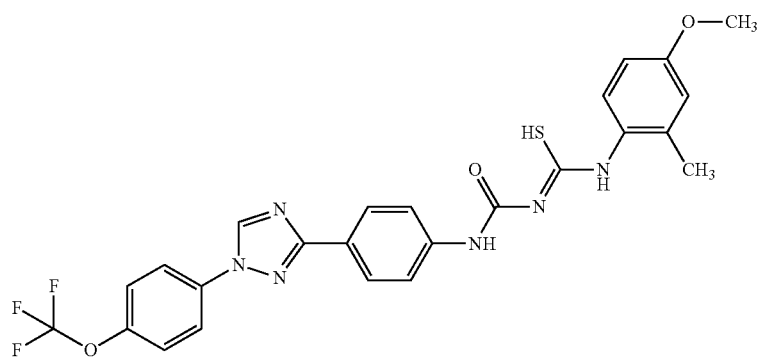 [SMILES: COc1ccc(N/C(S)=N/C(=O)Nc2ccc(-c3ncn(-c4ccc(OC(F)(F)F)cc4)n3)cc2)c(C)c1] |

-continued
| No. | Structure |
|---|---|
| A99 | 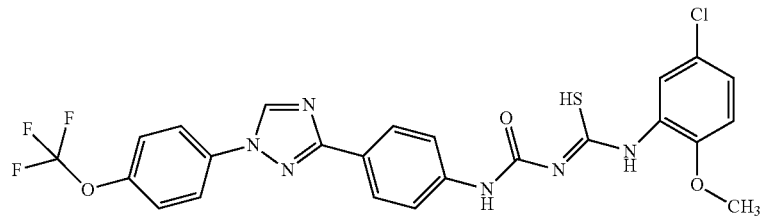 [SMILES: COc1ccc(Cl)cc1N/C(S)=N/C(=O)Nc1ccc(-c2ncn(-c3ccc(OC(F)(F)F)cc3)n2)cc1] |
| A100 | 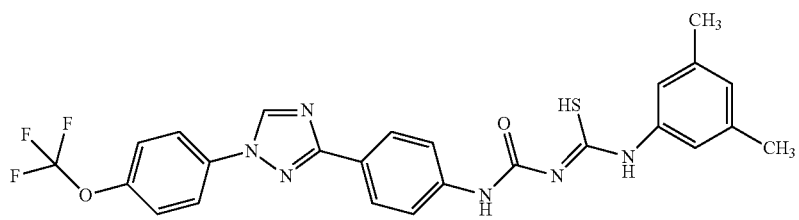 [SMILES: Cc1cc(C)cc(N/C(S)=N/C(=O)Nc2ccc(-c3ncn(-c4ccc(OC(F)(F)F)cc4)n3)cc2)c1] |
| A101 | 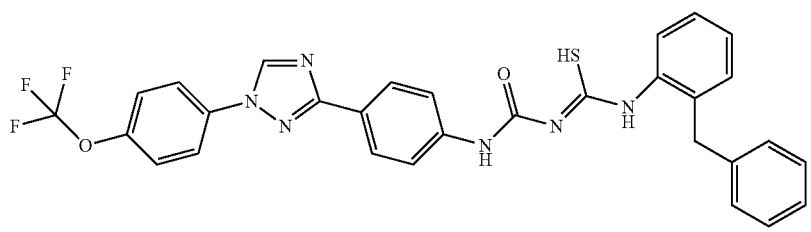 [SMILES: O=C(/N=C(\S)Nc1ccccc1Cc1ccccc1)Nc1ccc(-c2ncn(-c3ccc(OC(F)(F)F)cc3)n2)cc1] |
| A102 | 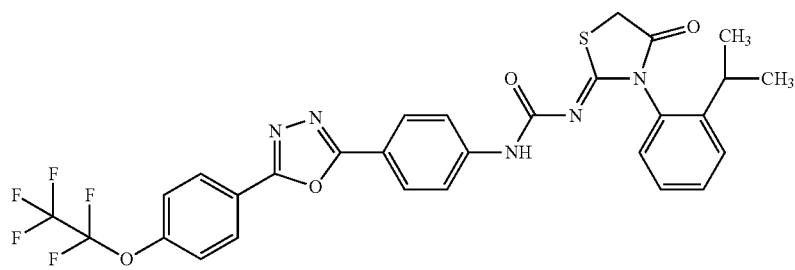 [SMILES: CC(C)c1ccccc1N1C(=O)CS/C1=N\C(=O)Nc1ccc(-c2nnc(-c3ccc(OC(F)(F)C(F)(F)F)cc3)o2)cc1] |
| A103 | 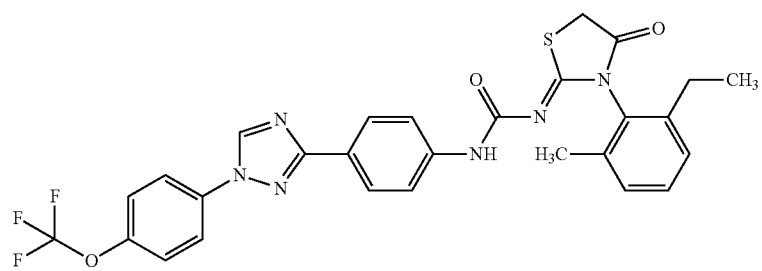 [SMILES: CCc1cccc(C)c1N1C(=O)CS/C1=N\C(=O)Nc1ccc(-c2ncn(-c3ccc(OC(F)(F)F)cc3)n2)cc1] |
| A104 | 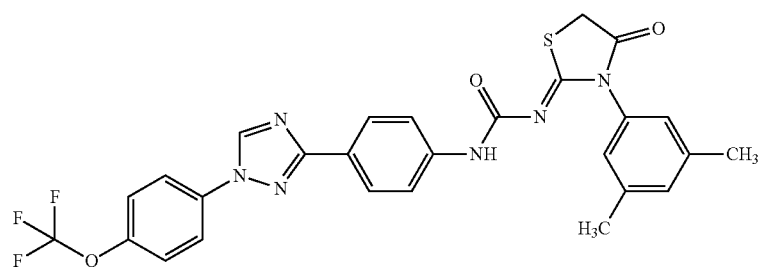 [SMILES: Cc1cc(C)cc(N2C(=O)CS/C2=N\C(=O)Nc2ccc(-c3ncn(-c4ccc(OC(F)(F)F)cc4)n3)cc2)c1] |

-continued

| No. | Structure |
|---|---|
| A105 | 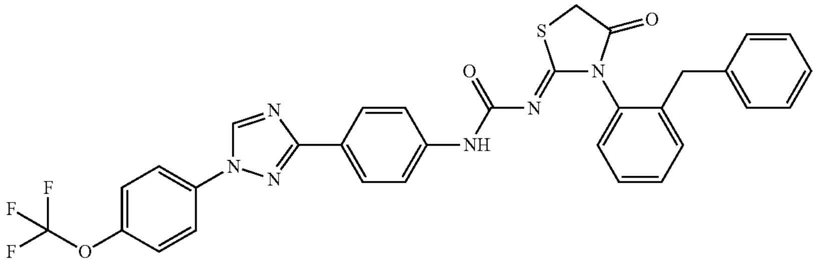 [SMILES: O=C(/N=C1\SCC(=O)N1c1ccccc1Cc1ccccc1)Nc1ccc(-c2ncn(-c3ccc(OC(F)(F)F)cc3)n2)cc1] |
| A106 | 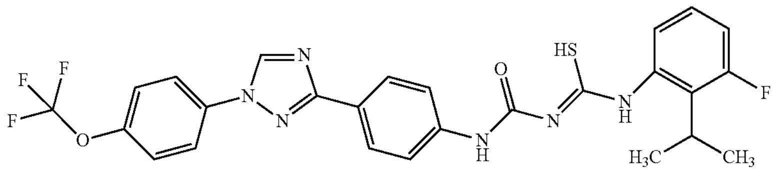 [SMILES: CC(C)c1c(F)cccc1N/C(S)=N/C(=O)Nc1ccc(-c2ncn(-c3ccc(OC(F)(F)F)cc3)n2)cc1] |
| A107 | 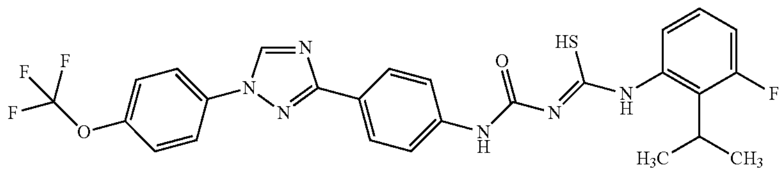 [SMILES: CC(C)c1c(F)cccc1N/C(S)=N/C(=O)Nc1ccc(-c2ncn(-c3ccc(OC(F)(F)F)cc3)n2)cc1] |
| A108 | 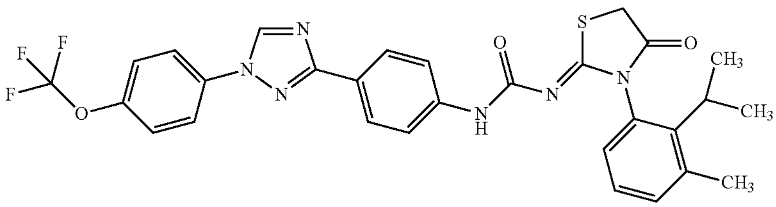 [SMILES: Cc1cccc(N2C(=O)CS/C2=N\C(=O)Nc2ccc(-c3ncn(-c4ccc(OC(F)(F)F)cc4)n3)cc2)c1C(C)C] |
| A109 | 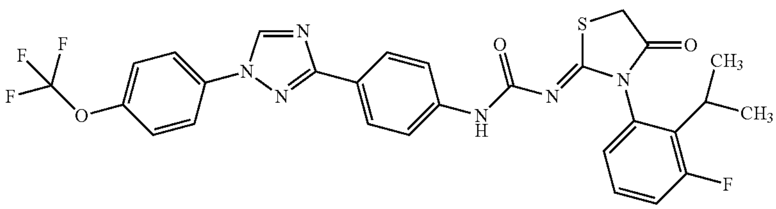 [SMILES: CC(C)c1c(F)cccc1N1C(=O)CS/C1=N\C(=O)Nc1ccc(-c2ncn(-c3ccc(OC(F)(F)F)cc3)n2)cc1] |
| A110 | 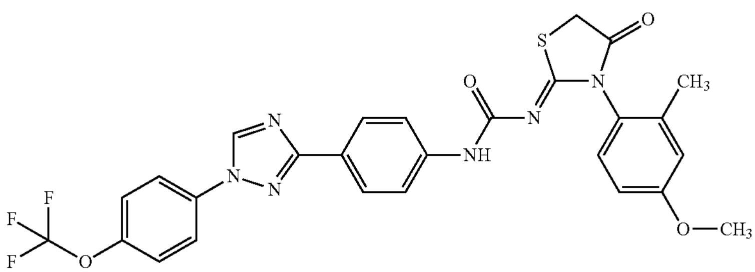 [SMILES: COc1ccc(N2C(=O)CS/C2=N\C(=O)Nc2ccc(-c3ncn(-c4ccc(OC(F)(F)F)cc4)n3)cc2)c(C)c1] |
| A111 | 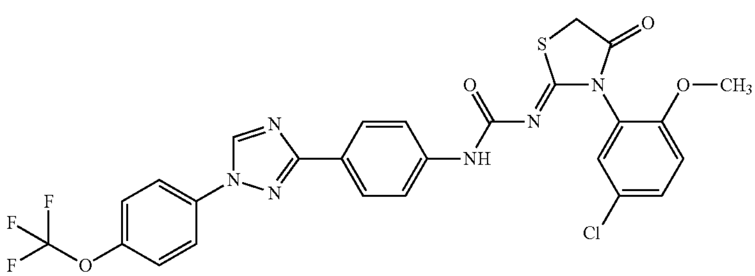 [SMILES: COc1ccc(Cl)cc1N1C(=O)CS/C1=N\C(=O)Nc1ccc(-c2ncn(-c3ccc(OC(F)(F)F)cc3)n2)cc1] |

| No. | Structure |
|---|---|
| A112 | 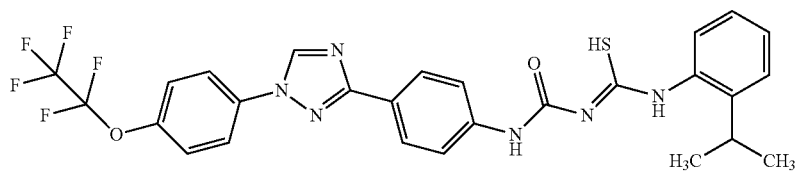 [SMILES: CC(C)c1ccccc1N/C(S)=N/C(=O)Nc1ccc(-c2ncn(-c3ccc(OC(F)(F)C(F)(F)F)cc3)n2)cc1] |
| A113 | 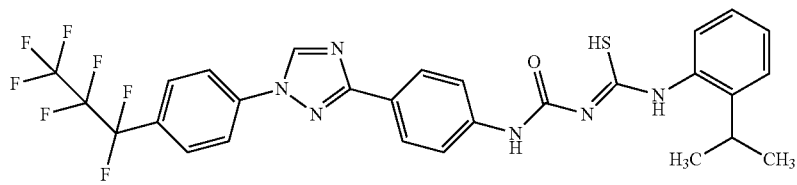 [SMILES: CC(C)c1ccccc1N/C(S)=N/C(=O)Nc1ccc(-c2ncn(-c3ccc(C(F)(F)C(F)(F)C(F)(F)F)cc3)n2)cc1] |
| A114 | 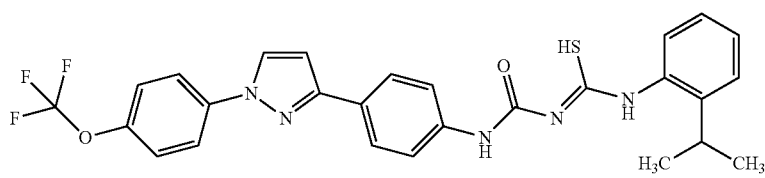 [SMILES: CC(C)c1ccccc1N/C(S)=N/C(=O)Nc1ccc(-c2ccn(-c3ccc(OC(F)(F)F)cc3)n2)cc1] |
| A115 | 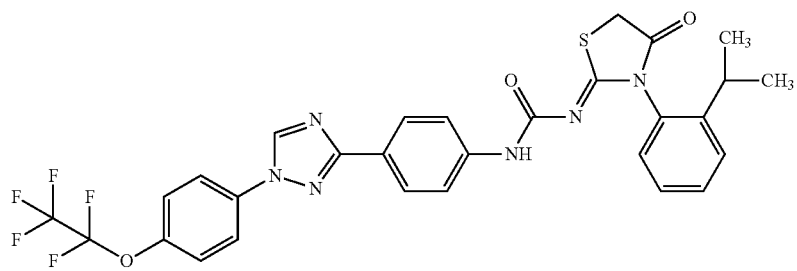 [SMILES: CC(C)c1ccccc1N1C(=O)CS/C1=N\C(=O)Nc1ccc(-c2ncn(-c3ccc(OC(F)(F)C(F)(F)F)cc3)n2)cc1] |
| A116 | 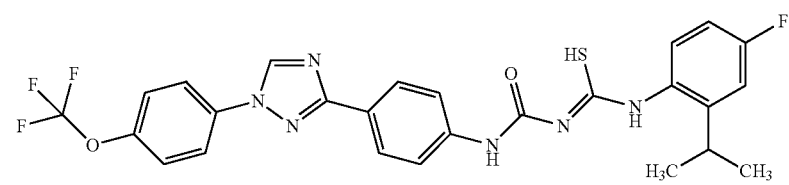 [SMILES: CC(C)c1cc(F)ccc1N/C(S)=N/C(=O)Nc1ccc(-c2ncn(-c3ccc(OC(F)(F)F)cc3)n2)cc1] |
| A117 | 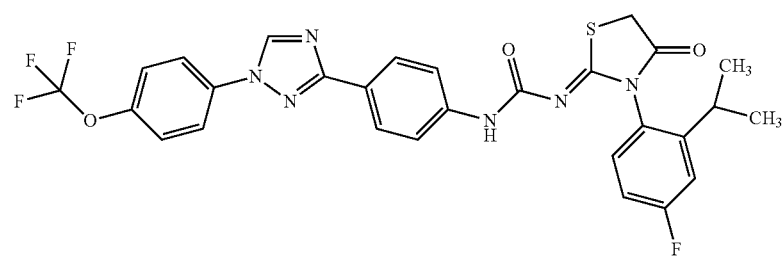 [SMILES: CC(C)c1cc(F)ccc1N1C(=O)CS/C1=N\C(=O)Nc1ccc(-c2ncn(-c3ccc(OC(F)(F)F)cc3)n2)cc1] |
| A118 | 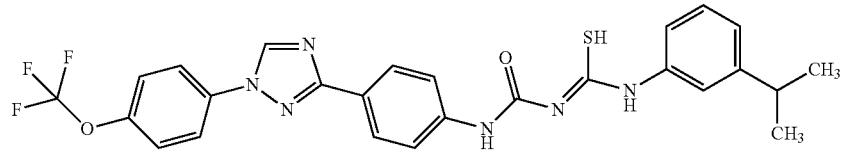 [SMILES: CC(C)c1cccc(N/C(S)=N/C(=O)Nc2ccc(-c3ncn(-c4ccc(OC(F)(F)F)cc4)n3)cc2)c1] |

-continued

| No. | Structure |
|---|---|
| A119 | 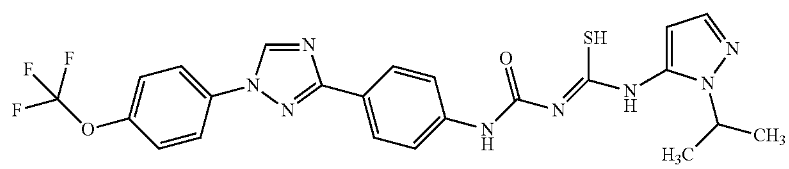 [SMILES: CC(C)n1nccc1N/C(S)=N/C(=O)Nc1ccc(-c2ncn(-c3ccc(OC(F)(F)F)cc3)n2)cc1] |
| A120 | 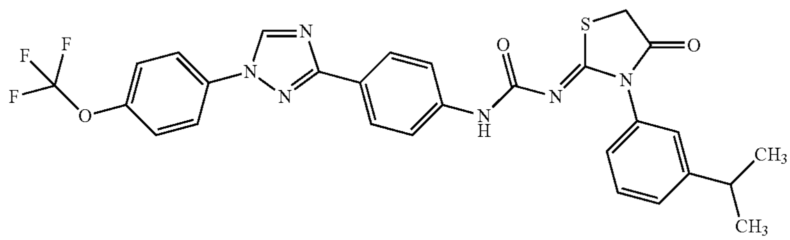 [SMILES: CC(C)c1cccc(N2C(=O)CS/C2=N\C(=O)Nc2ccc(-c3ncn(-c4ccc(OC(F)(F)F)cc4)n3)cc2)c1] |
| A121 | 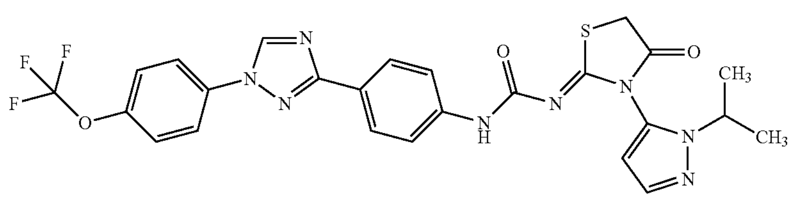 [SMILES: CC(C)n1nccc1N1C(=O)CS/C1=N\C(=O)Nc1ccc(-c2ncn(-c3ccc(OC(F)(F)F)cc3)n2)cc1] |
| A122 | 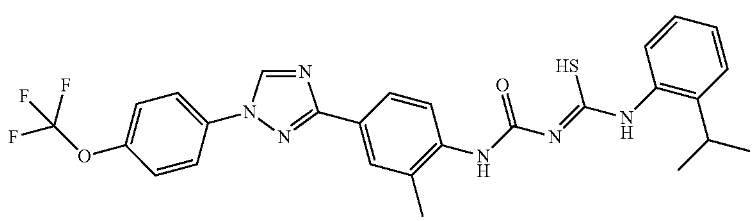 [SMILES: Cc1cc(-c2ncn(-c3ccc(OC(F)(F)F)cc3)n2)ccc1NC(=O)/N=C(\S)Nc1ccccc1C(C)C] |
| A123 | 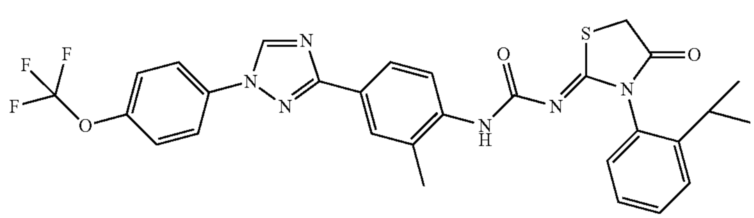 [SMILES: Cc1cc(-c2ncn(-c3ccc(OC(F)(F)F)cc3)n2)ccc1NC(=O)/N=C1\SCC(=O)N1c1ccccc1C(C)C] |
| A124 | 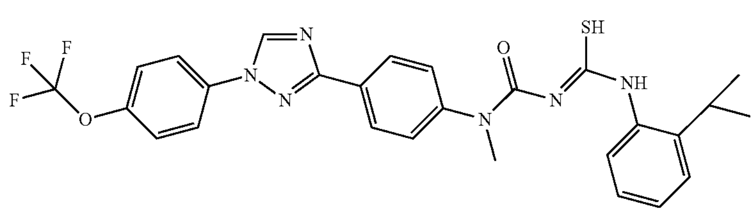 [SMILES: CC(C)c1ccccc1N/C(S)=N/C(=O)N(C)c1ccc(-c2ncn(-c3ccc(OC(F)(F)F)cc3)n2)cc1] |
| A125 | 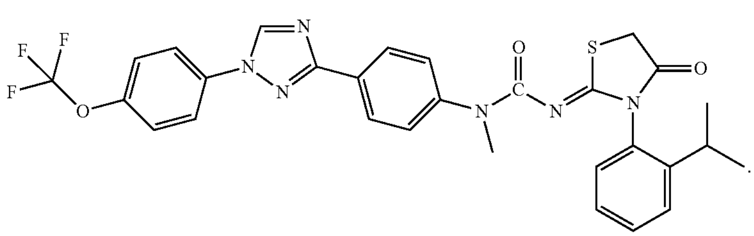 [SMILES: CC(C)c1ccccc1N1C(=O)CS/C1=N\C(=O)N(C)c1ccc(-c2ncn(-c3ccc(OC(F)(F)F)cc3)n2)cc1] |

12. A process comprising applying the composition of claim 10 to a locus to control a pest, in an amount sufficient to control such pest.

\* \* \* \* \*